US012435054B2

(12) United States Patent
Zbieg et al.

(10) Patent No.: US 12,435,054 B2
(45) Date of Patent: Oct. 7, 2025

(54) THERAPEUTIC COMPOUNDS AND METHODS OF USE

(71) Applicant: Genentech, Inc., South San Francisco, CA (US)

(72) Inventors: Jason R. Zbieg, Montara, CA (US); Paul Powell Beroza, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/472,105

(22) Filed: Sep. 21, 2023

(65) Prior Publication Data

US 2024/0208919 A1 Jun. 27, 2024

Related U.S. Application Data

(62) Division of application No. 17/383,422, filed on Jul. 22, 2021, now Pat. No. 11,787,775.

(60) Provisional application No. 63/056,498, filed on Jul. 24, 2020.

(51) Int. Cl.

| | |
|---|---|
| ***C07D 307/81*** | (2006.01) |
| ***C07D 213/74*** | (2006.01) |
| ***C07D 277/64*** | (2006.01) |
| ***C07D 405/10*** | (2006.01) |
| ***C07D 409/10*** | (2006.01) |
| ***C07D 417/10*** | (2006.01) |
| ***C07D 491/048*** | (2006.01) |
| ***C07F 5/02*** | (2006.01) |

(52) U.S. Cl.
CPC ......... *C07D 307/81* (2013.01); *C07D 213/74* (2013.01); *C07D 277/64* (2013.01); *C07D 405/10* (2013.01); *C07D 409/10* (2013.01); *C07D 417/10* (2013.01); *C07D 491/048* (2013.01); *C07F 5/025* (2013.01)

(58) Field of Classification Search
CPC .................................................... C07D 307/81
See application file for complete search history.

(56) References Cited

U.S. PATENT DOCUMENTS

| | | | | |
|---|---|---|---|---|
| 7,465,815 | B2 | 12/2008 | Ohkawa et al. | |
| 7,507,841 | B2 | 3/2009 | Ohkawa et al. | |
| 11,787,775 | B2 * | 10/2023 | Zbieg | C07D 307/81 514/64 |
| 2014/0232463 | A1 | 8/2014 | Matsuya | |
| 2021/0253518 | A1 | 8/2021 | Nishino et al. | |
| 2022/0017491 | A1 | 1/2022 | Lim et al. | |

FOREIGN PATENT DOCUMENTS

| | | | |
|---|---|---|---|
| CZ | 306434 | B6 | 1/2017 |
| CZ | 306987 | B6 | 11/2017 |
| JP | 2000-302778 | A | 10/2000 |
| JP | 2016-504289 | A | 2/2016 |
| WO | 02/055521 | A1 | 7/2002 |
| WO | 02/055524 | A1 | 7/2002 |
| WO | 2014/084778 | A1 | 6/2014 |
| WO | 2015/128333 | A1 | 9/2015 |
| WO | 2017/053706 | A1 | 3/2017 |
| WO | 2017/058716 | A1 | 4/2017 |
| WO | 2017/064277 | A1 | 4/2017 |
| WO | 2018/185266 | A1 | 10/2018 |
| WO | 2018/204532 | A1 | 11/2018 |
| WO | 2019/040380 | A1 | 2/2019 |
| WO | 2019/113236 | A1 | 6/2019 |
| WO | 2019/222431 | A1 | 11/2019 |
| WO | 2019/222431 | A9 | 11/2019 |
| WO | 2019/232216 | A1 | 12/2019 |
| WO | 2020/047037 | A1 | 3/2020 |
| WO | 2020/051099 | A1 | 3/2020 |
| WO | 2020/070181 | A1 | 4/2020 |
| WO | 2020/081572 | A1 | 4/2020 |
| WO | 2020/096416 | A1 | 5/2020 |
| WO | 2020/097389 | A1 | 5/2020 |
| WO | 2020/190774 | A1 | 9/2020 |
| WO | 2020/214734 | A1 | 10/2020 |
| WO | 2020/243423 | A1 | 12/2020 |
| WO | 2021/018869 | A1 | 2/2021 |
| WO | 2019/235569 | A1 | 7/2021 |

OTHER PUBLICATIONS

Aurora Fine Chemicals et al., CAS Registry Database, 1789004-01-8, (N-(3,4-Dimethylphenyl)-3-ethyl-3-oxetanecarboxamide; C14H19NO2), pp. 1Creation Date Jun. 26, 2015.
Aurora Fine Chemicals et al., CAS Registry Database, 1789643-92-0, (N-(3,4-Dimethoxyphenyl)-3-ethyl-3-oxetanecarboxamide; C14H19NO4), pp. 1Creation Date Jun. 26, 2015.
Caplus et al., CAS Registry Database, 1259431-81-6, (N-(3,5-Dicyano-6-methoxy-4-phenyl-2-pyridinyl)-2-oxetanecarboxamide; C18H14N4O3), pp. 1Creation Date Jan. 14, 2011.
Caplus et al., CAS Registry Database, 919004-97-0, (N-(6-Methyl-2-pyridinyl)-3-propenamide; C9H10N2O), pp. 1Creation Date Feb. 2, 2007.
Chemcats et al., CAS Registry Database, 2175703-05-4, (N-[3-(Hydroxymethyl)-4-methoxyphenyl]-3-oxetanecarboxamide; C13H17NO4), pp. 1Creation Date Feb. 18, 2019.
Chemcats et al., CAS Registry Database, 2320013-47-4, (N-(3,4-Dimethoxyphenyl)-3-(1-methylethyl)-3-oxetanecarboxamide; C15H21NO4), pp. 1Creation Date May 29, 2019.
Chemcats et al., CAS Registry Database, 2320057-01-8, (3-Oxetanecarboxamide, N-(3,4-diethoxyphenyl)-3-(1-methylethyl); C17 H25NO4), pp. 1Creation Date May 29, 2019.
FCH Group et al., CAS Registry Database, 1824536-47-1, (N-Cyano-N'-(3,4-Dimethylphenyl); C10H11N3O), pp. 1Creation Date Dec. 7, 2015.
Hammer et al., "Synthesis of 7-arylquinolinones and 6-arylindoles from 3-aminobiphenyls through regioselective cyclization reactions" Tetrahedron 70(43):8114-8121 ( 2014).

(Continued)

*Primary Examiner* — Golam M Shameem
(74) *Attorney, Agent, or Firm* — Eric E. Silverman

(57) ABSTRACT

The invention relates to compounds and methods of using said compounds, as well as pharmaceutical compositions containing such compounds, for treating diseases and conditions mediated by TEAD, such as cancer.

19 Claims, No Drawings

Specification includes a Sequence Listing.

(56) References Cited

OTHER PUBLICATIONS

Pubchem et al., CAS Registry Database, 17208-99-0, (N-(3-methoxyphenyl)prop-2-enamide; C10H11NO2), pp. 1-3Creation Date Sep. 13, 2005.
Pubchem et al., CAS Registry Database, 90357-51-0, CID 10149314 (N-(4-cyano-3-(trifluoromethyl)phenyl)-2-methyloxirane-2-carboxamide; C12H9F3N2O2), pp. 1-3Creation Date Oct. 25, 2006.
Pubchem—Chemieliva Pharmaceuticals Co, Ltd, CAS Registry Database, 821765-08-6, CID 45097465 ((2-Methyl-oxirane-2-carboxylic acid (4-cyano-3-methylphenylamide; C12H12N2O2), pp. 1-3Creation Date Mar. 30, 2010.
Ahn, E., et al., "Rassfia—Mediated Regulation of AREG via the Hippo Pathway in Hepatocellular Carcinoma" Mole Cancer Res 11(7):748-758 (Jul. 1, 2013).
Avruch, J., et al., "YAP oncogene overexpression supercharges colon cancer proliferation" Cell Cycle 11(6):1090-1096 (Mar. 15, 2012).
Baia, G., et al., "Yes-Associated Protein 1 is Activated and Functions as an Oncogene in Meningiomas" Mole Cancer Res 10(7):904-913 (Jul. 1, 2012).
Bao, Y., et al., "Mammalian Hippo pathway: from development to cancer and beyond" J Biochem-Oxford 149(4):361-379 (Apr. 1, 2011).
Chan, P., et al., "Autopalmitoylation of Tead proteins regulates transcriptional output of the Hippo pathway" Nat Chem Biol 12(4):282-289 (Apr. 1, 2016).
Chan, S., et al., "A Role for TAZ in Migration, Invasion, and Tumorigenesis of Breast Cancer Cells" Cancer Res 68(8):2592-2598 (Apr. 15, 2008).
Fujii, M., et al., "TGF-β synergizes with defects in the Hippo pathway to stimulate human malignant mesothelioma growth" J Exp Med 209(3):479-494 (Mar. 12, 2012).
Gasparotto, D., et al., "Overexpression of TWIST2 correlates with poor prognosis in Head and Neck Squamous Cell Carcinomas" Oncotarget 2(12):1165-1175 (Dec. 1, 2011).
Halder, G., et al., "Hippo signaling: growth control and beyond" Development 138(1):9-22 (Jan. 1, 2011).
Hall, C., et al., "Hippo Pathway Effector Yap is an Ovarian Cancer Oncogene" Cancer Res 70(21):8517-8525 (Oct. 31, 2010).
Harvey, K., et al., "The Hippo pathway and human cancer" Nat Rev Cancer 13(4):246-257 (Mar. 7, 2013).
"International Preliminary Report on Patentability—PCT/US2020/060264" (Report Issuance Date: May 17, 2022; Chapter I),:pp. 1-11 (May 27, 2022).
"International Preliminary Report on Patentability—PCT/US2021/042968":pp. 1-10 (Jan. 24, 2023).
"International Search Report & Written Opinion—PCT/US2021/042968" (Jul. 23, 2021).
"International Search Report—PCT/US2020/060264" (w/Written Opinion), :pp. 1-15 (Feb. 1, 2021).
Jie, L., et al., "The Hippo—Yes Association Protein Pathway in Liver Cancer" Gastroenterol Res Pract 2013:187070 (1-7) (Aug. 6, 2013).
Jimenez-Velasco, A., et al., "Downregulation of the large tumor suppressor 2 (LATS2/KPM) gene is associated with poor prognosis in acute lymphoblastic leukemia" Leukemia 19(12):2347-2350 (Dec. 1, 2005).
Karatas, H., et al., "Discovery of Covalent Inhibitors Targeting the Transcriptional Enhanced Associate Domain Central Pocket" J Med Chem 63(20):11972-11989 (Oct. 22, 2020).
Kurppa, K., et al., "Treatment-Induced Tumor Dormancy through YAP-Mediated Transcriptional Reprogramming of the Apoptotic Pathway" Cancer Cell 37(1):104-122.e.12 (Jan. 13, 2020).
Lamar, J., et al., "The Hippo pathway target, YAP, promotes metastasis through its Tead-interaction domain" PNAS USA 109(37):E2441-E2450 (Sep. 11, 2012).
Lei, Q., et al., "TAZ Promotes Cell Proliferation and Epithelial-Mesenchymal Transition and is Inhibited by the Hippo Pathway" Mol Cell Biol 28(7):2426-2436 (Apr. 1, 2008).
Liu,A., et al., "An update on targeting Hippo-YAP signaling in liver cancer" Expert Opin Ther Targets 16(3):243-247 (Feb. 16, 2012).
Lograsso, P., et al., "Inhibitors of c-jun-N-terminal kinase (JNK)" Mini Rev Med Chem 8(8):755-766 (Jul. 1, 2008).
Lu, W., et al., "Discovery and biological evaluation of vinylsulfonamide derivatives as highly potent, covalent TEAD autopalmitoylation inhibitors" Eur J Med Chem 184:111767 (1-15) (Dec. 15, 2019).
Mizuno, T., et al., "YAP induces malignant mesothelioma cell proliferation by upregulating transcription of cell cycle-promoting genes" Oncogene 31(49):5117-5122 (Dec. 6, 2012).
Orr, B., et al., "Yes-associated protein 1 is widely expressed in human brain tumors and promotes glioblastoma growth" J Neuropathol Exp Neurol 70(7):568-577 (Jul. 1, 2011).
Pobbati, A., et al., "Targeting the Central Pocket in Human Transcription Factor Tead as a Potential Cancer Therapeutic Strategy" Structure 23(11):2076-2086 (Nov. 3, 2015).
Seidel, C., et al., "Frequent hypermethylation of MST1 and MST2 in soft tissue sarcoma" Mol Carcinog 46(10):865-871 (Oct. 1, 2007).
Sekido, Y., "Inactivation of Merlin in malignant mesothelioma cells and the Hippo signaling cascade dysregulation" Pathol Int 61(6):331-344 (Jun. 1, 2011).
Siddiqui, M., et al., "Small Molecule JNK (c-Jun N-Terminal Kinase) Inhibitors" J Med Chem 53(8):3005-3012 (Feb. 10, 2010).
Steinhardt, A., et al., "Expression of Yes-associated protein in common solid tumors" Human Pathol 39(11):1582-1589 (Nov. 1, 2008).
Steinmann, K., et al., "Frequent promoter hypermethylation of tumor-related genes in head and neck squamous cell carcinoma" Onco Reports 22(6):1519-1526 (Dec. 1, 2009).
Striedinger, K., et al., "The Neurofibromatosis 2 Tumor Suppressor Gene Product, Merlin, Regulates Human Meningioma Cell Growth by Signaling through YAP" Neoplasia 10(11):1204-1212 (Nov. 1, 2008).
Vassilev, A., et al., "Tead/TEF transcription factors utilize the activation domain of YAP65, a Src/Yes-associated protein localized in the cytoplasm" Genes Development 15(10):1229-1241 (May 15, 2001).
Wang, X., et al., "Yes-associated protein promotes tumour development in luminal epithelial derived breast cancer" Eur J Cancer 48(8):1227-1284 (May 1, 2012).
Wang, Y., et al., "Overexpression of yes-associated protein contributes to progression and poor prognosis of non-small-cell lung cancer" Cancer Science 101(5):1279-1285 (May 1, 2010).
Yuen, H., et al., "TAZ expression as a prognostic indicator in colorectal cancer" LOS One 8(1):E54211 (1-17) (Jan. 23, 2013).
Zeng, Q., et al., "The emerging role of the hippo pathway in cell contact inhibition, organ size control, and cancer development in mammals" Cancer Cell 313:188-192 (Mar. 1, 2008).
Zhao, B., et al., "Both Tea-Binding and WW Domains are Required for the Growth Stimulation and Oncogenic Transformation Activity of Yes-Associated Protein" Cancer Res 69(3):1089-1098 (Feb. 1, 2009).
Zhao, B., et al., "Cell detachment activates the Hippo pathway via cytoskeleton reorganization to induce anoikis" Gene Development 26(1):54-68 (Jan. 1, 2012).
Zhao, B., et al., "Hippo signaling at a glance" J Cell Science 123(23):4001-4006 (Dec. 1, 2010).
Zhao, B., et al., "Inactivation of YAP oncoprotein by the Hippo pathway is involved in cell contact inhibition and tissue growth control" Gene Develop 21(21):2747-2761 (Nov. 1, 2007).
Zhao, B., et al., "The Hippo pathway in organ size control, tissue regeneration and stem cell self-renewal" Nat Cell Biol 13(8):877-883 (Aug. 1, 2011).
Zhao, B., et al., "The Hippo—YAP pathway in organ size control and tumorigenesis: an updated version" Genes Development 24(9):862-874 (May 1, 2010).
Zhou, Z., et al., "TAZ is a novel oncogene in non-small cell lung cancer" Oncogene 30(18):2181-2186 (May 5, 2011).
"RN1351602-75-9, Database Registry [Online], retrieved from STN": 1-2 (Dec. 22, 2011).
"RN1894921-48-2,CAS Database Registry [Online], retrieved from STN":1-2 (Apr. 21, 2016).

(56) References Cited

OTHER PUBLICATIONS

"RN1995594-90-5, Database Registry [Online], retrieved from STN":1-2 (Sep. 18, 2016).

* cited by examiner

SEQUENCE LISTING

```
Sequence total quantity: 18
SEQ ID NO: 1            moltype = AA  length = 440
FEATURE                 Location/Qualifiers
REGION                  1..440
                        note = Description of Artificial Sequence: Synthetic
                         polypeptide
source                  1..440
                        mol_type = protein
                        organism = synthetic construct
SEQUENCE: 1
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                            440

SEQ ID NO: 2            moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 2
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 3            moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 3
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
```

-continued

```
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 4           moltype = AA  length = 218
FEATURE                Location/Qualifiers
REGION                 1..218
                       note = Description of Artificial Sequence: Synthetic
                        polypeptide
source                 1..218
                       mol_type = protein
                       organism = synthetic construct
SEQUENCE: 4
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 5           moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 5
GFTFSDSWIH                                                         10

SEQ ID NO: 6           moltype = AA  length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 6
AWISPYGGST YYADSVKG                                                18

SEQ ID NO: 7           moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 7
RHWPGGFDY                                                          9

SEQ ID NO: 8           moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 8
RASQDVSTAV A                                                       11

SEQ ID NO: 9           moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 9
SASFLYS                                                            7

SEQ ID NO: 10          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 10
QQYLYHPAT                                                          9

SEQ ID NO: 11          moltype = AA  length = 118
```

```
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 11
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 12          moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 12
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 13          moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 13
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 14          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 14
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 15          moltype = AA  length = 449
FEATURE                Location/Qualifiers
REGION                 1..449
                       note = Description of Artificial Sequence: Synthetic
                        polypeptide
source                 1..449
                       mol_type = protein
                       organism = synthetic construct
SEQUENCE: 15
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 16          moltype = AA  length = 216
FEATURE                Location/Qualifiers
REGION                 1..216
                       note = Description of Artificial Sequence: Synthetic
                        polypeptide
source                 1..216
```

-continued

```
                        mol_type = protein
                        organism = synthetic construct
SEQUENCE: 16
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 17           moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 17
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 18           moltype = AA  length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 18
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215
```

THERAPEUTIC COMPOUNDS AND METHODS OF USE

CROSS REFERENCE TO RELATED APPLICATIONS

This application is a division of U.S. patent application Ser. No. 17/383,422, filed Jul. 22, 2021, which claims priority to and benefit of U.S. Provisional Patent Application No. 63/056,498, filed Jul. 24, 2020, the disclosures of which are hereby incorporated herein by reference in their entirety.

SEQUENCE LISTING

The instant application contains a Sequence Listing which has been submitted electronically in XML format and is hereby incorporated by reference in its entirety. Said XML copy, created on Aug. 31, 2023, is named P35669-US-2_SEQ_LIST.xml and is 27,320 bytes in size.

FIELD OF THE DISCLOSURE

The present disclosure relates to compounds useful for therapy and/or prophylaxis in a mammal, and in particular as inhibitors of TEAD useful for treating cancer.

BRIEF DESCRIPTION

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer. For reviews, see, for example, Halder et al., 2011, Development 138:9-22; Zhao et al., 2011, Nature Cell Biology 13:877-883; Bao et al., 2011, J. Biochem. 149:361-379; Zhao at al., 2010, J. Cell Sci. 123:4001-4006.

The Hippo signaling pathway is conserved from *Drosophila* to mammals (Vassilev et al., Genes and Development, 2001, 15, 1229-1241; Zeng and Hong, Cancer Cell, 2008, 13, 188-192). The core of the pathway consists of a cascade of kinases (Hippo-MST1-2 being upstream of Lats 1-2 and NDRI-2) leading to the phosphorylation of two transcriptional co-activators, YAP (Yes-Associated Protein) and TAZ (Transcription co-activator with PDZ binding motif or tafazzin; Zhao et al., Cancer Res., 2009, 69, 1089-1098; Lei et al., Mol. Cell. Biol., 2008, 28, 2426-2436).

Because the Hippo signaling pathway is a regulator of animal development, organ size control and stem cell regulation, it has been implicated in cancer development (Review in Harvey et al., Nat. Rev. Cancer, 2013, 13, 246-257; Zhao et al., Genes Dev. 2010, 24, 862-874). In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of malignancies, including with no limitations, lung cancer (NSCLC; Zhou et al., Oncogene, 2011, 30, 2181-2186; Wang et al., Cancer Sci., 2010, 101, 1279-1285), breast cancer (Chan et al., Cancer Res., 2008, 68, 2592-2598; Lamar et al., Proc. Natl. Acad. Sci, USA, 2012; 109, E2441-E2250; Wang et al., Eur. J. Cancer, 2012, 48, 1227-1234), head and neck cancer (Gasparotto et al., Oncotarget., 2011, 2, 1165-1175; Steinmann et al., Oncol. Rep., 2009, 22, 1519-1526), colon cancer (Angela et al., Hum. Pathol., 2008, 39, 1582-1589; Yuen et al., PLoS One, 2013, 8, e54211; Avruch et al., Cell Cycle, 2012, 11, 1090-1096), ovarian cancer (Angela et al., Hum. Pathol., 2008, 39, 1582-1589; Chad et al., Cancer Res., 2010, 70, 8517-8525; Hall et al., Cancer Res., 2010, 70, 8517-8525), liver cancer (Jie et al., Gastroenterol. Res. Pract., 2013, 2013, 187070; Ahn et al., Mol. Cancer. Res., 2013, 11, 748-758; Liu et al., Expert. Opin. Ther. Targets, 2012, 16, 243-247), brain cancer (Orr et al., J Neuropathol. Exp. Neurol. 2011, 70, 568-577; Baia et al., Mol. Cancer Res., 2012, 10, 904-913; Striedinger et al., Neoplasia, 2008, 10, 1204-1212) and prostate cancer (Zhao et al., Genes Dev., 2012, 26, 54-68; Zhao et al., Genes Dev., 2007, 21, 2747-2761), mesotheliomas (Fujii et al., J. Exp. Med., 2012, 209, 479-494; Mizuno et al., Oncogene, 2012, 31, 5117-5122; Sekido Y., Pathol. Int., 2011, 61, 331-344), sarcomas (Seidel et al., Mol. Carcinog., 2007, 46, 865-871) and leukemia (Jimenez-Velasco et al., Leukemia, 2005, 19, 2347-2350).

Two of the core components of the mammalian Hippo pathway are Lats1 and Lats2, which are nuclear Dbf2-related (NDR) family protein kinases homologous to *Drosophila* Warts (Wts). The Lats1/2 proteins are activated by association with the scaffold proteins Mob1A/B (Mps one binder kinase activator-like 1A and 1B), which are homologous to *Drosophila* Mats. Lats1/2 proteins are also activated by phosphorylation by the STE20 family protein kinases Mst1 and Mst2, which are homologous to *Drosophila* Hippo. Lats1/2 kinases phosphorylate the downstream effectors YAP (Yes-associated protein) and TAZ (transcriptional coactivator with PDZ-binding motif, WWTR1), which are homologous to *Drosophila* Yorkie. The phosphorylation of YAP and TAZ by Lats1/2 are crucial events within the Hippo signaling pathway. Lats1/2 phosphorylates YAP at multiple sites, but phosphorylation of Ser127 is critical for YAP inhibition. Phosphorylation of YAP generates a protein-binding motif for the 14-3-3 family of proteins, which upon binding of a 14-3-3 protein, leads to retention and/or sequestration of YAP in the cell cytoplasm. Likewise, Lats1/2 phosphorylates TAZ at multiple sites, but phosphorylation of Ser89 is critical for TAZ inhibition. Phosphorylation of TAZ leads to retention and/or sequestration of TAZ in the cell cytoplasm. In addition, phosphorylation of YAP and TAZ is believed to destabilize these proteins by activating phosphorylation-dependent degradation catalyzed by YAP or TAZ ubiquitination. Thus, when the Hippo pathway is "on", YAP and/or TAZ is phosphorylated, inactive, and generally sequestered in the cytoplasm; in contrast, when the Hippo pathway is "off", YAP and/or TAZ is non-phosphorylated, active, and generally found in the nucleus.

Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor γ (PPARγ), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor.

Hence, pharmacological targeting of the Hippo cascade through inhibition of TEAD would be a valuable approach for the treatment of cancers that harbor functional alterations of this pathway.

SUMMARY OF THE DISCLOSURE

In some aspects, a compound or a stereisomer, tautomer, or pharmaceutically acceptable salt thereof of the following formula (X) is provided:

(X)

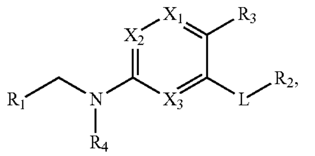

wherein:

$X_1$ is C—$R_5$, wherein the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more D;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, $S(O)_2$—$C_{1-6}$alkyl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

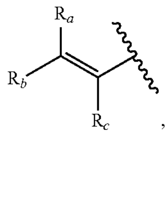

, wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

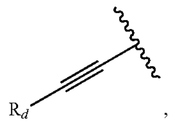

, wherein $R_d$ is selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$ alkyl, $C_{1-6}$haloalkyl, $C_{3-10}$cycloalkyl, $NO_2$, $N(R^e)(R^f)$, $O(R^e)$, and $S(R^g)_5$, then L is —CH═CH— or —C≡C—;

$R_4$ is H or $C_{1-6}$alkyl, wherein the $C_{1-6}$alkyl is optionally substituted with hydroxyl;

$R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl; and $R^g$ is halo.

In some aspects, a compound or a stereoisomer, tautomer, or pharmaceutically acceptable salt thereof of the following formula (I) is provided:

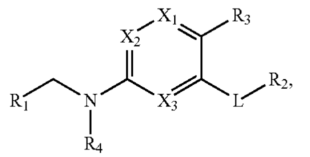

(I)

wherein:

$X_1$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$, or the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

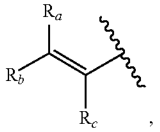

, wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

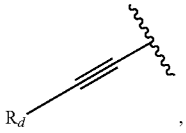

, wherein $R_d$ is selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, then L is —CH═CH— or —C≡C—;

$R_3$ is cyano, $C_{1-6}$alkyl, $C_{1-4}$alkoxy, or $C_{2-4}$alkenyl, wherein the $C_{2-4}$alkenyl is optionally substituted with $N(R^e)(R^f)$, or $R_3$ is taken together with $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl, or $R_3$ is taken together with the carbon atom of *—$CH_2$—O—** of L, and the atoms to which they are attached, to form a $C_6$aryl or a 6-membered heteroaryl;

$R_4$ is H or $C_{1-6}$alkyl, wherein the $C_{1-6}$alkyl is optionally substituted with hydroxyl; and $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl.

In some aspects, a pharmaceutical composition comprising a compound of formula (I) or a stereoisomer, tautomer, or pharmaceutically acceptable salt thereof, and a pharmaceutically acceptable carrier, diluent or excipient, is provided.

In some aspects, a compound of formula (X) or formula (I), or a stereoisomer, tautomer, or pharmaceutically acceptable salt thereof, is provided for use in medical therapy.

In some aspects, a compound of formula (X) or formula (I), or a stereoisomer, tautomer, or pharmaceutically acceptable salt thereof, is provided for the treatment or prophylaxis of cancer, mesothelioma, sarcoma, or leukemia.

In some aspects, a compound of formula (X) or formula (I), or a stereoisomer, tautomer, or pharmaceutically acceptable salt thereof, is provided for the preparation of a medicament for the treatment or prophylaxis of cancer, mesothelioma, sarcoma, or leukemia.

In some aspects, a method for treating cancer, mesothelioma, sarcoma, or leukemia in a mammal is provided, the method comprising, administering a compound of formula (X) or formula (I), or a stereoisomer, tautomer, or pharmaceutically acceptable salt thereof, to the mammal.

In some aspects, a method for treating cancer, mesothelioma, sarcoma, or leukemia in a mammal is provided, the method comprising administering a compound of formula (X) or formula (I), or a stereoisomer, tautomer, or pharmaceutically acceptable salt thereof, to the mammal in combination with a second therapeutic agent.

In some aspects, a compound of formula (X) or formula (I), or a stereoisomer, tautomer, or pharmaceutically acceptable salt thereof, is provided for modulating TEAD activity.

In some aspects, a compound of formula (X) or formula (I), or a stereoisomer, tautomer, or pharmaceutically acceptable salt thereof, is provided for the treatment or prophylaxis of a disease or condition mediated by TEAD activity.

In some aspects, a compound of formula (X) or formula (I), or a stereoisomer, tautomer, or pharmaceutically acceptable salt thereof, is provided for use for the preparation of a medicament for the treatment or prophylaxis of a disease or condition that is mediated by TEAD activity.

In some aspects, a method for modulating TEAD activity is provided, the method comprising contacting TEAD with a compound of formula (X) or formula (I), or a stereoisomer, tautomer, or pharmaceutically acceptable salt thereof.

In some aspects, a method for treating a disease or condition mediated by TEAD activity in a mammal is provided, the method comprising administering a compound of formula (X) or formula (I), or a stereoisomer, tautomer, or pharmaceutically acceptable salt thereof, to the mammal.

DETAILED DESCRIPTION

Definitions

Unless otherwise indicated, the following specific terms and phrases used in the description and claims are defined as follows.

The term "moiety" refers to an atom or group of chemically bonded atoms that is attached to another atom or molecule by one or more chemical bonds thereby forming part of a molecule.

The term "substituted" refers to the fact that at least one of the hydrogen atoms of that moiety is replaced by another substituent or moiety.

The term "alkyl" refers to an aliphatic straight-chain or branched-chain saturated hydrocarbon moiety having 1 to 20 carbon atoms, such as 1 to 12 carbon atoms, or 1 to 6 carbon atoms. Alkyl groups may be optionally substituted.

The term "cycloalkyl" means a saturated or partially unsaturated carbocyclic moiety having mono- or bicyclic (including bridged bicyclic) rings and 3 to 10 carbon atoms in the ring. In particular aspects, cycloalkyl may contain from 3 to 8 carbon atoms (i.e., ($C_3$-$C_8$)cycloalkyl). In other particular aspects cycloalkyl may contain from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a spirocycle fashion such as spirocyclopropyl:

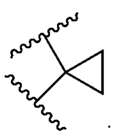 [SMILES: *C1(*)CC1]

The term "haloalkyl" refers to an alkyl group wherein one or more of the hydrogen atoms of the alkyl group has been replaced by the same or different halogen atoms, such as fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. Haloalkyl groups may be optionally substituted.

The term "alkenyl" refers to a straight or branched chain alkyl or substituted alkyl group as defined elsewhere herein having at least one carbon-carbon double bond. Alkenyl groups may be optionally substituted.

The term "alkynyl" refers to a straight or branched chain alkyl or substituted alkyl group as defined elsewhere herein having at least one carbon-carbon triple bond. Alkynyl groups may be optionally substituted.

The terms "heterocyclyl" and "heterocycle" refer to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4) heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted. The heterocycle can be attached to its pendant group at any heteroatom or carbon atom that results in a stable structure and any of the ring atoms can be optionally substituted. Examples of such saturated or partially unsaturated heterocycles include, without limitation, oxiranyl, oxetanyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazolyl, thiazepinyl, morpholinyl, and quinuclidinyl. The term heterocycle also includes groups in which a heterocycle is fused to one or more aryl, heteroaryl, or cycloalkyl rings, such as benzothiazolyl, benzofuranyl, furopyridinyl, indolinyl, 3H-indolyl, chromanyl, 2-azabicyclo[2.2.1]heptanyl, octahydroindolyl, or tetrahydroquinolinyl. Heterocyclyl groups may be optionally substituted.

The term "aryl" refers to a cyclic aromatic hydrocarbon moiety having a mono-, bi- or tricyclic aromatic ring of 5 to 20 carbon ring atoms. Examples of aryl moieties include, but are not limited to, phenyl, naphthyl, benzyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In some aspects, monocyclic aryl rings may have 5 or 6 carbon ring atoms. Aryl groups may be optionally substituted.

The term "heteroaryl" refers an aromatic heterocyclic mono- or bicyclic ring system of 1 to 20 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Heteroaryl groups may be optionally substituted.

The terms "halo" and "halogen" refer fluoro, chloro, bromo and iodo. In some aspects, halo is fluoro or chloro.

The term “oxo” refers to the =O moiety.

The term “cyano” refers to the —C≡N moiety.

The terms “spirocycle” and “spirocyclyl” refer to carbogenic bicyclic ring systems comprising between 5 and 13 carbon atoms with both rings connected through a single atom. The rings can be different in size and nature, or identical in size and nature. Examples include spiropentane, spirohexane, spiroheptane, spirooctane, spirononane, or spirodecane. One or more of the carbon atoms in the spirocycle can be substituted with a heteroatom (e.g., O, N, S, or P). Spirocycle groups may be optionally substituted.

The term “annular” refers to a moiety that is a member of a ring, including, but not limited to, a cycloalkyl ring, a cycloalkenyl ring, an aryl ring, a heteroaryl ring, a heterocyclyl ring, or a spirocyclyl ring. For example, if a heteroaryl ring is described as “comprising two or more annular heteroatoms”, two or more of the ring members of the heteroaryl ring will be heteroatoms.

The term “pharmaceutically acceptable salts” refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The term “prodrug” refers to those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

In some prodrug aspects, prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

In some other prodrug aspects, a free carboxyl group of a compound of the disclosure can be derivatized as an amide or alkyl ester. In yet other prodrug aspects, prodrugs comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 “Design and Application of Prodrugs,” by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present disclosure provides for metabolites of compounds of the disclosure. As used herein, a “metabolite” refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure can exist in multiple crystalline or amorphous forms. In general, all physical forms are equivalent for the uses contemplated by the present disclosure and are intended to be within the scope of the present disclosure.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain aspects the compound is enriched by at least about 90% by weight with a single diastereomer or enantiomer. In other aspects the compound is enriched by at least about 95%, 98%, or 99% by weight with a single diastereomer or enantiomer.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure may also exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise indicated, the term "a compound of the formula" or "a compound of formula" or "compounds of the formula" or "compounds of formula" refers to any compound selected from the genus of compounds as defined by the formula. In some embodiments or aspects, the term also includes a pharmaceutically acceptable salt or ester of any such compound, a stereoisomer, or a tautomer of such compound.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with a compound of the disclosure, use thereof in the compositions of the disclosure is contemplated. Supplementary active compounds can also be incorporated into the compositions.

Compounds

In some aspects, a compound or a stereisomer, tautomer, or pharmaceutically acceptable salt thereof of the following formula (X) is provided:

(X)

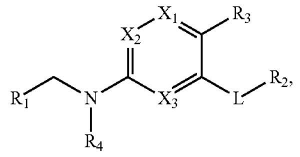

wherein:

$X_1$ is C—$R_5$, wherein the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more D;

$X_2$ is N or C—$R_5$, wherein each $R_5$ is independently selected from the group consisting of H, cyano, halo, C(O)$NH_2$, N($R^e$)($R^f$), $C_{3-10}$cycloalkyl, $C_{1-6}$alkoxy, $C_{6-20}$aryl, $S(O)_2$—$C_{1-6}$alkyl, and $C_{1-6}$alkyl, wherein the $C_{1-6}$alkyl of $R_5$ is optionally substituted with hydroxyl or N($R^e$)($R^f$);

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

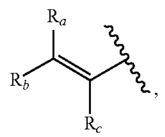

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

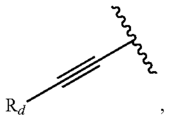

wherein $R_d$ is selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_5$. 13spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, then L is —CH═CH— or —C≡C—;

$R_4$ is H or $C_{1-6}$alkyl, wherein the $C_{1-6}$alkyl is optionally substituted with hydroxyl;

$R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl; and $R^g$ is halo.

In some aspects, a compound or a stereoisomer, tautomer, or pharmaceutically acceptable salt thereof of the following formula (I) is provided:

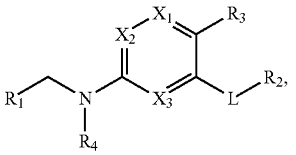

(I)

wherein:

$X_1$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$, or the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

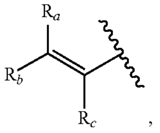

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

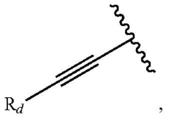

wherein $R_d$ is selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), and O($R^e$), provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), and O($R^e$), then L is —CH═CH— or —C≡C—;

$R_3$ is cyano, $C_{1-6}$alkyl, $C_{1-4}$alkoxy, or $C_{2-4}$alkenyl, wherein the $C_{2-4}$alkenyl is optionally substituted with N($R^e$)($R^f$), or $R_3$ is taken together with $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl, or $R_3$ is taken together with the carbon atom of *—$CH_2$—O—** of L, and the atoms to which they are attached, to form a $C_6$aryl or a 6-membered heteroaryl;

$R_4$ is H or $C_{1-6}$alkyl, wherein the $C_{1-6}$alkyl is optionally substituted with hydroxyl; and $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl.

In some embodiments, provided herein is a compound of formula (I), or a stereoisomer, tautomer, or pharmaceutically acceptable salt thereof, wherein $X_1$ is C—$R_5$, $X_2$ is C—$R_5$, and $X_3$ is C—H. In other embodiments, $X_1$ is C—$R_5$, $X_2$ is C—$R_5$, and $X_3$ is N. In still other embodiments, $X_1$ is C—$R_5$, $X_2$ is N, and $X_3$ is C—H. In some embodiments, $X_1$ is C—$R_5$, $X_2$ is N, and $X_3$ is N. In some embodiments, $X_1$ is N, $X_2$ is C—$R_5$, and $X_3$ is C—H.

In certain embodiments, provided herein is a compound of formula (X) or formula (I), or a stereoisomer, tautomer, or pharmaceutically acceptable salt thereof, wherein $X_1$ is C—$R_5$, and $R_3$ is taken together with the $R_5$ of $X_1$, and the atoms to which they are attached, to form a 5-membered heterocyclyl or a 5-membered heteroaryl, wherein the 5-membered heterocyclyl or 5-membered heteroaryl comprises 1, 2, or 3 annular heteroatoms. In certain embodiments, the 1, 2, or 3 heteroatoms are selected from the group consisting of O, N, and S. In embodiments, the 5-membered heterocyclyl or 5-membered heteroaryl is optionally substituted with one or more $C_{1-6}$ alkyl. In some embodiments, the 5-membered heterocyclyl or 5-membered heteroaryl is unsubstituted. In some embodiments, the 5-membered heterocyclyl or 5-membered heteroaryl is substituted with one or more D.

In some embodiments of formula (X) or formula (I), $X_1$ is C—$R_5$, and $R_3$ is taken together with the $R_5$ of $X_1$, and the atoms to which they are attached, to form a 5-membered heteroaryl, wherein the 5-membered heteroaryl comprises at least two annular heteroatoms. In some embodiments, $X_1$ is C—$R_5$, and $R_3$ is taken together with the $R_5$ of $X_1$, and the atoms to which they are attached, to form a 5-membered heteroaryl, wherein the 5-membered heteroaryl comprises one annular sulfur atom and one annular nitrogen atom. In embodiments, the 5-membered heteroaryl is optionally substituted with one or more $C_{1-6}$alkyl. In some embodiments, the 5-membered heteroaryl is unsubstituted. In some embodiments, the 5-membered heteroaryl is substituted with one or more D.

In certain embodiments of formula (X) or formula (I), $X_1$ is C—$R_5$, and $R_3$ is taken together with the $R_5$ of $X_1$, and the atoms to which they are attached, to form a 5-membered heterocyclyl, wherein the 5-membered heteroaryl comprises at least one annular heteroatom. In some embodiments, the $X_1$ is C—$R_5$, and $R_3$ is taken together with the $R_5$ of $X_1$, and the atoms to which they are attached, to form a 5-membered heterocyclyl that comprises one annular oxygen atom. In some embodiments, the 5-membered heterocyclyl is optionally substituted with one or more $C_{1-6}$alkyl. In some embodiments, the 5-membered heterocyclyl is unsubstituted. In some embodiments, the 5-membered heterocyclyl is substituted with one or more D.

In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form an unsubstituted 5-membered heterocyclyl or an unsubstituted 5-membered heteroaryl; $X^2$ is N; and $X^3$ is N. In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form a 5-membered heterocyclyl or a 5-membered heteroaryl, wherein the 5-membered heterocyclyl or 5-membered heteroaryl is substituted with one or more D; $X^2$ is N; and $X^3$ is N.

In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form an unsubstituted 5-membered heterocyclyl; $X^2$ is N; and $X^3$ is N. In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form a 5-membered heterocyclyl, wherein the 5-membered heterocyclyl is substituted with one or more D; $X^2$ is N; and $X^3$ is N In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form an unsubstituted 5-membered heterocyclyl or an unsubstituted 5-membered heteroaryl; and L is O. In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form a 5-membered heterocyclyl or a 5-membered heteroaryl, wherein the 5-membered heterocyclyl or 5-membered heteroaryl is substituted with one or more D; and L is O.

In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form an unsubstituted 5-membered heterocyclyl; and L is O. In one embodiment of formula (I), or a stereoisomer, tautomer, or pharmaceutically acceptable salt thereof: $X_1$ is C—$R_5$; $R_3$ is taken together with the $R_5$ of $X_1$, and the atoms to which they are attached, to form a 5-membered heterocyclyl, wherein the 5-membered heterocyclyl is substituted with one or more D; and L is O.

In some embodiments, provided herein is a compound of formula (X) or formula (I), or a stereoisomer, tautomer, or pharmaceutically acceptable salt thereof, wherein the compound of formula (X) or formula (I) is a compound of formula (IA):

(IA)

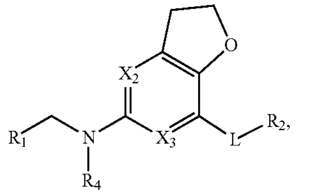

or a stereoisomer, tautomer, or pharmaceutically acceptable salt thereof.

In some embodiments, provided herein is a compound of formula (X), formula (I), or formula (IA), or a stereoisomer, tautomer, or pharmaceutically acceptable salt thereof, wherein $X_2$ is C—$R_5$, and the $R_5$ of $X_2$ is H, cyano, halo, $S(O)_2$—$C_{1-6}$alkyl, or $C_{1-6}$alkyl, wherein the $C_{1-6}$alkyl is optionally substituted with one or more hydroxyl. In some embodiments, provided herein is a compound of formula (X), formula (I), or formula (IA), or a stereoisomer, tautomer, or pharmaceutically acceptable salt thereof, wherein $X_2$ is C—$R_5$, and the $R_5$ of $X_2$ is H, cyano, halo, or $C_{1-6}$alkyl, wherein the $C_{1-6}$alkyl is optionally substituted with one or more hydroxyl. In certain embodiments, the $R_5$ of $X_2$ is cyano. In other embodiments, the $R_5$ of $X_2$ is H. In still other embodiments, the $R_5$ of $X_2$ is F. In some embodiments, the $R_5$ of $X_2$ is $C_{1-6}$alkyl, wherein the $C_{1-6}$ alkyl is optionally substituted with one or more hydroxyl. In other embodiments, the $R_5$ of $X_2$ is —$CH_2OH$. In some embodiments, the $R_5$ of $X_2$ is $S(O)_2$—$C_{1-6}$alkyl. In some embodiments, the $R_5$ of $X_2$ is $S(O)_2$—$CH_3$.

In some embodiments, provided herein is a compound of formula (X), formula (I), or formula (IA), or a stereoisomer, tautomer, or pharmaceutically acceptable salt thereof, wherein L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule. In some embodiments, L is absent.

In some embodiments, provided herein is a compound of formula (X), formula (I), or formula (IA), or a stereoisomer, tautomer, or pharmaceutically acceptable salt thereof, wherein $R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, then L is —CH═CH— or —C≡C—. In some embodiments, $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$ or $C_{1-6}$alkyl, wherein the $C_{1-6}$alkyl is further optionally substituted with one or more halo. In other embodiments, $R_2$ is $C_{6-20}$aryl, wherein the $C_{6-20}$aryl of $R_2$ is independently optionally substituted with one or more $O(R^e)$, $S(R^g)_5$, or $C_{1-6}$ alkyl, wherein the $C_{1-6}$alkyl is further optionally substituted with one or more halo. In some embodiments, $R_2$ is $C_{6-20}$aryl, wherein the $C_{6-20}$aryl of $R_2$ is independently optionally substituted with one or more $C_{1-6}$alkyl. In certain embodiments, $R_2$ is phenyl substituted with isopropyl. In some embodiments, $R_2$ is $C_{6-20}$aryl, wherein the $C_{6-20}$aryl of $R_2$ is independently optionally substituted with one or more $S(R^g)_5$. In certain embodiments, $R_2$ is phenyl substituted with $SF_5$. In some embodiments, $R_2$ is phenyl substituted with $O(R^e)$. In some embodiments, $R_2$ is phenyl substituted with $OCF_3$.

In some embodiments, provided herein is a compound of formula (X), formula (I), or formula (IA), or a stereoisomer, tautomer, or pharmaceutically acceptable salt thereof, wherein $R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, then L is —CH═CH— or —C≡C—. In some embodiments, $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$ or $C_{1-6}$alkyl, wherein the $C_{1-6}$alkyl is further optionally substituted with one or more halo. In other embodiments, $R_2$ is $C_{6-20}$aryl, wherein the $C_{6-20}$aryl of $R_2$ is independently optionally substituted with one or more $O(R^e)$ or $C_{1-6}$alkyl, wherein the $C_{1-6}$alkyl is further optionally substituted with one or more halo. In some embodiments, $R_2$ is $C_{6-20}$aryl, wherein the $C_{6-20}$aryl of $R_2$ is independently optionally substituted with one or more $C_{1-6}$alkyl. In certain embodiments, $R_2$ is phenyl substituted with isopropyl.

In some embodiments, provided herein is a compound of formula (X), formula (I), or formula (IA), or a stereoisomer, tautomer, or pharmaceutically acceptable salt thereof, wherein L is absent and $R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, then L is —CH═CH— or —C≡C—. In some embodiments, L is absent and $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$ or $C_{1-6}$alkyl, wherein the $C_{1-6}$alkyl is further optionally substituted with one or more halo. In other embodiments, $R_2$ is $C_{6-20}$aryl, wherein the $C_{6-20}$aryl of $R_2$ is independently optionally substituted with one or more $O(R^e)$ or $C_{1-6}$alkyl, wherein the $C_{1-6}$alkyl is further optionally substituted with one or more halo. In some embodiments, L is absent and $R_2$ is $C_{6-20}$aryl, wherein the $C_{6-20}$aryl of $R_2$ is independently optionally substituted with one or more $C_{1-6}$alkyl. In certain embodiments, L is absent and $R_2$ is phenyl substituted with isopropyl. In some embodiments, L is absent and $R_2$ is $C_{6-20}$aryl, wherein the $C_{6-20}$aryl of $R_2$ is independently optionally substituted with one or more $S(R^g)_5$. In certain embodiments, L is absent and $R_2$ is phenyl substituted with $SF_5$. In some embodiments, L is absent and $R_2$ is phenyl substituted with $O(R^e)$. In some embodiments, L is absent and $R_2$ is phenyl substituted with $OCF_3$.

In some embodiments, provided herein is a compound of formula (X), formula (I), or formula (IA), or a stereoisomer, tautomer, or pharmaceutically acceptable salt thereof, wherein L is absent and $R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, then L is —CH═CH— or —C≡C—. In some embodiments, L is absent and $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$ or $C_{1-6}$alkyl, wherein the $C_{1-6}$alkyl is further optionally substituted with one or more halo. In other embodiments, $R_2$ is $C_{6-20}$aryl, wherein the $C_{6-20}$aryl of $R_2$ is independently optionally substituted with one or more $O(R^e)$ or $C_{1-6}$alkyl, wherein the $C_{1-6}$alkyl is further optionally substituted with one or more halo. In some embodiments, L is absent and $R_2$ is $C_{6-20}$aryl, wherein the $C_{6-20}$aryl of $R_2$ is independently optionally substituted with one or more $C_{1-6}$alkyl. In certain embodiments, L is absent and $R_2$ is phenyl substituted with isopropyl.

In some embodiments, provided herein is a compound of formula (X) or formula (I), or a stereoisomer, tautomer, or pharmaceutically acceptable salt thereof, wherein L is absent, such that the compound of formula (I) is a compound of formula (IA-1):

(IA-1)

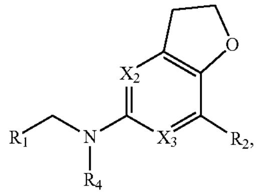

or a stereoisomer, tautomer, or pharmaceutically acceptable salt thereof.

In some embodiments, provided herein is a compound of formula (X), formula (I), or formula (IA-1), or a stereoisomer, tautomer, or pharmaceutically acceptable salt thereof, wherein $X_2$ is C—$R_5$, and the $R_5$ of $X_2$ is H, cyano, halo, or $S(O)_2$—$C_{1-6}$alkyl, $C_{1-6}$alkyl, wherein the $C_{1-6}$alkyl is optionally substituted with one or more hydroxyl. In some embodiments, provided herein is a compound of formula (X), formula (I), or formula (IA-1), or a stereoisomer, tautomer, or pharmaceutically acceptable salt thereof, wherein $X_2$ is C—$R_5$, and the $R_5$ of $X_2$ is H, cyano, halo, or $C_{1-6}$alkyl, wherein the $C_{1-6}$alkyl is optionally substituted with one or more hydroxyl. In certain embodiments, the $R_5$ of $X_2$ is cyano. In other embodiments, the $R_5$ of $X_2$ is H. In still other embodiments, the $R_5$ of $X_2$ is F. In some embodiments, the $R_5$ of $X_2$ is $C_{1-6}$alkyl, wherein the $C_{1-6}$ alkyl is optionally substituted with one or more hydroxyl. In other embodiments, the $R_5$ of $X_2$ is —$CH_2OH$. In some embodiments, the $R_5$ of $X_2$ is $S(O)_2$—$C_{1-6}$alkyl. In some embodiments, the $R_5$ of $X_2$ is $S(O)_2$—$CH_3$.

In some embodiments, provided herein is a compound of formula (X), formula (I), or formula (IA-1), or a stereoisomer, tautomer, or pharmaceutically acceptable salt thereof, wherein $R_2$ is phenyl, wherein the phenyl is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$. In some embodiments, the phenyl is independently optionally substituted with one or more $O(R^e)$, $S(R^g)_5$, or $C_{1-6}$alkyl, wherein the $C_{1-6}$alkyl is further optionally substituted with one or more halo. In certain embodiments, the phenyl is substituted with isopropyl. In some embodiments, the phenyl is substituted with $S(R^g)_5$. In some embodiments, the phenyl is substituted with $SF_5$. In some embodiments, the phenyl is substituted with $O(R^e)$. In some embodiments, the phenyl is substituted with $OCF_3$.

In some embodiments, provided herein is a compound of formula (X), formula (I), or formula (IA-1), or a stereoisomer, tautomer, or pharmaceutically acceptable salt thereof, wherein $R_2$ is phenyl, wherein the phenyl is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$. In some embodiments, the phenyl is independently optionally substituted with one or more $O(R^e)$ or $C_{1-6}$alkyl, wherein the $C_{1-6}$alkyl is further optionally substituted with one or more halo. In certain embodiments, the phenyl is substituted with isopropyl.

In some embodiments, provided herein is a compound of formula (X), formula (I), or formula (IA-1), or a stereoisomer, tautomer, or pharmaceutically acceptable salt thereof, wherein $R_1$ is

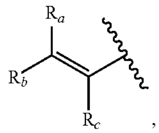

, wherein $R_a$, $R_b$, and $R_c$ are each independently selected from the group consisting of H, $B(OH)_2$, C(O)—OH, C(O)—N$(R^e)(R^f)$, C(O)—$C_{1-6}$alkoxy and C(O)—$C_{1-6}$alkyl, and $R_4$ is H or $C_{1-6}$ alkyl, wherein $R^e$ and $R^f$ are, independently of each other and independently at each occurrence, selected from the group consisting of H, hydroxyl, and $C_{1-6}$alkyl. In embodiments, the $C_{1-6}$alkyl is methyl or isopropyl. In embodiments, the $C_{1-6}$alkoxy of the C(O)—$C_{1-6}$alkoxy is methoxy.

In some embodiments, provided herein is a compound of formula (X), formula (I), or formula (IA-1), or a stereoisomer, tautomer, or pharmaceutically acceptable salt thereof, wherein $R_1$ is

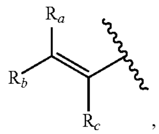

, wherein $R_a$, $R_b$, and $R_c$ are each independently selected from the group consisting of H, $B(OH)_2$, C(O)—OH, C(O)—N$(R^e)(R^f)$, C(O)—$C_{1-6}$alkoxy and C(O)—$C_{1-6}$alkyl, and $R_4$ is H or $C_{1-6}$ alkyl, wherein $R^e$ and $R^f$ are, independently of each other and independently at each occurrence, selected from the group consisting of H, hydroxyl, $C_{1-6}$alkoxy, and $C_{1-6}$alkyl. In embodiments, the $C_{1-6}$alkyl is methyl or isopropyl. In embodiments, the $C_{1-6}$alkoxy is methoxy.

In embodiments, provided herein is a compound of formula (X), formula (I), or formula (IA-1), or a stereoisomer, tautomer, or pharmaceutically acceptable salt thereof, wherein $X_2$ is C—$R_5$, wherein $R_5$ is independently selected from the group consisting of H, cyano, halo, $S(O)_2$—$C_{1-6}$alkyl, and $C_{1-6}$alkyl, wherein the $C_{1-6}$alkyl of $R_5$ is optionally substituted with hydroxyl. In embodiments, provided herein is a compound of formula (X), formula (I), or formula (IA-1), or a stereoisomer, tautomer, or pharmaceutically acceptable salt thereof, wherein $X_2$ is C—$R_5$, wherein $R_5$ is independently selected from the group consisting of H, cyano, halo and $C_{1-6}$alkyl, wherein the $C_{1-6}$ alkyl of $R_5$ is optionally substituted with hydroxyl. In embodiments, $R_5$ is H. In embodiments, $R_5$ is cyano. In embodiments, $R_5$ is $C_{1-6}$alkyl substituted with hydroxyl. In embodiments, $R_5$ is $CH_2$—OH. In some embodiments, $R_5$ is $S(O)_2$—$C_{1-6}$alkyl. In some embodiments, $R_5$ is $S(O)_2$—$CH_3$.

In embodiments, provided herein is a compound of formula (X), formula (I), or formula (IA-1), or a stereoisomer, tautomer, or pharmaceutically acceptable salt thereof, wherein $X_3$ is C—H.

In embodiments, provided herein is a compound of formula (X), formula (I), or formula (IA-1), or a stereoisomer, tautomer, or pharmaceutically acceptable salt thereof, wherein $R_1$ is

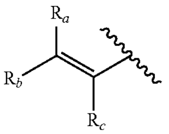

, wherein $R_a$, $R_b$, and $R_c$ are each independently selected from the group consisting of H, $B(OH)_2$, C(O)—OH, C(O)—N$(R^e)(R^f)$, C(O)—$C_{1-6}$alkoxy, C(O)—$C_{1-6}$alkyl, and wherein $R^e$ and $R^f$ are, independently of each other and independently at each occurrence, selected from the group consisting of H, hydroxyl, $C_{1-6}$alkoxy, and $C_{1-6}$alkyl optionally substituted with one or more halo substituents. In embodiments, provided herein is a compound of formula (X), formula (I), or formula (IA-1), or a stereoisomer, tautomer, or pharmaceutically acceptable salt thereof, wherein $R_1$ is

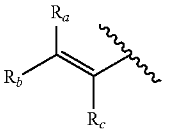

, wherein $R_a$, $R_b$, and $R_c$ are each independently selected from the group consisting of H, $B(OH)_2$, C(O)—OH, C(O)—N$(R^e)(R^f)$, C(O)—$C_{1-6}$alkoxy, C(O)—$C_{1-6}$alkyl, and wherein $R^e$ and $R^f$ are, independently of each other and independently at each occurrence, selected from the group consisting of H, hydroxyl and $C_{1-6}$alkyl optionally substituted with one or more halo substituents. In embodiments, $R_a$ and $R_b$ are each H. In embodiments, $R_a$ and $R_b$ are each H, and $R^e$ is selected from the group consisting of H, $B(OH)_2$, C(O)—OH, C(O)—N$(R^e)(R^f)$, C(O)—$C_{1-6}$alkoxy and C(O)—$C_{1-6}$alkyl. In embodiments, the $C_{1-6}$alkyl is methyl. In embodiments, the $C_{1-6}$alkoxy is methoxy. In embodiments, $R^e$ is C(O)—OH. In embodiments, $R^e$ is C(O)—N$(R^e)(R^f)$. In embodiments, $R^e$ and $R^f$ are each H. In embodiments, one of $R^e$ and $R^f$ is H, and the other of $R^e$ and $R^f$ is $C_{1-6}$alkyl. In embodiments, one of $R^e$ and $R^f$ is H, and the other of $R^e$ and $R^f$ is methyl. In embodiments, one of $R^e$ and $R^f$ is H, and the other of $R^e$ and $R^f$ is OH.

In embodiments, provided herein is a compound of formula (X), formula (I), or formula (IA-1), or a stereoisomer, tautomer, or pharmaceutically acceptable salt thereof, wherein $R_2$ is $C_{6-20}$aryl optionally substituted with one or more substituents selected from the group consisting of $C_{1-6}$alkyl, $C_{1-6}$haloalkyl, $O(R^e)$, and $S(R^g)_5$. In embodiments, provided herein is a compound of formula (X), formula (I), or formula (IA-1), or a stereoisomer, tautomer, or pharmaceutically acceptable salt thereof, wherein $R_2$ is $C_{6-20}$aryl optionally substituted with one or more substituents selected from the group consisting of $C_{1-6}$alkyl, $C_{1-6}$haloalkyl, and $O(R^e)$. In embodiments, $R_2$ is phenyl. In embodiments, $R_2$ is phenyl substituted with $C_{1-6}$alkyl. In embodiments, $R_2$ is phenyl substituted with isopropyl. In embodiments, $R_2$ is phenyl substituted with $C_{1-6}$haloalkyl. In embodiments, $R_2$ is phenyl substituted with —$CF_3$. In embodiments, $R_2$ is phenyl substituted with —$CH_2(CH_3)CF_3$. In embodiments, $R_2$ is phenyl substituted with $O(R^e)$, wherein $R^e$ is $C_{1-6}$alkyl substituted with one or more halo substituents. In embodiments, $R^e$ is —$CF_3$. In embodiments, $R_2$ is phenyl substituted with $S(R^g)_5$. In embodiments, $R_2$ is phenyl substituted with $SF_5$.

In embodiments, provided herein is a compound of formula (X), formula (I), or formula (IA-1), or a stereoisomer, tautomer, or pharmaceutically acceptable salt thereof, wherein $R_4$ is H or $C_{1-6}$alkyl. In embodiments, $R_4$ is H. In embodiments, $R_4$ is methyl.

In embodiments, provided herein is a compound of formula (I), or formula (IA-1), or a stereoisomer, tautomer, or pharmaceutically acceptable salt thereof, wherein $X_2$ is C—$R_5$, wherein $R_5$ is H; $X_3$ is C—H; $R_1$ is

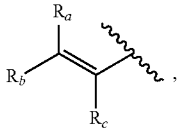

wherein $R_a$ and $R_b$ are each H, and $R^e$ is H, $B(OH)_2$, C(O)—OH, C(O)—N($R^e$)($R^f$), C(O)—$C_{1-6}$alkoxy, C(O)—$C_{1-6}$alkyl, and wherein $R^e$ and $R^f$ are, independently of each other and independently at each occurrence, selected from the group consisting of H, hydroxyl and $C_{1-6}$alkyl; $R_2$ is phenyl substituted with $C_{1-6}$alkyl, $C_{1-6}$haloalkyl, and O($R^e$), wherein $R^e$ is $C_{1-6}$alkyl substituted with one or more halo substituents; and $R_4$ is H.

In embodiments, $X_2$ is C—$R_5$, wherein $R_5$ is cyano; $X_3$ is C—H; $R_1$ is

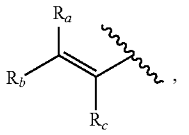

wherein $R_a$ and $R_b$ are each H, and $R^e$ is H, $B(OH)_2$, C(O)—OH, C(O)—N($R^e$)($R^f$), C(O)—$C_{1-6}$alkoxy, C(O)—$C_{1-6}$alkyl, and wherein $R^e$ and $R^f$ are, independently of each other and independently at each occurrence, selected from the group consisting of H, hydroxyl and $C_{1-6}$alkyl; $R_2$ is phenyl substituted with $C_{1-6}$alkyl, $C_{1-6}$haloalkyl, and O($R^e$), wherein $R^e$ is $C_{1-6}$alkyl substituted with one or more halo substituents; and $R_4$ is H.

In some embodiments, provided herein is a compound of formula (X) or formula (I), such as a compound of formula (IA) or formula (IA-1), or a stereoisomer, tautomer, or pharmaceutically acceptable salt thereof, wherein the compound is selected from the group consisting of

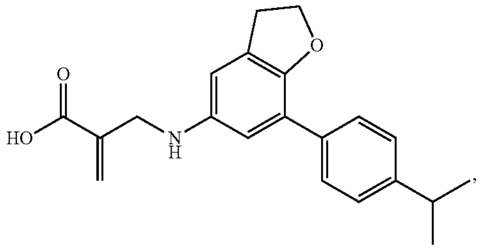

-continued

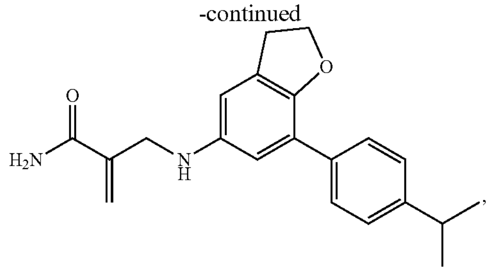

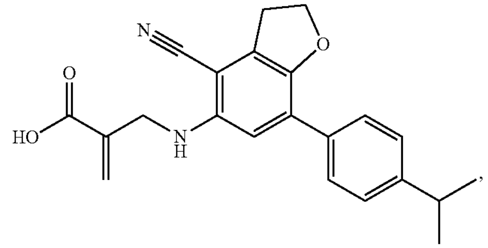

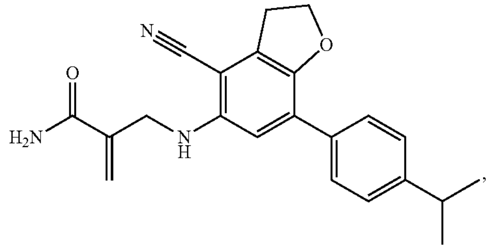

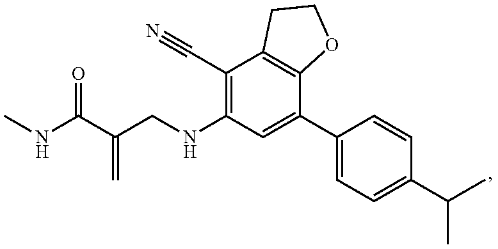

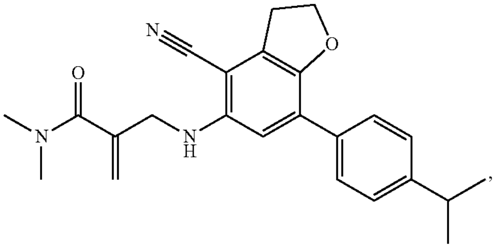

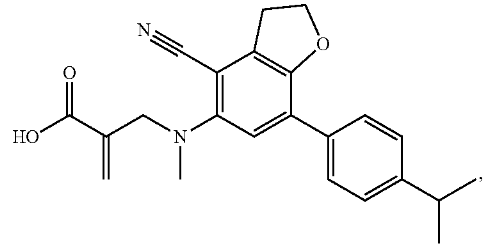

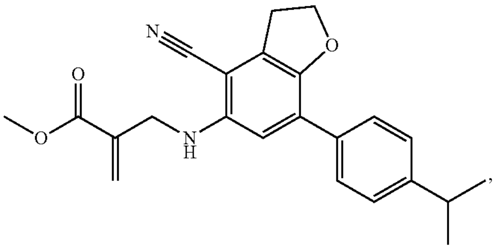

-continued
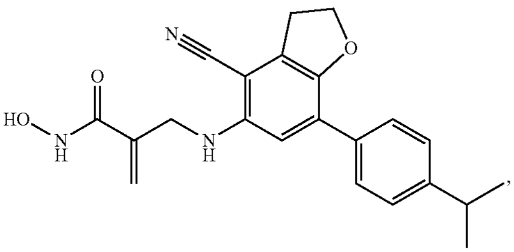
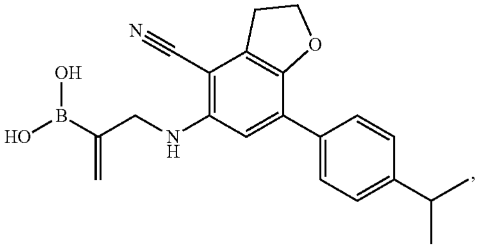
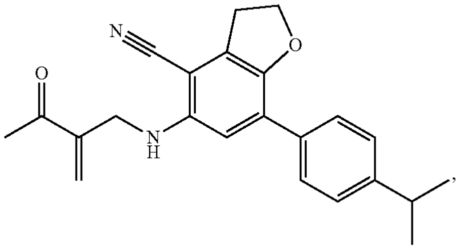
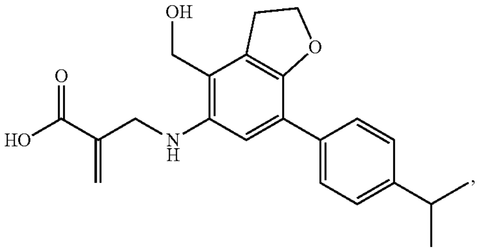
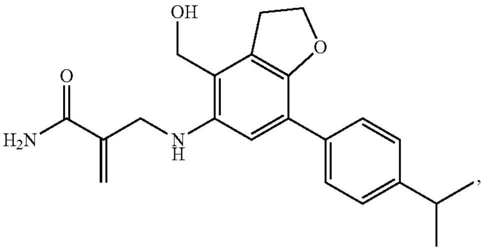
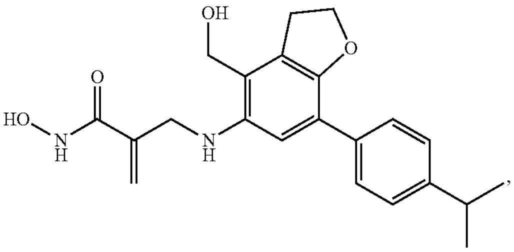
-continued
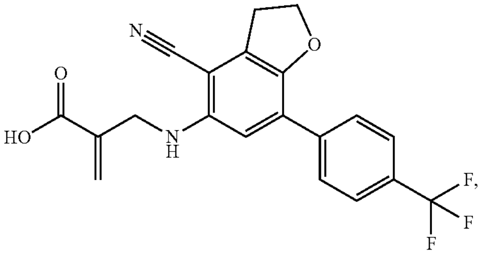
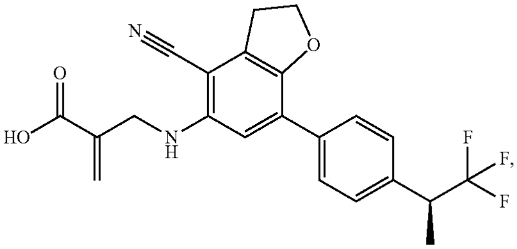
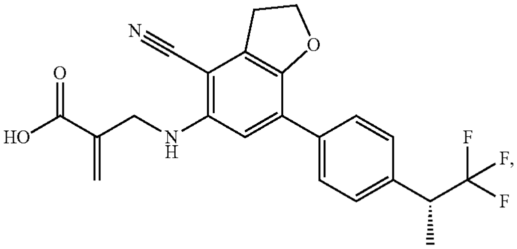
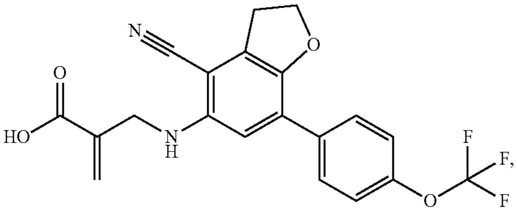
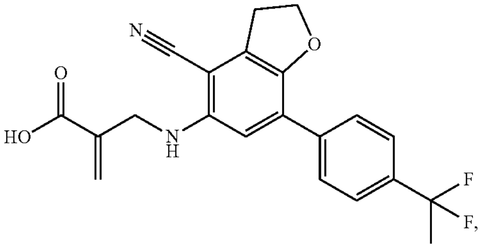
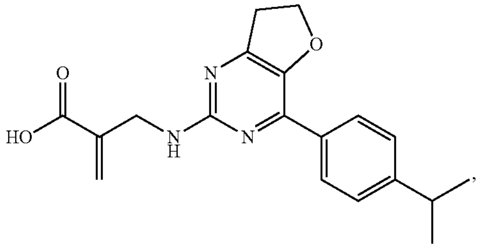
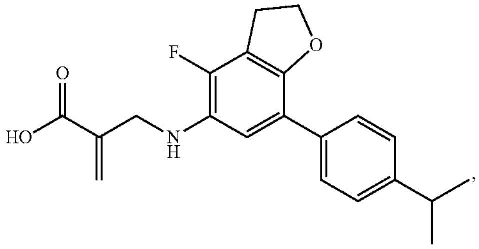

-continued
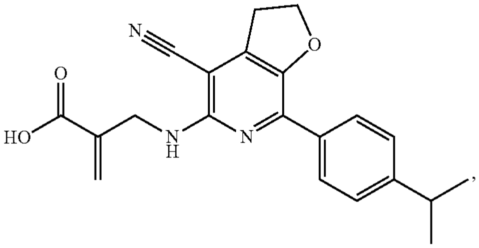
,
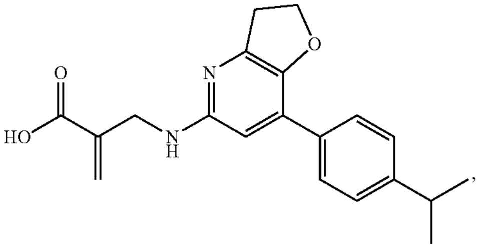
,
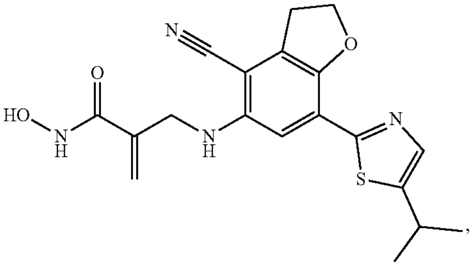
,
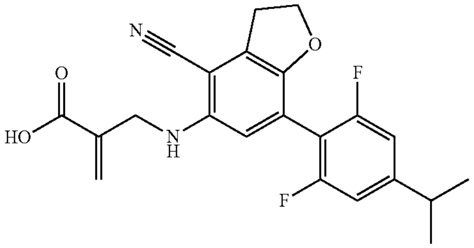
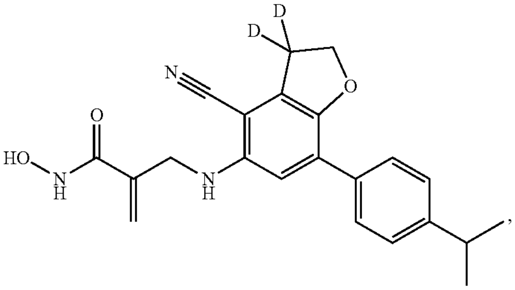
,
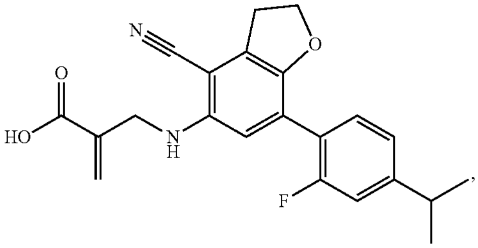
,
-continued
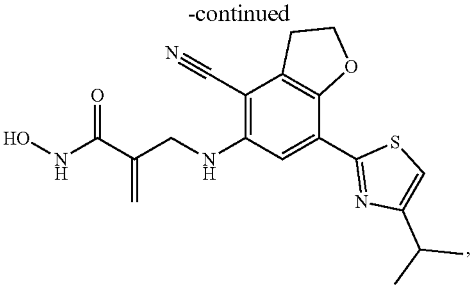
,
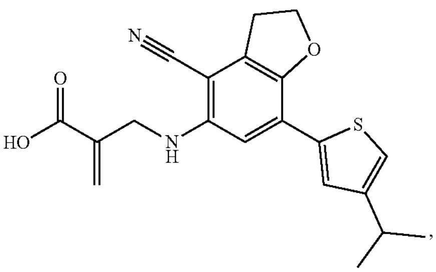
,
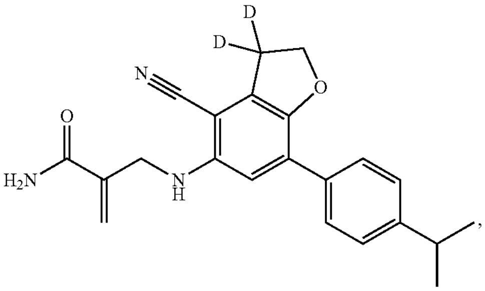
,
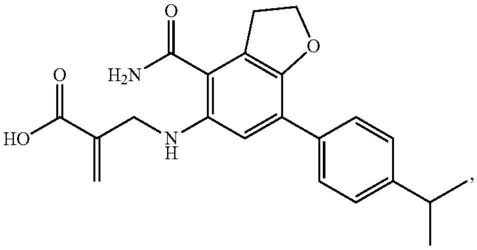
,
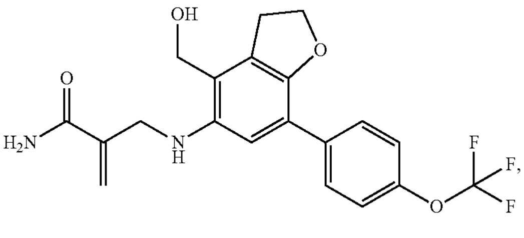
,
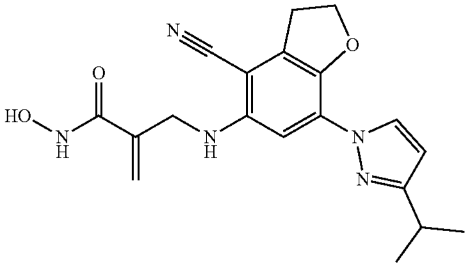

-continued
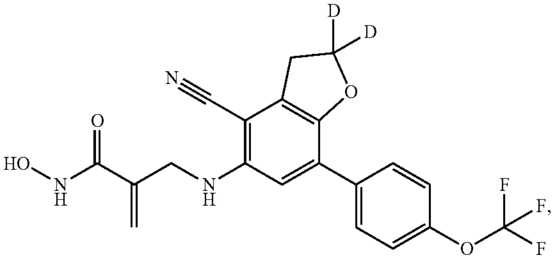
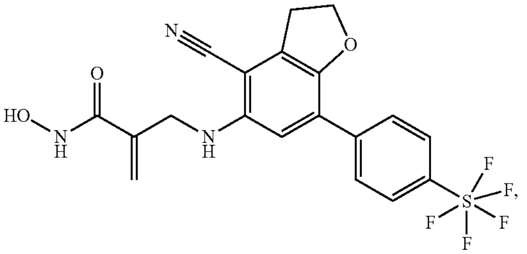
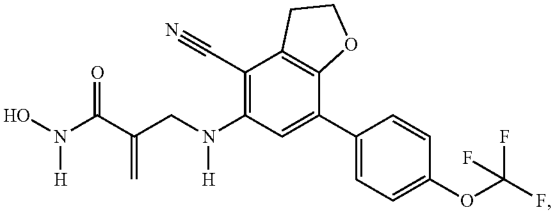
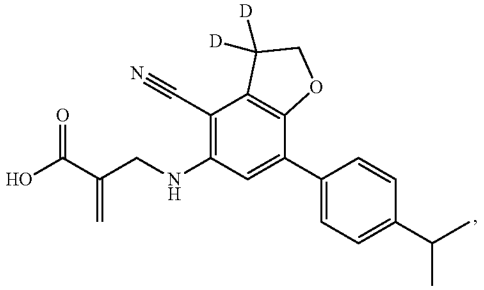
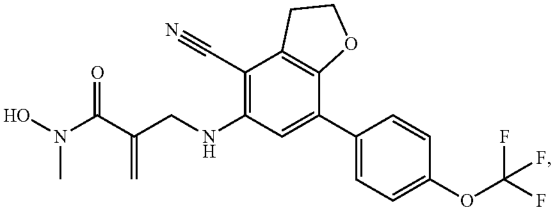
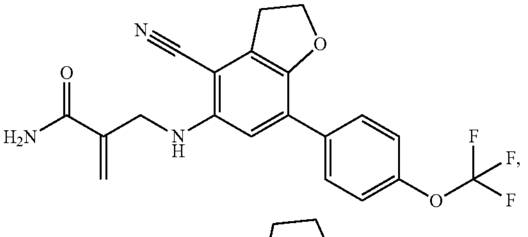
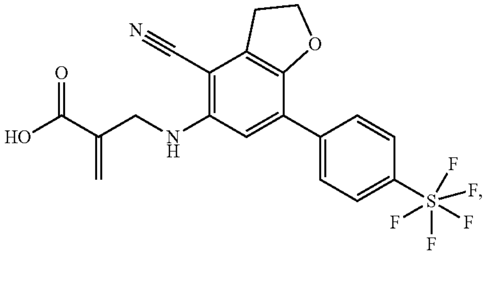
-continued
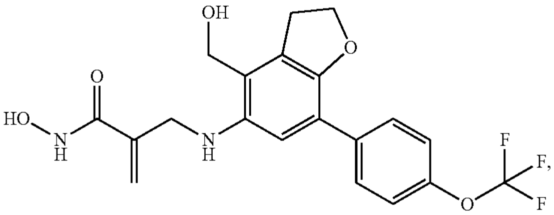
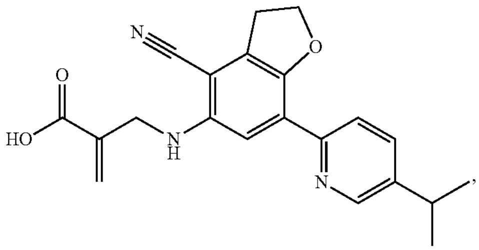
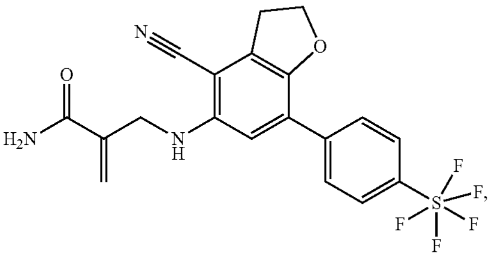
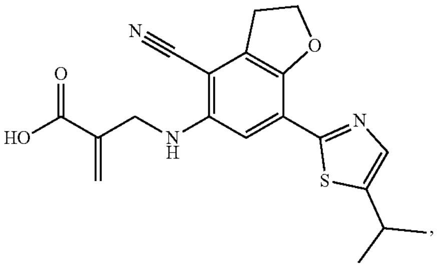
and
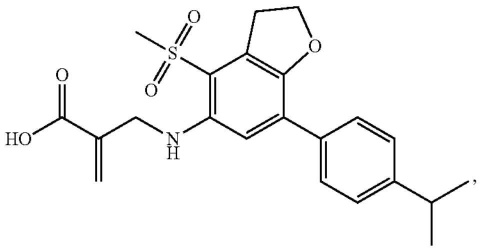
or a stereoisomer, tautomer, or pharmaceutically acceptable salt thereof.
In some embodiments, provided herein is a compound of formula (X) or formula (I), such as a compound of formula (IA) or formula (IA-1), or a stereoisomer, tautomer, or pharmaceutically acceptable salt thereof, wherein the compound is selected from the group consisting of

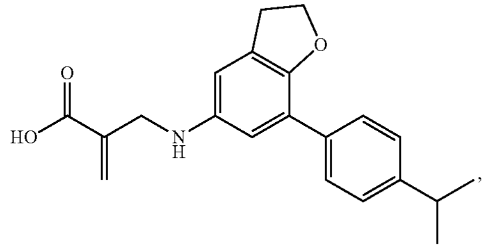,
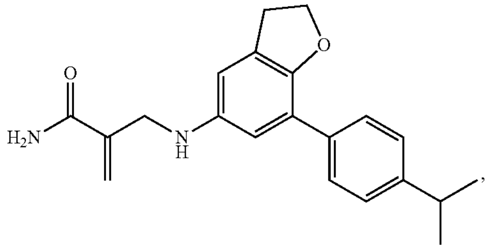,
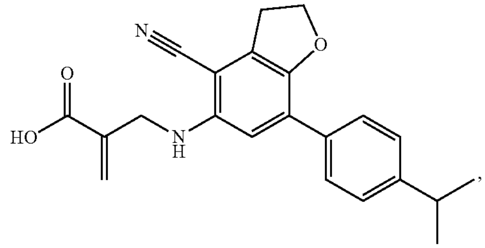,
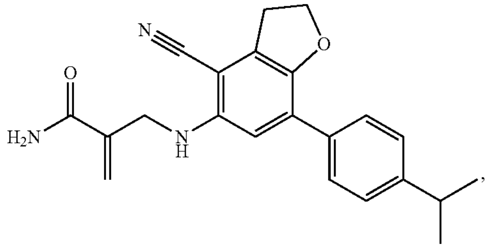,
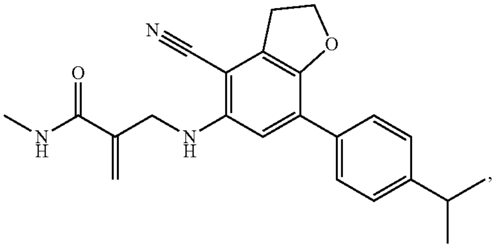,
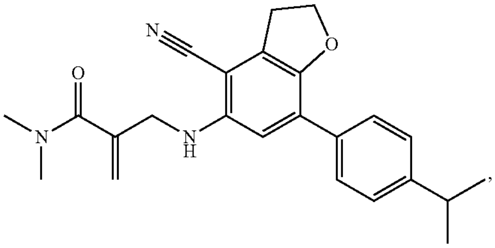,
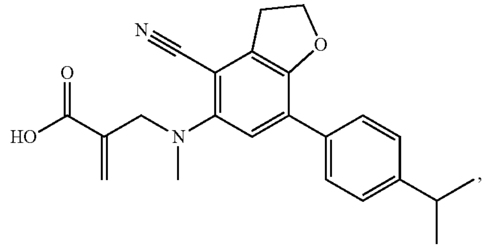,
-continued
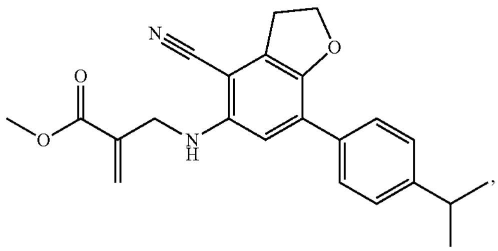,
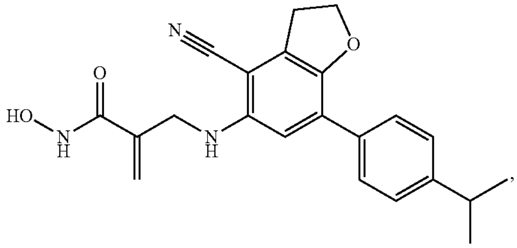,
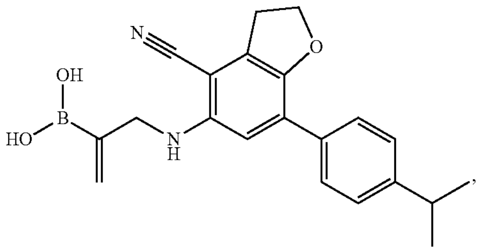,
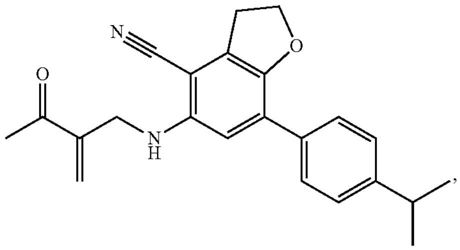,
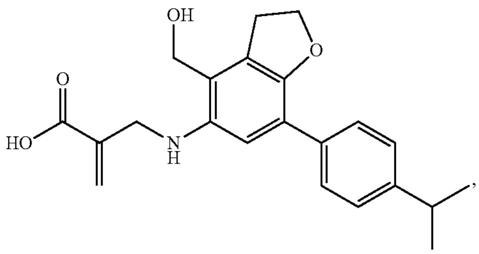,
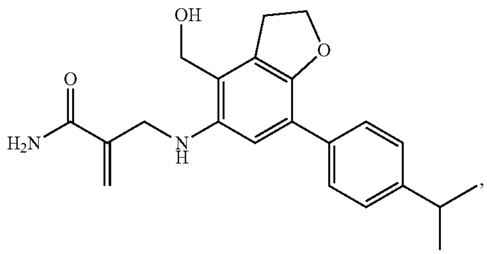, -continued

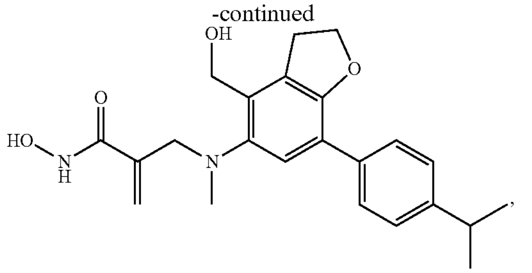

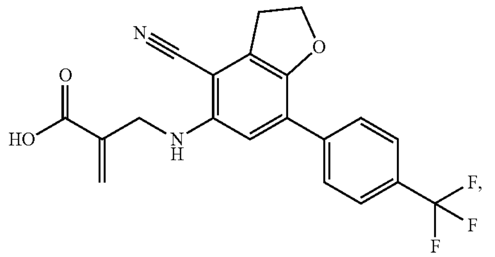

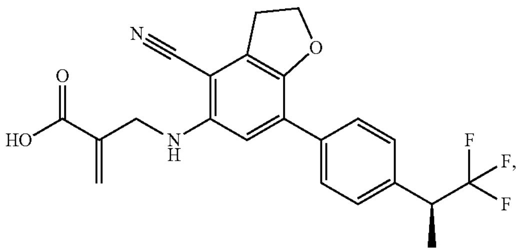

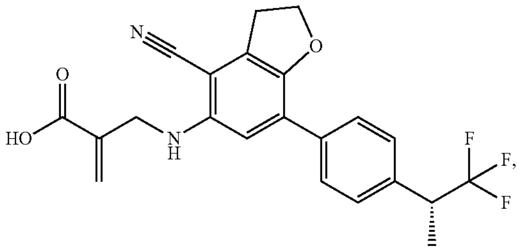

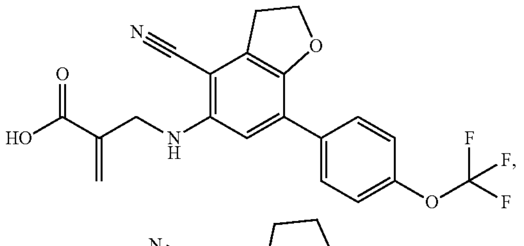

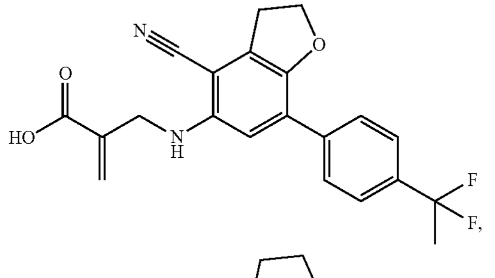

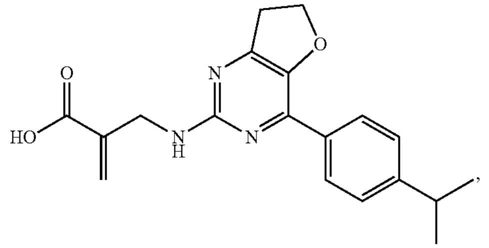

-continued

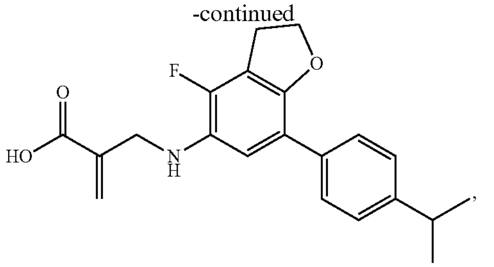

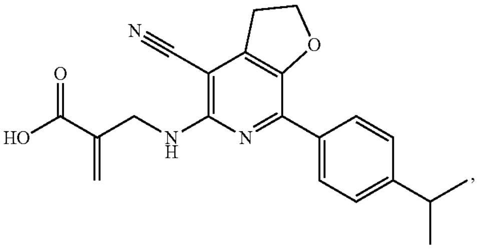

and

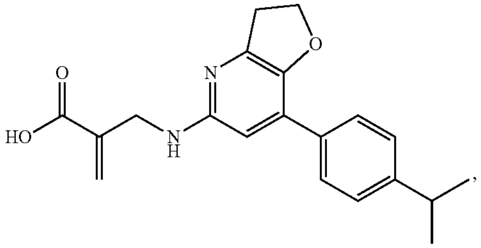

or a stereoisomer, tautomer, or pharmaceutically acceptable salt thereof.

In some embodiments, provided herein is a compound of formula (X), formula (I), or formula (IA), or a stereoisomer, tautomer, or pharmaceutically acceptable salt thereof, wherein $X_1$ is C—$R_5$, and $R_3$ is taken together with the $R_5$ of $X_1$, and the atoms to which they are attached, to form a 5-membered heterocyclyl or a 5-membered heteroaryl, L is absent, and $R_2$ is $C_{6-20}$aryl, wherein the $C_{6-20}$aryl of $R_2$ is independently optionally substituted with one or more $C_{1-6}$alkyl. In certain embodiments, provided herein is a compound of formula (X), formula (I), or formula (IA), or a stereoisomer, tautomer, or pharmaceutically acceptable salt thereof, wherein the compound of formula (X), formula (I), or formula (IA) is a compound of formula (IB):

(IB)

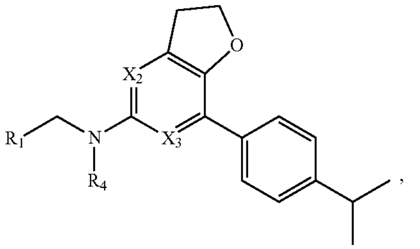

or a stereoisomer, tautomer, or pharmaceutically acceptable salt thereof.

In some embodiments, provided herein is a compound of formula (X), formula (I), formula (IA), or formula (IB), or a stereoisomer, tautomer, or pharmaceutically acceptable salt thereof, wherein $R_1$ is a 3-5 membered saturated heterocyclyl comprising at least one annular oxygen atom, wherein the 3-5 membered saturated heterocyclyl is optionally substituted with one or more $C_{1-6}$alkyl. In certain embodiments, $R_1$ is a 3-membered saturated heterocyclyl comprising at least one annular oxygen atom, wherein the 3-membered saturated heterocyclyl is optionally substituted with one or more $C_{1-6}$alkyl. In some embodiments, $R_1$ is oxiranyl, wherein the oxiranyl is optionally substituted with one or more $C_{1-6}$alkyl. In some embodiments, $R_1$ is

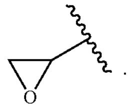 [SMILES: *C1CO1]

In other embodiments, $R_1$ is

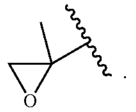

In some embodiments, provided herein is a compound of formula (X), formula (I), formula (IA), or formula (IB), or a stereoisomer, tautomer, or pharmaceutically acceptable salt thereof, wherein $R_1$ is $N(R^e)(R^f)$, wherein $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl. In some embodiments, provided herein is a compound of formula (X), formula (I), formula (IA), or formula (IB), or a stereoisomer, tautomer, or pharmaceutically acceptable salt thereof, wherein $R_1$ is $N(R^e)(R^f)$, wherein $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl. In certain embodiments, $R^e$ and $R^f$ are, independently of each other and independently at each occurrence, selected from the group consisting of H, cyano, and $C_{1-6}$alkyl.

In some embodiments, provided herein is a compound of formula (X), formula (I), formula (IA), or formula (IB), or a stereoisomer, tautomer, or pharmaceutically acceptable salt thereof, wherein $R_1$ is

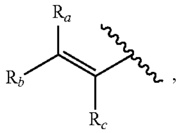

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl. In certain embodiments, at least two of $R_a$, $R_b$, and $R_c$ are H. In some embodiments, exactly two of $R_a$, $R_b$, and $R^c$ are H, and exactly one of $R_a$, $R_b$, and $R^c$ is $B(OH)_2$, C(O)—OH, C(O)—$N(R^e)(R^f)$, C(O)—$C_{1-6}$alkoxy, or C(O)—$C_{1-6}$alkyl. In some embodiments, $R_a$ and $R_b$ are both H and $R^e$ is $B(OH)_2$, C(O)—OH, C(O)—$N(R^e)(R^f)$, C(O)—$C_{1-6}$alkoxy, or C(O)—$C_{1-6}$alkyl. In some embodiments, exactly two of $R_a$, $R_b$, and $R_c$ are H, and exactly one of $R_a$, $R_b$, and $R_c$ is C(O)—OH. In certain embodiments, $R_a$ and $R_b$ are both H and $R^e$ is C(O)—OH. In some embodiments, wherein $R_a$, $R_b$, or $R^e$ is C(O)—$N(R^e)(R^f)$, the $R^e$ and $R^f$ of C(O)—$N(R^e)(R^f)$ are each independently H, $C_{1-6}$alkyl, or hydroxyl. In some embodiments, wherein $R_a$, $R_b$, or $R^e$ is C(O)—$N(R^e)(R^f)$, the $R^e$ and $R^f$ of C(O)—$N(R^e)(R^f)$ are each independently H, $C_{1-6}$alkyl, $C_{1-6}$alkoxy, or hydroxyl.

In some embodiments, provided herein is a compound of formula (X), formula (I), formula (IA), or formula (IB), or a stereoisomer, tautomer, or pharmaceutically acceptable salt thereof, wherein the compound is selected from the group consisting of

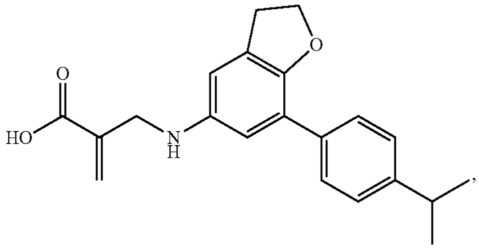

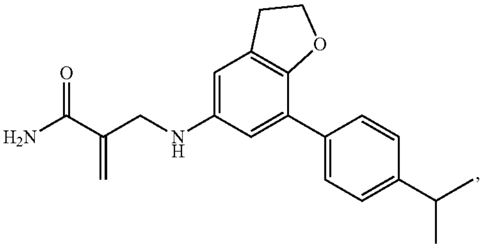

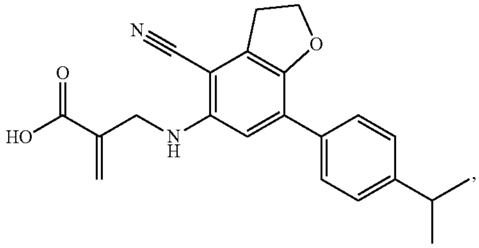

-continued
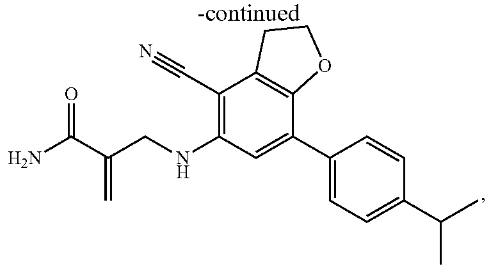,
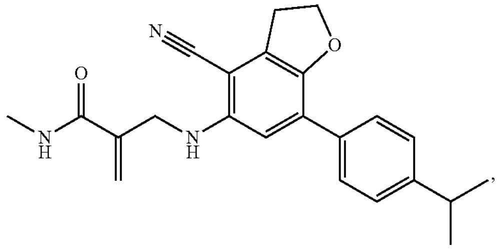,
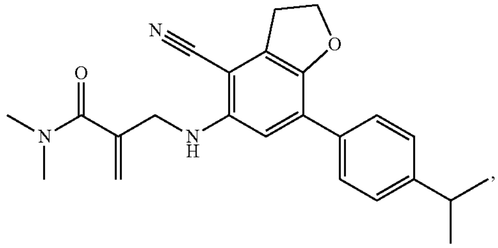,
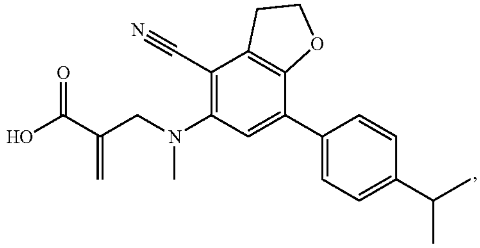,
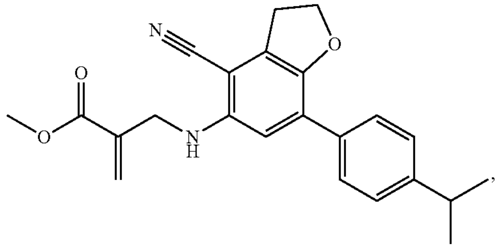,
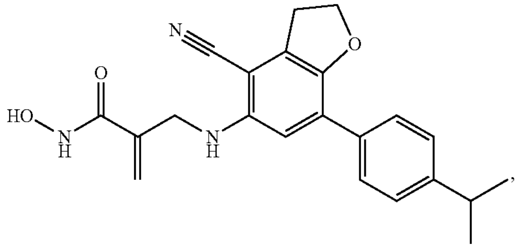,
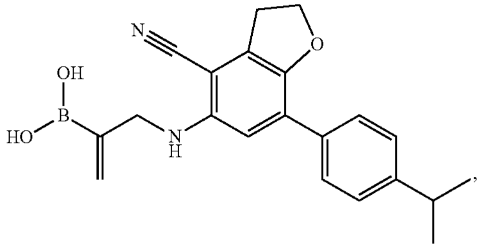,
-continued
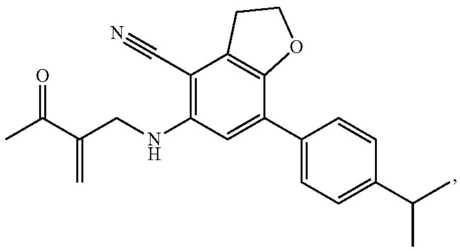,
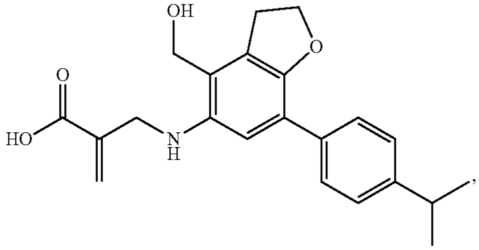,
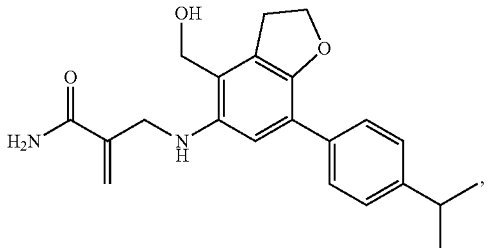,
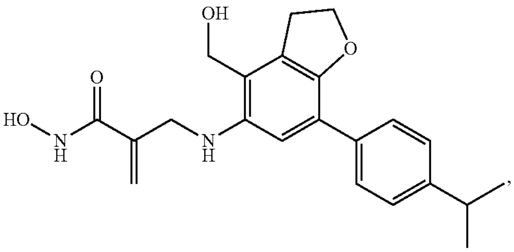,
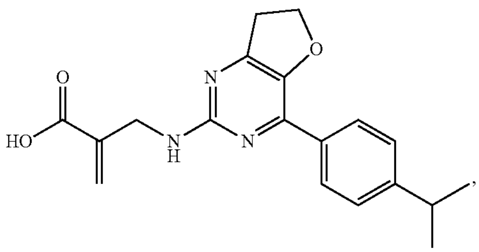,
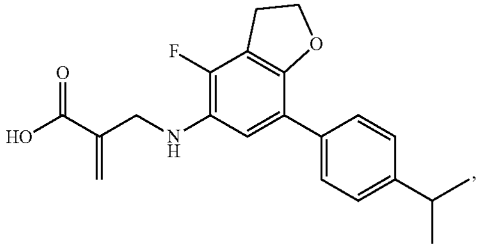, -continued
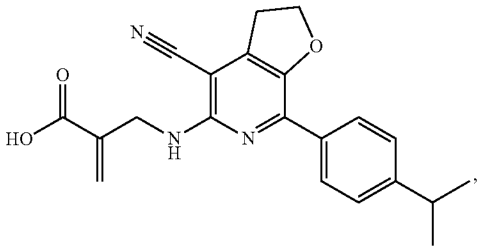
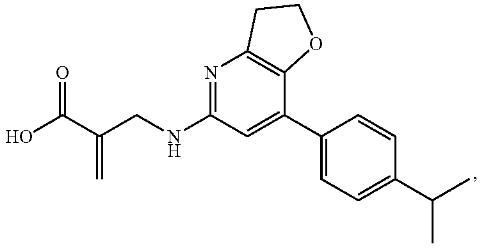
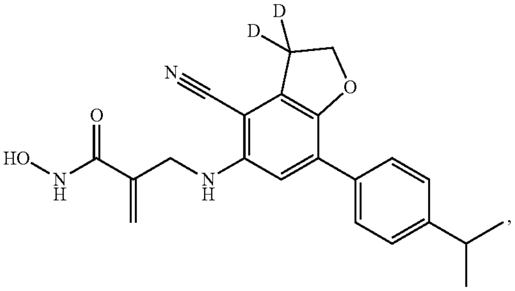
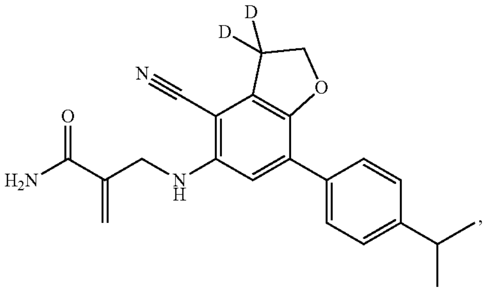
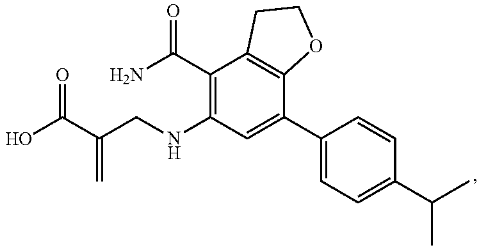
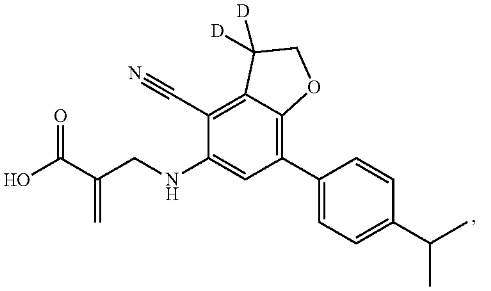
and
-continued
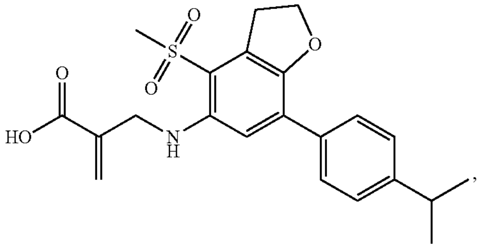
or a stereoisomer, tautomer, or pharmaceutically acceptable salt thereof.
In some embodiments, provided herein is a compound of formula (X), formula (I), formula (IA), or formula (IB), or a stereoisomer, tautomer, or pharmaceutically acceptable salt thereof, wherein the compound is selected from the group consisting of
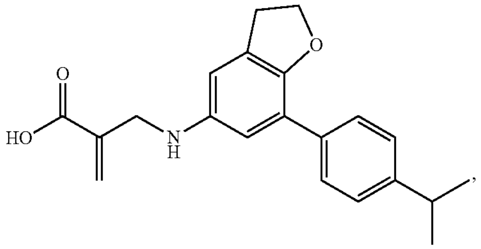
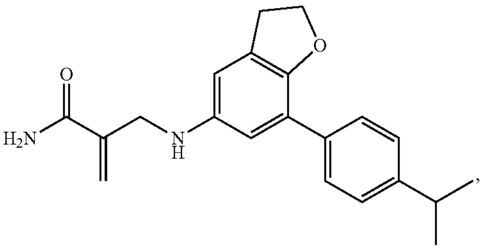
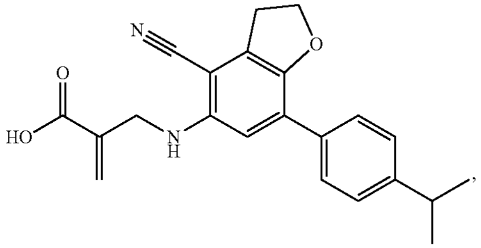
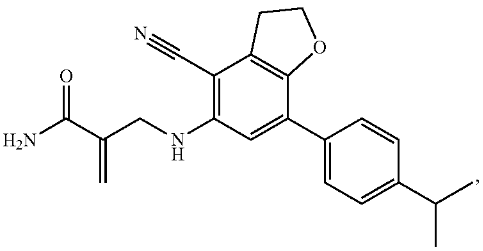

-continued
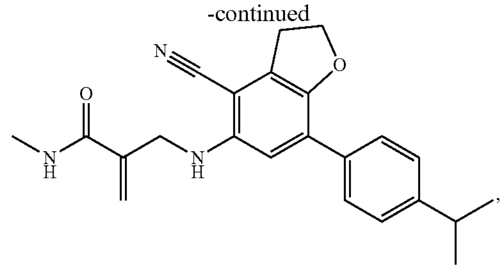
,
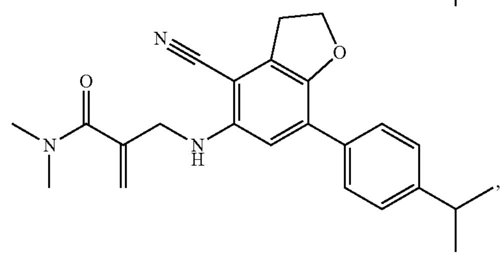
,
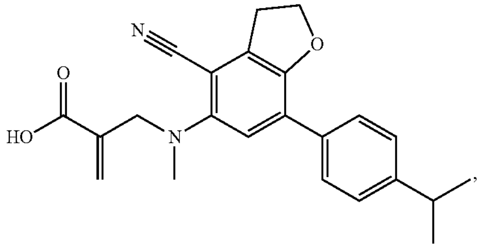
,
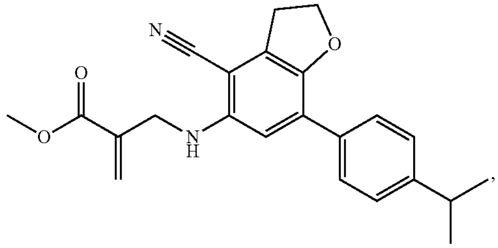
,
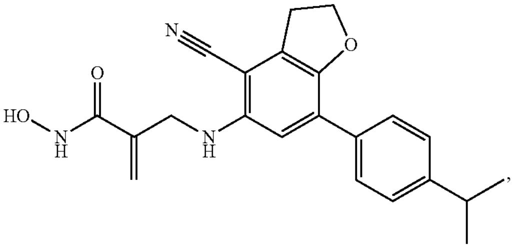
,
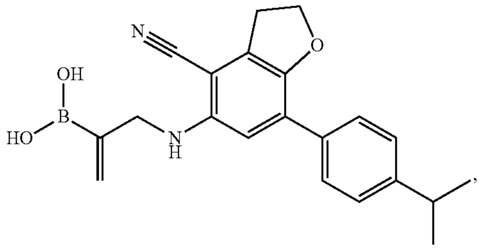
,
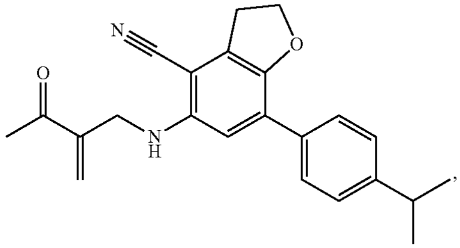
,
-continued
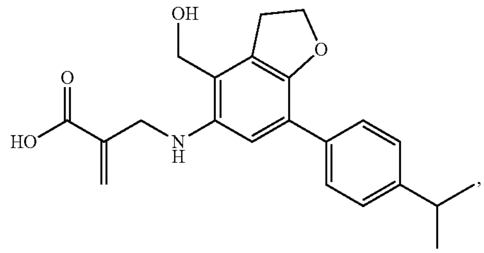
,
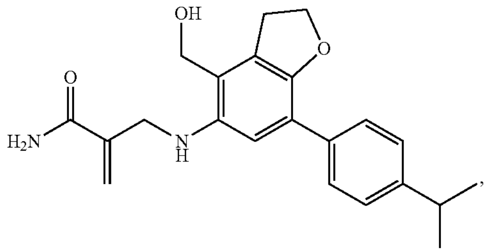
,
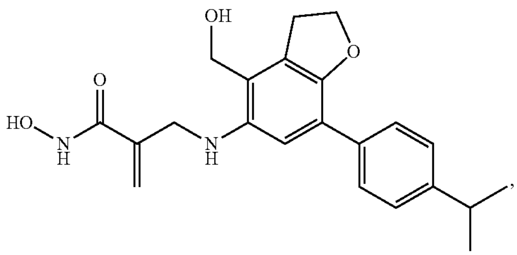
,
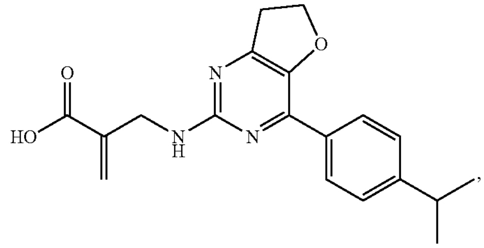
,
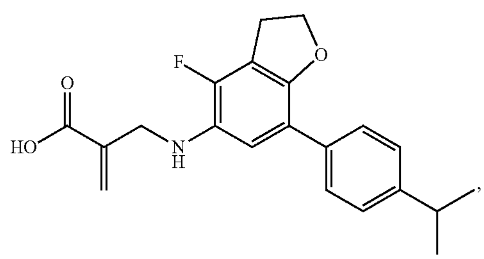
,
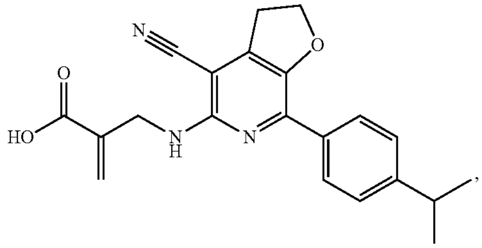
, and -continued

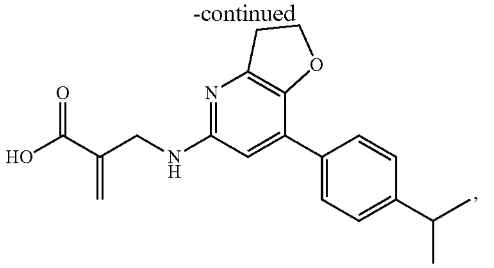

or a stereoisomer, tautomer, or pharmaceutically acceptable salt thereof.

In some embodiments, provided herein is a compound of formula (X), formula (I), formula (IA), or formula (IB), or a stereoisomer, tautomer, or pharmaceutically acceptable salt thereof, wherein the compound of formula (X), formula (I), formula (IA), or formula (IB) is a compound of formula (IC):

(IC)

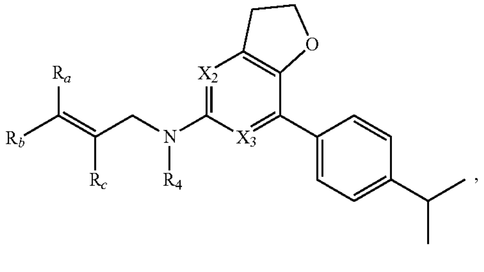

or a stereoisomer, tautomer, or pharmaceutically acceptable salt thereof.

In some embodiments, provided herein is a compound of formula (IC), or a stereoisomer, tautomer, or pharmaceutically acceptable salt thereof, wherein $X_2$ is C—$R_5$ and $X_3$ is C—H. In some embodiments, $X_2$ is C—$R_5$, wherein $R_5$ is H, cyano, halo, or $C_{1-6}$alkyl, wherein the $C_{1-6}$ alkyl is optionally substituted with hydroxyl, and $X_3$ is C—H. In other embodiments, $X_2$ is C—$R_5$, wherein $R_5$ is cyano, and $X_3$ is C—H. In other embodiments, $X_2$ is C—$R_5$, wherein $R_5$ is cyano, and $X_3$ is N. In still other embodiments, $X_2$ is N and $X_3$ is C—H. In certain embodiments, $X_2$ is N and $X_3$ is N.

In some embodiments, provided herein is a compound of formula (IC), or a stereoisomer, tautomer, or pharmaceutically acceptable salt thereof, wherein $R_4$ is H. In other embodiments, $R_4$ is $C_{1-6}$alkyl, wherein the $C_{1-6}$alkyl is optionally substituted with hydroxyl. In certain embodiments, $R_4$ is methyl. In some embodiments, provided herein is a compound of formula (IC), or a stereoisomer, tautomer, or pharmaceutically acceptable salt thereof, wherein $X_2$ is C—$R_5$, wherein $R_5$ is H, cyano, halo, or $C_{1-6}$alkyl, wherein the $C_{1-6}$alkyl is optionally substituted with hydroxyl, $X_3$ is C—H, and $R_4$ is H. In other embodiments, provided herein is a compound of formula (IC), or a stereoisomer, tautomer, or pharmaceutically acceptable salt thereof, wherein $X_2$ is C—$R_5$, wherein $R_5$ is cyano, $X_3$ is C—H, and $R_4$ is H.

In some embodiments, provided herein is a compound of formula (IC), or a stereoisomer, tautomer, or pharmaceutically acceptable salt thereof, wherein at least two of $R_a$, $R_b$, and $R^e$ are H. In some embodiments, exactly two of $R_a$, $R_b$, and $R_c$ are H, and exactly one of $R_a$, $R_b$, and $R^e$ is $B(OH)_2$, C(O)—OH, C(O)—N($R^e$)($R^f$), C(O)—$C_{1-6}$alkoxy, or C(O)—$C_{1-6}$alkyl, wherein the $R^e$ and $R^f$ of C(O)—N($R^e$)($R^f$) are each independently H, $C_{1-6}$alkyl, $C_{1-6}$alkoxy, or hydroxyl. In some embodiments, exactly two of $R_a$, $R_b$, and $R_c$ are H, and exactly one of $R_a$, $R_b$, and $R_c$ is $B(OH)_2$, C(O)—OH, C(O)—N($R^e$)($R^f$), C(O)—$C_{1-6}$alkoxy, or C(O)—$C_{1-6}$alkyl, wherein the $R^e$ and $R^f$ of C(O)—N($R^e$)($R^f$) are each independently H, $C_{1-6}$alkyl, or hydroxyl. In some embodiments, exactly two of $R_a$, $R_b$, and $R_c$ are H, and exactly one of $R_a$, $R_b$, and $R_c$ is C(O)—OH. In some embodiments, $R_a$ is H, $R_b$ is H, and $R^e$ is C(O)—OH. In some embodiments, $R_a$ is H, $R_b$ is H, and $R^e$ is C(O)—NH(OH).

In certain embodiments, provided herein is a compound of formula (IC), or a stereoisomer, tautomer, or pharmaceutically acceptable salt thereof, wherein $X_2$ is C—$R_5$, wherein $R_5$ is H, cyano, halo, $S(O)_2$—$C_{1-6}$alkyl, or $C_{1-6}$alkyl, wherein the $C_{1-6}$alkyl is optionally substituted with hydroxyl, $X_3$ is C—H, $R_4$ is H, and at least two of $R_a$, $R_b$, and $R_c$ are H. In certain embodiments, provided herein is a compound of formula (IC), or a stereoisomer, tautomer, or pharmaceutically acceptable salt thereof, wherein $X_2$ is C—$R_5$, wherein $R_5$ is H, cyano, halo, or $C_{1-6}$alkyl, wherein the $C_{1-6}$alkyl is optionally substituted with hydroxyl, $X_3$ is C—H, $R_4$ is H, and at least two of $R_a$, $R_b$, and $R^e$ are H. In certain embodiments, provided herein is a compound of formula (IC), or a stereoisomer, tautomer, or pharmaceutically acceptable salt thereof, wherein $X_2$ is C—$R_5$, wherein $R_5$ is H, cyano, halo, $S(O)_2$—$C_{1-6}$alkyl, or $C_{1-6}$alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is $B(OH)_2$, C(O)—OH, C(O)—N($R^e$)($R^f$), C(O)—$C_{1-6}$alkoxy, or C(O)—$C_{1-6}$alkyl, wherein the $R^e$ and $R^f$ of C(O)—N($R^e$)($R^f$) are each independently H, $C_{1-6}$alkyl, or hydroxyl. In certain embodiments, provided herein is a compound of formula (IC), or a stereoisomer, tautomer, or pharmaceutically acceptable salt thereof, wherein $X_2$ is C—$R_5$, wherein $R_5$ is H, cyano, halo, or $C_{1-6}$alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is $B(OH)_2$, C(O)—OH, C(O)—N($R^e$)($R^f$), C(O)—$C_{1-6}$ alkoxy, or C(O)—$C_{1-6}$ alkyl, wherein the $R^e$ and $R^f$ of C(O)—N($R^e$)($R^f$) are each independently H, $C_{1-6}$alkyl, or hydroxyl. In some embodiments, provided herein is a compound of formula (IC), or a stereoisomer, tautomer, or pharmaceutically acceptable salt thereof, wherein $X_2$ is C—$R_5$, wherein $R_5$ is H, cyano, halo, $S(O)_2$—$C_{1-6}$alkyl, or $C_{1-6}$alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is C(O)—OH. In some embodiments, provided herein is a compound of formula (IC), or a stereoisomer, tautomer, or pharmaceutically acceptable salt thereof, wherein $X_2$ is C—$R_5$, wherein $R_5$ is H, cyano, halo, or $C_{1-6}$ alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is C(O)—OH. In some embodiments, provided herein is a compound of formula (IC), or a stereoisomer, tautomer, or pharmaceutically acceptable salt thereof, wherein $X_2$ is C—$R_5$, wherein $R_5$ is H, cyano, halo, $S(O)_2$—$C_{1-6}$alkyl, or $C_{1-6}$ alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is C(O)—NH(OH). In some embodiments, provided herein is a compound of formula (IC), or a stereoisomer, tautomer, or pharmaceutically acceptable salt thereof, wherein $X_2$ is C—$R_5$, wherein $R_5$ is H, cyano, halo, or $C_{1-6}$alkyl, wherein the $C_{1-6}$alkyl is optionally substituted with hydroxyl, $X_3$ is C—H, $R_4$ is H, exactly two of $R_a$, $R_b$, and $R_c$ are H, and exactly one of $R_a$, $R_b$, and $R_c$ is C(O)—NH(OH).
In some embodiments, provided herein is a compound of formula (IC), or a stereoisomer, tautomer, or pharmaceutically acceptable salt thereof, wherein the compound of formula (IC) is selected from the group consisting of
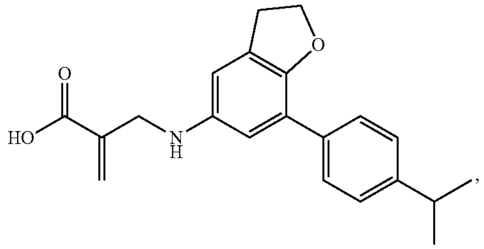
,
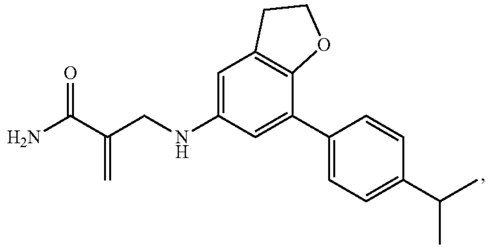
,
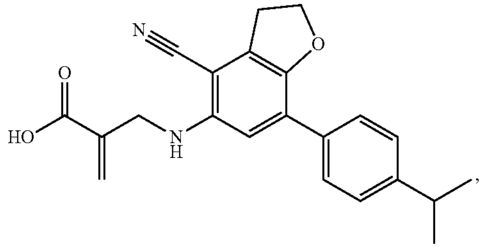
,
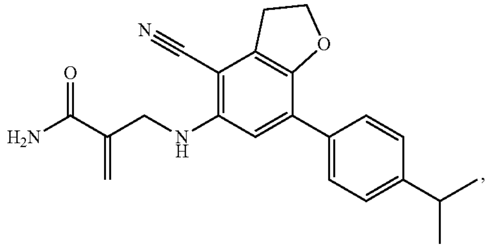
,
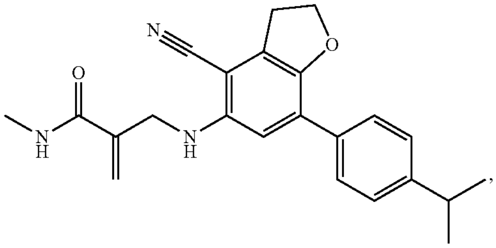
,
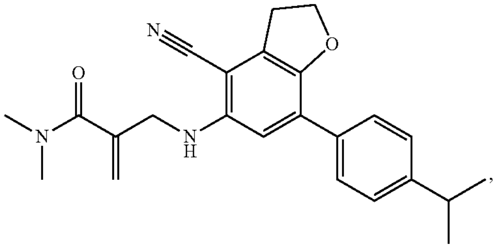
,
-continued
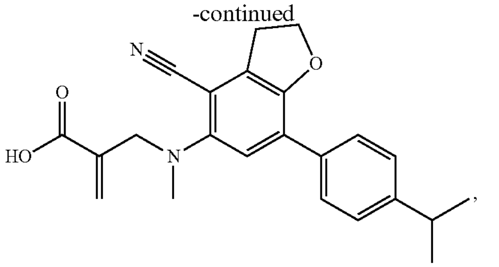
,
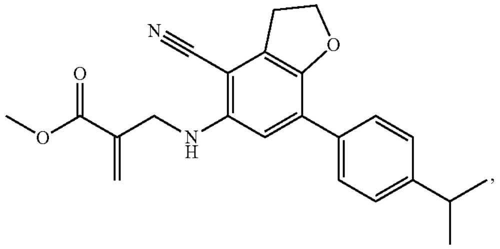
,
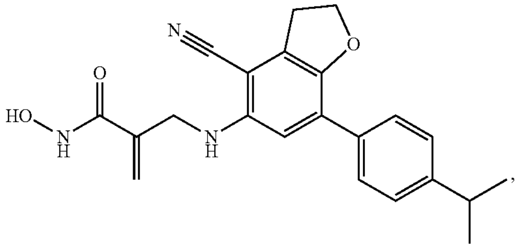
,
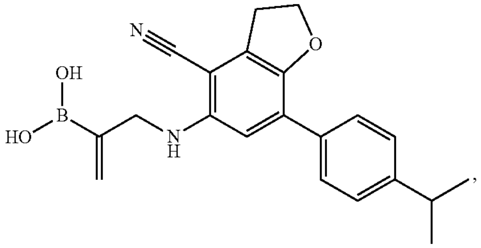
,
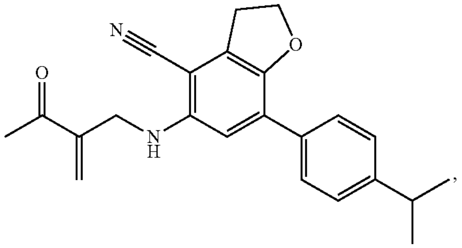
,
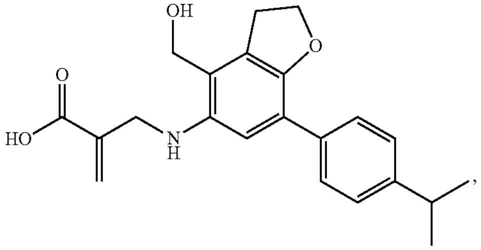
,
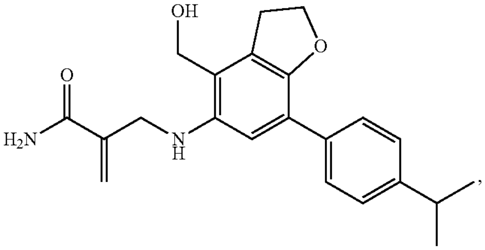
, -continued
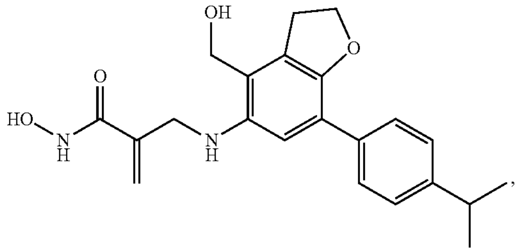
,
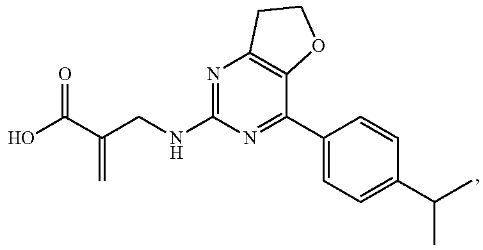
,
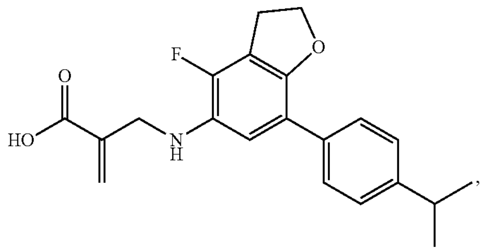
,
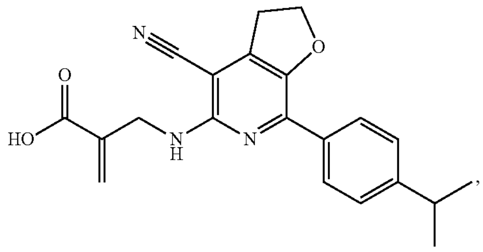
,
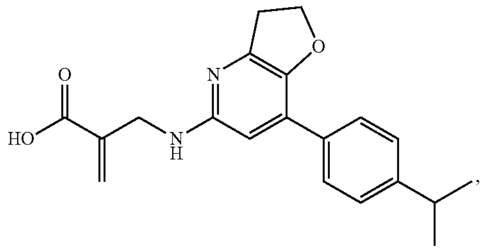 [SMILES: C=C(CNc1cc(-c2ccc(C(C)C)cc2)c2c(n1)CCO2)C(=O)O]
,
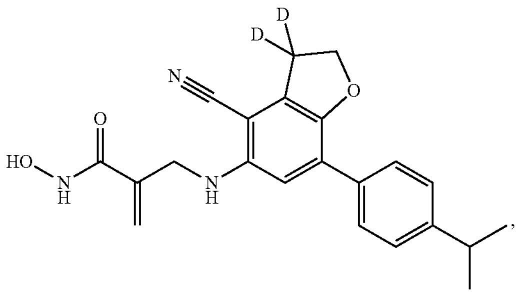
,
-continued
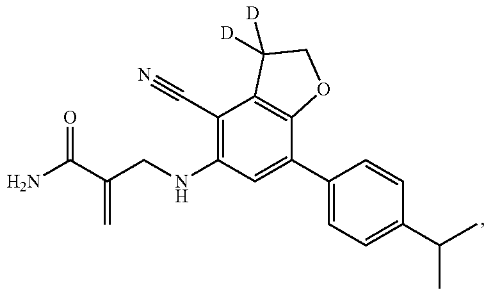
,
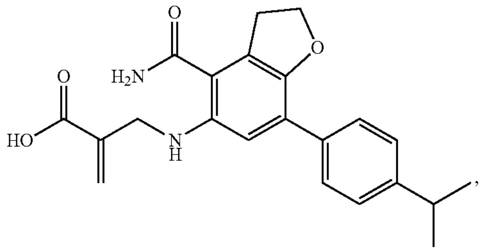
,
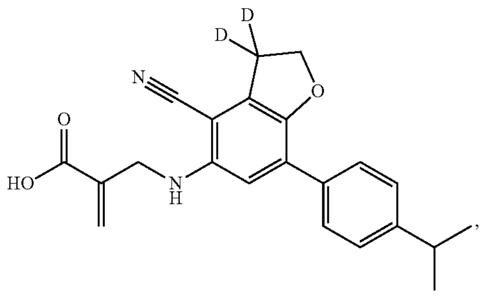
, and
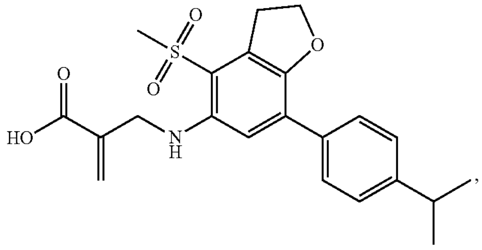
,
or a stereoisomer, tautomer, or pharmaceutically acceptable salt thereof.
In some embodiments, provided herein is a compound of formula (IC), or a stereoisomer, tautomer, or pharmaceutically acceptable salt thereof, wherein the compound of formula (IC) is selected from the group consisting of
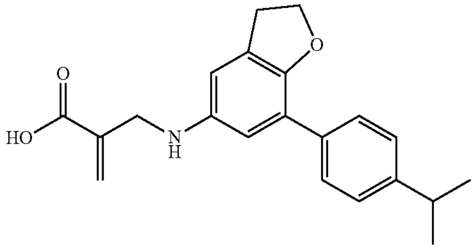
, -continued
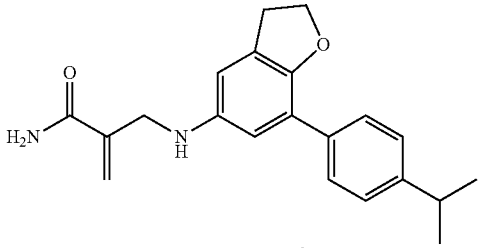
,
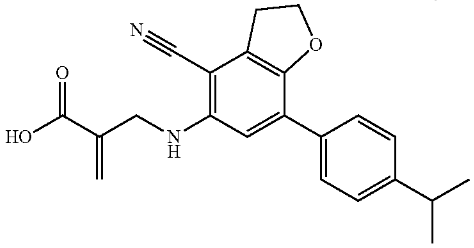
,
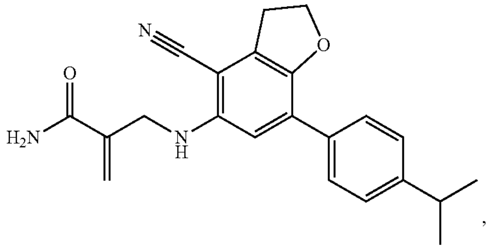
,
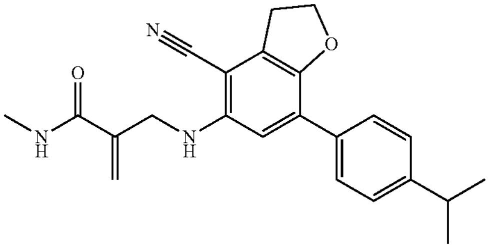
,
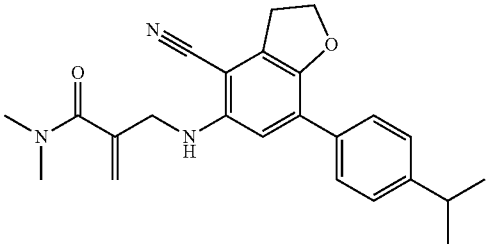
,
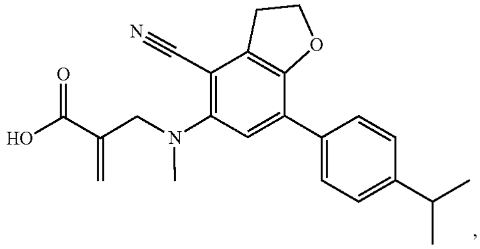
,
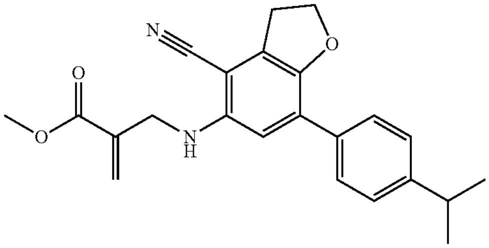
,
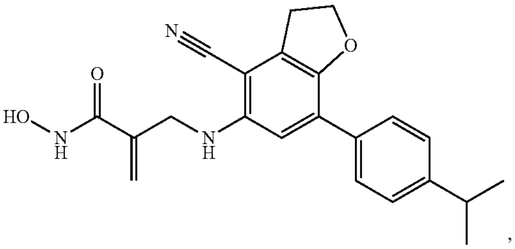
,
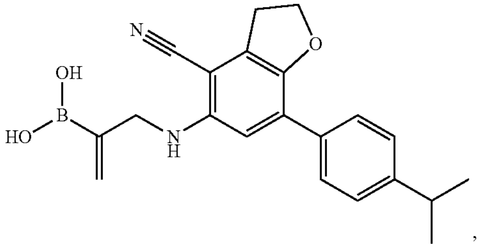
,
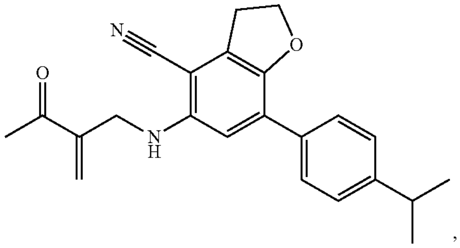
,
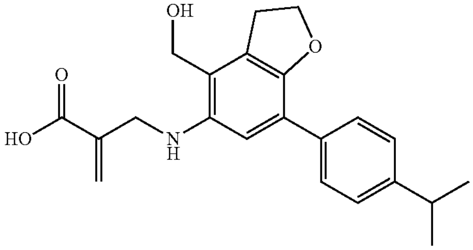
,
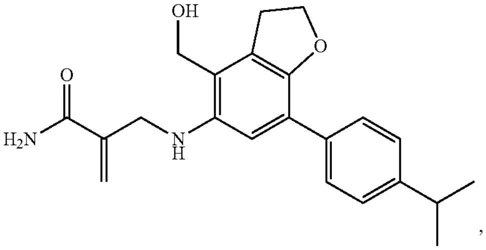
,
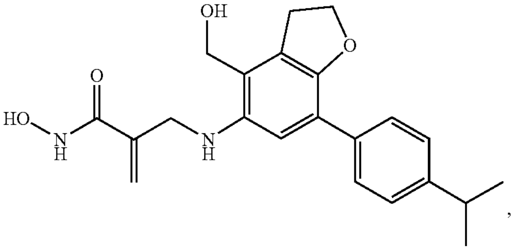
, -continued

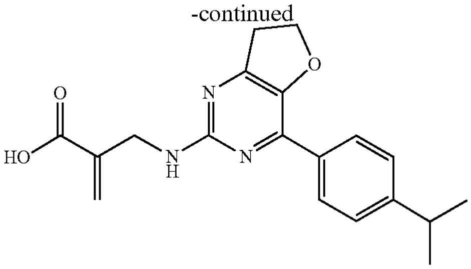

,

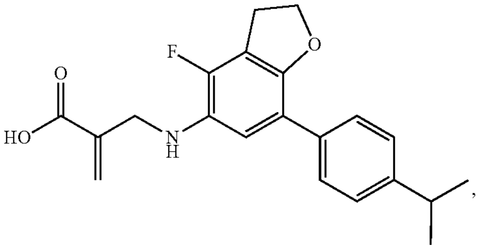

,

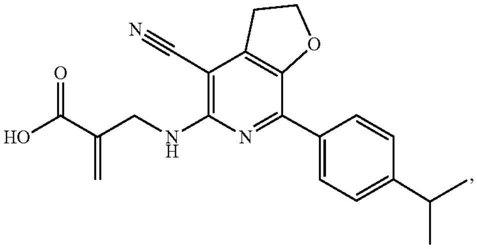

, and

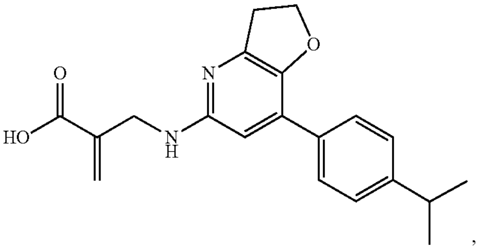

, or a stereoisomer, tautomer, or pharmaceutically acceptable salt thereof.

In some embodiments, provided herein is a compound of formula (X), formula (I), formula (IA), or formula (IB), or a stereoisomer, tautomer, or pharmaceutically acceptable salt thereof, wherein $R_1$ is

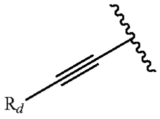

, wherein $R_d$ is selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl.

In some embodiments, provided herein is a compound of formula (I), formula (IA), or formula (IB), or a stereoisomer, tautomer, or pharmaceutically acceptable salt thereof, wherein $R_3$ is cyano, $C_{1-6}$alkyl, $C_{1-4}$alkoxy, or $C_{2-4}$alkenyl, wherein the $C_{2-4}$alkenyl is optionally substituted with N($R^e$)($R^f$). In some embodiments, $R_3$ is cyano. In other embodiments, $R_3$ is $C_{1-4}$alkoxy.

In some embodiments, provided herein is a compound of formula (I), or a stereoisomer, tautomer, or pharmaceutically acceptable salt thereof, wherein $R_3$ is taken together with the carbon atom of *—$CH_2$—O—** of L, and the atoms to which they are attached, to form a $C_6$aryl or a 6-membered heteroaryl. In some embodiments, $R_3$ is taken together with the carbon atom of *—$CH_2$—O—** of L, and the atoms to which they are attached, to form a $C_6$aryl. In other embodiments, $R_3$ is taken together with the carbon atom of *—$CH_2$—O—** of L, and the atoms to which they are attached, to form a 6-membered heteroaryl.

In some embodiments, provided herein is a compound of formula (X), formula (I), formula (IA), formula (IB), or formula (IC), or a stereoisomer, tautomer, or pharmaceutically acceptable salt thereof, wherein $R_4$ is H or $C_{1-6}$alkyl, wherein the $C_{1-6}$alkyl is optionally substituted with hydroxyl. In other embodiments, $R_4$ is H.

In one embodiment, provided herein is a compound of formula (X), or a stereoisomer, tautomer, or pharmaceutically acceptable salt thereof, wherein: $X_1$ is C—$R_5$, wherein the $R_5$ of $X_1$ is taken together with $R_3$, and the atoms to which they are attached, to form a 5-membered heterocyclyl or a 5-membered heteroaryl that is optionally substituted with one more D; $X_2$ is N or C—$R_5$, wherein each $R_5$ is independently selected from the group consisting of H, cyano, halo, $C(O)NH_2$, $S(O)_2$—$C_{1-6}$alkyl, and $C_{1-6}$alkyl, wherein the $C_{1-6}$alkyl of $R_5$ is optionally substituted with hydroxyl; $X_3$ is N or C—H; $R_1$ is

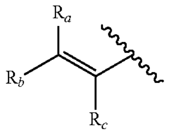

, wherein $R_a$ and $R_b$ are each H, and $R_c$ is selected from the group consisting of H, $B(OH)_2$, C(O)—OH, C(O)—N($R^e$)($R^f$), C(O)—$C_{1-6}$alkoxy, and C(O)—$C_{1-6}$alkyl; L is absent; $R_2$ is $C_{6-20}$aryl or 5-20 membered heteroaryl, wherein the $C_{6-20}$aryl or 5-20 membered heteroaryl of $R_2$ is independently optionally substituted with one or more substituents selected from the group consisting of halo, $C_{1-6}$alkyl, $C_{1-6}$haloalkyl, O($R^e$), and S($R^g$)$_5$, wherein $R^e$ and $R^f$ are, independently of each other and independently at each occurrence, selected from the group consisting of H, hydroxyl, and $C_{1-6}$alkyl, wherein the $C_{1-6}$alkyl of $R^e$ or $R^f$ is optionally substituted with one or more halo, and $R^g$ is halo.

In some embodiments of the foregoing, provided herein is a compound of formula (X), or a stereoisomer, tautomer, or pharmaceutically acceptable salt thereof, wherein $X_1$ is C—$R_5$, wherein the $R_5$ of $X_1$ is taken together with $R_3$, and the atoms to which they are attached, to form a 5-membered heterocyclyl that is optionally substituted with one or more D; $X_2$ is C—$R_5$, wherein $R_5$ is independently selected from the group consisting of H or cyano; $X_3$ is C—H.

In some embodiments of the foregoing, provided herein is a compound of formula (X), or a stereoisomer, tautomer, or pharmaceutically acceptable salt thereof, wherein the $R_5$ of $X_1$ is taken together with $R_3$, and the atoms to which they are attached, to form a tetrahydrofuranyl that is optionally substituted with one or more D. In some embodiments, the tetrahydrofuranyl is unsubstituted.

In some embodiments of the foregoing, provided herein is a compound of formula (X), or a stereoisomer, tautomer, or pharmaceutically acceptable salt thereof, wherein the $R_5$ of $X_1$ is taken together with $R_3$, and the atoms to which they are attached, to form a thiazolyl that is optionally substituted with one or more D. In some embodiments, the thiazolyl is unsubstituted.

In some embodiments of the foregoing, provided herein is a compound of formula (X), or a stereoisomer, tautomer, or pharmaceutically acceptable salt thereof, wherein $R_1$ is

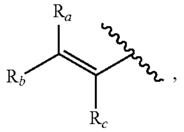

wherein $R_a$ and $R_b$ are each H, and $R_c$ is selected from the group consisting $B(OH)_2$, C(O)—OH, C(O)—$N(R^e)(R^f)$, C(O)—$C_{1-6}$alkoxy, C(O)—$C_{1-6}$alkyl, wherein $R^e$ and $R^f$ are, independently of each other and independently at each occurrence, selected from the group consisting of H, hydroxyl, and $C_{1-6}$alkyl.

In some embodiments of the foregoing, provided herein is a compound of formula (X), or a stereoisomer, tautomer, or pharmaceutically acceptable salt thereof, wherein L is absent, and $R_2$ is phenyl optionally substituted with one or more substituents selected from the group consisting of $C_{1-6}$alkyl, $C_{1-6}$haloalkyl, $O(R^e)$, and $S(R^g)_5$, wherein $R^e$ is selected from the group consisting of H and $C_{1-6}$alkyl, wherein the $C_{1-6}$alkyl of $R^e$ is optionally substituted with one or more halo, and $R^g$ is halo.

In some embodiments of the foregoing, provided herein is a compound of formula (X), or a stereoisomer, tautomer, or pharmaceutically acceptable salt thereof, L is absent, and $R_2$ is selected from the group consisting of phenyl, thiazolyl, thienyl, pyridyl, pyrazolyl, and furanyl, wherein the phenyl, thiazolyl, thienyl, pyridyl, pyrazolyl, or furanyl of $R_2$ is independently optionally substituted. In some embodiments, L is absent, and $R_2$ is selected from the group consisting of phenyl, thiazolyl, thienyl, pyridyl, pyrazolyl, and furanyl, wherein the phenyl, thiazolyl, thienyl, pyridyl, pyrazolyl, or furanyl of $R_2$ is independently optionally substituted with one or more substituents selected from the group consisting of $C_{1-6}$alkyl, $C_{1-6}$haloalkyl, $O(R^e)$, and $S(R^g)_5$, wherein $R^e$ is selected from the group consisting of H and $C_{1-6}$alkyl, wherein the $C_{1-6}$alkyl of $R^e$ is optionally substituted with one or more halo, and $R^g$ is halo.

In some aspects, compounds of formula (X) or formula (I), or any variation or embodiment thereof, as appropriate, are selected from the compounds listed in Table 1 below, including racemic mixtures and resolved isomers:

TABLE 1

| Compound Number | Structure | Compound Name |
|---|---|---|
| 1 | 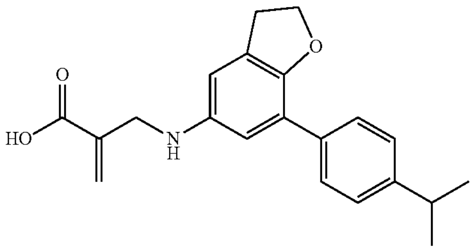 | 2-[[[7-(4-isopropylphenyl)-2,3-dihydrobenzofuran-5-yl]amino]methyl]prop-2-enoic acid |
| 2 | 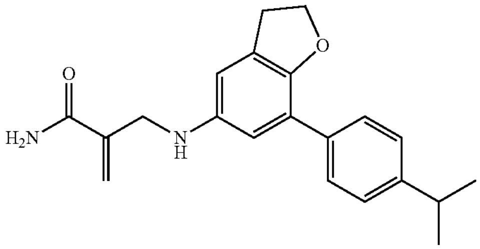 [SMILES: C=C(CNc1cc2c(c(-c3ccc(C(C)C)cc3)c1)OCC2)C(N)=O] | 2-[[[7-(4-isopropylphenyl)-2,3-dihydrobenzofuran-5-yl]amino]methyl]prop-2-enamide |
| 3 | 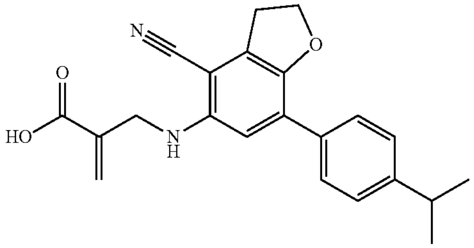 | 2-[[[4-cyano-7-(4-isopropylphenyl)-2,3-dihydrobenzofuran-5-yl]amino]methyl]prop-2-enoic acid |

TABLE 1-continued

| Compound Number | Structure | Compound Name |
|---|---|---|
| 4 | 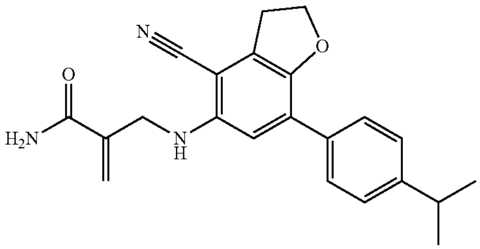 [SMILES: C=C(CNc1cc(-c2ccc(C(C)C)cc2)c2c(c1C#N)CCO2)C(N)=O] | 2-[[[4-cyano-7-(4-isopropylphenyl)-2,3-dihydrobenzofuran-5-yl]amino]methyl]prop-2-enamide |
| 5 | 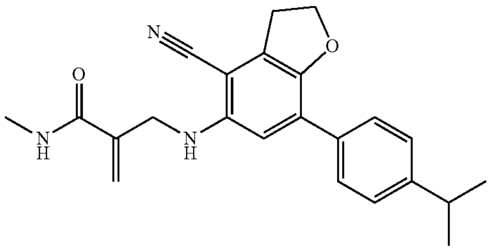 [SMILES: C=C(CNc1cc(-c2ccc(C(C)C)cc2)c2c(c1C#N)CCO2)C(=O)NC] | 2-[[[4-cyano-7-(4-isopropylphenyl)-2,3-dihydrobenzofuran-5-yl]amino]methyl]-N-methyl-prop-2-enamide |
| 6 | 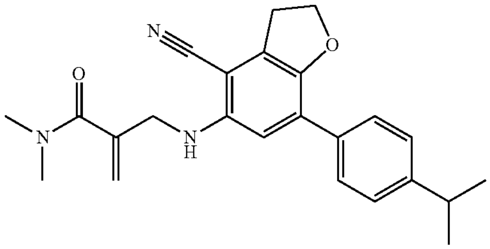 [SMILES: C=C(CNc1cc(-c2ccc(C(C)C)cc2)c2c(c1C#N)CCO2)C(=O)N(C)C] | 2-[[[4-cyano-7-(4-isopropylphenyl)-2,3-dihydrobenzofuran-5-yl]amino]methyl]-N,N-dimethyl-prop-2-enamide |
| 7 | 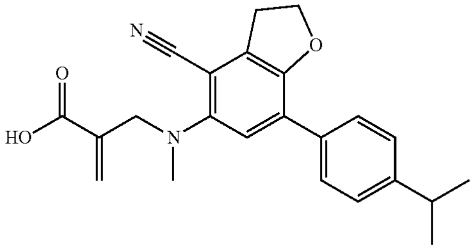 [SMILES: C=C(CN(C)c1cc(-c2ccc(C(C)C)cc2)c2c(c1C#N)CCO2)C(=O)O] | 2-[[[4-cyano-7-(4-isopropylphenyl)-2,3-dihydrobenzofuran-5-yl]-methyl-amino]methyl]prop-2-enoic acid |
| 8 | 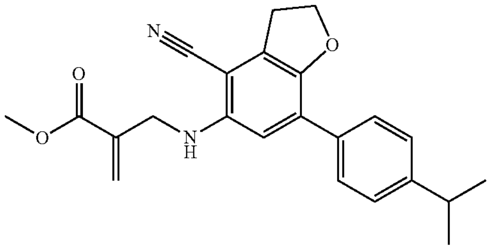 [SMILES: C=C(CNc1cc(-c2ccc(C(C)C)cc2)c2c(c1C#N)CCO2)C(=O)OC] | methyl 2-[[[4-cyano-7-(4-isopropylphenyl)-2,3-dihydrobenzofuran-5-yl]amino]methyl]prop-2-enoate |
| 9 | 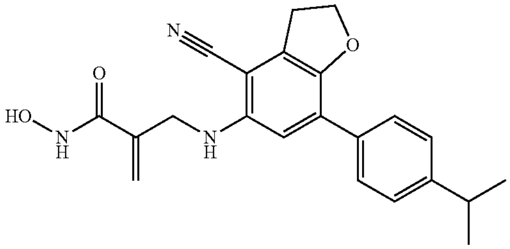 [SMILES: C=C(CNc1cc(-c2ccc(C(C)C)cc2)c2c(c1C#N)CCO2)C(=O)NO] | 2-[[[4-cyano-7-(4-isopropylphenyl)-2,3-dihydrobenzofuran-5-yl]amino]methyl]prop-2-enehydroxamic acid |

TABLE 1-continued

| Compound Number | Structure | Compound Name |
|---|---|---|
| 10 | 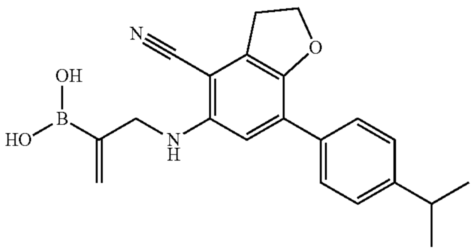 [SMILES: C=C(CNc1cc(-c2ccc(C(C)C)cc2)c2c(c1C#N)CCO2)B(O)O] | 1-[[[4-cyano-7-(4-isopropylphenyl)-2,3-dihydrobenzofuran-5-yl]amino]methyl]vinylboronic acid |
| 11 | 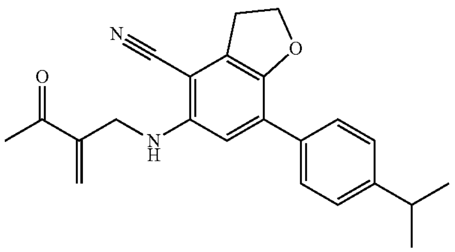 [SMILES: C=C(CNc1cc(-c2ccc(C(C)C)cc2)c2c(c1C#N)CCO2)C(C)=O] | 7-(4-isopropylphenyl)-5-[(2-methylene-3-oxo-butyl)amino]-2,3-dihydrobenzofuran-4-carbonitrile |
| 12 | 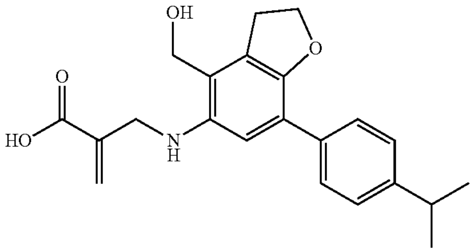 [SMILES: C=C(CNc1cc(-c2ccc(C(C)C)cc2)c2c(c1CO)CCO2)C(=O)O] | 2-[[[4-(hydroxymethyl)-7-(4-isopropylphenyl)-2,3-dihydrobenzofuran-5-yl]amino]methyl]prop-2-enoic acid |
| 13 | 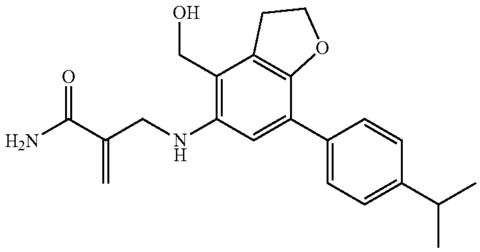 [SMILES: C=C(CNc1cc(-c2ccc(C(C)C)cc2)c2c(c1CO)CCO2)C(N)=O] | 2-[[[4-(hydroxymethyl)-7-(4-isopropylphenyl)-2,3-dihydrobenzofuran-5-yl]amino]methyl]prop-2-enamide |
| 14 | 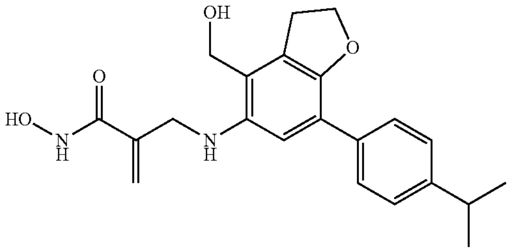 [SMILES: C=C(CNc1cc(-c2ccc(C(C)C)cc2)c2c(c1CO)CCO2)C(=O)NO] | 2-[[[4-(hydroxymethyl)-7-(4-isopropylphenyl)-2,3-dihydrobenzofuran-5-yl]amino]methyl]prop-2-enehydroxamic acid |
| 15 | 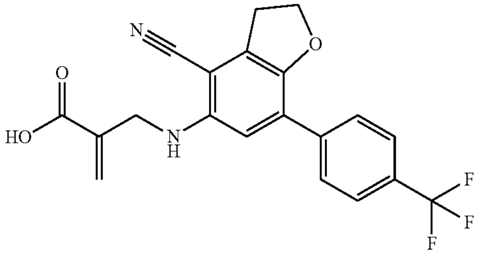 [SMILES: C=C(CNc1cc(-c2ccc(C(F)(F)F)cc2)c2c(c1C#N)CCO2)C(=O)O] | 2-[[[4-cyano-7-[4-(trifluoromethyl)phenyl]-2,3-dihydrobenzofuran-5-yl]amino]methyl]prop-2-enoic acid |

TABLE 1-continued

| Compound Number | Structure | Compound Name |
| --- | --- | --- |
| 16 | 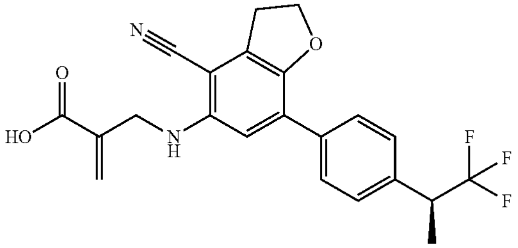 [SMILES: C=C(CNc1cc(-c2ccc([C@H](C)C(F)(F)F)cc2)c2c(c1C#N)CCO2)C(=O)O] | 2-[[[4-cyano-7-[4-[(1S)-2,2,2-trifluoro-1-methyl-ethyl]phenyl]-2,3-dihydrobenzofuran-5-yl]amino]methyl]prop-2-enoic acid |
| 17 | 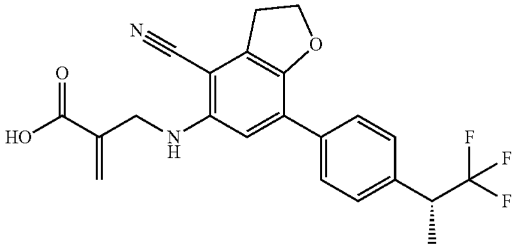 [SMILES: C=C(CNc1cc(-c2ccc([C@@H](C)C(F)(F)F)cc2)c2c(c1C#N)CCO2)C(=O)O] | 2-[[[4-cyano-7-[4-[(1R)-2,2,2-trifluoro-1-methyl-ethyl]phenyl]-2,3-dihydrobenzofuran-5-yl]amino]methyl]prop-2-enoic acid |
| 18 | 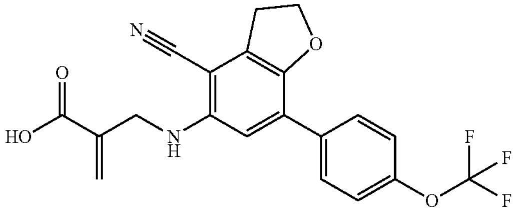 [SMILES: C=C(CNc1cc(-c2ccc(OC(F)(F)F)cc2)c2c(c1C#N)CCO2)C(=O)O] | 2-[[[4-cyano-7-[4-(trifluoromethoxy)phenyl]-2,3-dihydrobenzofuran-5-yl]amino]methyl]prop-2-enoic acid |
| 19 | 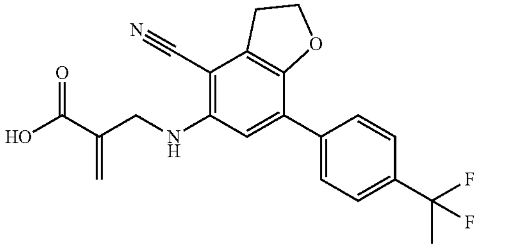 [SMILES: C=C(CNc1cc(-c2ccc(C(C)(F)F)cc2)c2c(c1C#N)CCO2)C(=O)O] | 2-[[[4-cyano-7-[4-(1,1-difluoroethyl)phenyl]-2,3-dihydrobenzofuran-5-yl]amino]methyl]prop-2-enoic acid |
| 20 | 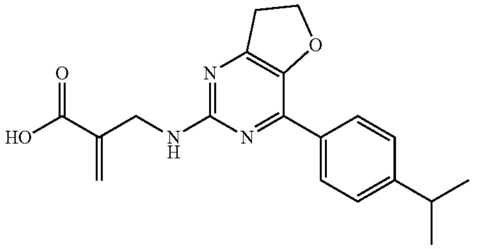 | 2-[[[4-(4-isopropylphenyl)-6,7-dihydrofuro[3,2-d]pyrimidin-2-yl]amino]methyl]prop-2-enoic acid |
| 21 | 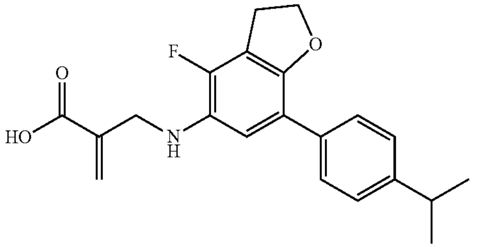 [SMILES: C=C(CNc1cc(-c2ccc(C(C)C)cc2)c2c(c1F)CCO2)C(=O)O] | 2-[[[4-fluoro-7-(4-isopropylphenyl)-2,3-dihydrobenzofuran-5-yl]amino]methyl]prop-2-enoic acid |

TABLE 1-continued

| Compound Number | Structure | Compound Name |
|---|---|---|
| 22 | 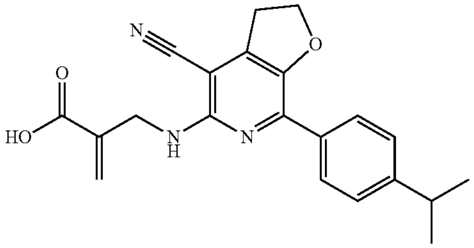 [SMILES: C=C(CNc1nc(-c2ccc(C(C)C)cc2)c2c(c1C#N)CCO2)C(=O)O] | 2-[[[4-cyano-7-(4-isopropylphenyl)-2,3-dihydrofuro[2,3-c]pyridin-5-yl]amino]methyl]prop-2-enoic acid |
| 23 | 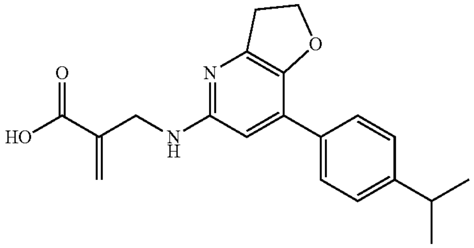 [SMILES: C=C(CNc1cc(-c2ccc(C(C)C)cc2)c2c(n1)CCO2)C(=O)O] | 2-[[[7-(4-isopropylphenyl)-2,3-dihydrofuro[3,2-b]pyridin-5-yl]amino]methyl]prop-2-enoic acid |
| 24 | 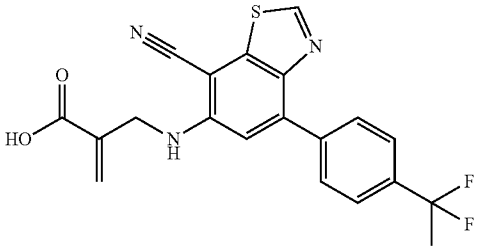 [SMILES: C=C(CNc1cc(-c2ccc(C(C)(F)F)cc2)c2ncsc2c1C#N)C(=O)O] | 2-[[[7-cyano-4-[4-(1,1-difluoroethyl)phenyl]-1,3-benzothiazol-6-yl]amino]methyl]prop-2-enoic acid |
| 25 | 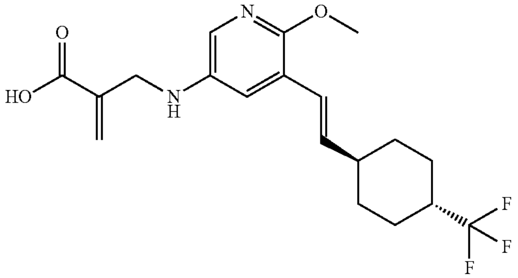 [SMILES: C=C(CNc1cnc(OC)c(/C=C/[C@H]2CC[C@H](C(F)(F)F)CC2)c1)C(=O)O] | 2-[[[6-methoxy-5-[(E)-2-[trans-4-(trifluoromethyl)cyclohexyl]vinyl]-3-pyridyl]amino]methyl]prop-2-enoic acid |
| 26 | 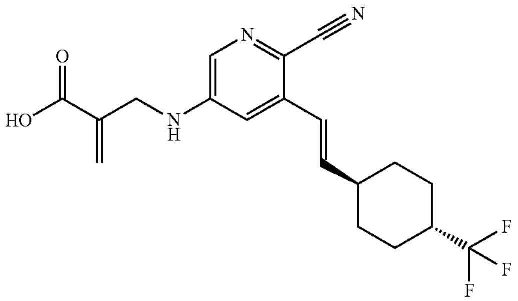 [SMILES: C=C(CNc1cnc(C#N)c(/C=C/[C@H]2CC[C@H](C(F)(F)F)CC2)c1)C(=O)O] | 2-[[[6-cyano-5-[(E)-2-[trans-4-(trifluoromethyl)cyclohexyl]vinyl]-3-pyridyl]amino]methyl]prop-2-enoic acid |

TABLE 1-continued

| Compound Number | Structure | Compound Name |
|---|---|---|
| 27 | 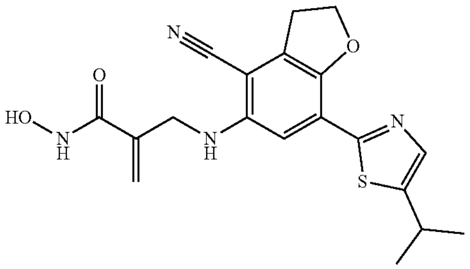 [SMILES: C=C(CNc1cc(-c2ncc(C(C)C)s2)c2c(c1C#N)CCO2)C(=O)NO] | 2-[[[4-cyano-7-(5-isopropylthiazol-2-yl)-2,3-dihydrobenzofuran-5-yl]amino]methyl]prop-2-enehydroxamic acid |
| 28 | 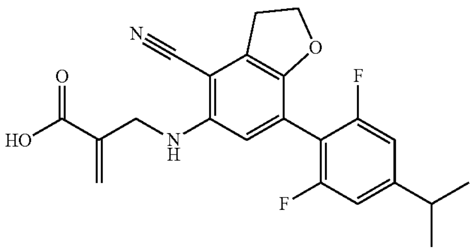 [SMILES: C=C(CNc1cc(-c2c(F)cc(C(C)C)cc2F)c2c(c1C#N)CCO2)C(=O)O] | 2-[[[4-cyano-7-(2,6-difluoro-4-isopropyl-phenyl)-2,3-dihydrobenzofuran-5-yl]amino]methyl]prop-2-enoic acid |
| 29 | 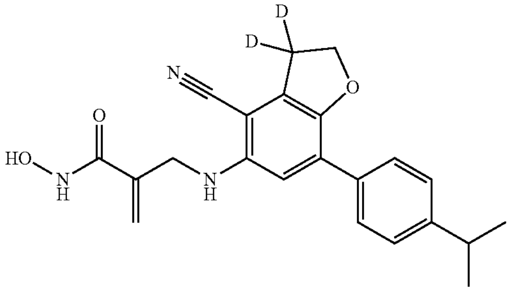 [SMILES: [2H]C1([2H])COc2c(-c3ccc(C(C)C)cc3)cc(NCC(=C)C(=O)NO)c(C#N)c21] | 2-[[[4-cyano-3,3-dideuterio-7-(4-isopropylphenyl)-2H-benzofuran-5-yl]amino]methyl]prop-2-enehydroxamic acid |
| 30 | 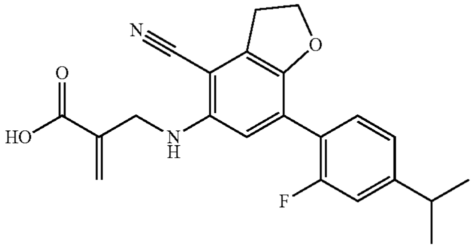 [SMILES: C=C(CNc1cc(-c2ccc(C(C)C)cc2F)c2c(c1C#N)CCO2)C(=O)O] | 2-[[[4-cyano-7-(2-fluoro-4-isopropyl-phenyl)-2,3-dihydrobenzofuran-5-yl]amino]methyl]prop-2-enoic acid |
| 31 | 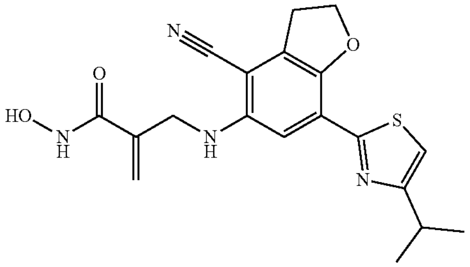 [SMILES: C=C(CNc1cc(-c2nc(C(C)C)cs2)c2c(c1C#N)CCO2)C(=O)NO] | 2-[[[4-cyano-7-(4-isopropylthiazol-2-yl)-2,3-dihydrobenzofuran-5-yl]amino]methyl]prop-2-enehydroxamic acid |

TABLE 1-continued

| Compound Number | Structure | Compound Name |
|---|---|---|
| 32 | 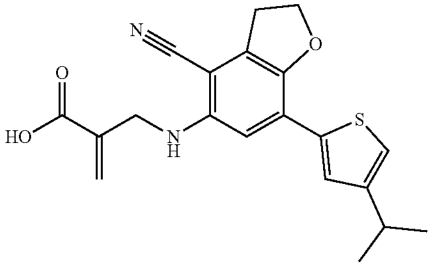 [SMILES: C=C(CNc1cc(-c2cc(C(C)C)cs2)c2c(c1C#N)CCO2)C(=O)O] | 2-[[[4-cyano-7-(4-isopropyl-2-thienyl)-2,3-dihydrobenzofuran-5-yl]amino]methyl]prop-2-enoic acid |
| 33 | 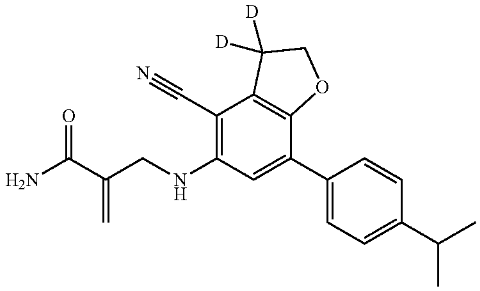 [SMILES: [2H]C1([2H])COc2c(-c3ccc(C(C)C)cc3)cc(NCC(=C)C(N)=O)c(C#N)c21] | 2-[[[4-cyano-3,3-dideuterio-7-(4-isopropylphenyl)-2H-benzofuran-5-yl]amino]methyl]prop-2-enamide |
| 34 | 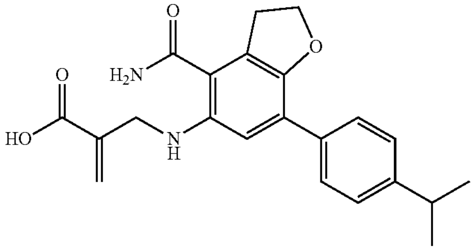 [SMILES: C=C(CNc1cc(-c2ccc(C(C)C)cc2)c2c(c1C(N)=O)CCO2)C(=O)O] | 2-[[[4-carbamoyl-7-(4-isopropylphenyl)-2,3-dihydrobenzofuran-5-yl]amino]methyl]prop-2-enoic acid |
| 35 | 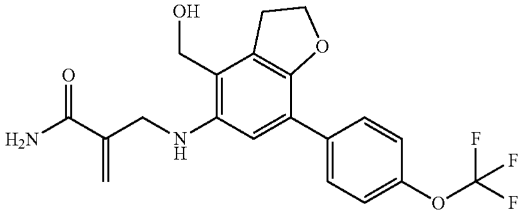 [SMILES: C=C(CNc1cc(-c2ccc(OC(F)(F)F)cc2)c2c(c1CO)CCO2)C(N)=O] | 2-[[[4-(hydroxymethyl)-7-[4-(trifluoromethoxy)phenyl]-2,3-dihydrobenzofuran-5-yl]amino]methyl]prop-2-enamide |
| 36 | 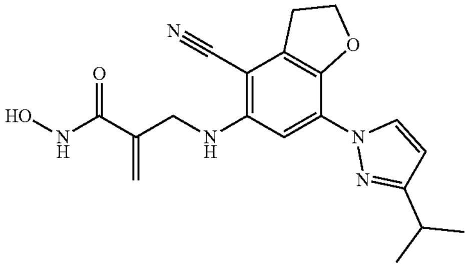 [SMILES: C=C(CNc1cc(-n2ccc(C(C)C)n2)c2c(c1C#N)CCO2)C(=O)NO] | 2-[[[4-cyano-7-(3-isopropylpyrazol-1-yl)-2,3-dihydrobenzofuran-5-yl]amino]methyl]prop-2-enehydroxamic acid |

TABLE 1-continued

| Compound Number | Structure | Compound Name |
|---|---|---|
| 37 | 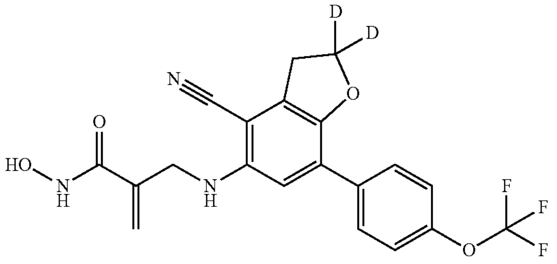 [SMILES: [2H]C1([2H])Cc2c(C#N)c(NCC(=C)C(=O)NO)cc(-c3ccc(OC(F)(F)F)cc3)c2O1] | 2-[[[4-cyano-2,2-dideuterio-7-[4-(trifluoromethoxy)phenyl]-3H-benzofuran-5-yl]amino]methyl]prop-2-enehydroxamic acid |
| 38 | 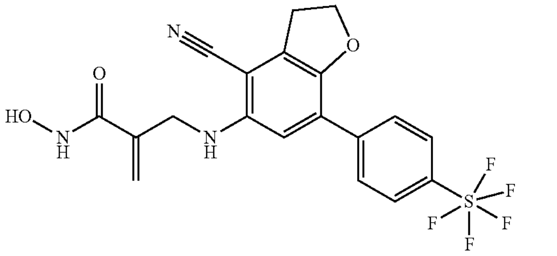 [SMILES: C=C(CNc1cc(-c2ccc(S(F)(F)(F)(F)F)cc2)c2c(c1C#N)CCO2)C(=O)NO] | 2-[[[4-cyano-7-[4-(pentafluoro-lambda6-sulfanyl)phenyl]-2,3-dihydrobenzofuran-5-yl]amino]methyl]prop-2-enehydroxamic acid |
| 39 | 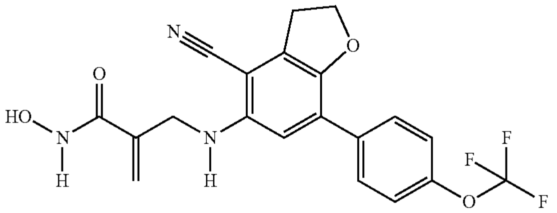 [SMILES: C=C(CNc1cc(-c2ccc(OC(F)(F)F)cc2)c2c(c1C#N)CCO2)C(=O)NO] | 2-[[[4-cyano-7-[4-(trifluoromethoxy)phenyl]-2,3-dihydrobenzofuran-5-yl]amino]methyl]prop-2-enehydroxamic acid |
| 40 | 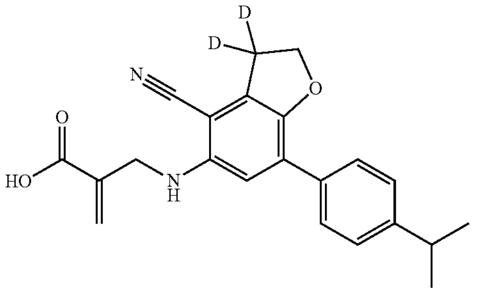 [SMILES: [2H]C1([2H])COc2c(-c3ccc(C(C)C)cc3)cc(NCC(=C)C(=O)O)c(C#N)c21] | 2-[[[4-cyano-3,3-dideuterio-7-(4-isopropylphenyl)-2H-benzofuran-5-yl]amino]methyl]prop-2-enoic acid |
| 41 | 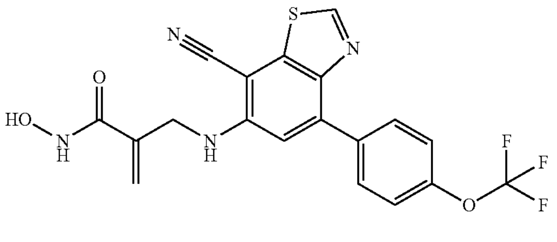 [SMILES: C=C(CNc1cc(-c2ccc(OC(F)(F)F)cc2)c2ncsc2c1C#N)C(=O)NO] | 2-[[[7-cyano-4-[4-(trifluoromethoxy)phenyl]-1,3-benzothiazol-6-yl]amino]methyl]prop-2-enehydroxamic acid |
| 42 | 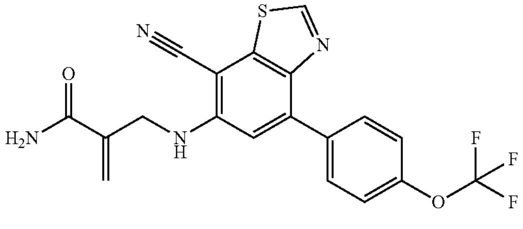 [SMILES: C=C(CNc1cc(-c2ccc(OC(F)(F)F)cc2)c2ncsc2c1C#N)C(N)=O] | 2-[[[7-cyano-4-[4-(trifluoromethoxy)phenyl]-1,3-benzothiazol-6-yl]amino]methyl]prop-2-enamide |

TABLE 1-continued

| Compound Number | Structure | Compound Name |
|---|---|---|
| 43 | 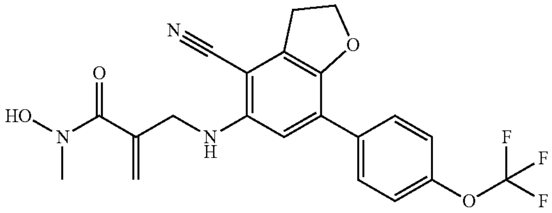 [SMILES: C=C(CNc1cc(-c2ccc(OC(F)(F)F)cc2)c2c(c1C#N)CCO2)C(=O)N(C)O] | 2-[[[4-cyano-7-[4-(trifluoromethoxy)phenyl]-2,3-dihydrobenzofuran-5-yl]amino]methyl]-N-hydroxy-N-methyl-prop-2-enamide |
| 44 | 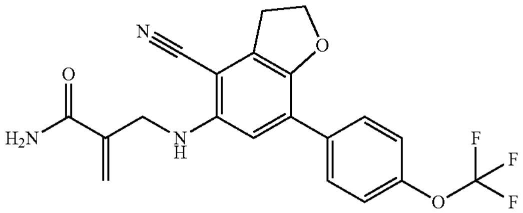 [SMILES: C=C(CNc1cc(-c2ccc(OC(F)(F)F)cc2)c2c(c1C#N)CCO2)C(N)=O] | 2-[[[4-cyano-7-[4-(trifluoromethoxy)phenyl]-2,3-dihydrobenzofuran-5-yl]amino]methyl]prop-2-enamide |
| 45 | 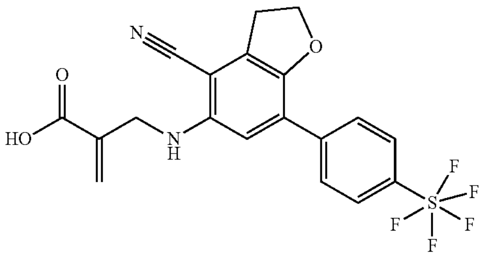 [SMILES: C=C(CNc1cc(-c2ccc(S(F)(F)(F)(F)F)cc2)c2c(c1C#N)CCO2)C(=O)O] | 2-[[[4-cyano-7-[4-(pentafluoro-lambda6-sulfanyl)phenyl]-2,3-dihydrobenzofuran-5-yl]amino]methyl]prop-2-enoic acid |
| 46 | 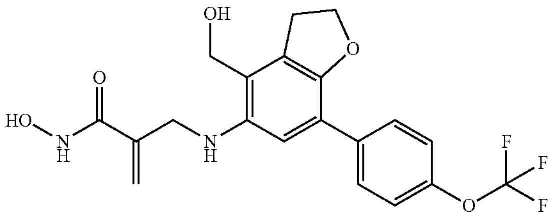 [SMILES: C=C(CNc1cc(-c2ccc(OC(F)(F)F)cc2)c2c(c1CO)CCO2)C(=O)NO] | 2-[[[4-(hydroxymethyl)-7-[4-(trifluoromethoxy)phenyl]-2,3-dihydrobenzofuran-5-yl]amino]methyl]prop-2-enehydroxamic acid |
| 47 | 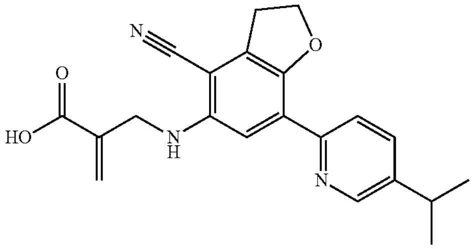 | 2-[[[4-cyano-7-(5-isopropyl-2-pyridyl)-2,3-dihydrobenzofuran-5-yl]amino]methyl]prop-2-enoic acid |
| 48 | 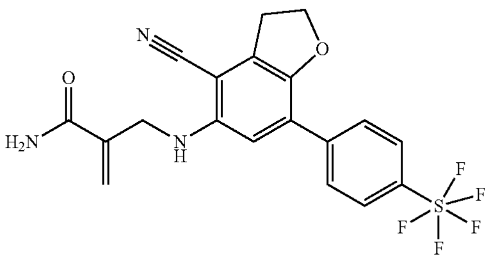 [SMILES: C=C(CNc1cc(-c2ccc(S(F)(F)(F)(F)F)cc2)c2c(c1C#N)CCO2)C(N)=O] | 2-[[[4-cyano-7-[4-(pentafluoro-lambda6-sulfanyl)phenyl]-2,3-dihydrobenzofuran-5-yl]amino]methyl]prop-2-enamide |

TABLE 1-continued

| Compound Number | Structure | Compound Name |
|---|---|---|
| 49 | 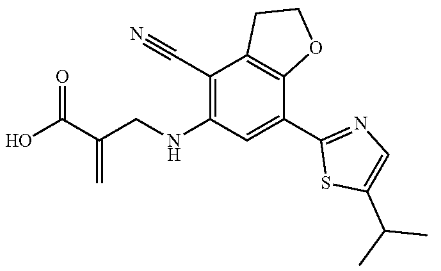 [SMILES: C=C(CNc1cc(-c2ncc(C(C)C)s2)c2c(c1C#N)CCO2)C(=O)O] | 2-[[[4-cyano-7-(5-isopropylthiazol-2-yl)-2,3-dihydrobenzofuran-5-yl]amino]methyl]prop-2-enoic acid |
| 50 | 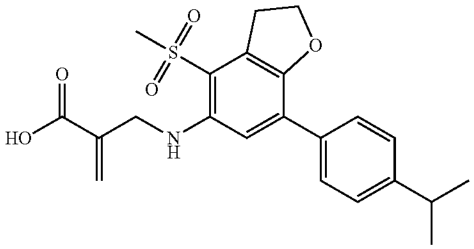 [SMILES: C=C(CNc1cc(-c2ccc(C(C)C)cc2)c2c(c1S(C)(=O)=O)CCO2)C(=O)O] | 2-[[[7-(4-isopropylphenyl)-4-methylsulfonyl-2,3-dihydrobenzofuran-5-yl]amino]methyl]prop-2-enoic acid |
| 51 | 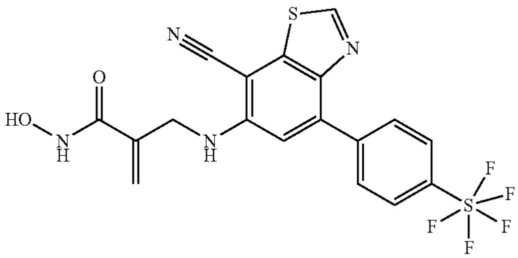 [SMILES: C=C(CNc1cc(-c2ccc(S(F)(F)(F)(F)F)cc2)c2ncsc2c1C#N)C(=O)NO] | 2-[[[7-cyano-4-[4-(pentafluoro-lambda6-sulfanyl)phenyl]-1,3-benzothiazol-6-yl]amino]methyl]prop-2-enehydroxamic acid |

Provided herein is a compound selected from the group consisting of:

2-[[[7-(4-isopropylphenyl)-2,3-dihydrobenzofuran-5-yl]amino]methyl]prop-2-enoic acid;

2-[[[7-(4-isopropylphenyl)-2,3-dihydrobenzofuran-5-yl]amino]methyl]prop-2-enamide;

2-[[[4-cyano-7-(4-isopropylphenyl)-2,3-dihydrobenzofuran-5-yl]amino]methyl]prop-2-enoic acid;

2-[[[4-cyano-7-(4-isopropylphenyl)-2,3-dihydrobenzofuran-5-yl]amino]methyl]prop-2-enamide;

2-[[[4-cyano-7-(4-isopropylphenyl)-2,3-dihydrobenzofuran-5-yl]amino]methyl]-N-methyl-prop-2-enamide;

2-[[[4-cyano-7-(4-isopropylphenyl)-2,3-dihydrobenzofuran-5-yl]amino]methyl]-N,N-dimethyl-prop-2-enamide;

2-[[[4-cyano-7-(4-isopropylphenyl)-2,3-dihydrobenzofuran-5-yl]-methyl-amino]methyl]prop-2-enoic acid;

methyl 2-[[[4-cyano-7-(4-isopropylphenyl)-2,3-dihydrobenzofuran-5-yl]amino]methyl]prop-2-enoate;

2-[[[4-cyano-7-(4-isopropylphenyl)-2,3-dihydrobenzofuran-5-yl]amino]methyl]prop-2-enehydroxamic acid;

1-[[[4-cyano-7-(4-isopropylphenyl)-2,3-dihydrobenzofuran-5-yl]amino]methyl]vinylboronic acid;

7-(4-isopropylphenyl)-5-[(2-methylene-3-oxo-butyl)amino]-2,3-dihydrobenzofuran-4-carbonitrile;

2-[[[4-(hydroxymethyl)-7-(4-isopropylphenyl)-2,3-dihydrobenzofuran-5-yl]amino]methyl]prop-2-enoic acid;

2-[[[4-(hydroxymethyl)-7-(4-isopropylphenyl)-2,3-dihydrobenzofuran-5-yl]amino]methyl]prop-2-enamide;

2-[[[4-(hydroxymethyl)-7-(4-isopropylphenyl)-2,3-dihydrobenzofuran-5-yl]amino]methyl]prop-2-enehydroxamic acid;

2-[[[4-cyano-7-[4-(trifluoromethyl)phenyl]-2,3-dihydrobenzofuran-5-yl]amino]methyl]prop-2-enoic acid;

2-[[[4-cyano-7-[4-[2,2,2-trifluoro-1-methyl-ethyl]phenyl]-2,3-dihydrobenzofuran-5-yl]amino]methyl]prop-2-enoic acid;

2-[[[4-cyano-7-[4-[2,2,2-trifluoro-1-methyl-ethyl]phenyl]-2,3-dihydrobenzofuran-5-yl]amino]methyl]prop-2-enoic acid;

2-[[[4-cyano-7-[4-(trifluoromethoxy)phenyl]-2,3-dihydrobenzofuran-5-yl]amino]methyl]prop-2-enoic acid;

2-[[[4-cyano-7-[4-(1,1-difluoroethyl)phenyl]-2,3-dihydrobenzofuran-5-yl]amino]methyl]prop-2-enoic acid;

2-[[[4-(4-isopropylphenyl)-6,7-dihydrofuro[3,2-d]pyrimidin-2-yl]amino]methyl]prop-2-enoic acid;

2-[[[4-fluoro-7-(4-isopropylphenyl)-2,3-dihydrobenzofuran-5-yl]amino]methyl]prop-2-enoic acid;

2-[[[4-cyano-7-(4-isopropylphenyl)-2,3-dihydrofuro[2,3-c]pyridin-5-yl]amino]methyl]prop-2-enoic acid;

2-[[[7-(4-isopropylphenyl)-2,3-dihydrofuro[3,2-b]pyridin-5-yl]amino]methyl]prop-2-enoic acid;

2-[[[7-cyano-4-[4-(1,1-difluoroethyl)phenyl]-1,3-benzothiazol-6-yl]amino]methyl]prop-2-enoic acid;

2-[[[6-methoxy-5-[2-[4-(trifluoromethyl)cyclohexyl]vinyl]-3-pyridyl]amino]methyl]prop-2-enoic acid;

2-[[[6-cyano-5-[2-[4-(trifluoromethyl)cyclohexyl]vinyl]-3-pyridyl]amino]methyl]prop-2-enoic acid;

2-[[[4-cyano-7-(5-isopropylthiazol-2-yl)-2,3-dihydrobenzofuran-5-yl]amino]methyl]prop-2-enehydroxamic acid;

2-[[[4-cyano-7-(2,6-difluoro-4-isopropyl-phenyl)-2,3-dihydrobenzofuran-5-yl]amino]methyl]prop-2-enoic acid;

2-[[[4-cyano-3,3-dideuterio-7-(4-isopropylphenyl)-2H-benzofuran-5-yl]amino]methyl]prop-2-enehydroxamic acid;

2-[[[4-cyano-7-(2-fluoro-4-isopropyl-phenyl)-2,3-dihydrobenzofuran-5-yl]amino]methyl]prop-2-enoic acid;

2-[[[4-cyano-7-(4-isopropylthiazol-2-yl)-2,3-dihydrobenzofuran-5-yl]amino]methyl]prop-2-enehydroxamic acid;

2-[[[4-cyano-7-(4-isopropyl-2-thienyl)-2,3-dihydrobenzofuran-5-yl]amino]methyl]prop-2-enoic acid;

2-[[[4-cyano-3,3-dideuterio-7-(4-isopropylphenyl)-2H-benzofuran-5-yl]amino]methyl]prop-2-enamide;

2-[[[4-carbamoyl-7-(4-isopropylphenyl)-2,3-dihydrobenzofuran-5-yl]amino]methyl]prop-2-enoic acid;

2-[[[4-(hydroxymethyl)-7-[4-(trifluoromethoxy)phenyl]-2,3-dihydrobenzofuran-5-yl]amino]methyl]prop-2-enamide;

2-[[[4-cyano-7-(3-isopropylpyrazol-1-yl)-2,3-dihydrobenzofuran-5-yl]amino]methyl]prop-2-enehydroxamic acid;

2-[[[4-cyano-2,2-dideuterio-7-[4-(trifluoromethoxy)phenyl]-3H-benzofuran-5-yl]amino]methyl]prop-2-enehydroxamic acid;

2-[[[4-cyano-7-[4-(pentafluoro-lambda6-sulfanyl)phenyl]-2,3-dihydrobenzofuran-5-yl]amino]methyl]prop-2-enehydroxamic acid;

2-[[[4-cyano-7-[4-(trifluoromethoxy)phenyl]-2,3-dihydrobenzofuran-5-yl]amino]methyl]prop-2-enehydroxamic acid;

2-[[[4-cyano-3,3-dideuterio-7-(4-isopropylphenyl)-2H-benzofuran-5-yl]amino]methyl]prop-2-enoic acid;

2-[[[7-cyano-4-[4-(trifluoromethoxy)phenyl]-1,3-benzothiazol-6-yl]amino]methyl]prop-2-enehydroxamic acid;

2-[[[7-cyano-4-[4-(trifluoromethoxy)phenyl]-1,3-benzothiazol-6-yl]amino]methyl]prop-2-enamide;

2-[[[4-cyano-7-[4-(trifluoromethoxy)phenyl]-2,3-dihydrobenzofuran-5-yl]amino]methyl]-N-hydroxy-N-methyl-prop-2-enamide;

2-[[[4-cyano-7-[4-(trifluoromethoxy)phenyl]-2,3-dihydrobenzofuran-5-yl]amino]methyl]prop-2-enamide;

2-[[[4-cyano-7-[4-(pentafluoro-lambda6-sulfanyl)phenyl]-2,3-dihydrobenzofuran-5-yl]amino]methyl]prop-2-enoic acid;

2-[[[4-(hydroxymethyl)-7-[4-(trifluoromethoxy)phenyl]-2,3-dihydrobenzofuran-5-yl]amino]methyl]prop-2-enehydroxamic acid;

2-[[[4-cyano-7-(5-isopropyl-2-pyridyl)-2,3-dihydrobenzofuran-5-yl]amino]methyl]prop-2-enoic acid;

2-[[[4-cyano-7-[4-(pentafluoro-lambda6-sulfanyl)phenyl]-2,3-dihydrobenzofuran-5-yl]amino]methyl]prop-2-enamide;

2-[[[4-cyano-7-(5-isopropylthiazol-2-yl)-2,3-dihydrobenzofuran-5-yl]amino]methyl]prop-2-enoic acid;

2-[[[7-(4-isopropylphenyl)-4-methylsulfonyl-2,3-dihydrobenzofuran-5-yl]amino]methyl]prop-2-enoic acid; and 2-[[[7-cyano-4-[4-(pentafluoro-lambda6-sulfanyl)phenyl]-1,3-benzothiazol-6-yl]amino]methyl]prop-2-enehydroxamic acid, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, tautomers, or mixtures thereof in any ratio, including racemic mixtures.

Also provided herein is a compound selected from the group consisting of:

2-[[[7-(4-isopropylphenyl)-2,3-dihydrobenzofuran-5-yl]amino]methyl]prop-2-enoic acid;

2-[[[7-(4-isopropylphenyl)-2,3-dihydrobenzofuran-5-yl]amino]methyl]prop-2-enamide;

2-[[[4-cyano-7-(4-isopropylphenyl)-2,3-dihydrobenzofuran-5-yl]amino]methyl]prop-2-enoic acid;

2-[[[4-cyano-7-(4-isopropylphenyl)-2,3-dihydrobenzofuran-5-yl]amino]methyl]prop-2-enamide;

2-[[[4-cyano-7-(4-isopropylphenyl)-2,3-dihydrobenzofuran-5-yl]amino]methyl]-N-methyl-prop-2-enamide;

2-[[[4-cyano-7-(4-isopropylphenyl)-2,3-dihydrobenzofuran-5-yl]amino]methyl]-N,N-dimethyl-prop-2-enamide;

2-[[[4-cyano-7-(4-isopropylphenyl)-2,3-dihydrobenzofuran-5-yl]-methyl-amino]methyl]prop-2-enoic acid;

methyl 2-[[[4-cyano-7-(4-isopropylphenyl)-2,3-dihydrobenzofuran-5-yl]amino]methyl]prop-2-enoate;

2-[[[4-cyano-7-(4-isopropylphenyl)-2,3-dihydrobenzofuran-5-yl]amino]methyl]prop-2-enehydroxamic acid;

1-[[[4-cyano-7-(4-isopropylphenyl)-2,3-dihydrobenzofuran-5-yl]amino]methyl]vinylboronic acid; 7-(4-isopropylphenyl)-5-[(2-methylene-3-oxo-butyl)amino]-2,3-dihydrobenzofuran-4-carbonitrile;

2-[[[4-(hydroxymethyl)-7-(4-isopropylphenyl)-2,3-dihydrobenzofuran-5-yl]amino]methyl]prop-2-enoic acid;

2-[[[4-(hydroxymethyl)-7-(4-isopropylphenyl)-2,3-dihydrobenzofuran-5-yl]amino]methyl]prop-2-enamide;

2-[[[4-(hydroxymethyl)-7-(4-isopropylphenyl)-2,3-dihydrobenzofuran-5-yl]amino]methyl]prop-2-enehydroxamic acid;

2-[[[4-cyano-7-[4-(trifluoromethyl)phenyl]-2,3-dihydrobenzofuran-5-yl]amino]methyl]prop-2-enoic acid;

2-[[[4-cyano-7-[4-[2,2,2-trifluoro-1-methyl-ethyl]phenyl]-2,3-dihydrobenzofuran-5-yl]amino]methyl]prop-2-enoic acid;

2-[[[4-cyano-7-[4-[2,2,2-trifluoro-1-methyl-ethyl]phenyl]-2,3-dihydrobenzofuran-5-yl]amino]methyl]prop-2-enoic acid;

2-[[[4-cyano-7-[4-(trifluoromethoxy)phenyl]-2,3-dihydrobenzofuran-5-yl]amino]methyl]prop-2-enoic acid;

2-[[[4-cyano-7-[4-(1,1-difluoroethyl)phenyl]-2,3-dihydrobenzofuran-5-yl]amino]methyl]prop-2-enoic acid;

2-[[[4-(4-isopropylphenyl)-6,7-dihydrofuro[3,2-d]pyrimidin-2-yl]amino]methyl]prop-2-enoic acid;

2-[[[4-fluoro-7-(4-isopropylphenyl)-2,3-dihydrobenzofuran-5-yl]amino]methyl]prop-2-enoic acid;

2-[[[4-cyano-7-(4-isopropylphenyl)-2,3-dihydrofuro[2,3-c]pyridin-5-yl]amino]methyl]prop-2-enoic acid;

2-[[[7-(4-isopropylphenyl)-2,3-dihydrofuro[3,2-b]pyridin-5-yl]amino]methyl]prop-2-enoic acid;

2-[[[7-cyano-4-[4-(1,1-difluoroethyl)phenyl]-1,3-benzothiazol-6-yl]amino]methyl]prop-2-enoic acid;

2-[[[4-cyano-7-(5-isopropylthiazol-2-yl)-2,3-dihydrobenzofuran-5-yl]amino]methyl]prop-2-enehydroxamic acid;

2-[[[4-cyano-7-(2,6-difluoro-4-isopropyl-phenyl)-2,3-dihydrobenzofuran-5-yl]amino]methyl]prop-2-enoic acid;

2-[[[4-cyano-3,3-dideuterio-7-(4-isopropylphenyl)-2H-benzofuran-5-yl]amino]methyl]prop-2-enehydroxamic acid;

2-[[[4-cyano-7-(2-fluoro-4-isopropyl-phenyl)-2,3-dihydrobenzofuran-5-yl]amino]methyl]prop-2-enoic acid;

2-[[[4-cyano-7-(4-isopropylthiazol-2-yl)-2,3-dihydrobenzofuran-5-yl]amino]methyl]prop-2-enehydroxamic acid;

2-[[[4-cyano-7-(4-isopropyl-2-thienyl)-2,3-dihydrobenzofuran-5-yl]amino]methyl]prop-2-enoic acid;

2-[[[4-cyano-3,3-dideuterio-7-(4-isopropylphenyl)-2H-benzofuran-5-yl]amino]methyl]prop-2-enamide;

2-[[[4-carbamoyl-7-(4-isopropylphenyl)-2,3-dihydrobenzofuran-5-yl]amino]methyl]prop-2-enoic acid;

2-[[[4-(hydroxymethyl)-7-[4-(trifluoromethoxy)phenyl]-2,3-dihydrobenzofuran-5-yl]amino]methyl]prop-2-enamide;

2-[[[4-cyano-7-(3-isopropylpyrazol-1-yl)-2,3-dihydrobenzofuran-5-yl]amino]methyl]prop-2-enehydroxamic acid;

2-[[[4-cyano-2,2-dideuterio-7-[4-(trifluoromethoxy)phenyl]-3H-benzofuran-5-yl]amino]methyl]prop-2-enehydroxamic acid;

2-[[[4-cyano-7-[4-(pentafluoro-lambda6-sulfanyl)phenyl]-2,3-dihydrobenzofuran-5-yl]amino]methyl]prop-2-enehydroxamic acid;

2-[[[4-cyano-7-[4-(trifluoromethoxy)phenyl]-2,3-dihydrobenzofuran-5-yl]amino]methyl]prop-2-enehydroxamic acid;

2-[[[4-cyano-3,3-dideuterio-7-(4-isopropylphenyl)-2H-benzofuran-5-yl]amino]methyl]prop-2-enoic acid;

2-[[[7-cyano-4-[4-(trifluoromethoxy)phenyl]-1,3-benzothiazol-6-yl]amino]methyl]prop-2-enehydroxamic acid;

2-[[[7-cyano-4-[4-(trifluoromethoxy)phenyl]-1,3-benzothiazol-6-yl]amino]methyl]prop-2-enamide;

2-[[[4-cyano-7-[4-(trifluoromethoxy)phenyl]-2,3-dihydrobenzofuran-5-yl]amino]methyl]-N-hydroxy-N-methyl-prop-2-enamide;

2-[[[4-cyano-7-[4-(trifluoromethoxy)phenyl]-2,3-dihydrobenzofuran-5-yl]amino]methyl]prop-2-enamide;

2-[[[4-cyano-7-[4-(pentafluoro-lambda6-sulfanyl)phenyl]-2,3-dihydrobenzofuran-5-yl]amino]methyl]prop-2-enoic acid;

2-[[[4-(hydroxymethyl)-7-[4-(trifluoromethoxy)phenyl]-2,3-dihydrobenzofuran-5-yl]amino]methyl]prop-2-enehydroxamic acid;

2-[[[4-cyano-7-(5-isopropyl-2-pyridyl)-2,3-dihydrobenzofuran-5-yl]amino]methyl]prop-2-enoic acid;

2-[[[4-cyano-7-[4-(pentafluoro-lambda6-sulfanyl)phenyl]-2,3-dihydrobenzofuran-5-yl]amino]methyl]prop-2-enamide;

2-[[[4-cyano-7-(5-isopropylthiazol-2-yl)-2,3-dihydrobenzofuran-5-yl]amino]methyl]prop-2-enoic acid;

2-[[[7-(4-isopropylphenyl)-4-methylsulfonyl-2,3-dihydrobenzofuran-5-yl]amino]methyl]prop-2-enoic acid; and 2-[[[7-cyano-4-[4-(pentafluoro-lambda6-sulfanyl)phenyl]-1,3-benzothiazol-6-yl]amino]methyl]prop-2-enehydroxamic acid, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, tautomers, or mixtures thereof in any ratio, including racemic mixtures.

In one aspect, provided herein is a compound, or a stereoisomer, tautomer, or pharmaceutically acceptable salt thereof, selected from the group consisting of:

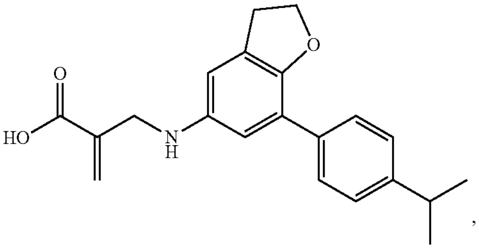
,

-continued

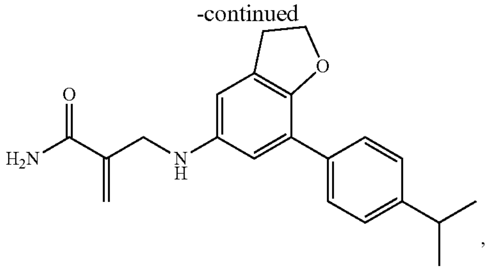
,

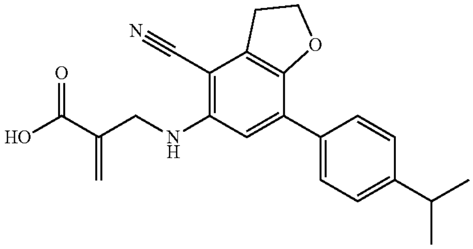
,

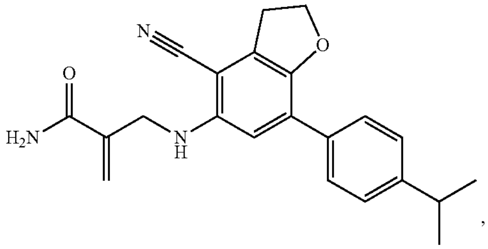
,

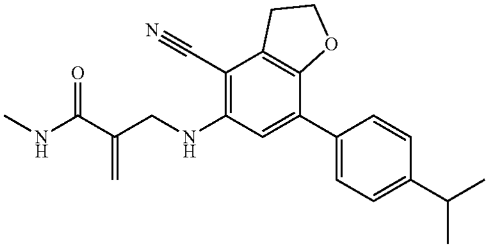
,

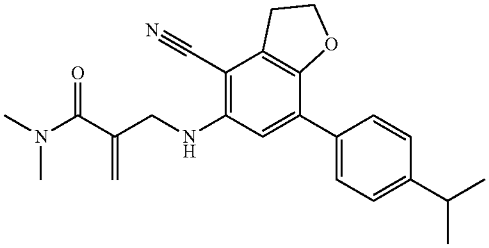
,

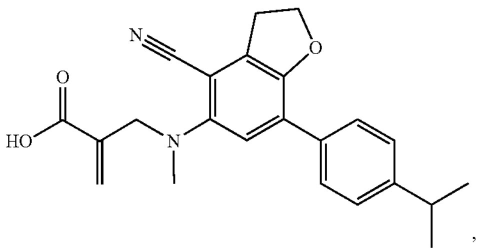
,

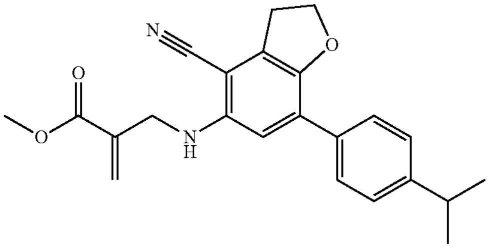
,

-continued
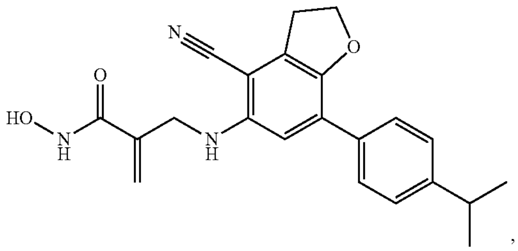
,
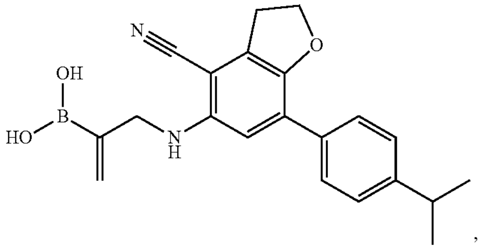
,
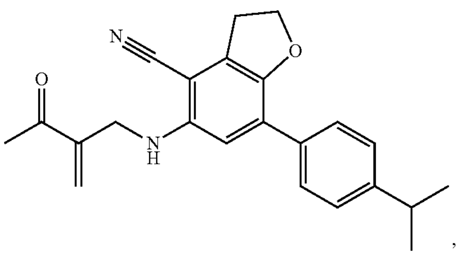
,
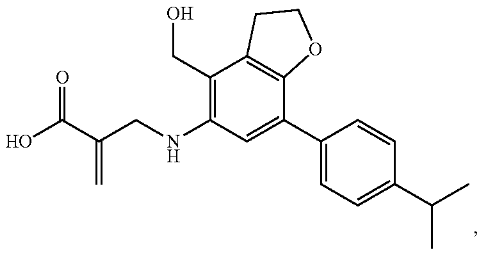
,
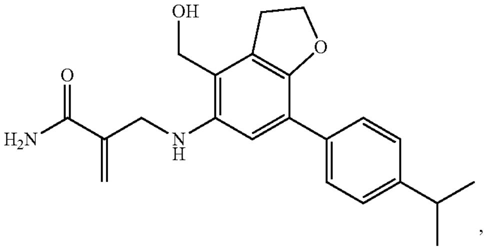
,
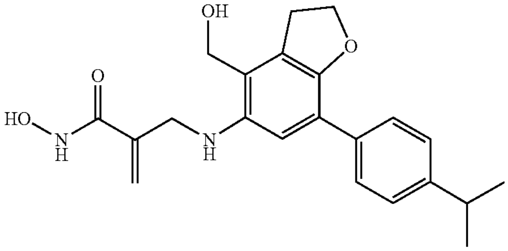
,
-continued
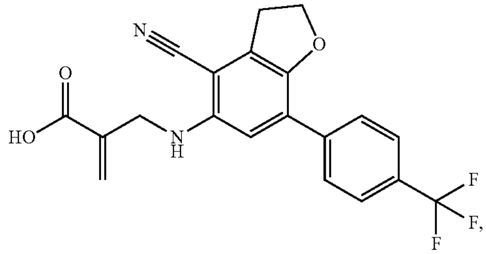
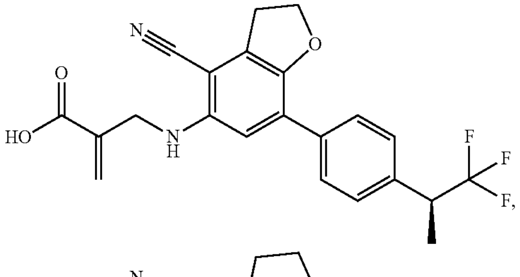
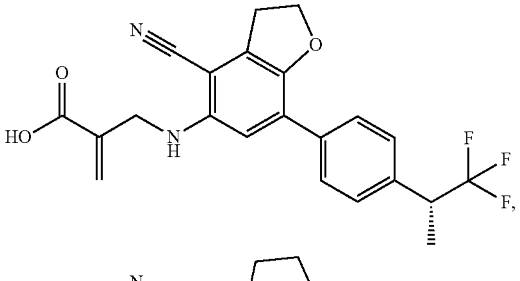
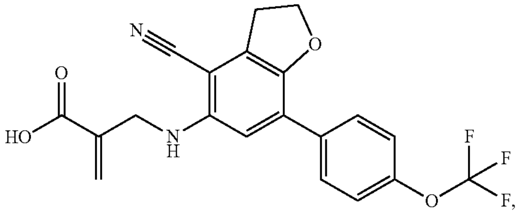
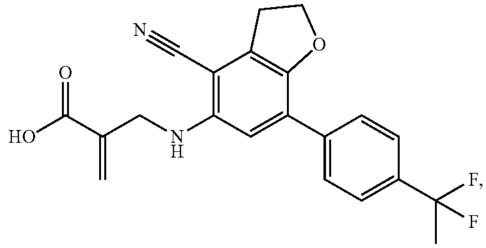
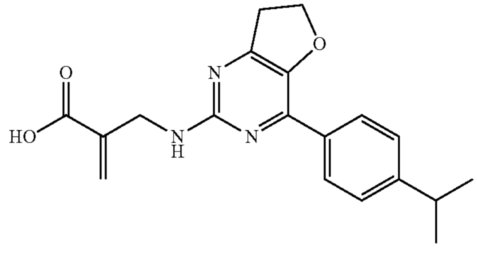
,
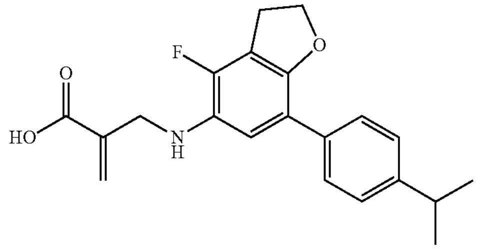
, -continued
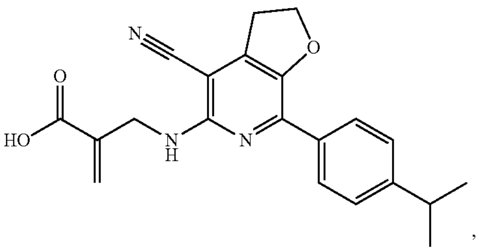
,
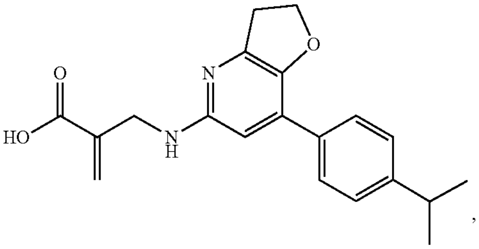
,
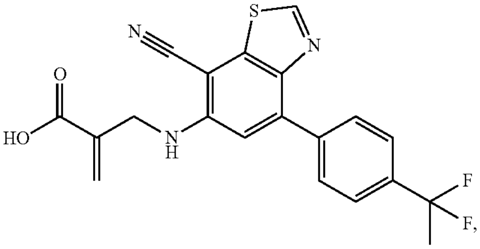
,
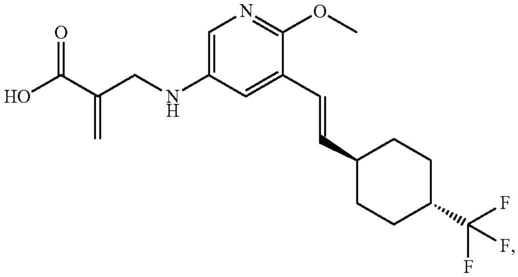
,
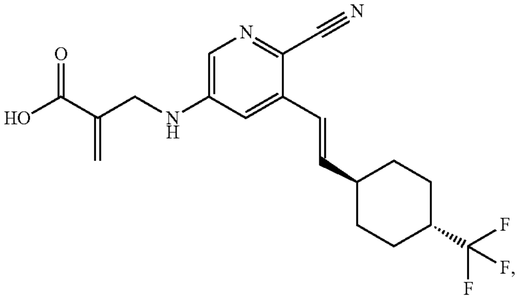
,
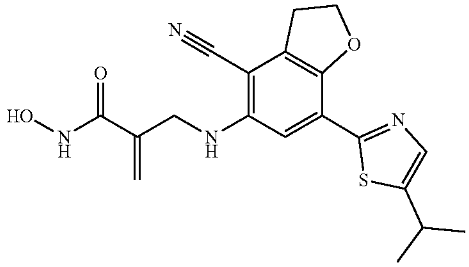
,
-continued
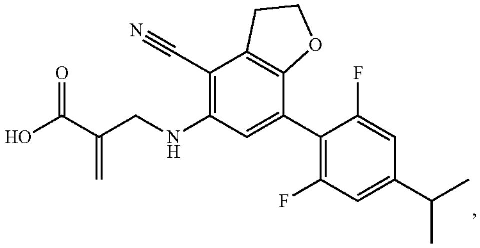
,
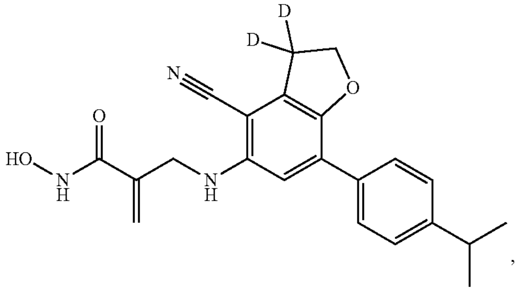
,
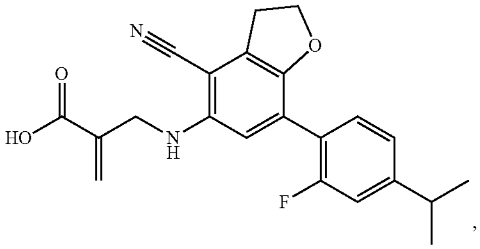
,
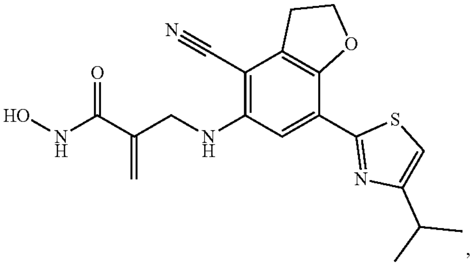
,
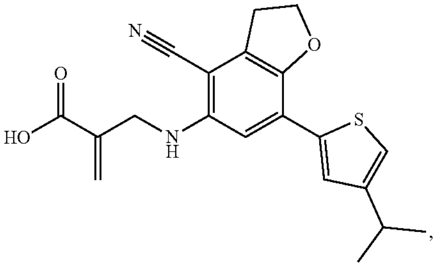
,
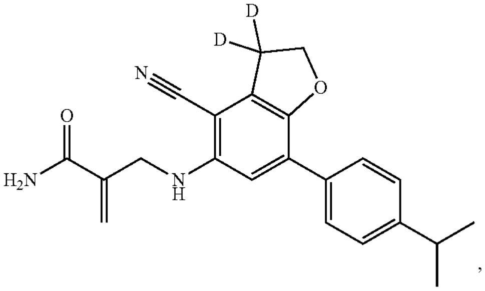
, -continued
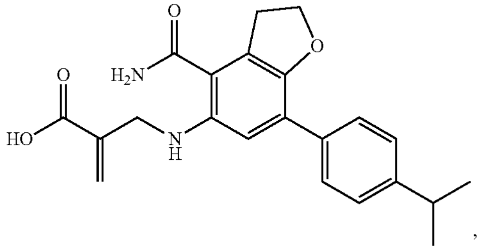
,
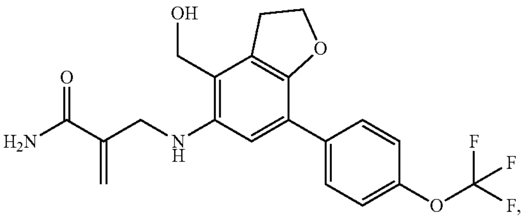
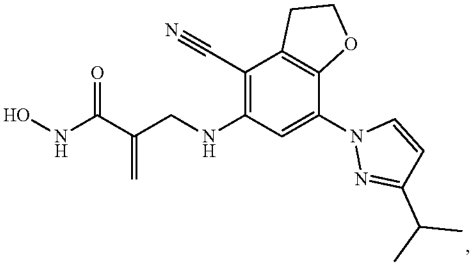
,
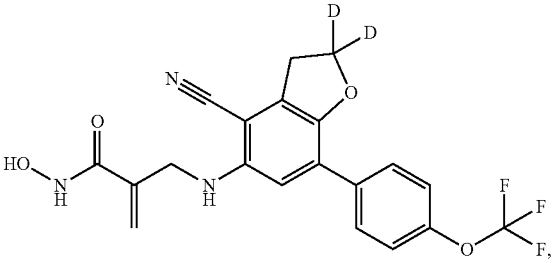
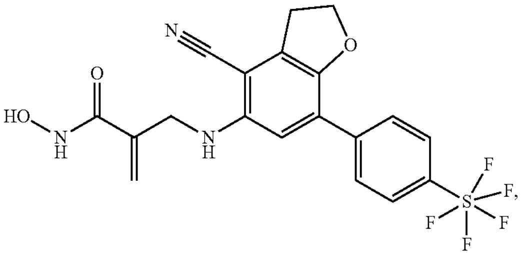
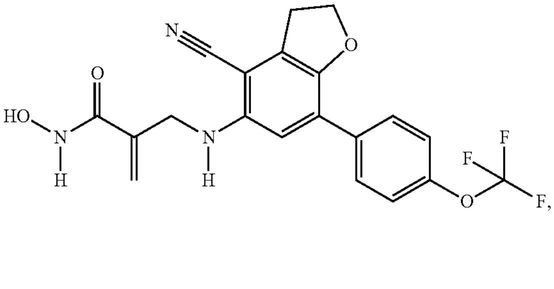
-continued
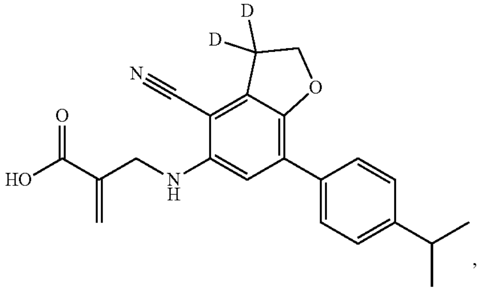
,
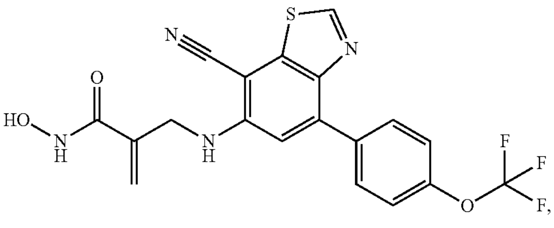
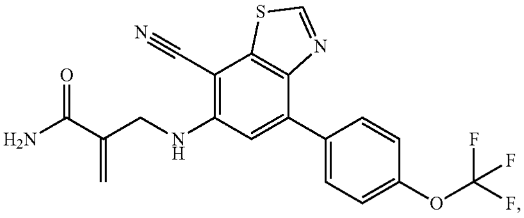
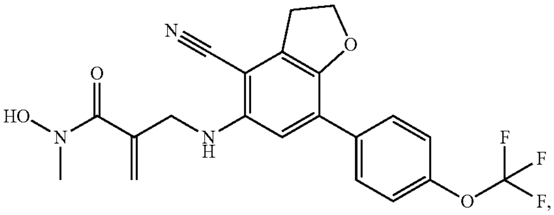
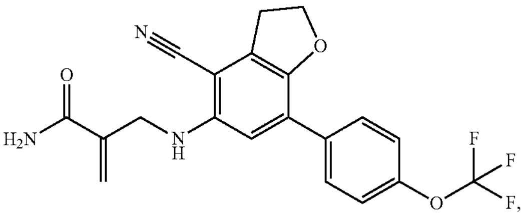
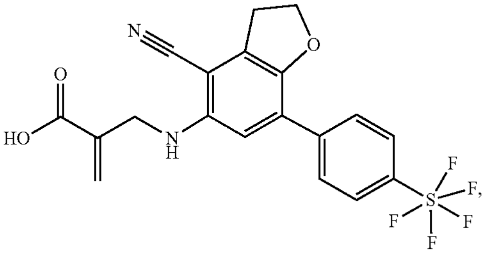
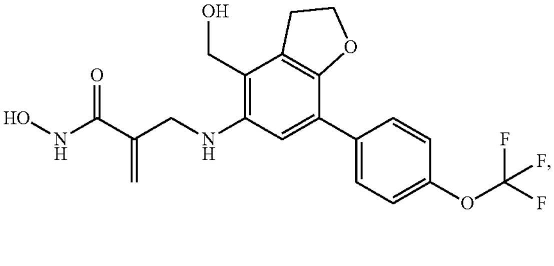

-continued
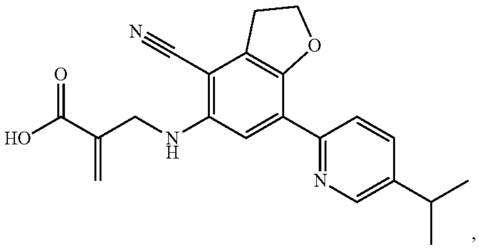
,
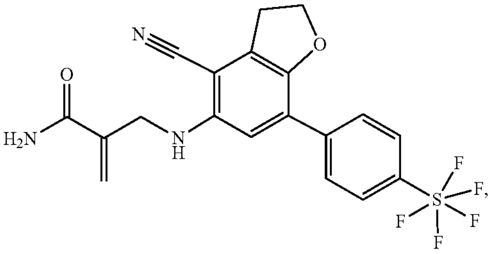
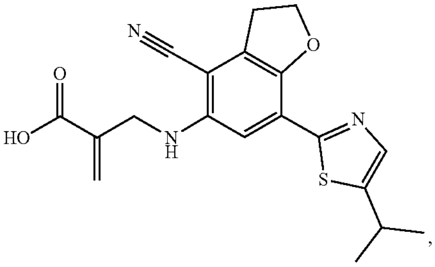
,
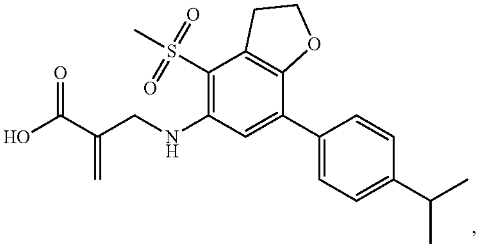
, and
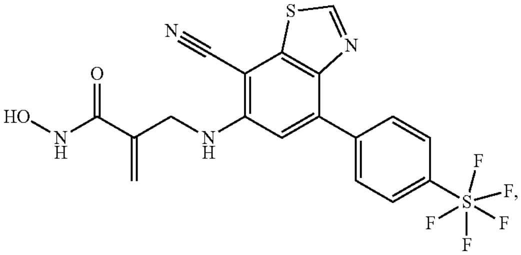
or a stereoisomer, tautomer, or pharmaceutically acceptable salt thereof.
In one aspect, provided herein is a compound, or a stereoisomer, tautomer, or pharmaceutically acceptable salt thereof, selected from the group consisting of:
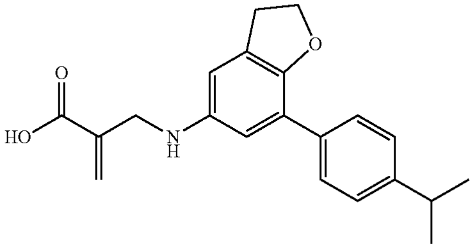
,
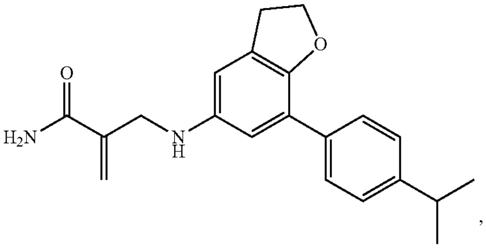
,
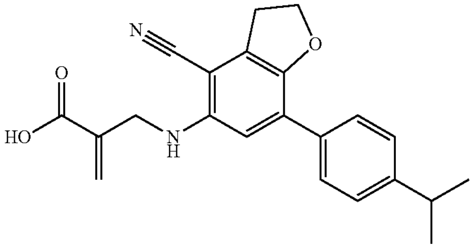
,
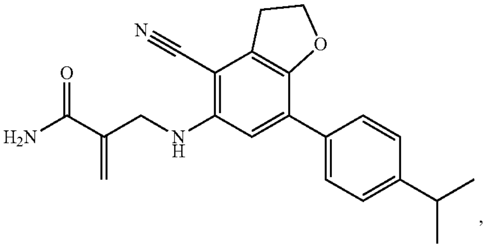
,
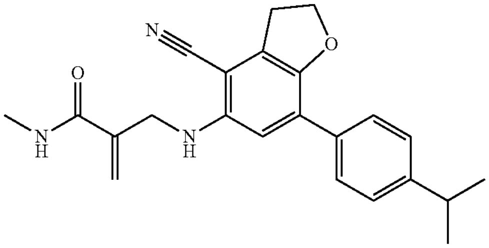
,
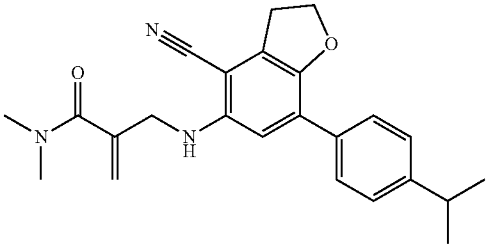
,
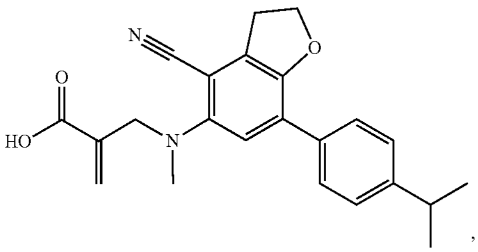
, -continued
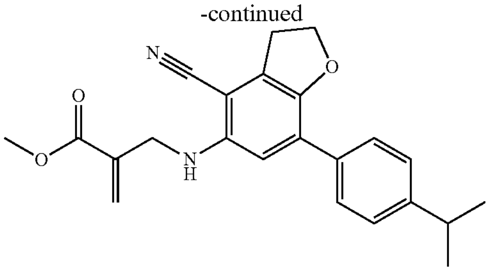
,
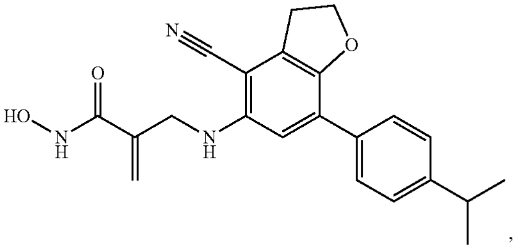
,
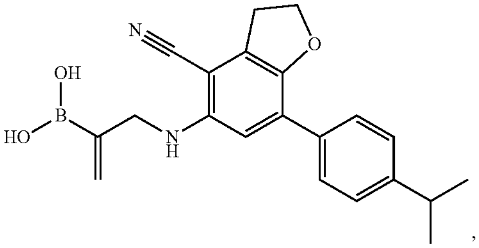
,
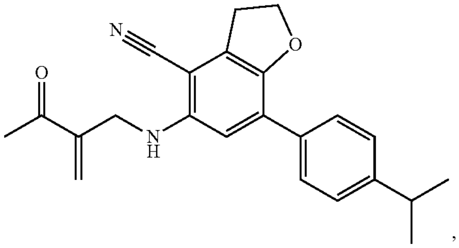
,
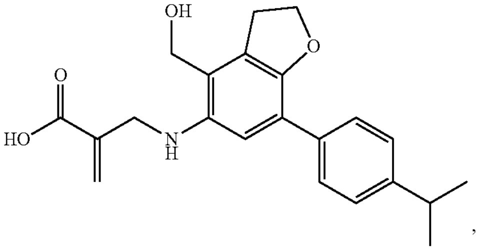
,
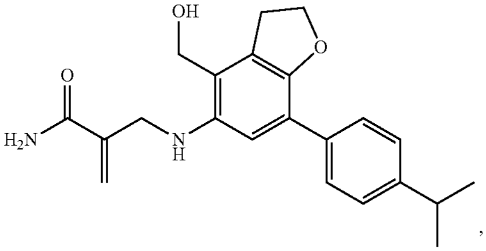
,
-continued
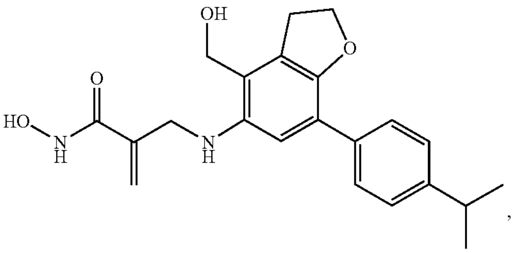
,
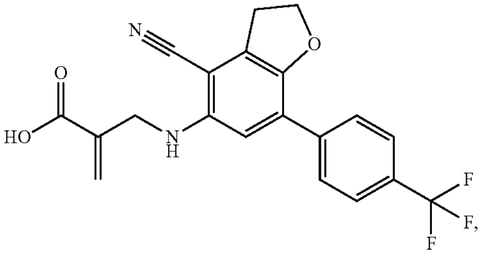
,
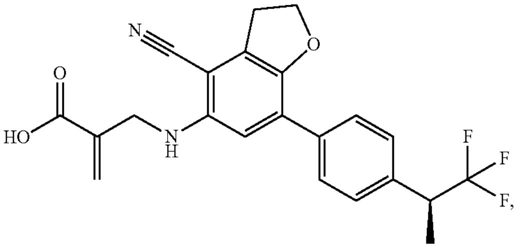
,
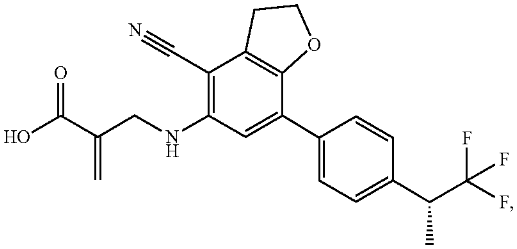
,
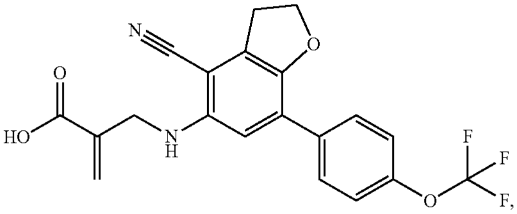
,
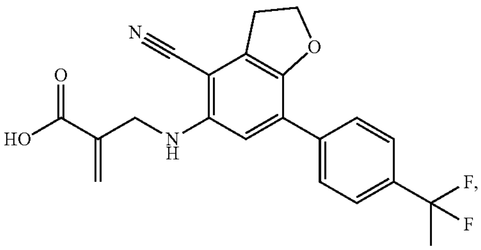
,
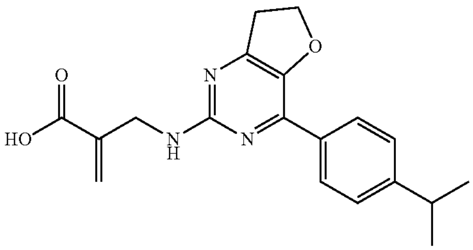
,

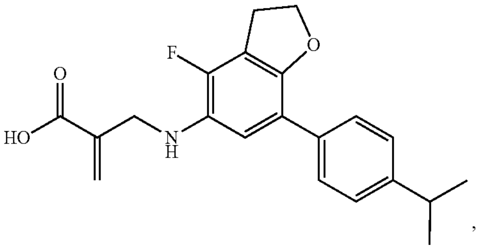
,
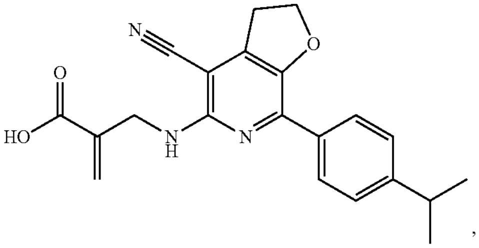
,
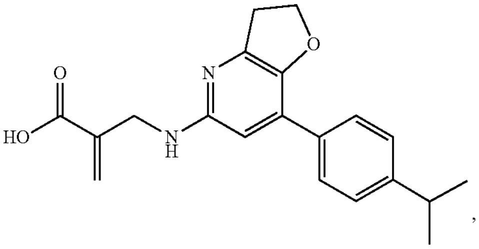
,
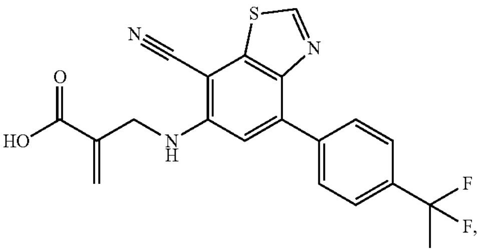
,
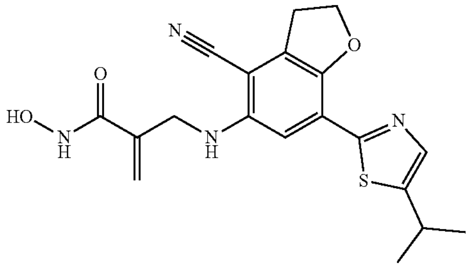
,
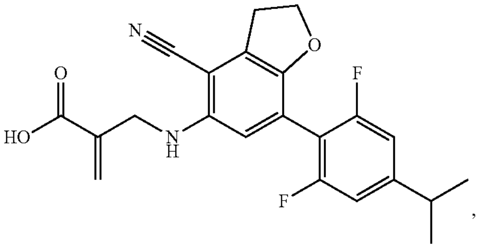
,
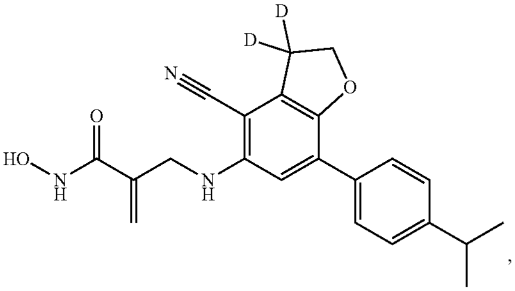
,
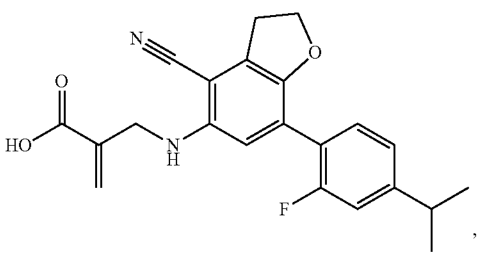
,
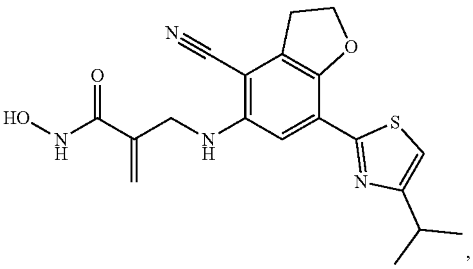
,
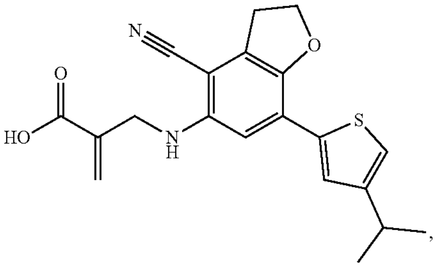
,
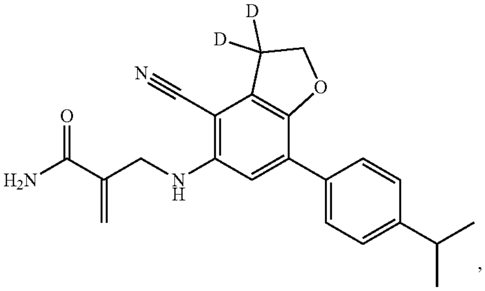
,
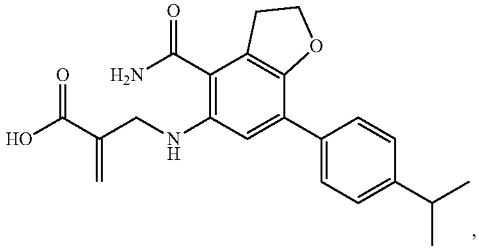
, -continued
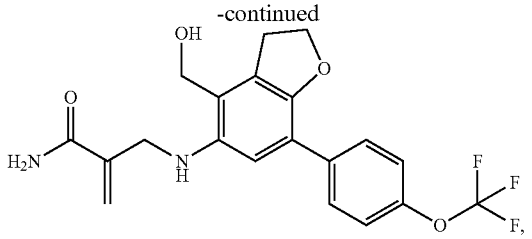
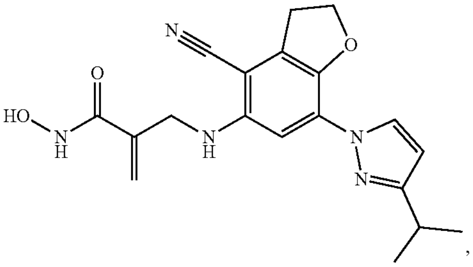
,
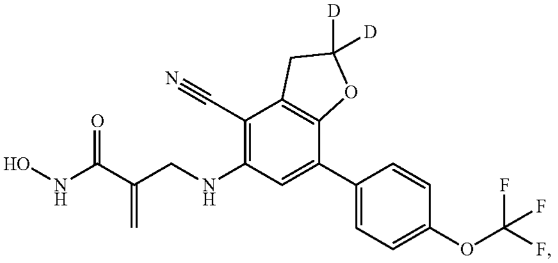
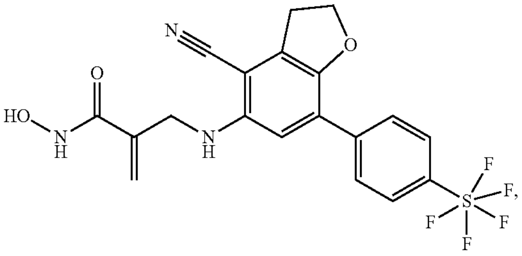
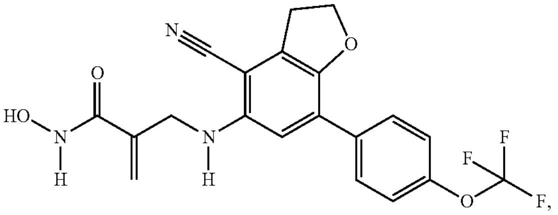
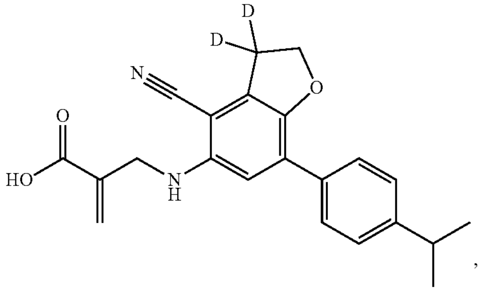
,
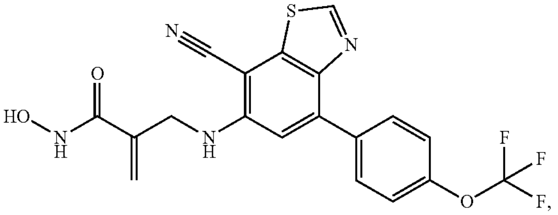
-continued
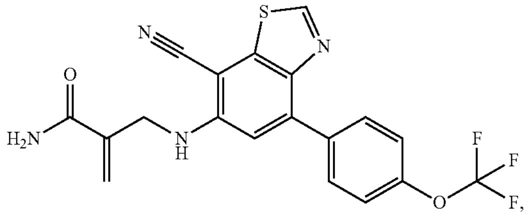
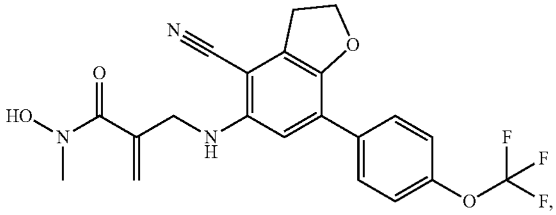
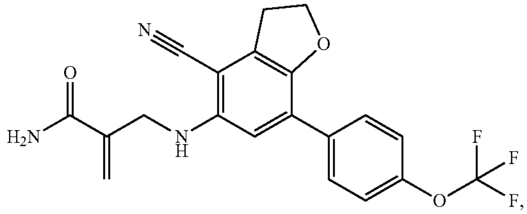
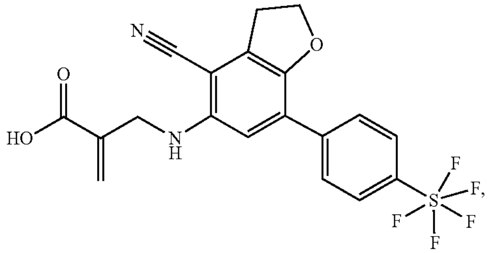
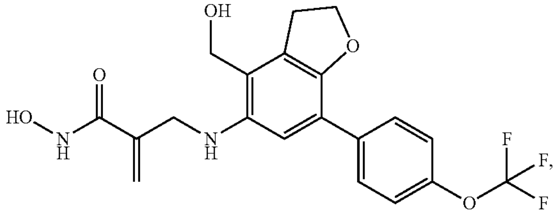
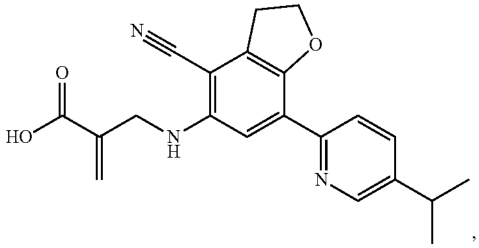
,
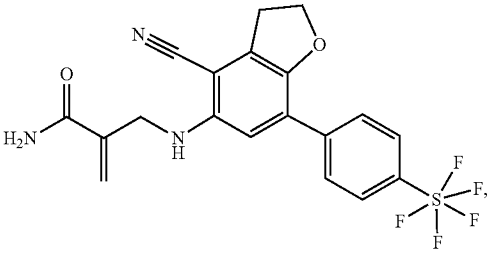

-continued
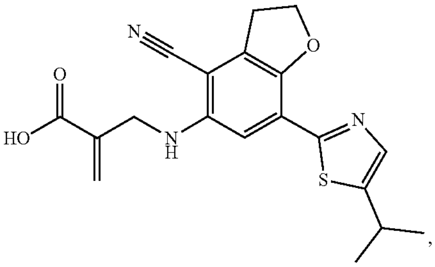
,
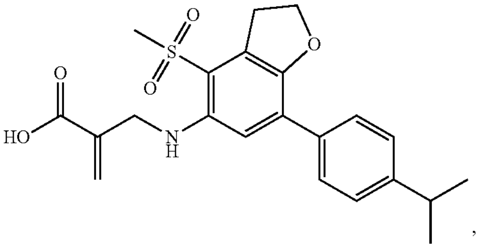
, and
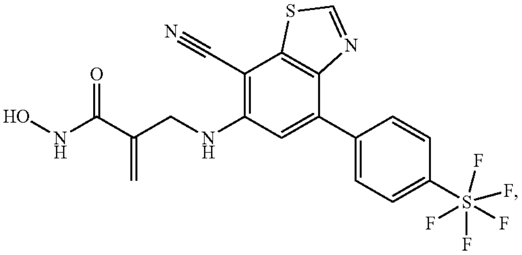
or a stereoisomer, tautomer, or pharmaceutically acceptable salt thereof.
In one aspect, the compound or a pharmaceutically acceptable salt thereof of formula (I), or a stereoisomer, tautomer, or pharmaceutically acceptable salt thereof, is selected from the group consisting of
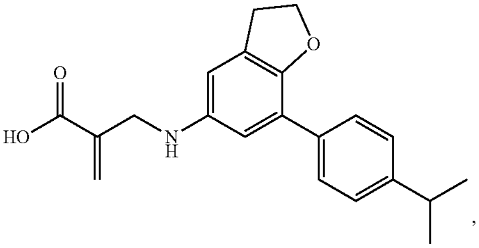
,
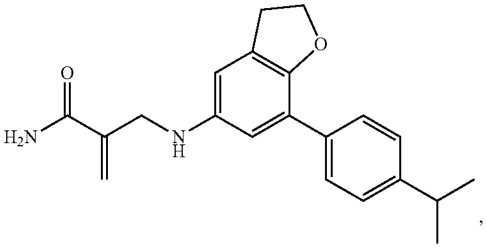
,
-continued
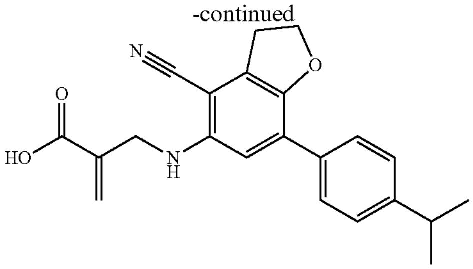
,
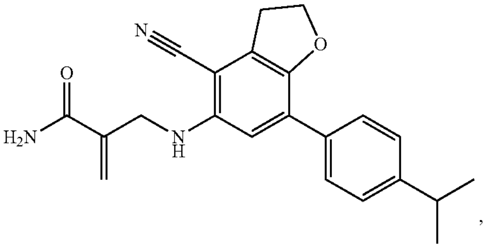
,
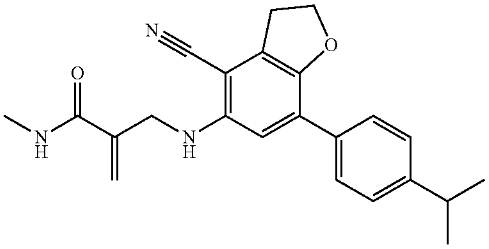
,
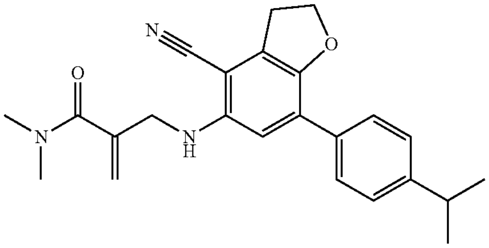
,
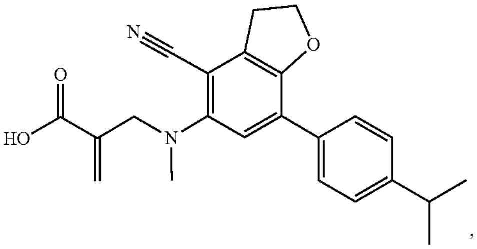
,
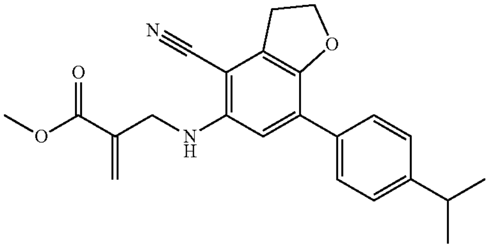
,
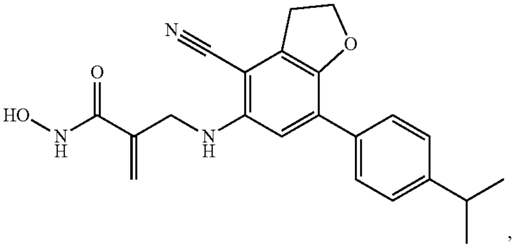
, -continued
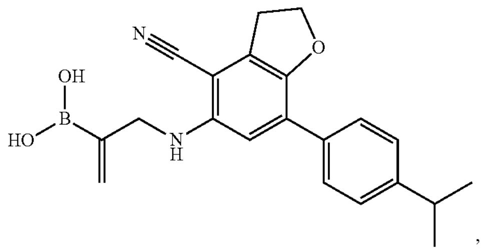
,
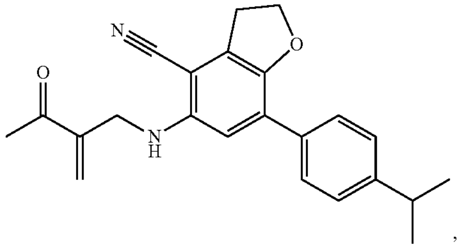
,
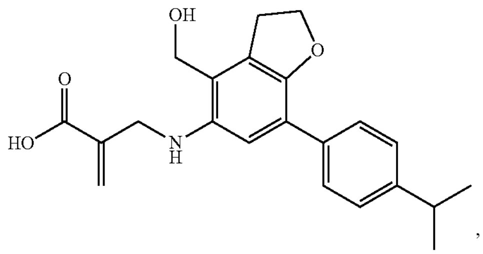
,
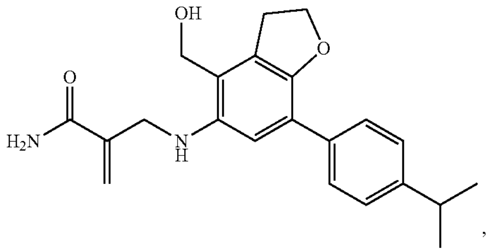
,
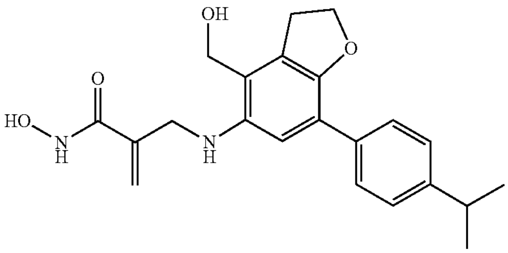
,
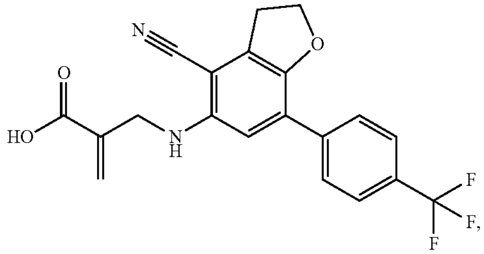
,
-continued
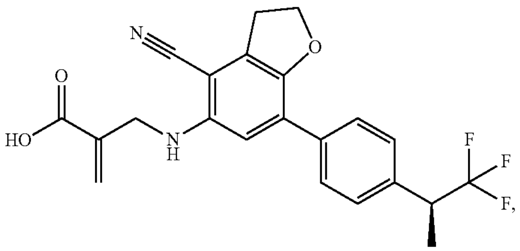
,
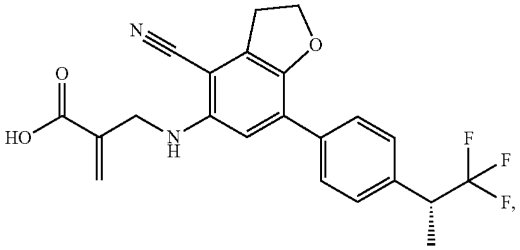
,
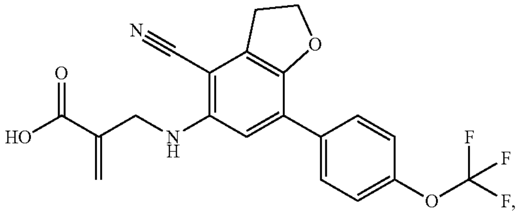
,
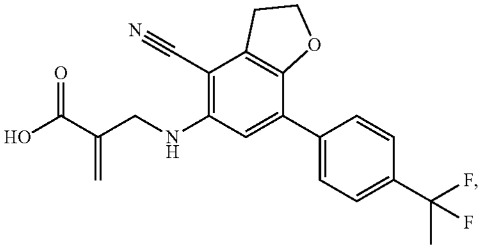
,
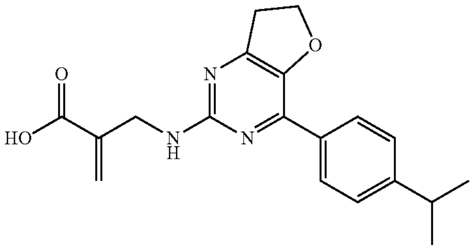
,
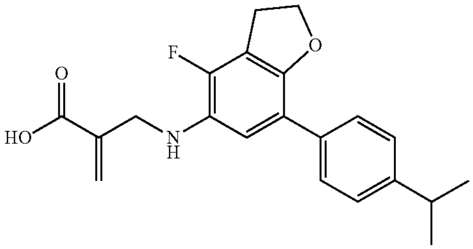
,
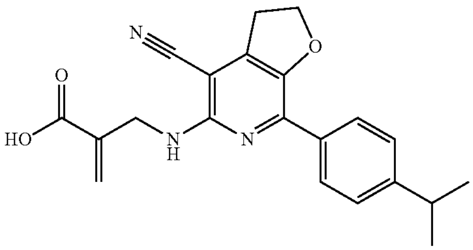
, -continued
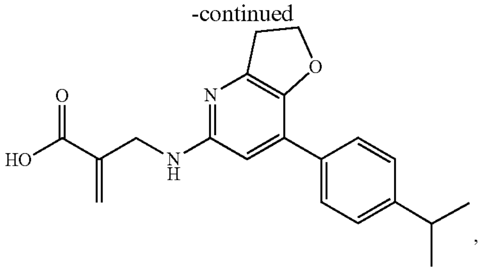
,
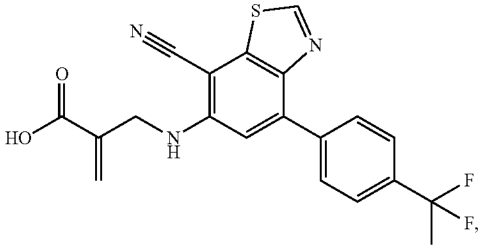
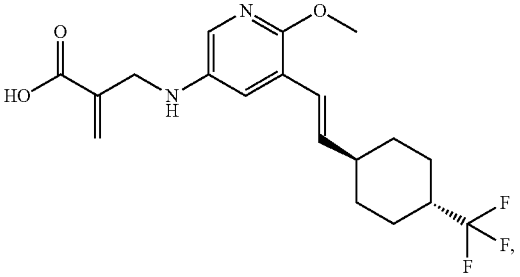
and
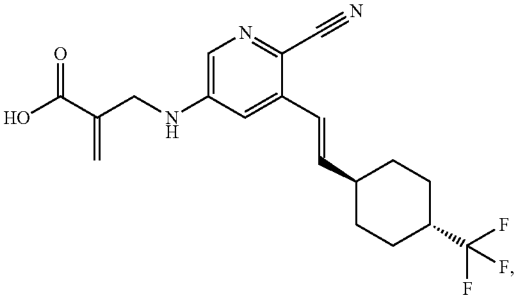
or a stereoisomer, tautomer, or pharmaceutically acceptable salt thereof.
In one aspect, the compound or a pharmaceutically acceptable salt thereof of formula (X) or formula (I), or a stereoisomer, tautomer, or pharmaceutically acceptable salt thereof, is selected from the group consisting of:
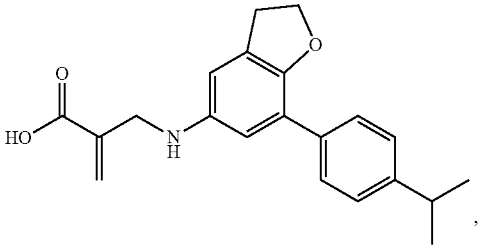
,
-continued
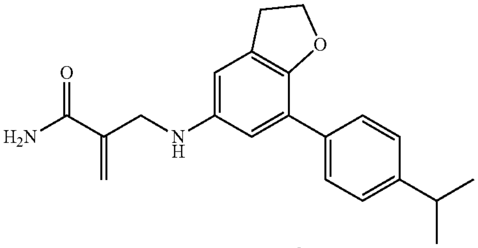
,
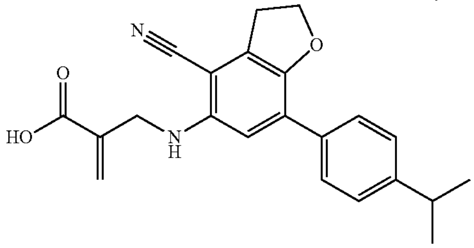
,
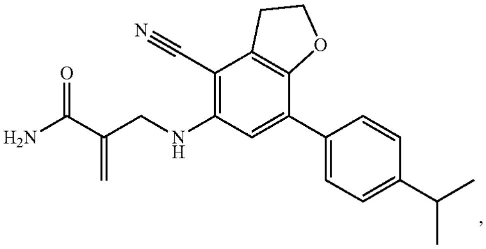
,
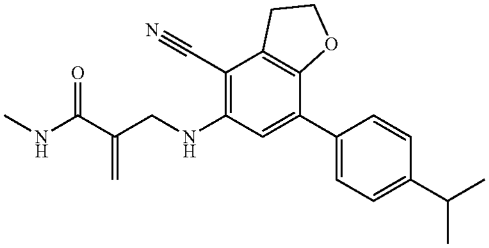
,
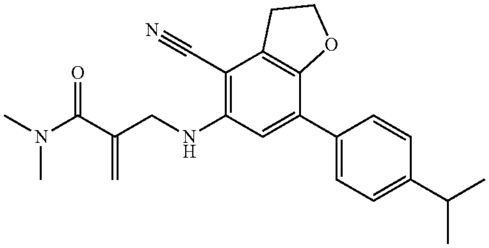
,
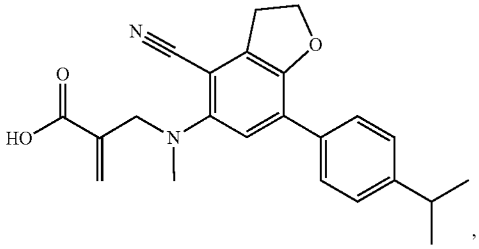
,
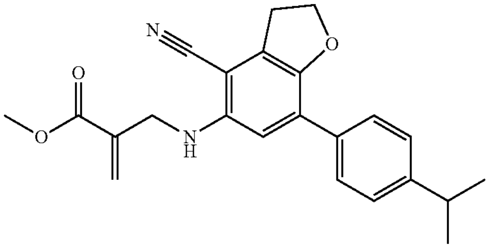
, -continued
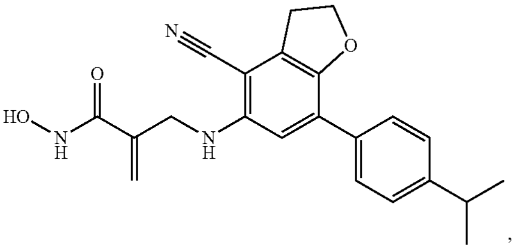
,
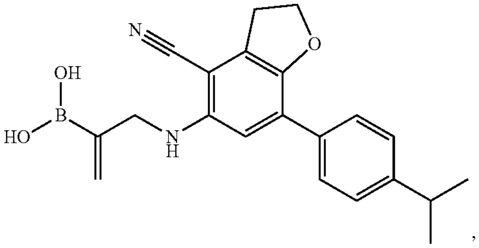
,
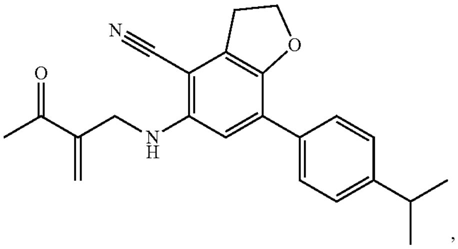
,
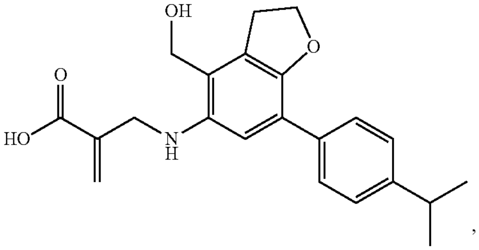
,
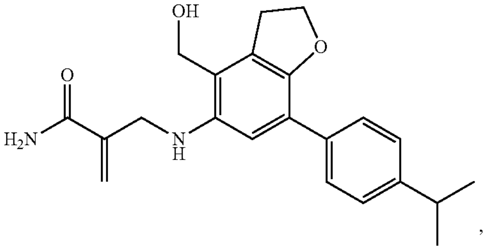
,
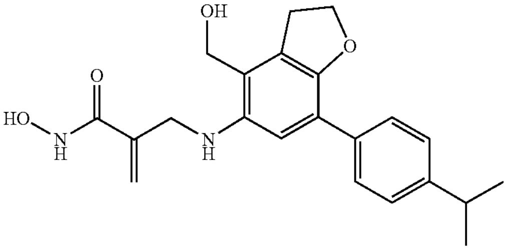
,
-continued
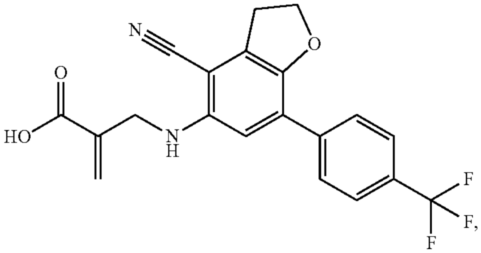
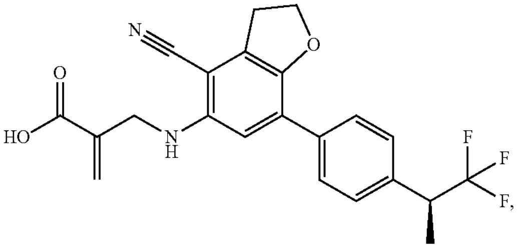
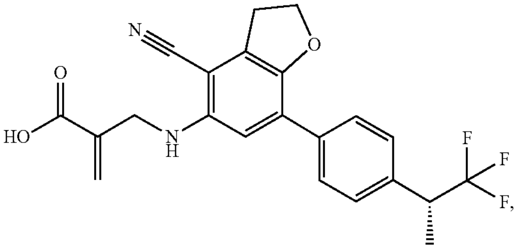
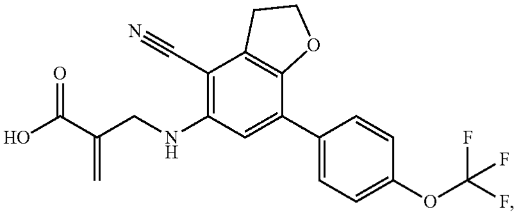
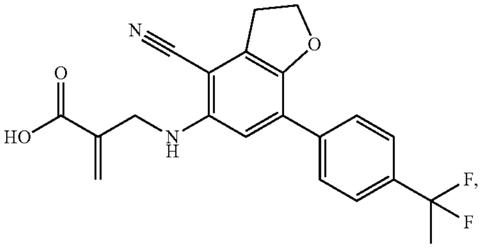
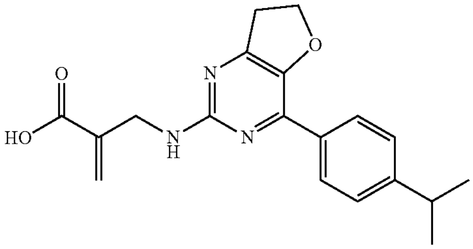
,
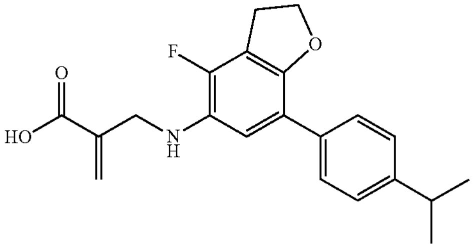
, -continued

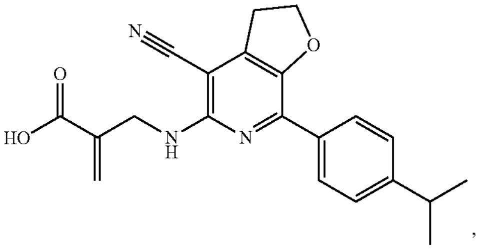

,

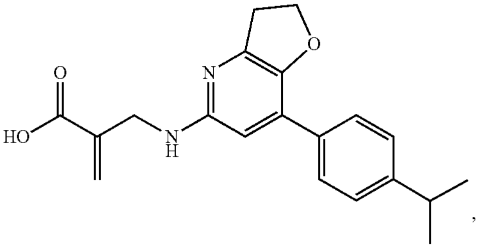

, and

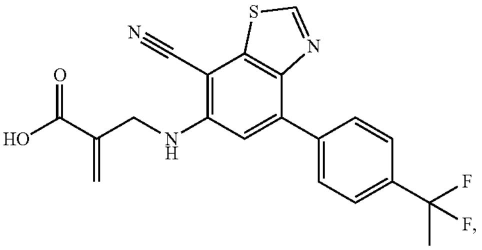

or a stereoisomer, tautomer, or pharmaceutically acceptable salt thereof.

In one aspect, the compounds of formula (I) include 2-[[[6-methoxy-5-[(E)-2-[trans-4-(trifluoromethyl)cyclohexyl]vinyl]-3-pyridyl]amino]methyl]prop-2-enoic acid and 2-[[[6-cyano-5-[(E)-2-[trans-4-(trifluoromethyl)cyclohexyl]vinyl]-3-pyridyl]amino]methyl]prop-2-enoic acid, and stereoisomers, tautomers, and pharmaceutically acceptable salts thereof. In another aspect, the compounds of formula (I) do not include 2-[[[6-methoxy-5-[(E)-2-[trans-4-(trifluoromethyl)cyclohexyl]vinyl]-3-pyridyl]amino]methyl]prop-2-enoic acid or 2-[[[6-cyano-5-[(E)-2-[trans-4-(trifluoromethyl)cyclohexyl]vinyl]-3-pyridyl]amino]methyl]prop-2-enoic acid, or stereoisomers, tautomers, or pharmaceutically acceptable salts thereof.

In one aspect, the compounds of formula (I) include

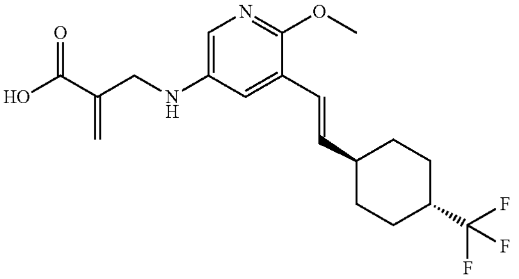

and

-continued

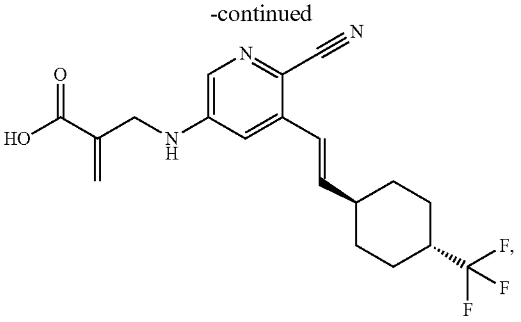

and stereoisomers, tautomers, and pharmaceutically acceptable salts thereof. In another aspect, the compounds of formula (I) do not include

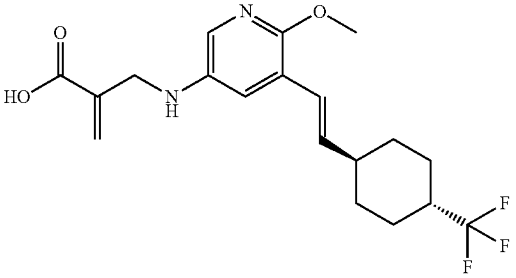

or

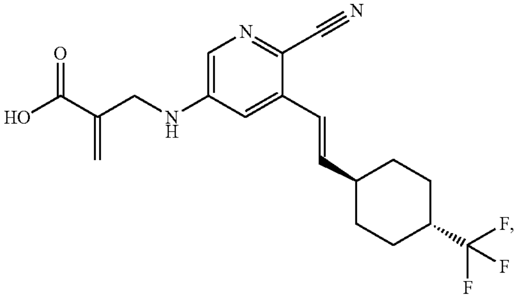 [SMILES: C=C(CNc1cnc(C#N)c(/C=C/[C@H]2CC[C@H](C(F)(F)F)CC2)c1)C(=O)O]

or stereoisomers, tautomers, or pharmaceutically acceptable salts thereof.

In some aspects, the compounds of the disclosure are isotopically labeled by having one or more atoms therein replaced by an atom having a different atomic mass or mass number. Such isotopically-labeled (i.e., radiolabeled) compounds of formula (X) or formula (I) are considered to be within the scope of this disclosure. Examples of isotopes that can be incorporated into the compounds of formula (X) or formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}I$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action, or binding affinity to TEAD. Certain isotopically-labeled compounds of formula (X) or formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (X) or formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (X) or formula (I) can generally be prepared by conventional techniques known to those skilled in the art or by processes analogous to those described in the Examples as set out below using an appropriate isotopically-labeled reagent in place of the non-labeled reagent previously employed.

Also provided herein is a pharmaceutically acceptable salt or ester of any compound provided herein, as well as a stereoisomer, a geometric isomer, a tautomer, a solvate, a metabolite, an isotope or a prodrug of such compound or a pharmaceutically acceptable salt of such compound.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the disclosure also provides for compositions and medicaments comprising a compound of the present disclosure or an embodiment or aspect thereof and at least one pharmaceutically acceptable carrier. The compositions of the disclosure can be used to selectively inhibit TEAD in patients (e.g., humans).

In one aspect, the disclosure provides for pharmaceutical compositions or medicaments comprising a compound of the disclosure (or embodiments and aspects thereof including stereoisomers, geometric isomers, tautomers, solvates, metabolites, isotopes, pharmaceutically acceptable salts, and prodrugs) and a pharmaceutically acceptable carrier, diluent or excipient. In another aspect, the disclosure provides for preparing compositions (or medicaments) comprising compounds of the disclosure. In another aspect, the disclosure provides for administering compounds of the disclosure and compositions comprising compounds of the disclosure to a patient (e.g., a human patient) in need thereof.

The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of a compound of the disclosure which are prepared by dissolving solid compounds of the disclosure in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of a compound of the disclosure together with a suitable carrier so as to prepare the proper dosage form for proper administration to the recipient.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TEAD activity as required to prevent or treat the undesired disease or disorder, such as for example, pain. For example, such amount may be below the amount that is toxic to normal cells, or the mammal as a whole.

In one example, the therapeutically effective amount of the compound of the disclosure administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain aspects, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compositions comprising compounds of the disclosure (or embodiments or aspects thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present disclosure and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the disclosure (e.g., a compound of formula (I), or an embodiment or aspect thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, PA. The particular carrier, diluent or excipient used will depend upon the means and purpose for which a compound of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Sustained-release preparations of a compound of the disclosure (e.g., compound of formula (X) or formula (I), or an embodiment or aspect thereof) can be prepared. Suitable examples of sustained-release preparations include semipermeable matrices of solid hydrophobic polymers containing a compound of formula (X) or formula (I), or an embodiment or aspect thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of the disclosure or an embodiment or aspect thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the disclosure (or an embodiment or aspect thereof) is formulated in an acetate buffer, at pH 5. In another aspect, the compounds of the disclosure or an embodiment thereof are sterile. The compound may be stored, for example, as a solid or amorphous composition, as a lyophilized formulation or as an aqueous solution Formulations of a compound of the disclosure suitable for oral administration can be prepared as discrete units such as pills, capsules, cachets or tablets each containing a predetermined amount of a compound of the disclosure.

Compressed tablets can be prepared by compressing in a suitable machine a compound of the disclosure in a free-flowing form such as a powder or granules, optionally mixed with a binder, lubricant, inert diluent, preservative, surface active or dispersing agent. Molded tablets can be made by molding in a suitable machine a mixture of a powdered compound of the disclosure moistened with an inert liquid diluent. The tablets can optionally be coated or scored and optionally are formulated so as to provide slow or controlled release of a compound of the disclosure therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the disclosure intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing a compound of the disclosure in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment or aspect thereof) of the disclosure compounded with a filler (e.g., lactose, such as about 90-30 mg anhydrous lactose), a disintegrant (e.g, croscarellose, such as about 5-40 mg sodium croscarmellose), a polymer (e.g. polyvinylpyrrolidone (PVP), a cellulose (e.g., hydroxypropylmethyl cellulose (HPMC), and/or copovidone, such as about 5-30 mg PVP, HPMC or copovidone), and a lubricant (e.g., magnesium stearate, such as about 1-10 mg). Wet granulation, dry granulation or dry blending may be used. In one wet granulation aspect, powdered ingredients are first mixed together and then mixed with a solution or suspension of the polymer (e.g., PVP). The resulting composition can be dried, granulated, mixed with lubricant and compressed to tablet form using conventional equipment. An example of an aerosol formulation can be prepared by dissolving the compound, for example 5-400 mg, of the disclosure in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the compounds of the disclosure in an amount of, for example, 0.075 to 20% w/w. When formulated in an ointment, the compounds of the disclosure can be employed with either a paraffinic or a water-miscible ointment base. Alternatively, the compounds of the disclosure can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of a compound of the disclosure through the skin or other affected areas. Examples of such dermal penetration enhancers include dimethyl sulfoxide and related analogs.

For topical formulations, it is desired to administer an effective amount of a pharmaceutical composition according to the disclosure to target area, e.g., skin surfaces, mucous membranes, and the like, which are adjacent to peripheral neurons which are to be treated. This amount will generally range from about 0.0001 mg to about 1 g of a compound of the disclosure (or an embodiment or aspect thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of a compound of the disclosure is used per cc of ointment base. The pharmaceutical composition can be formulated as transdermal compositions or transdermal delivery devices ("patches"). Such compositions include, for example, a backing, compound of the disclosure reservoir, a control membrane, liner and contact adhesive. Such transdermal patches may be used to provide continuous pulsatile, or on demand delivery of the compounds of the present disclosure as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of a compound of the disclosure.

When the binding target is located in the brain, certain aspects of the disclosure provide for a compound of the disclosure (or an embodiment or aspect thereof) to traverse the blood-brain barrier. Certain neurodegenerative diseases are associated with an increase in permeability of the blood-brain barrier, such that a compound of the disclosure (or an embodiment or aspect thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of the disclosure (or an embodiment or aspect thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula of the disclosure (or an embodiment or aspect thereof) across the blood-brain barrier include, but are not limited to, encapsulating the a compound of the disclosure (or an embodiment or aspect thereof) in liposomes that are coupled to antibody binding fragments that bind to receptors on the vascular endothelium of the blood-brain barrier (see, e.g., U.S. Patent Application Publication No. 2002/0025313), and coating a compound of the disclosure (or an embodiment or aspect thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of the disclosure (or an embodiment or aspect thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of the disclosure (or an embodiment or aspect thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain aspects, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic mini pumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the disclosure have been shown to modulate TEAD activity.

In In some embodiments, a compound that modulates TEAD activity is a compound of formula (B), or a stereoisomer, tautomer, or pharmaceutically acceptable salt thereof:

(B)

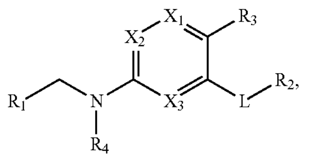

wherein:

- $X_1$ is C—$R_5$, wherein the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more D;
- $X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, $S(O)_2$—$C_{1-6}$alkyl, and $C_{1-6}$alkyl, wherein the $C_{1-6}$alkyl of $R_5$ is optionally substituted with hydroxyl or $N(R^e)(R^f)$;
- $X_3$ is N or C—H;
- $R_1$ is:
  - (i) a 3-5 membered saturated heterocyclyl comprising at least one annular oxygen atom, wherein the 3-5 membered saturated heterocyclyl is optionally substituted with one or more $C_{1-6}$alkyl, or
  - (ii) $N(R^e)(R^f)$, or
  - (iii)

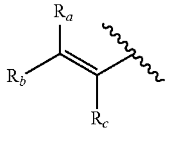, wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

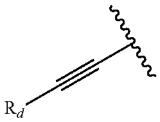, wherein $R_d$ is selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

- L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;
- $R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl,
  - wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$;
- $R_4$ is H or $C_{1-6}$alkyl, wherein the $C_{1-6}$alkyl is optionally substituted with hydroxyl;
- $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl; and $R^g$ is halo.

In some embodiments, a compound that modulates TEAD activity is a compound of formula (A), or a stereoisomer, tautomer, or pharmaceutically acceptable salt thereof:

(A)

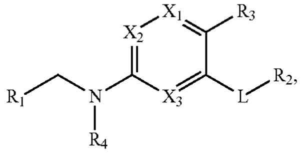

wherein:

- $X_1$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$,
- or the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

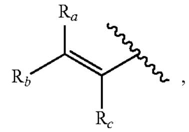

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

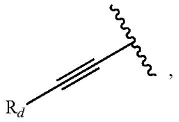

wherein $R_d$ is selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$;

$R_3$ is cyano, $C_{1-6}$alkyl, $C_{1-4}$alkoxy, or $C_{2-4}$alkenyl, wherein the $C_{2-4}$alkenyl is optionally substituted with $N(R^e)(R^f)$, or $R_3$ is taken together with $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl, or $R_3$ is taken together with the carbon atom of *—$CH_2$—O—** of L, and the atoms to which they are attached, to form a $C_6$aryl or a 6-membered heteroaryl;

$R_4$ is H or $C_{1-6}$alkyl, wherein the $C_{1-6}$alkyl is optionally substituted with hydroxyl; and $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl.

In some embodiments, a compound that modulates TEAD activity is a compound of formula (X), or a stereoisomer, tautomer, or pharmaceutically acceptable salt thereof:

(X)

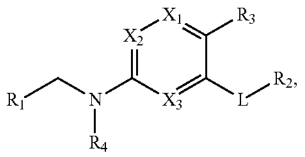

wherein:

$X_1$ is C—$R_5$, wherein the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more D;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, $S(O)_2$—$C_{1-6}$alkyl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

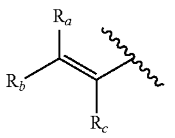

wherein $R_a$, $R_b$, and $R_c$ are each independently selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

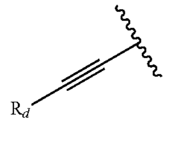

, wherein $R_d$ is selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_1$-6alkyl is further optionally substituted with hydroxyl; L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_5$. 13spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), O($R^e$), and S($R^g$)$_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), O($R^e$), and S($R^g$)$_5$, then L is —CH═CH— or —C≡C—;

$R_4$ is H or $C_{1-6}$alkyl, wherein the $C_{1-6}$alkyl is optionally substituted with hydroxyl;

$R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl; and $R^g$ is halo.

In some embodiments, a compound that modulates TEAD activity is a compound of formula (I), or a stereoisomer, tautomer, or pharmaceutically acceptable salt thereof:

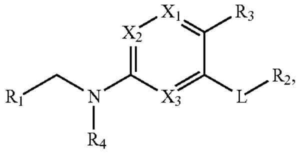

(I)

wherein:

$X_1$ is N or C—$R_5$, wherein each $R_5$ is independently selected from the group consisting of H, cyano, halo, $C(O)NH_2$, N($R^e$)($R^f$), $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or N($R^e$)($R^f$), or the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl;

$X_2$ is N or C—$R_5$, wherein each $R_5$ is independently selected from the group consisting of H, cyano, halo, $C(O)NH_2$, N($R^e$)($R^f$), $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or N($R^e$)($R^f$);

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) N($R^e$)($R^f$), or (iii)

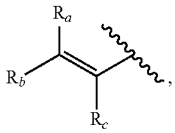

, wherein $R_a$, $R_b$, and $R_c$ are each independently selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

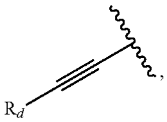

, wherein $R_d$ is selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, and $O(R^e)$, then L is —CH═CH— or —C≡C—;

$R_3$ is cyano, $C_{1-6}$alkyl, $C_{1-4}$alkoxy, or $C_{2-4}$alkenyl, wherein the $C_{2-4}$alkenyl is optionally substituted with $N(R^e)(R^f)$, or $R_3$ is taken together with $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl, or $R_3$ is taken together with the carbon atom of *—$CH_2$—O—** of L, and the atoms to which they are attached, to form a $C_6$aryl or a 6-membered heteroaryl;

$R_4$ is H or $C_{1-6}$alkyl, wherein the $C_{1-6}$alkyl is optionally substituted with hydroxyl; and $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl.

The compounds of the disclosure (or any embodiment or aspect thereof) are useful as a medical therapy for treating diseases and conditions mediated by TEAD activity. Such diseases and conditions include but are not limited to cancers including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In a specific embodiment, compounds of the disclosure (or any embodiment or aspect thereof) can be administered as a medical therapy to treat proliferative disorders including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstom's macroglobulinemia, testicular tumors, uterine cancer and Wilms' tumor.

In one specific aspect, compounds of the disclosure (or any embodiment or aspect thereof) are administered as a medical therapy to treat acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for a method for treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor, comprising the step of administering a therapeutically effective amount of a compound according to formula (A) or formula (I) (or an embodiment or aspect thereof) as described elsewhere herein to a subject in need thereof.

In another aspect, the disclosure provides for a compound of formula (B), formula (A), formula (X), or formula (I) as described elsewhere herein (or any embodiment or aspect thereof) for modulating TEAD activity. In some embodiments, the disclosure provides for a pharmaceutically acceptable salt of a compound of formula (B), formula (A), formula (X), or formula (I) for modulating TEAD activity.

In another aspect, the disclosure provides for a compound of formula (B), formula (A), formula (X), or formula (I) as described elsewhere herein, or an embodiment or aspect thereof, such as a pharmaceutically acceptable salt thereof, for use in medical therapy.

In another aspect, the disclosure provides for a method for treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor, comprising the step of administering a therapeutically effective amount of a compound according to formula (A) or formula (I) (or an embodiment or aspect thereof) as described elsewhere herein, to a subject in need thereof.

In another aspect, the disclosure provides for a compound of formula (B), formula (A), formula (X), or formula (I), as described elsewhere herein, or an embodiment or aspect thereof, such as a pharmaceutically acceptable salt thereof, for the treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for the use of a compound of formula (B), formula (A), formula (X), or formula (I), as described elsewhere herein, or an embodiment or aspect thereof, such as a pharmaceutically acceptable salt thereof, for the preparation of a medicament for the treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for a method for treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor in a mammal (e.g., a human) comprising administering a compound of formula (A) or formula (I) as described elsewhere herein or an embodiment or aspect thereof such as a pharmaceutically acceptable salt thereof to the mammal.

In another aspect, the disclosure provides for a method for modulating TEAD activity, comprising contacting TEAD with a compound of formula (B), formula (A), formula (X), or formula (I), as described elsewhere herein, or an embodiment or aspect thereof, such as a pharmaceutically acceptable salt thereof.

In another aspect, the disclosure provides for a compound of formula (B), formula (A), formula (X), or formula (I), as described elsewhere herein, or an embodiment or aspect thereof, such as a pharmaceutically acceptable salt thereof, for the treatment or prophylaxis of a disease or condition mediated by TEAD activity. Within aspects of this embodiment, the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for the use of a compound of formula (B), formula (A), formula (X), or formula (I), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one aspect, compounds of the disclosure demonstrate higher potency as compared to other analogues.

Combination Therapy

The compounds of formula (B), (A), (X), (I), (IA), (IB), or (IC), or stereoisomers, tautomers, or pharmaceutically acceptable salts thereof, may be employed alone or in combination with other agents for treatment. For example, the second agent of the pharmaceutical combination formulation or dosing regimen may have complementary activities to the compound of formula (B), (A), (X), (I), (IA), (IB), or (IC), such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (B), (A), (X), (I), (IA), (IB), or (IC), or stereoisomers, tautomers, or pharmaceutically acceptable salts thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I or formula II, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (B), (A), (X), (I), (IA), (IB), or (IC), or stereoisomers, tautomers, or pharmaceutically acceptable salts thereof, and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CBT-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ $\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc.); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP- 358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3-fluorophenyl)methoxy]phenyl]-6[5[[[2methylsulfonyl) ethyl]amino]methyl]-2-furanyl]-4-quinazolinamine).

Chemotherapeutic agents also include “tyrosine kinase inhibitors” including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc.); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof, autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGFR); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; famesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinirole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using a compound of formula (B), (A), (X), (I), (IA), (IB), or (IC), or a stereoisomer, tautomer, or pharmaceutically acceptable salt thereof, as described elsewhere herein, or an embodiment or aspect thereof, to treat cancer in combination with a PD-1 axis binding antagonist.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. Specific examples of PD-1 binding antagonists are provided infra.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. Specific examples of PD-L1 binding antagonists are provided infra.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 Axis Binding Antagonists

Provided herein are methods for treating cancer in an individual comprising administering to the individual an effective amount of a PD-1 axis binding antagonist and a compound of formula (B), (A), (I), (X), (IA), (IB), or (IC), or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (B), (A), (I), (X), (IA), (IB), or (IC), or a stereoisomer, tautomer, or pharmaceutically acceptable salt thereof, as described elsewhere herein.

In such methods, the PD-1 axis binding antagonist includes a PD-1 binding antagonist, a PDL1 binding antagonist, and/or a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partner(s). In a specific aspect the PD-1 ligand binding partners are PDL1 and/or PDL2. In another embodiment, a PDL1 binding antagonist is a molecule that inhibits the binding of PDL1 to its binding partner(s). In a specific aspect, PDL1 binding partner(s) are PD-1 and/or B7-1. In another embodiment, the PDL2 binding antagonist is a molecule that inhibits the binding of PDL2 to its binding partner(s). In a specific aspect, a PDL2 binding partner is PD-1. The antagonist may be an antibody, an antigen binding fragment thereof, an immunoadhesin, a fusion protein, an oligopeptide or a small molecule. If the antagonist is an antibody, in some embodiments the antibody comprises a human constant region selected from the group consisting of IgG1, IgG2, IgG3 and IgG4

Anti-PD-1 Antibodies

In some embodiments, the PD-1 binding antagonist is an anti-PD-1 antibody. A variety of anti-PDL1 antibodies can be utilized in the methods disclosed herein. In any of the embodiments herein, the PD-1 antibody can bind to a human PD-1 or a variant thereof. In some embodiments the anti-PD-1 antibody is a monoclonal antibody. In some embodiments, the anti-PD-1 antibody is an antibody fragment selected from the group consisting of Fab, Fab', Fab'-SH, Fv, scFv, and $(Fab')_2$ fragments. In some embodiments, the anti-PD-1 antibody is a chimeric or humanized antibody. In other embodiments, the anti-PD-1 antibody is a human antibody.

In some embodiments, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO2006/121168.

Nivolumab comprises a heavy chain and a light chain sequence, wherein:

(a) the heavy chain comprises the amino acid sequence.

```
                                             (SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDE

EKPSNTKVDKRVESKYGPPCPPCPAPEFLGGPSVFLFPPKPKDTLMISRT

PEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQE

EMTKNQVSLTCLVKGFYPSDIAVEWESNGQPENNYKTTPPVLDSDGSFFL

YSRLTVDKSRWQEGNVFSCSVMREALHNHYTQKSLSLSLGK,
```

and (b) the light chain comprises the amino acid sequence:

(SEQ ID NO: 2)
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKEIKVYACEVTHQ
GLSSPVTKSFNRGEC.

In some embodiments, the anti-PD-1 antibody comprises the six HVR sequences from SEQ ID NO:1 and SEQ ID NO:2 (e.g., the three heavy chain HVRs from SEQ ID NO:1 and the three light chain HVRs from SEQ ID NO:2). In some embodiments, the anti-PD-1 antibody comprises the heavy chain variable domain from SEQ ID NO:1 and the light chain variable domain from SEQ ID NO:2.

In some embodiments, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA® is an anti-PD-1 antibody described in WO2009/114335. Pembrolizumab comprises a heavy chain and a light chain sequence, wherein:

(a) the heavy chain comprises the amino acid sequence:

(SEQ ID NO: 3)
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDEEKPSNTKVDKRVESKYGPPCPPCPAPEFLGGPSVFLFPPKPKD
TLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK, and (b) the light chain comprises the amino acid sequence:

(SEQ ID NO: 4)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC.

In some embodiments, the anti-PD-1 antibody comprises the six HVR sequences from SEQ ID NO:3 and SEQ ID NO:4 (e.g., the three heavy chain HVRs from SEQ ID NO:3 and the three light chain HVRs from SEQ ID NO:4). In some embodiments, the anti-PD-1 antibody comprises the heavy chain variable domain from SEQ ID NO:3 and the light chain variable domain from SEQ ID NO:4.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD1 antibody that blocks the binding of PDL1 and PDL2 to PD-1.

In some embodiments, the anti-PD-1 antibody is REGN2810 (Regeneron). REGN2810 is a human anti-PD1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD1 antibody.

In some embodiments, the anti-PD-1 antibody is STI-A1110 (Sorrento). STI-A1110 is a human anti-PD1 antibody.

In some embodiments, the anti-PD-1 antibody is INCSHR-1210 (Incyte). INCSHR-1210 is a human IgG4 anti-PD1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD1 antibody that inhibits PD-1 function without blocking binding of PDL1 to PD-1.

In some embodiments, the anti-PD-1 antibody is ENUM 388D4 (Enumeral Biomedical Holdings). ENUM 388D4 is an anti-PD1 antibody that competitively inhibits binding of PDL1 to PD-1.

In some embodiments, the PD-1 antibody comprises the six HVR sequences (e.g., the three heavy chain HVRs and the three light chain HVRs) and/or the heavy chain variable domain and light chain variable domain from a PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

Anti-PDL1 Antibodies

In some embodiments, the PD-1 axis binding antagonist is an anti-PDL1 antibody. A variety of anti-PDL1 antibodies are contemplated and described herein. In any of the embodiments herein, the isolated anti-PDL1 antibody can bind to a human PDL1, for example a human PDL1 as shown in UniProtKB/Swiss-Prot Accession No. Q9NZQ7.1, or a variant thereof. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and $(Fab')_2$ fragments. In some embodiments, the anti-PDL1 antibody is a chimeric or humanized antibody. In some embodiments, the anti-PDL1 antibody is a human antibody. Examples of anti-PDL1 antibodies useful in the methods of this invention and methods of making them are described in PCT patent application WO 2010/077634 and U.S. Pat. No. 8,217,149, both of which are incorporated herein.

In some embodiments, the anti-PDL1 antibody is atezolizumab (CAS Registry Number: 1422185-06-5). Atezolizumab (Genentech), also known as MPDL3280A, is an anti-PDL1 antibody.

Atezolizumab comprises:

(a) an HVR—H1, HVR—H2, and HVR-H3 sequence of GFTFSDSWIH (SEQ ID NO:5), AWISPYGGSTYYADSVKG (SEQ ID NO:6) and RHWPGGFDY (SEQ ID NO:7), respectively, and (b) an HVR-L1, HVR-L2, and HVR-L3 sequence of RASQDVSTAVA (SEQ ID NO:8), SASFLYS (SEQ ID NO:9) and QQYLYHPAT (SEQ ID NO:10), respectively.

Atezolizumab comprises a heavy chain and a light chain sequence, wherein:

(a) the heavy chain variable region sequence comprises the amino acid sequence:

```
                                    (SEQ ID NO: 11
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS,
```

and (b) the light chain variable region sequence comprises the amino acid sequence:

```
                                    (SEQ ID NO: 12)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYIIPATFG

QGTKVEIKR.
```

Atezolizumab comprises a heavy chain and a light chain sequence, wherein:

(a) the heavy chain comprises the amino acid sequence:

```
                                    (SEQ ID NO: 13)
EVQLVESGGGLVQPGGSLRLSCAASGFTFSDSWITIWVRQAPGKGLEWVA

WISPYGGSTYYADSVKGRFTISADTSKNTAYLQMNSLRAEDTAVYYCARR

HWPGGFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG,
```

and (b) the light chain comprises the amino acid sequence:

```
                                    (SEQ ID NO: 14)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYEEPATFG

QGTKVEIKRTVAAPSVFIFPPSDEQLKSGTASVVCLLNNFYPREAKVQWK

VDNALQSGNSQESVTEQDSKDSTYSLSSTLTLSKADYEKEIKVYACEVTH

QGLSSPVTKSFNRGEC.
```

In some embodiments, the anti-PDL1 antibody is avelumab (CAS Registry Number: 1537032-82-8). Avelumab, also known as MSB0010718C, is a human monoclonal IgG1 anti-PDL1 antibody (Merck KGaA, Pfizer). Avelumab comprises a heavy chain and a light chain sequence, wherein:

(a) the heavy chain comprises the amino acid sequence:

```
                                    (SEQ ID NO: 15)
EVQLLESGGGLVQPGGSLRLSCAASGFTFSSYEVIMWVRQAPGKGLEWV

SSIYPSGGITFYADTVKGRFTISRDNSKNTLYLQMNSLRAEDTAVYYCA

RIKLGTVTTVDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNRKPSNTKVDKKVEPKSCDKTHTCPPCPAPELLGGPSVF

LFPPKPKDTLMISRTPEVTCVVVDVSREDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG,
```

and (b) the light chain comprises the amino acid sequence:

```
                                    (SEQ ID NO: 16)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVLGQPKANPTVTLFPPSSEELQANKATLVCLISDFYPGAVTV

AWKADGSPVKAGVETTKPSKQSNNKYAASSYLSLTPEQWKSEIRSYSCQV

TREGSTVEKTVAPTECS.
```

In some embodiments, the anti-PDL1 antibody comprises the six HVR sequences from SEQ ID NO:15 and SEQ ID NO:16 (e.g., the three heavy chain HVRs from SEQ ID NO:15 and the three light chain HVRs from SEQ ID NO:16). In some embodiments, the anti-PDL1 antibody comprises the heavy chain variable domain from SEQ ID NO:15 and the light chain variable domain from SEQ ID NO:16.

In some embodiments, the anti-PDL1 antibody is durvalumab (CAS Registry Number: 1428935-60-7). Durvalumab, also known as MEDI4736, is an Fc-optimized human monoclonal IgG1 kappa anti-PDL1 antibody (MedImmune, AstraZeneca) described in WO2011/066389 and US2013/034559. Durvalumab comprises a heavy chain and a light chain sequence, wherein:

(a) the heavy chain comprises the amino acid sequence:

```
                                          (SEQ ID NO: 17)
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNEEKPSNTKVDKRVEPKSCDKTHTCPPCPAPEFEGGPSVFLFPP

KPKDTLMISRTPEVTCVVVDVSEEEDPEVKFNWYVDGVEVHNAKTKPREE

QYNSTYRVVSVLTVLHQDWLNGKEYKCKVSNKALPASIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG,
```

and (b) the light chain comprises the amino acid sequence:

```
                                          (SEQ ID NO: 18)
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIKRTVAAPSVFIFPPSDEQLKSGTASVVCLLNNFYPREAKVQWK

VDNALQSGNSQESVTEQDSKDSTYSLSSTLTLSKADYEKEIKVYACEVTH

QGLSSPVTKSFNRGEC.
```

In some embodiments, the anti-PDL1 antibody comprises the six HVR sequences from SEQ ID NO:17 and SEQ ID NO:18 (e.g., the three heavy chain HVRs from SEQ ID NO:17 and the three light chain HVRs from SEQ ID NO:18). In some embodiments, the anti-PDL1 antibody comprises the heavy chain variable domain from SEQ ID NO:17 and the light chain variable domain from SEQ ID NO:18.

In some embodiments, the anti-PDL1 antibody is MDX-1105 (Bristol Myers Squibb). MDX-1105, also known as BMS-936559, is an anti-PDL1 antibody described in WO2007/005874.

In some embodiments, the anti-PDL1 antibody is LY3300054 (Eli Lilly).

In some embodiments, the anti-PDL1 antibody is STI-A1014 (Sorrento). STI-A1014 is a human anti-PDL1 antibody.

In some embodiments, the anti-PDL1 antibody is KN035 (Suzhou Alphamab). KN035 is single-domain antibody (dAB) generated from a camel phage display library.

In some embodiments, the anti-PDL1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PDL1 antibody is CX-072 (CytomX Therapeutics).

In some embodiments, the PDL1 antibody comprises the six HVR sequences (e.g., the three heavy chain HVRs and the three light chain HVRs) and/or the heavy chain variable domain and light chain variable domain from a PDL1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In a still further specific aspect, the PD-1 or PDL1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PDL1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

Other PD-1 Antagonists

In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. AMP-224 (CAS Registry No. 1422184-00-6; GlaxoSmithKline/MedImmune), also known as B7-DCIg, is a PDL2-Fc fusion soluble receptor described in WO2010/027827 and WO2011/066342.

In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699.

In some embodiments, the PDL1 binding antagonist is a small molecule that inhibits PD-1. In some embodiments, the PDL1 binding antagonist is a small molecule that inhibits PDL1. In some embodiments, the PDL1 binding antagonist is a small molecule that inhibits PDL1 and VISTA. In some embodiments, the PDL1 binding antagonist is CA-170 (also known as AUPM-170). In some embodiments, the PDL1 binding antagonist is a small molecule that inhibits PDL1 and TIM3. In some embodiments, the small molecule is a compound described in WO2015/033301 and WO2015/033299.

In some embodiments, the treatment method includes the co-administration of a compound of formula (B), (A), (I), (X), (IA), (IA-1), (IB), or (IC), or stereoisomers or tautomers thereof, or pharmaceutically acceptable salts of any of the foregoing, and at least one mitogen-activated protein kinase (MAPK) inhibitor. In some embodiments, the treatment method includes the co-administration of a compound of formula (B), (A), (I), (X), (IA), (IA-1), (IB), or (IC), or stereoisomers or tautomers thereof, or pharmaceutically acceptable salts of any of the foregoing, and at least one inhibitor of the RAS/MAPK pathway. In some embodiments, the treatment method includes the co-administration of a compound of formula (B), (A), (I), (X), (IA), (IA-1), (IB), or (IC), or stereoisomers or tautomers thereof, or pharmaceutically acceptable salts of any of the foregoing, and at least one epidermal growth factor receptor (EGFR) inhibitor. In some embodiments, the inhibitor of the RAS/MAPK pathway is a KRAS inhibitor, a RAF inhibitor, such as a BRAF monomer or RAF dimer inhibitor, a MEK inhibitor, an ERK inhibitor, an EGFR inhibitor, or a MAPK inhibitor, or any combination thereof. In certain embodiments, the inhibitor of the RAS/MAPK pathway is an EGFR inhibitor or a MAPK inhibitor, or a combination thereof. Examples of EGFR inhibitors, MAPK inhibitors, and/or RAS/MAPK pathway inhibitors are disclosed in Moore, A. R., Rosenberg, S. C., McCormick, F. et al. RAS-targeted therapies: is the undruggable drugged?. *Nat Rev Drug Discov* (2020), incorporated herein by reference and include, but are not limited to: sotorasib (AMG 510 from Amgen), MRTX849 (from Mirati Therapeutics), JNJ-74699157/ARS-3248 (from J&J Wellspring Biosciences), LY3499446 (from Eli Lilly), GDCBI 1701963 (from Boehringer Ingelheim), mRNA-5671 (from Moderna Therapeutics), G12D inhibitor (from Mirati Therapeutics), RAS(ON) inhibitors (from Revolution Medicines), BBP-454 (from BridgeBio Pharma), SP600125, PLX4032, GW5074, AZD6244, PD98059, simvastatin, alisertib, teriflunomide, NSC95397, PD325901, PD98059, lovastatin, sorafenib (NEXAVAR®, Bayer Labs), vermurafenib (ZELBORAF®, Hoffman La Roche Inc.), dabrafenib (TAFLINAR®, Novartis Pharmaceuticals Corportation), selumetinib (KOSELUGO™, AstraZeneca Pharmaceuticals LP), trametinib (MEKINIST®, Novartis Pharmaceuticals Corporation), ulixertinib, silimarin, sirolimus (RAPAMUNE®, PV Prism CV), lapatinib (TYKERB®/TYVERB®, GlaxoSmithKline), crizotinib (XALKORI®, PF Prism CV), taselisib (Roche), PF-0491502, PF502, enterolactone, PLX4720, PD0325901, PD184352, SC-514, alisterib (MLN8237), SB415286, PLX4720, obtaoclax (GX15-070), pimasterib, venetoclax (ABT-199/VENCLEXTA®/VENCLYXTO®), eprenetapopt (APR-246), gemcitabine (GEMZAR®), birinapant (TL32711), pexmetinib (ARRY-614), afuresertib, ralimetinib (LY2228820, Eli Lilly), cobimetinib (COTELLIC®, Exelixis/Genentech), prexasertib (LY2606368), erlotinib (TARCEVA®, OSI Pharmaceuticals), bevacizumab (AVASTIN®, Genentech), belvarafenib (Hanmi Pharm./Genentech, Inc.), and binimetinib (MEKTOVI®, Array Biopharma Inc.).

As used herein "combination" refers to any mixture or permutation of one or more compounds of the disclosure (or an embodiment or aspect thereof) and one or more other compounds of the disclosure or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the disclosure with another therapeutic agent. Unless the context makes clear otherwise, "combination" may include routes of administration of a compound of the disclosure with another therapeutic agent. Unless the context makes clear otherwise, "combination" may include formulations of a compound of the disclosure with another therapeutic agent. Dosage forms, routes of administration and pharmaceutical compositions include, but are not limited to, those described herein.

Enumerated Embodiments

The following enumerated embodiments are representative of some aspects of the invention.

1. A compound of formula (I):

(I)

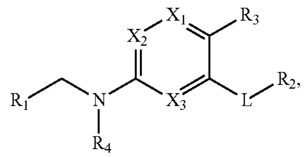

or a stereoisomer, tautomer, or pharmaceutically acceptable salt thereof, wherein:

$X_1$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$, or the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

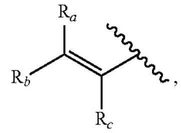

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

(iv)

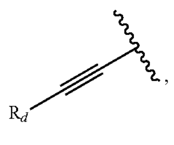

wherein $R_d$ is selected from the group consisting of H, halo, cyano, hydroxyl, $B(OH)_2$, C(O)—OH, C(O)—N($R^e$)($R^f$), C(O)—$C_{1-6}$alkoxy, C(O)—$C_{1-6}$ alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), and O($R^e$), provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, N($R^e$)($R^f$), and O($R^e$), then L is —CH═CH— or —C≡C—;

$R_3$ is cyano, $C_{1-6}$alkyl, $C_{1-4}$alkoxy, or $C_{2-4}$alkenyl, wherein the $C_{2-4}$alkenyl is optionally substituted with N($R^e$)($R^f$), or $R_3$ is taken together with $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl, or $R_3$ is taken together with the carbon atom of *—$CH_2$—O—** of L, and the atoms to which they are attached, to form a $C_6$aryl or a 6-membered heteroaryl;

$R_4$ is H or $C_{1-6}$alkyl, wherein the $C_{1-6}$alkyl is optionally substituted with hydroxyl; and $R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl.

2. The compound of embodiment 1, or a stereoisomer, tautomer, or pharmaceutically acceptable salt thereof, wherein $X_1$ is C—$R_5$, $X_2$ is C—$R_5$, and $X_3$ is C—H.

3. The compound of embodiment 1, or a stereoisomer, tautomer, or pharmaceutically acceptable salt thereof, wherein $X_1$ is C—$R_5$, $X_2$ is C—$R_5$, and $X_3$ is N.

4. The compound of embodiment 1, or a stereoisomer, tautomer, or pharmaceutically acceptable salt thereof, wherein $X_1$ is C—$R_5$, $X_2$ is N, and $X_3$ is C—H.

5. The compound of embodiment 1, or a stereoisomer, tautomer, or pharmaceutically acceptable salt thereof, wherein $X_1$ is C—$R_5$, $X_2$ is N, and $X_3$ is N.

6. The compound of any one of embodiments 1-5, or a stereoisomer, tautomer, or pharmaceutically acceptable salt thereof, wherein $X_1$ is C—$R_5$, and $R_3$ is taken together with the $R_5$ of $X_1$, and the atoms to which they are attached, to form a 5-membered heterocyclyl or a 5-membered heteroaryl, wherein the 5-membered heterocyclyl or 5-membered heteroaryl is optionally substituted with one or more $C_{1-6}$alkyl.

7. The compound of any one of embodiments 1-5, or a stereoisomer, tautomer, or pharmaceutically acceptable salt thereof, wherein $X_1$ is C—$R_5$ and $R_3$ is taken together with the $R_5$ of $X_1$, and the atoms to which they are attached, to form a 5-membered heterocyclyl.

8. The compound of embodiment 1, or a stereoisomer, tautomer, or pharmaceutically acceptable salt thereof, wherein $X_1$ is C—$R_5$, and $R_3$ is taken together with the $R_5$ of $X_1$, and the atoms to which they are attached, to form a 5-membered heterocyclyl, such that the compound of formula (I) is a compound of formula (IA):

(IA)

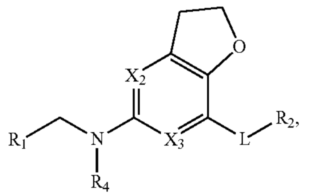

or a stereoisomer, tautomer, or pharmaceutically acceptable salt thereof.

9. The compound of embodiment 8, or a stereoisomer, tautomer, or pharmaceutically acceptable salt thereof, wherein L is absent.

10. The compound of embodiment 8 or embodiment 9, or a stereoisomer, tautomer, or pharmaceutically acceptable salt thereof, wherein the compound of formula (IA) is a compound of formula (IA-1):

(IA-1)

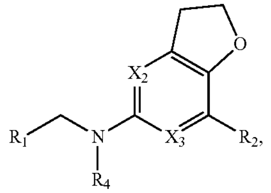

or a stereoisomer, tautomer, or pharmaceutically acceptable salt thereof.

11. The compound of any one of embodiments 8-10, or a stereoisomer, tautomer, or pharmaceutically acceptable salt thereof, wherein $X_2$ is C—$R_5$, wherein the $R_5$ of $X_2$ is H, cyano, halo, or $C_{1-6}$alkyl, wherein the $C_{1-6}$alkyl is optionally substituted with one or more hydroxyl.

12. The compound of any one of embodiments 1-3 or 6-8, or a stereoisomer, tautomer, or pharmaceutically acceptable salt thereof, wherein the $R_5$ of $X_2$ is cyano.

13. The compound of any one of embodiments 8-11, or a stereoisomer, tautomer, or pharmaceutically acceptable salt thereof, wherein the compound is selected from the group consisting of -continued
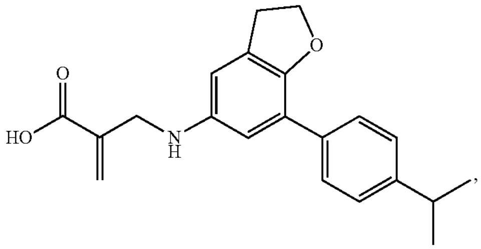
,
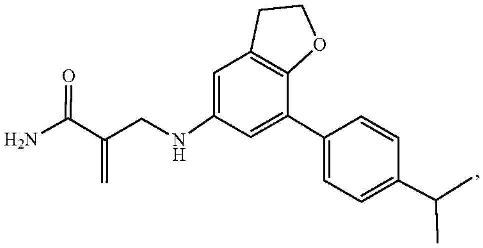
,
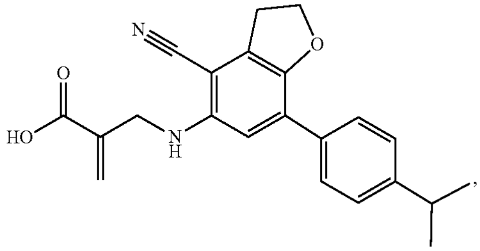
,
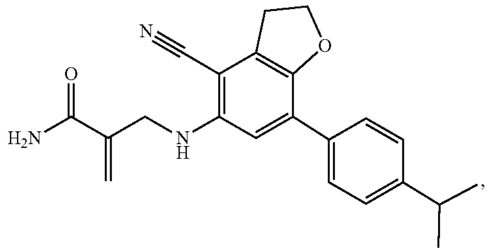
,
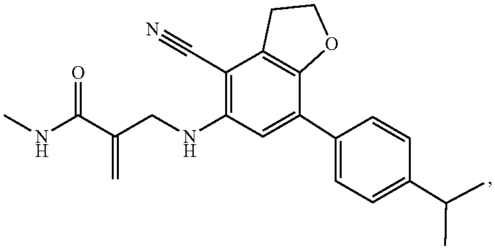
,
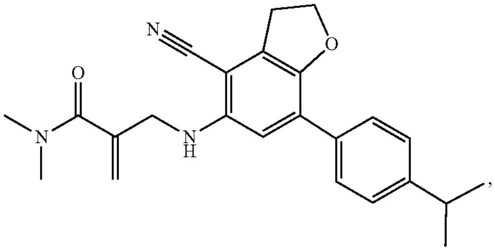
,
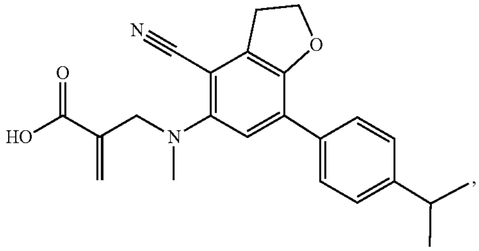
,
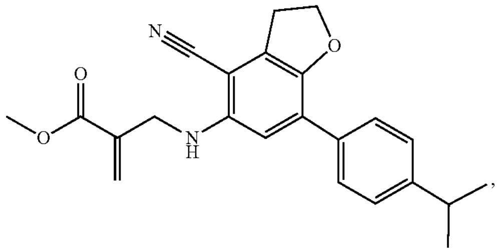
,
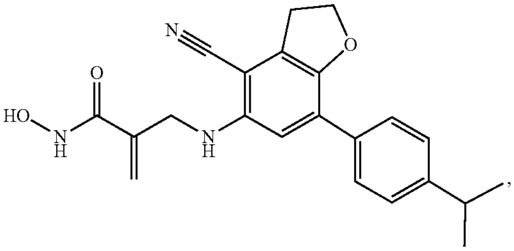
,
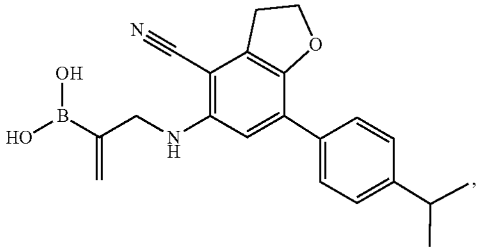
,
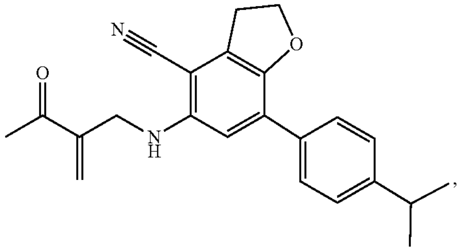
,
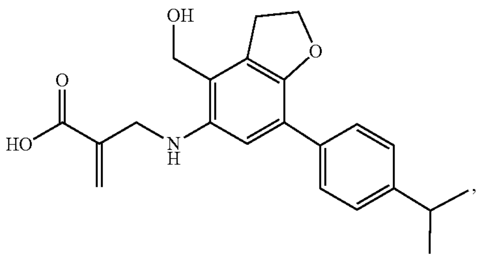
, -continued

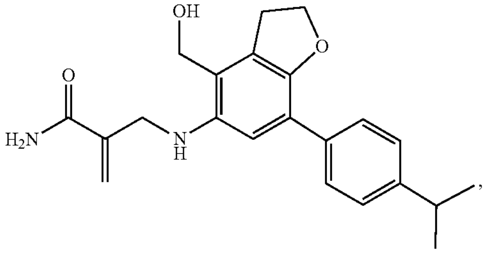

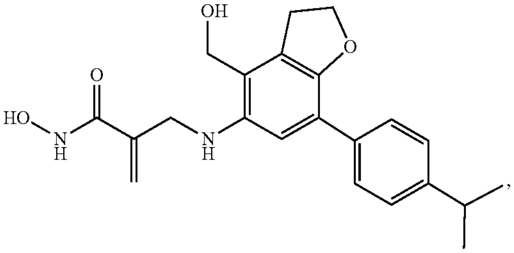

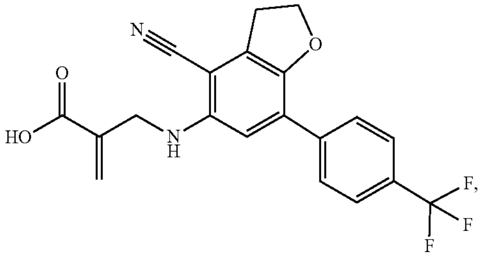

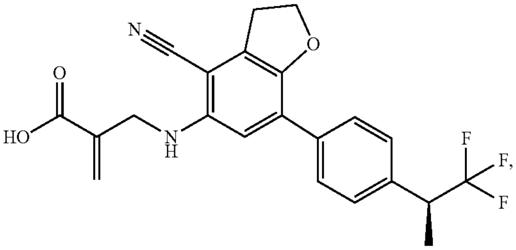

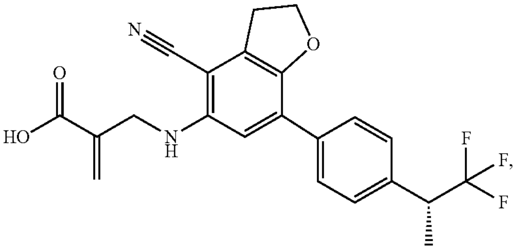

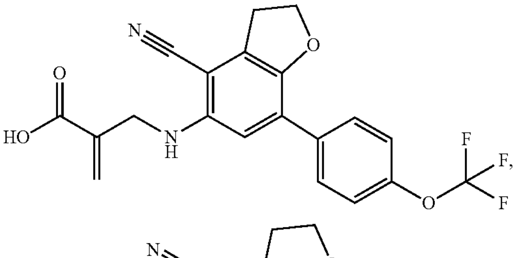

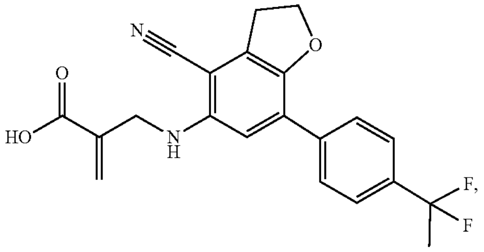

-continued

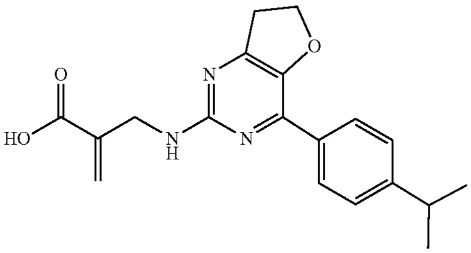

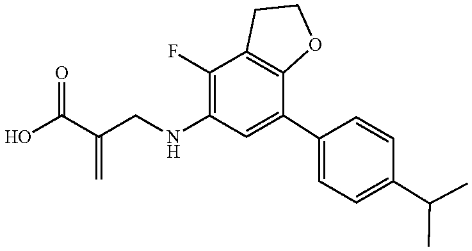

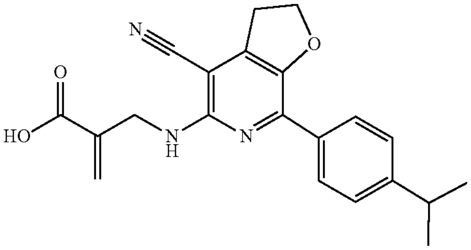

, and

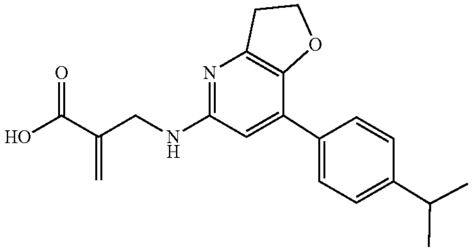

or a stereoisomer, tautomer, or pharmaceutically acceptable salt thereof.

14. The compound of any one of embodiments 8-12, or a stereoisomer, tautomer, or pharmaceutically acceptable salt thereof, wherein $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$ or $C_{1-6}$ alkyl, wherein the $C_{1-6}$alkyl is further optionally substituted with one or more halo.

15. The compound of any one of embodiments 1-12, or a stereoisomer, tautomer, or pharmaceutically acceptable salt thereof, wherein $R_2$ is $C_{6-20}$aryl, wherein the $C_{6-20}$aryl of $R_2$ is independently optionally substituted with one or more $C_{1-6}$alkyl.

16. The compound of any one of embodiments 8-12 and 14-15, or a stereoisomer, tautomer, or pharmaceutically acceptable salt thereof, wherein the compound has the structure of formula (IB).

(IB)
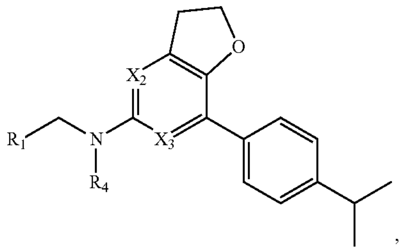,
or a stereoisomer, tautomer, or pharmaceutically acceptable salt thereof.
17. The compound of embodiment 16, or a stereoisomer, tautomer, or pharmaceutically acceptable salt thereof, wherein the compound of formula (IB) is selected from the group consisting of
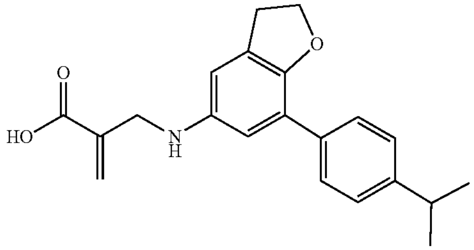,
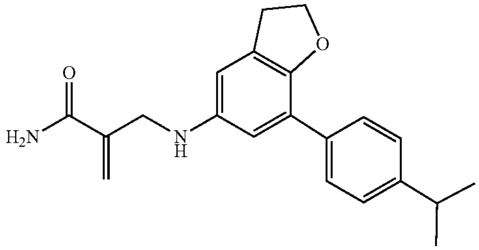,
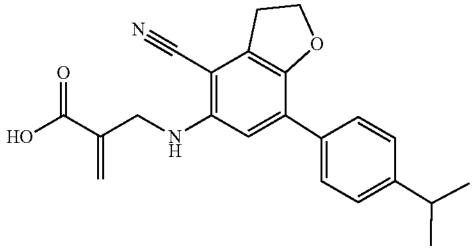,
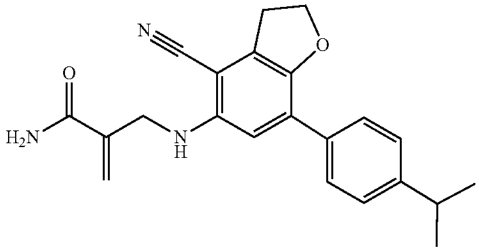,
-continued
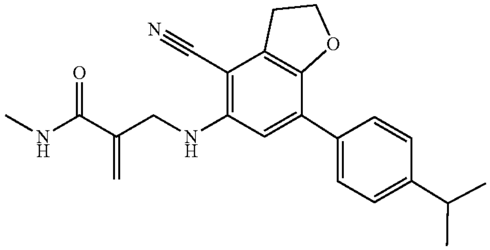,
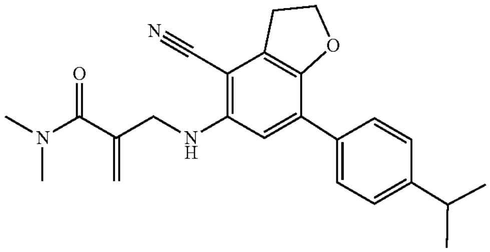,
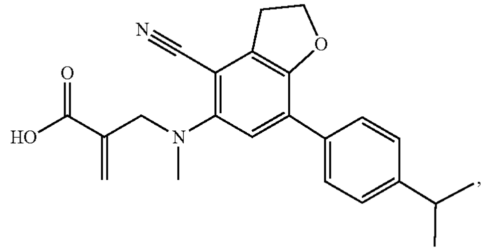,
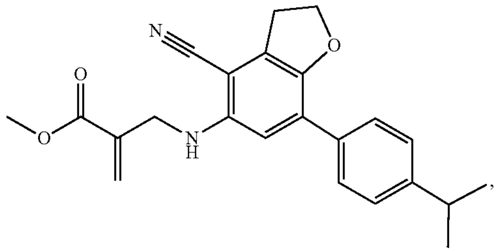,
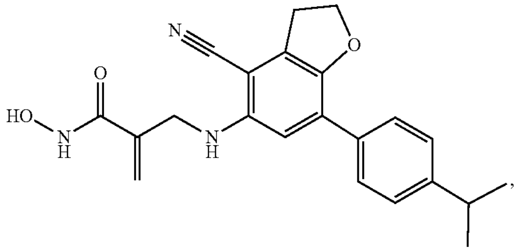,
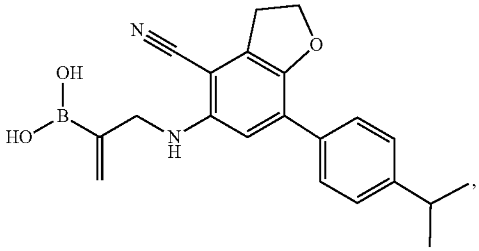, -continued

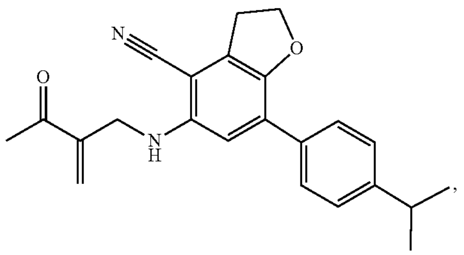

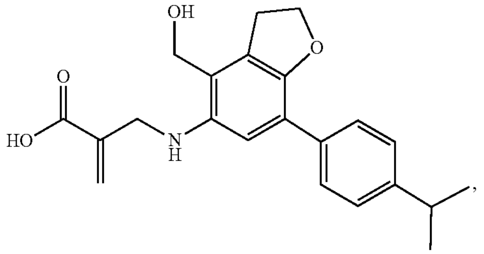

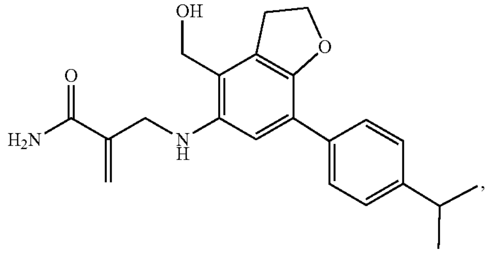

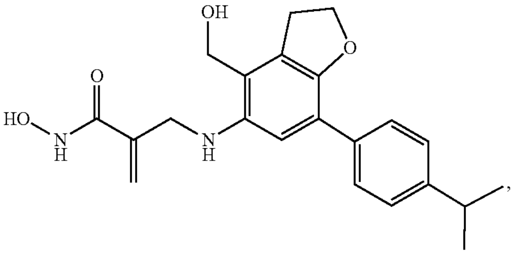

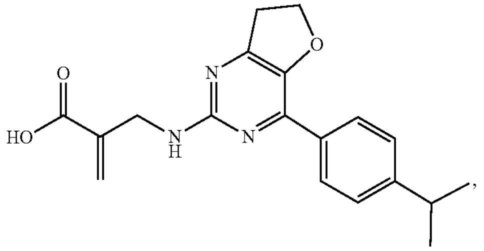

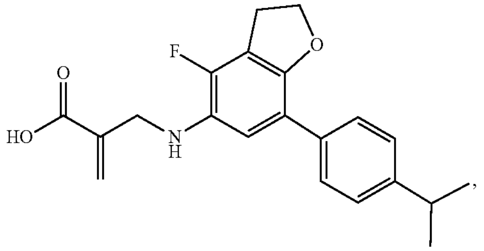

-continued

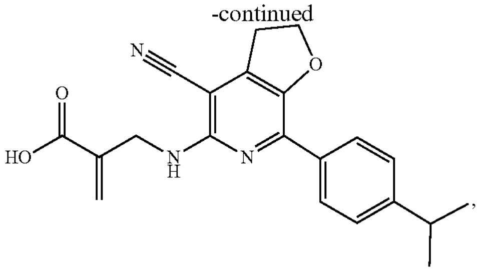

, and

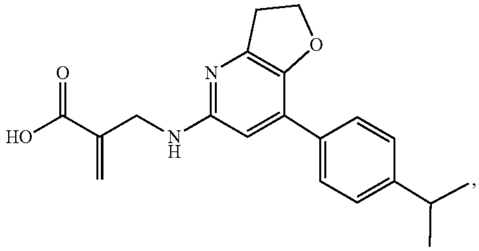

or a stereoisomer, tautomer, or pharmaceutically acceptable salt thereof.

18. The compound of any one of embodiments 1-11, and 14-16, or a stereoisomer, tautomer, or pharmaceutically acceptable salt thereof, wherein $R_1$ is

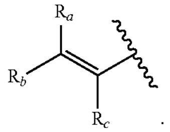

19. The compound of embodiment 18, or a stereoisomer, tautomer, or pharmaceutically acceptable salt thereof, wherein the compound has the structure of formula (IC):

(IC)

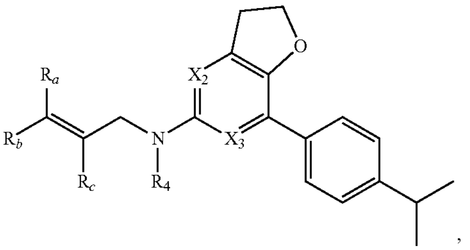

or a stereoisomer, tautomer, or pharmaceutically acceptable salt thereof.

20. The compound of embodiment 18 or embodiment 19, or a stereoisomer, tautomer, or pharmaceutically acceptable salt thereof, wherein at least two of $R_a$, $R_b$, and $R_c$ are H.

21. The compound of any one of embodiments 18-20, or a stereoisomer, tautomer, or pharmaceutically acceptable salt thereof, wherein exactly two of $R_a$, $R_b$, and $R_c$ are H, and exactly one of $R_a$, $R_b$, and $R_c$ is $B(OH)_2$, C(O)—OH, C(O)—N($R^e$)($R^f$), C(O)—$C_{1-6}$alkoxy, or C(O)—$C_{1-6}$alkyl.

22. The compound of embodiment 21, or a stereoisomer, tautomer, or pharmaceutically acceptable salt thereof, wherein the $R^e$ and $R^f$ of C(O)—N($R^e$)($R^f$) are each independently H, $C_{1-6}$alkyl, or hydroxyl.

23. The compound of any one of embodiments 18-20, or a stereoisomer, tautomer, or pharmaceutically acceptable salt thereof, wherein exactly two of $R_a$, $R_b$, and $R_c$ are H, and exactly one of $R_a$, $R_b$, and $R_c$ is C(O)—OH.

24. The compound of any one of embodiments 18-20, or a stereoisomer, tautomer, or pharmaceutically acceptable salt thereof, wherein $R_a$ and $R_b$ are each H, and $R_c$ is C(O)—OH.

25. The compound of embodiment 22, wherein the compound of formula (IC), or a stereoisomer, tautomer, or pharmaceutically acceptable salt thereof, is selected from the group consisting of

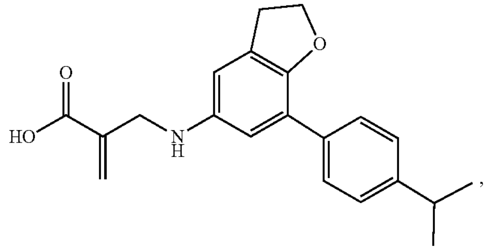
,

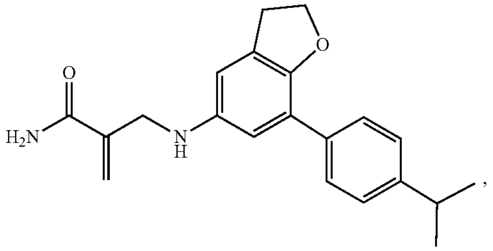
,

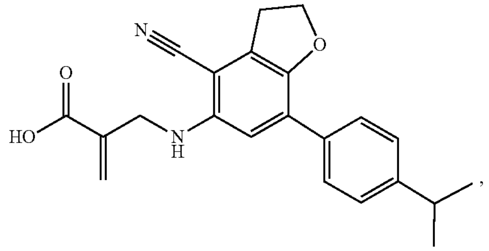
,

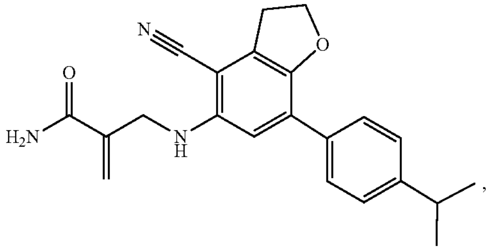
,

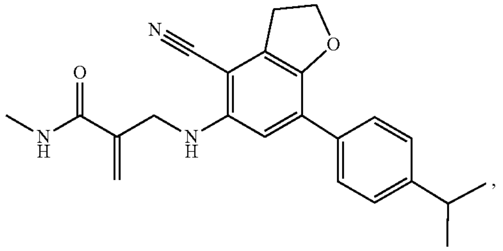
,

-continued

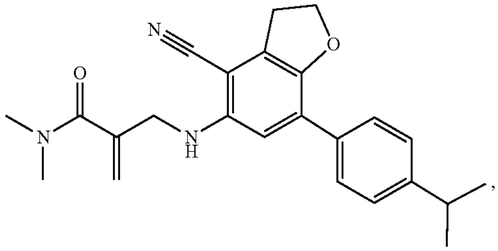
,

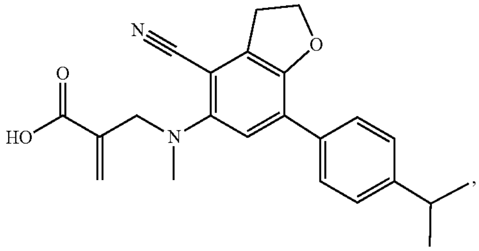
,

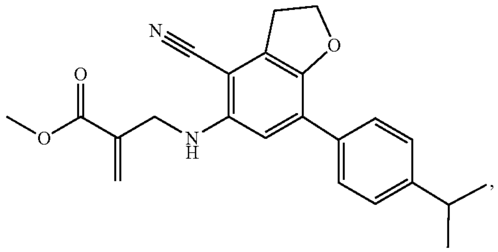
,

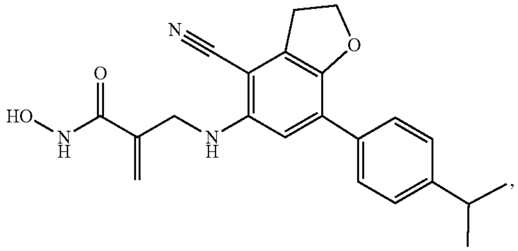
,

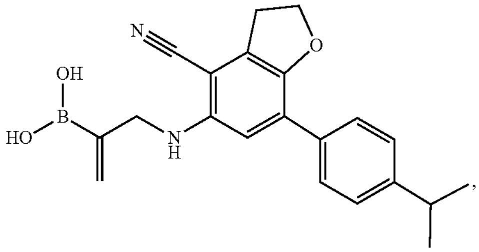
,

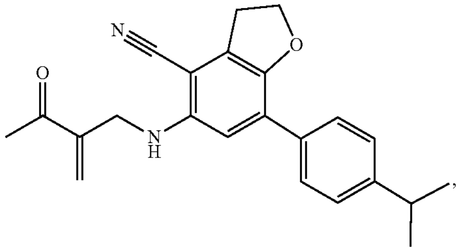
,

-continued
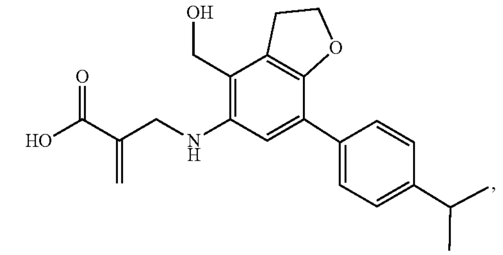
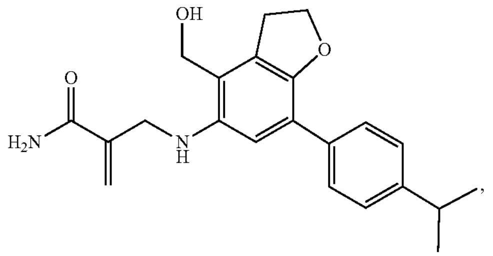
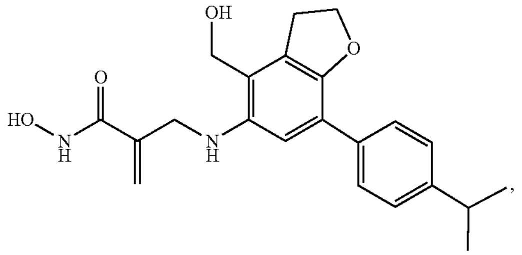
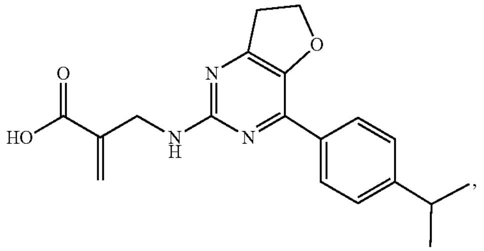
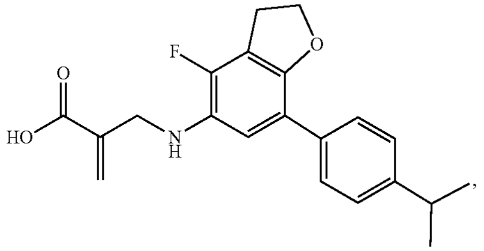
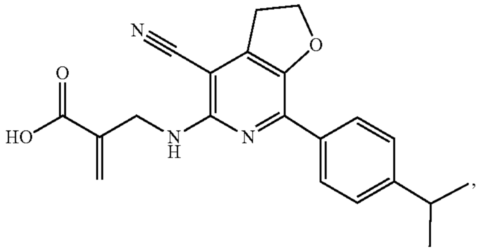
, and
-continued
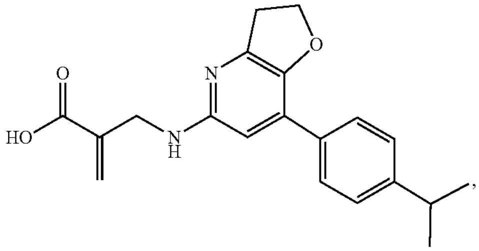
or a stereoisomer, tautomer, or pharmaceutically acceptable salt thereof.
26. The compound of any one of embodiments 1-12, 14-16, and 18-24, or a stereoisomer, tautomer, or pharmaceutically acceptable salt thereof, wherein $R_4$ is H.
27. A compound, or a stereoisomer, tautomer, or pharmaceutically acceptable salt thereof, selected from the group consisting of
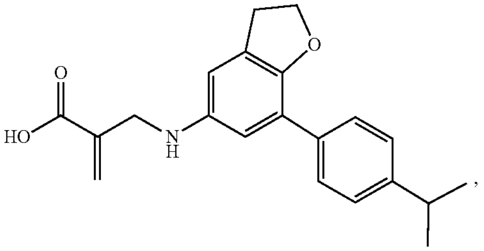
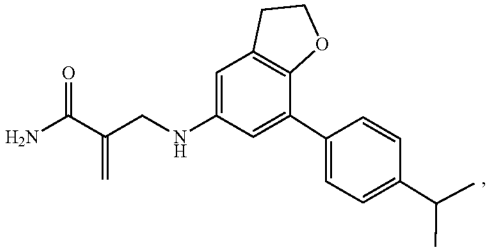
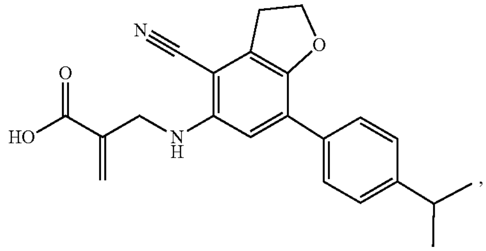
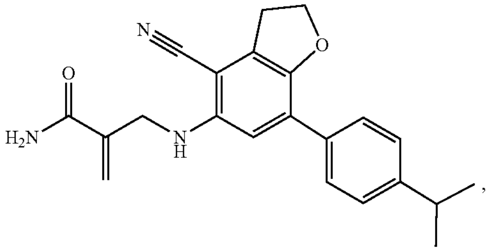

-continued
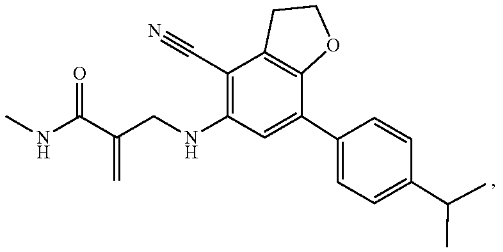
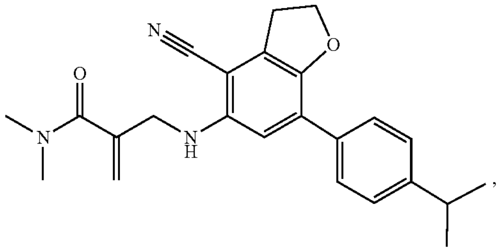
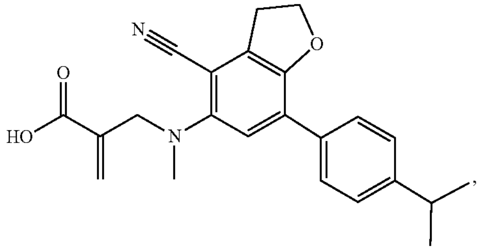
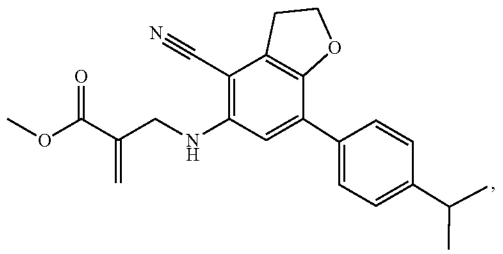
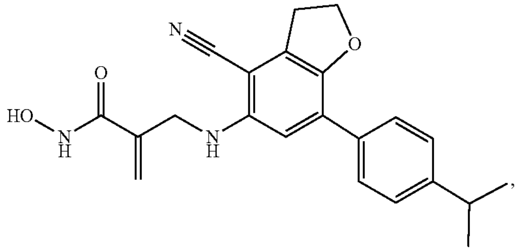
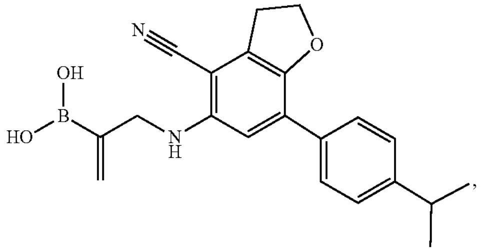
-continued
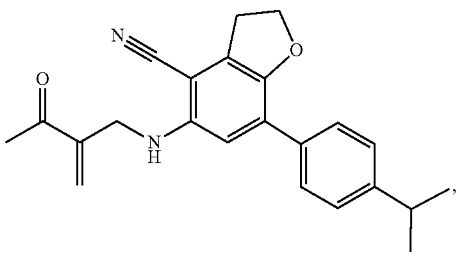
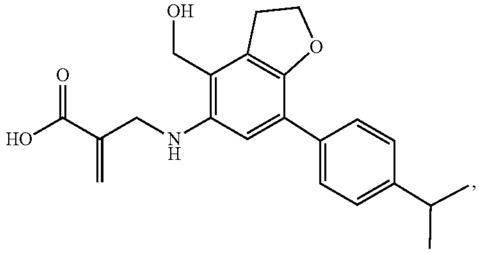
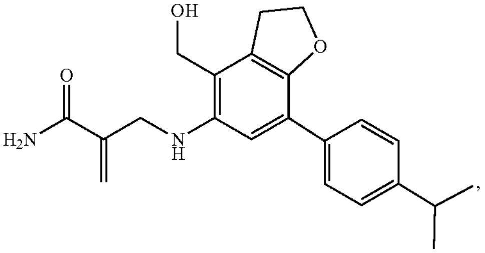
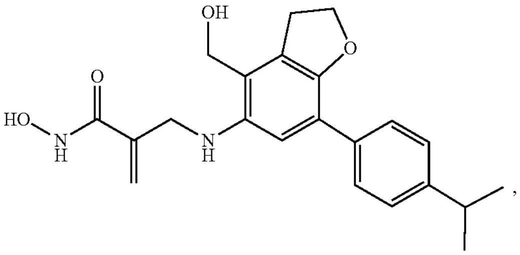
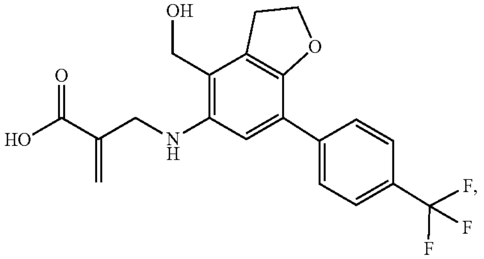
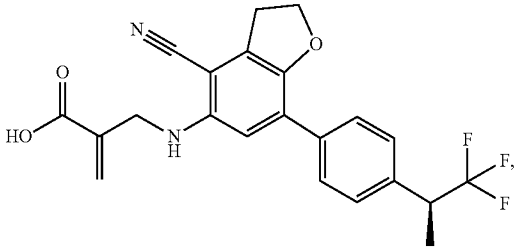

-continued
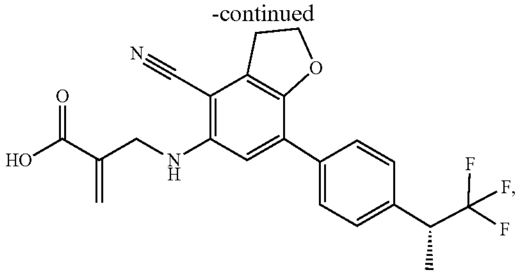
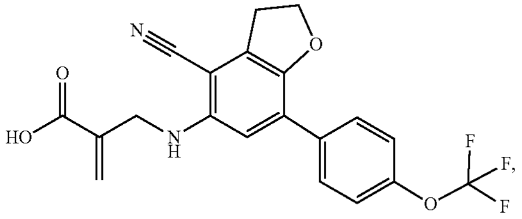
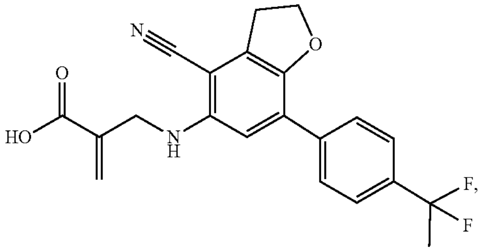
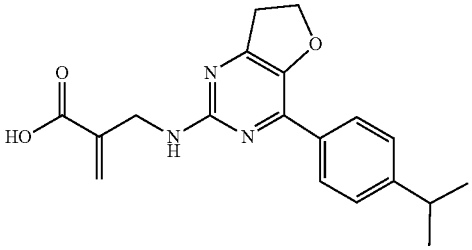
,
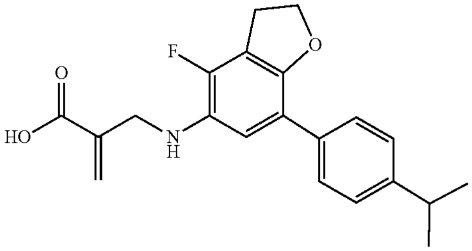
,
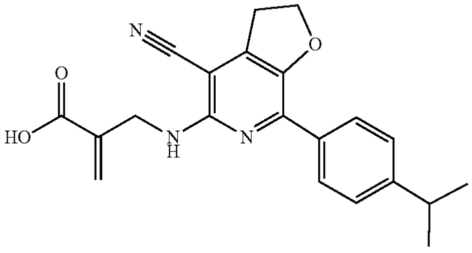
,
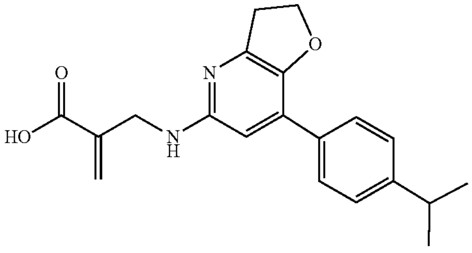
,
-continued
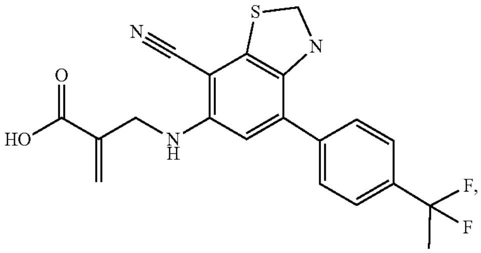
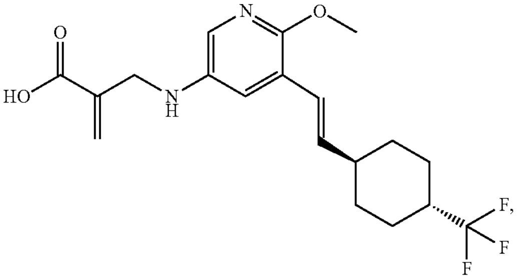
and
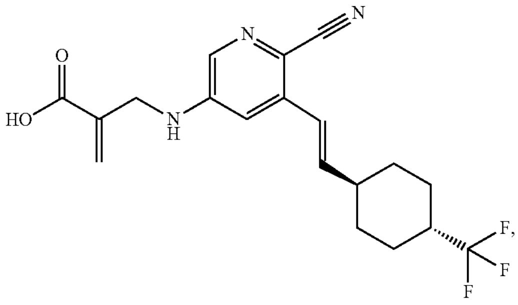
or a stereoisomer, tautomer, or pharmaceutically acceptable salt thereof.
28. A compound, or a stereoisomer, tautomer, or pharmaceutically acceptable salt thereof, selected from the group consisting of
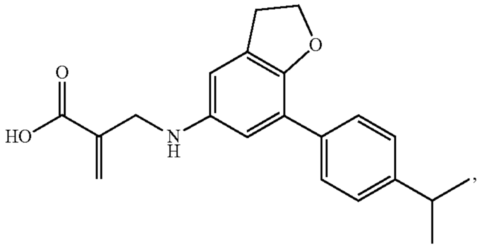
,
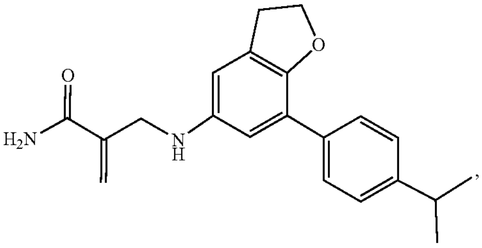
, -continued
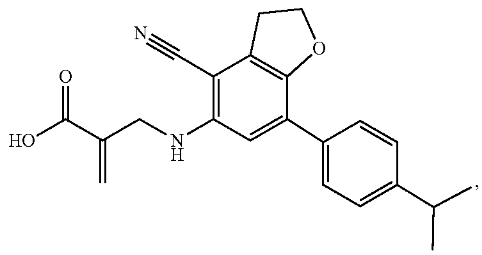,
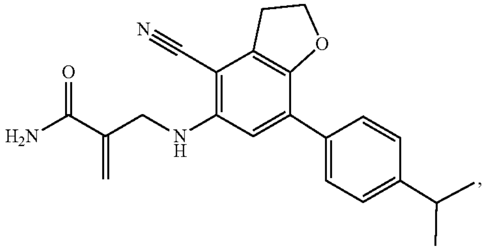,
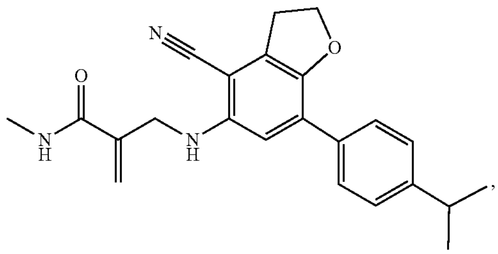,
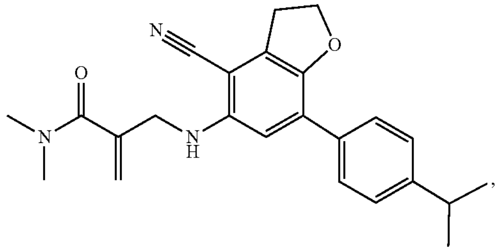,
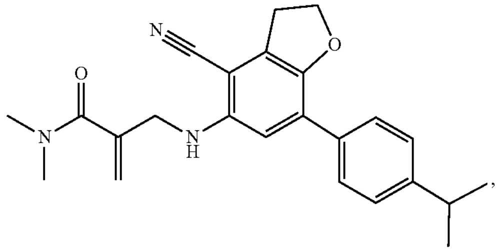,
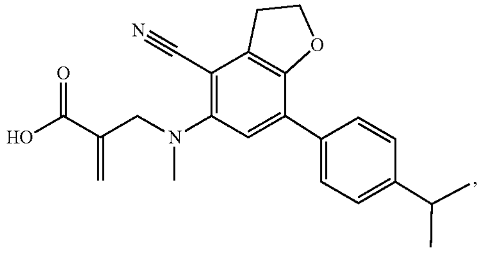,
-continued
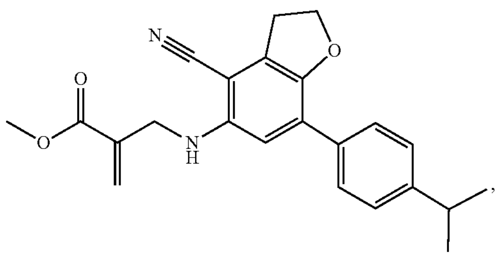,
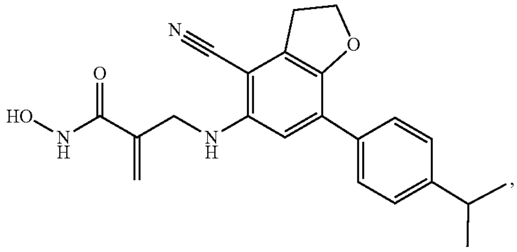,
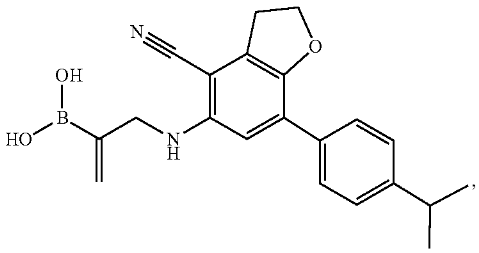,
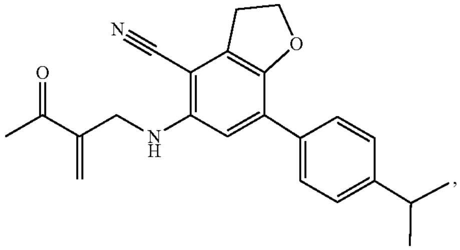,
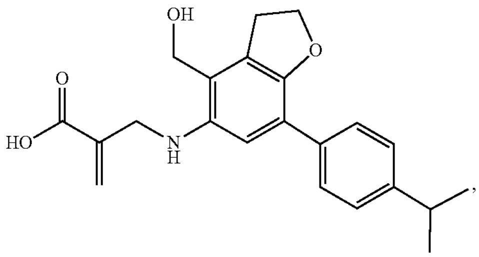,
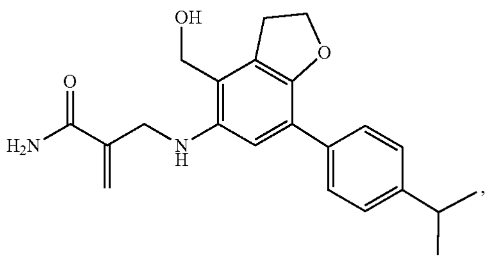, -continued

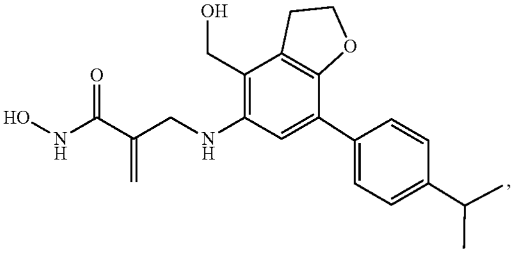

,

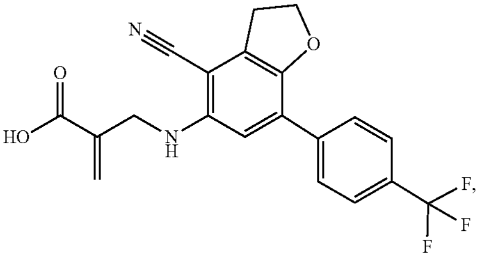

,

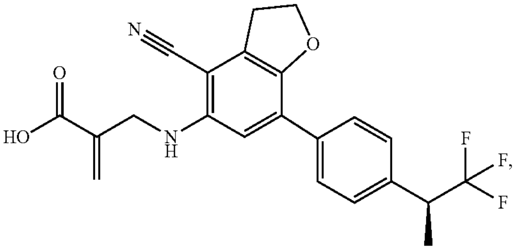

,

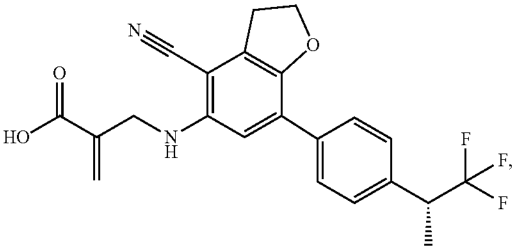

,

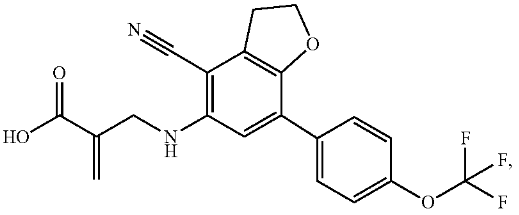

,

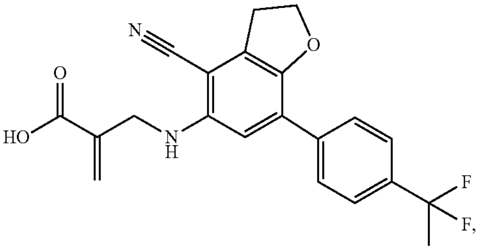

,

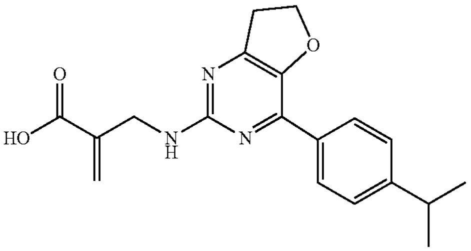

,

-continued

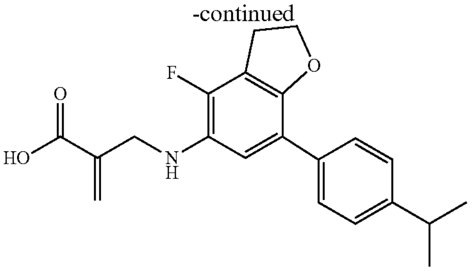

,

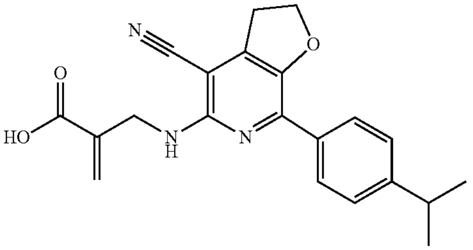

,

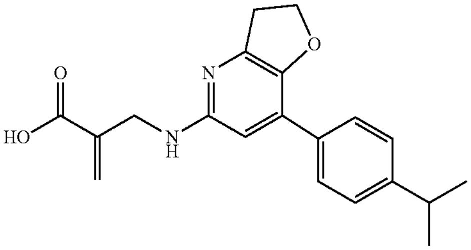

, and

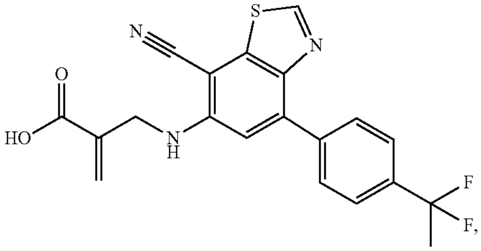

, or a stereoisomer, tautomer, or pharmaceutically acceptable salt thereof.

29. The compound of embodiment 1, or a stereoisomer, tautomer, or pharmaceutically acceptable salt thereof, wherein $X_1$ is N, $X_2$ is C—$R_5$, and $X_3$ is C—H.

30. A pharmaceutical composition, comprising (i) a compound as described in any one of embodiments 1-29, or a stereoisomer, tautomer, or pharmaceutically acceptable salt thereof, and (ii) a pharmaceutically acceptable carrier, diluent, or excipient.

31. A compound as described in any one of embodiments 1-29, or a stereoisomer, tautomer, or pharmaceutically acceptable salt thereof, for use in medical therapy.

32. A compound as described in any one of embodiments 1-29, or a stereoisomer, tautomer, or pharmaceutically acceptable salt thereof, for use in the treatment and/or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

33. A method for treating cancer in a mammal, comprising administering a compound as described in any one of embodiments 1-29, or a stereoisomer, tautomer, or pharmaceutically acceptable salt thereof, to the mammal.

34. A compound as described in any one of embodiments 1-29, or a stereoisomer, tautomer, or pharmaceutically acceptable salt thereof, for use in modulating TEAD activity.

35. A compound as described in any one of embodiments 1-29, or a stereoisomer, tautomer, or pharmaceutically acceptable salt thereof, for use in the treatment and/or prophylaxis of a disease or condition mediated by TEAD activity.

36. The compound for the use of embodiment 35, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

37. The use of a compound as described in any one of embodiments 1-29, or a stereoisomer, tautomer, or pharmaceutically acceptable salt thereof, for the preparation of a medicament for the treatment of prophylaxis of a disease or condition that is mediated by TEAD activity.

38. The use of embodiment 33, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

39. A method for modulating TEAD activity, comprising contacting TEAD with a compound as described in any one of embodiments 1-29, or a stereoisomer, tautomer, or pharmaceutically acceptable salt thereof.

40. A method for treating a disease or condition mediated by TEAD activity in a mammal, comprising administering a compound as described in any one of embodiments 1-29, or a pharmaceutically acceptable salt thereof, to the mammal.

41. The method of embodiment 40, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

42. The use of a compound as described in any one of embodiments 1-29, or a stereoisomer, tautomer, or pharmaceutically acceptable salt thereof, for modulating TEAD activity.

43. The use of a compound as described in any one of embodiments 1-29, or a stereoisomer, tautomer, or pharmaceutically acceptable salt thereof, for the treatment and/or prophylaxis of a disease or condition mediated by TEAD activity.

44. The use of embodiment 43, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

45. A process for preparing a compound of formula (I):

(I)

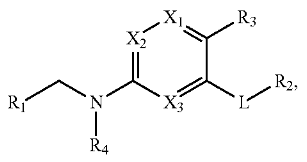

or a stereoisomer, tautomer, or pharmaceutically acceptable salt thereof, comprising

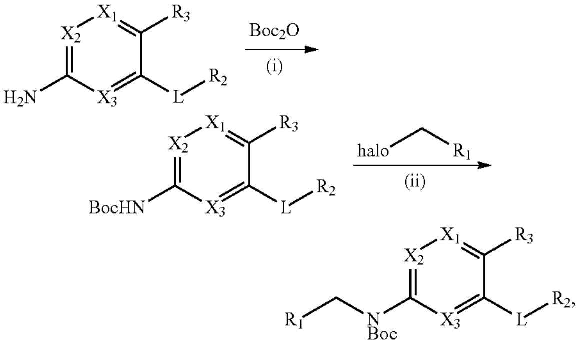

wherein Boc is a tert-butyloxycarbonyl group, and halo is halogen.

46. A compound, or a stereoisomer, tautomer, or pharmaceutically acceptable salt thereof, prepared by the process of embodiment 45.

47. The invention as described hereinbefore.

Preparation of Compounds

The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography, and/or by Preparative Thin Layer Chromatography (Prep TLC).

Mass spectrometry (MS) was performed using a (1) Sciex 15 mass spectrometer in ES+ mode, or (2) Shimadzu liquid chromatography-mass spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The following generalized schemes are used to prepare the disclosed compounds, intermediates, and pharmaceutically acceptable salts thereof. Disclosed compounds and intermediates may be prepared using standard organic synthetic techniques and from commerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the following general schemes. It is also to be understood that any of the steps shown in any of the following general schemes may be used in any combination and in any order that is chemically feasible to achieve a desired intermediate or disclosed compound.

SCHEME 1

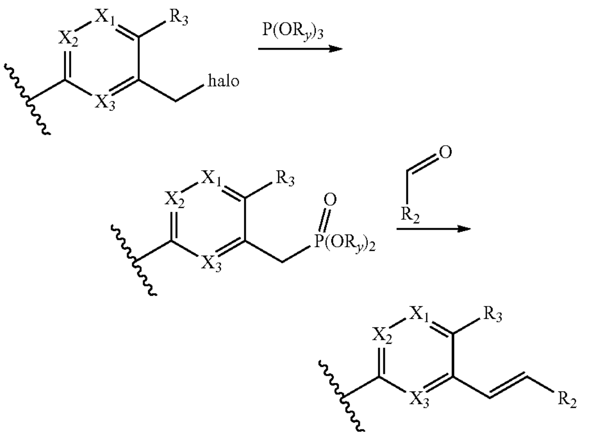

Scheme 1 describes a general synthetic route for converting a —$CH_2$-halo group to a —CH═$CHR_2$ moiety using a phosphate compound and an aldehyde compound. $R_2$, $R_3$, $X_1$, $X_2$, and $X_3$ are as defined above for formula (B), (A), (X), or (I). Halo refers to any halogen. In some embodiments, the halogen is chlorine, bromine, or iodine. In some embodiments, the phosphate compound is $P(OR_y)_3$, wherein $R_y$ is any suitable atom or group, including, for example, $C_{1-8}$ alkyl. In certain variations, the phosphate compound is $P(OEt)_3$. The

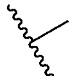

moiety may be any suitable atom or group, including, for example: a halogen, such a chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$.

SCHEME 2

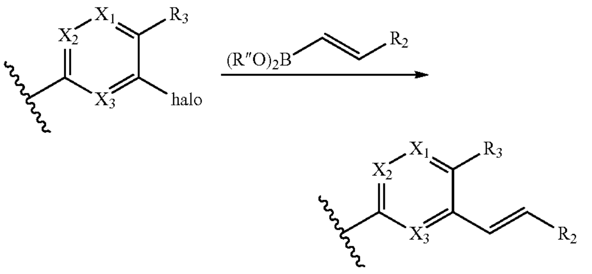

Scheme 2 describes a general synthetic route for converting a —$CH_2$—OH group to a —CH═$CHR_2$ moiety using a phosphate compound and an aldehyde compound. $R_2$, $R_3$, $X_1$, $X_2$, and $X_3$ are as defined above for formula (B), (A), (X), or (I). Halo refers to any halogen. In some embodiments, the halogen is chlorine, bromine, or iodine. In some embodiments, the phosphate compound is $P(OR_y)_3$, wherein $R_y$ is any suitable atom or group, including, for example, $C_{1-8}$ alkyl. In certain variations, the phosphate compound is $P(OEt)_3$. The

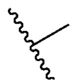

moiety may be any suitable atom or group, including, for example: a halogen, such a chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$.

SCHEME 3

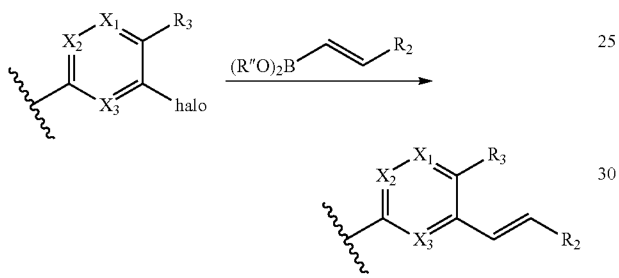

Scheme 3 describes a general synthetic route for converting a halogen (halo) group to a —CH═CHR$_2$ moiety using a boronic acid or a boronic ester compound. Halo refers to any halogen. In some embodiments, the halogen group is chlorine, bromine, or iodine. $R_2$, $R_3$, $X_1$, $X_2$, and $X_3$ are as defined above for formula (B), (A), (X), or (I). R" may be any suitable atom or group, including, for example, hydrogen. In certain embodiments, the R" substituents, together with the atoms to which they are attached, may form a ring structure. In some embodiments, the compound of formula

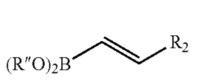

is

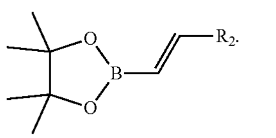

The

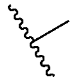

moiety may be any suitable atom or group, including, for example, a halogen, such as chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$.

SCHEME 4

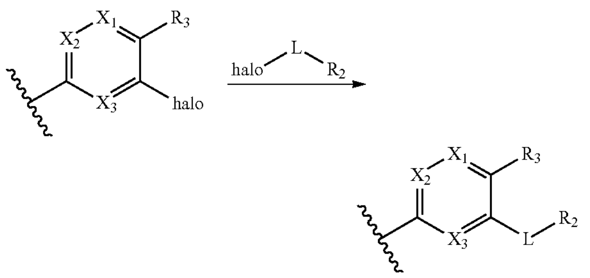

Scheme 4 describes a general synthetic route for converting a halogen (halo) group to the -L-$R_2$ moiety defined above for formula (B), (A), (X), or (I), using a halo compound. Halo refers to any halogen. In some embodiments, the halogen is chlorine, bromine, or iodine. $R_2$, $R_3$, $X_1$, $X_2$, and $X_3$ are as defined above for formula (B), (A), (X), or (I). The

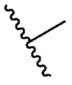

moiety may be any suitable atom or group, including, for example, a halogen, such as chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$.

SCHEME 5

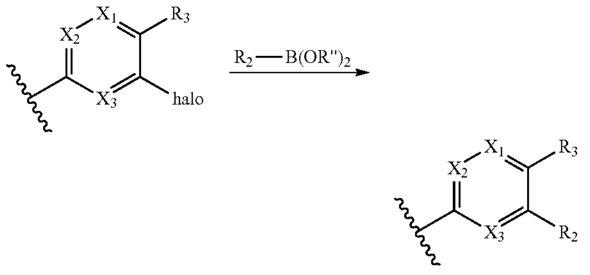

Scheme 5 describes a general synthetic route for converting a halogen (halo) group to the $R_2$ moiety defined above for formula (B), (A), (X), or (I), using a boronic acid or a boronic ester compound. Halo refers to any halogen. In some embodiments, the halogen group is chlorine, bromine, or iodine. $R_2$, $R_3$, $X_1$, $X_2$, and $X_3$ are as defined above for formula (A) or formula (I). R" may be any suitable atom or group, including, for example, hydrogen. The

moiety may be any suitable atom or group, including, for example, a halogen, such as chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, $—NR^sR^t$ is $—NO_2$.

SCHEME 6

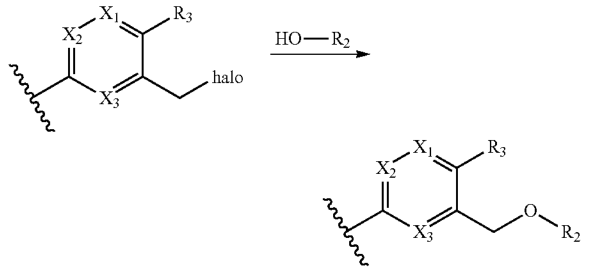

Scheme 6 describes a general synthetic route for converting a $—CH_2$-halo group to a $—CH_2—O—R_2$ moiety using a halo compound. Halo refers to any halogen. In some embodiments, the halogen is chlorine, bromine, or iodine. $R_2$, $R_3$, $X_1$, $X_2$, and $X_3$ are as defined above for formula (B), (A), (X), or (I). The

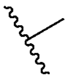

moiety may be any suitable atom or group, including, for example, a halogen, such as chlorine, bromine, or iodine; or $—NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, $—NR^sR^t$ is $—NO_2$.

SCHEME 7

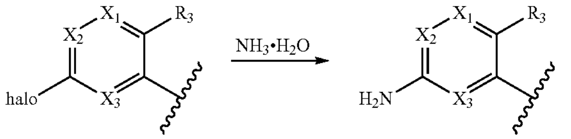

Scheme 7 describes a general synthetic route for converting a halogen (halo) group to an amino ($NH_2$) moiety. Halo refers to any halogen. In some embodiments, the halogen is chlorine, bromine, or iodine. $R_3$, $X_1$, $X_2$, and $X_3$ are as defined above for formula (B), (A), (X), or (I). The

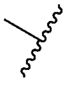

moiety may be any suitable atom or group, including, for example: a halogen, such as chlorine, bromine, or iodine; or the -L-$R_2$ moiety as defined above for formula (B), (A), (X), or (I). In one embodiment, the halogen (halo) group is converted to the amino ($NH_2$) moiety in the presence of a suitable catalyst such as CuI, a suitable base such as $K_3PO_4$, and $NH_3·H_2O$, and $N^1,N^2$-bis(5-methyl-[1,1'-biphenyl]-2-yl)oxalamide.

SCHEME 8

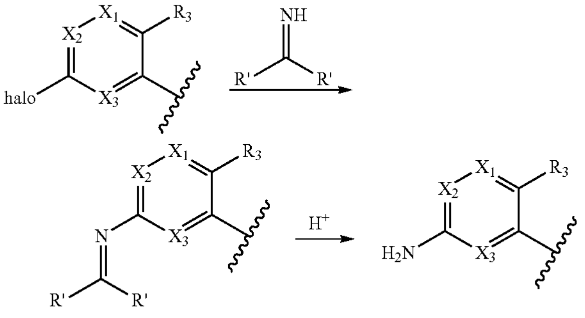

Scheme 8 describes a general synthetic route for converting a halogen (halo) group to an amino ($NH_2$) group using an imine compound. $R_3$, $X_1$, $X_2$, and $X_3$ are as defined above for formula (A) or formula (I). R' is any suitable atom or group, including, for example, $C_{6-20}$aryl. The

moiety may be any suitable atom or group, including, for example: a halogen, such as chlorine, bromine, or iodine; or the -L-$R_2$ moiety as defined above for formula (B), (A), (X), or (I).

SCHEME 9

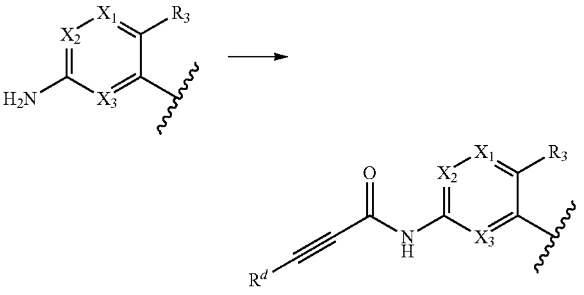

Scheme 9 describes a general synthetic route for converting an amino ($NH_2$) group to the

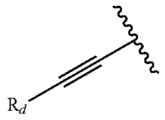

moiety as defined above for formula (B), (A), (X), or (I). $R_3$, $X_1$, $X_2$, and $X_3$ are as defined above for formula (B), (A), (X), or (I). The

moiety may be any suitable atom or group, including, for example: a halogen, such as chlorine, bromine, or iodine; or the -L-$R_2$ moiety as defined above for formula (B), (A), (X), or (I). In one embodiment, the amino ($NH_2$) moiety is converted to the

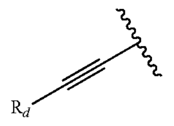

moiety in the presence of

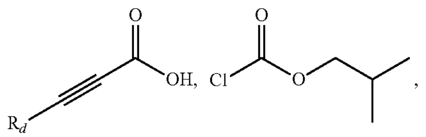

and N-methylmorpholine.

SCHEME 10

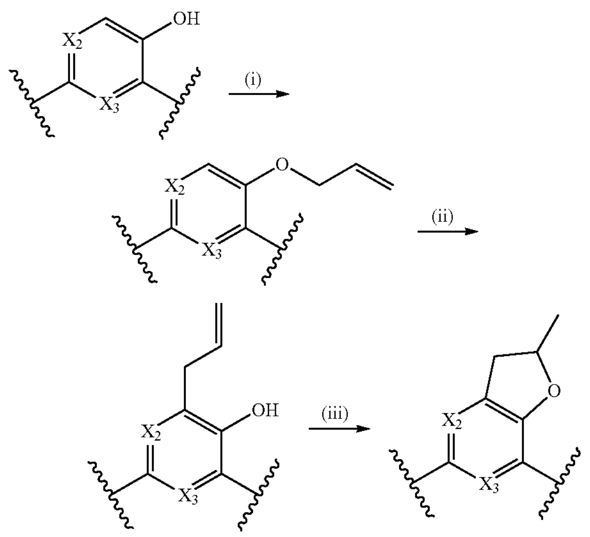

Scheme 10 describes a general synthetic route for forming a compound of formula (A) or formula (I) wherein $R_3$ is taken together with $R_5$ of $X_1$, and the atoms to which they are attached, to form a 5-membered heterocyclyl. $X_2$ and $X_3$ are as defined above for formula (B), (A), (X), or (I). The

moiety may be any suitable atom or group, including, for example: a halogen, such as chlorine, bromine, or iodine; or the -L-$R_2$ moiety as defined above for formula (B), (A), (X), or (I). The

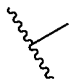

moiety may be any suitable atom or group, including, for example: H; a halogen, such a chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$. In one embodiment, the three steps outlined in Scheme 10 are carried out sequentially in the presence of (i) a suitable electrophile such as

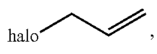

(ii) a utiable acid such as diethylaluminum chloride, and (iii) a suitable acid such as aluminum trifluoromethanesulfonate (aluminum triflate).

SCHEME 11

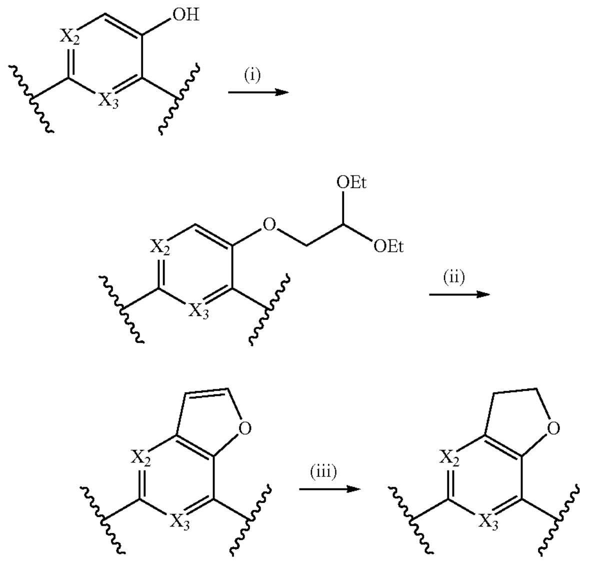

Scheme 11 describes a general synthetic route for forming a compound of formula (B), (A), (X), or (I) wherein $R_3$ is taken together with $R_5$ of $X_1$, and the atoms to which they are attached, to form a 5-membered heterocyclyl. $X_2$ and $X_3$ are as defined above for formula (B), (A), (X), or (I). The

moiety may be any suitable atom or group, including, for example: a halogen, such as chlorine, bromine, or iodine; or the -L-$R_2$ moiety as defined above for formula (B), (A), (X), or (I). The

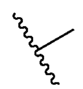

moiety may be any suitable atom or group, including, for example: H; a halogen, such a chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$. In one embodiment, the three steps outlined in Scheme 11 are carried out sequentially in the presence of (i) a suitable electrophile such as 2-bromo-1,1-diethoxyethane, (ii) a suitable acid such as phenylpropanolamine (PPA), and (iii) a suitable catalyst such as Rh/C.

SCHEME 12

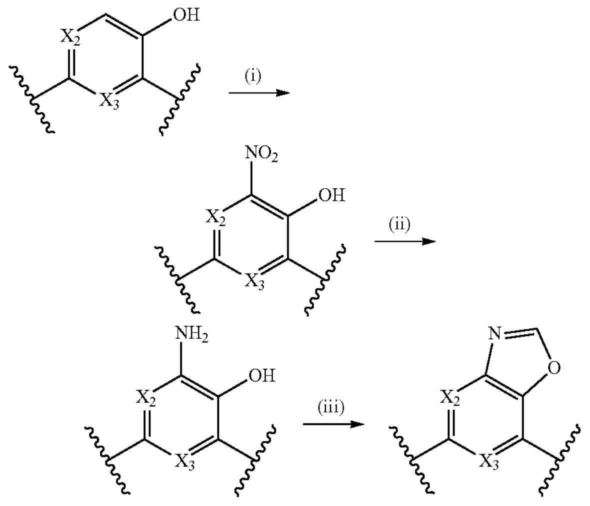

Scheme 12 describes a general synthetic route for forming a compound of formula (B), (A), (X), or (I), wherein $R_3$ is taken together with $R_5$ of $X_1$, and the atoms to which they are attached, to form a 5-membered heteroaryl. $X_2$ and $X_3$ are as defined above for formula (B), (A), (X), or (I). The

moiety may be any suitable atom or group, including, for example: $C_{1-6}$alkyl, such as methyl; a halogen, such as chlorine, bromine, or iodine; or the -L-$R_2$ moiety as defined above for formula (B), (A), (X), or (I). The

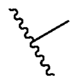

moiety may be any suitable atom or group, including, for example: H; a halogen, such a chlorine, bromine, or iodine; or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$. In one embodiment, the three steps outlined in Scheme 12 are carried out sequentially in the presence of (i) a suitable acid such as $HNO_3$, (ii) a suitable catalyst such as Fe, and (iii) a suitable nucleophile such as $NH_4C_1$.

SCHEME 13

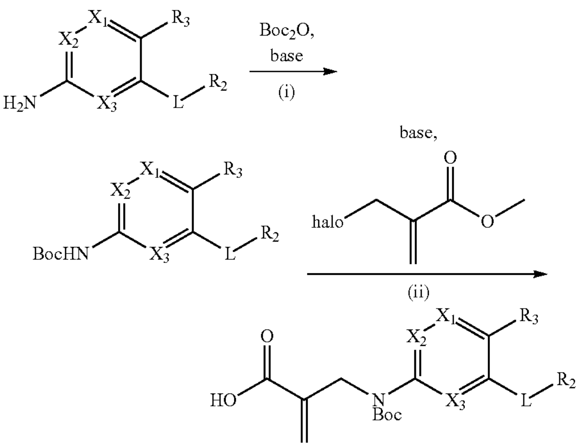

Scheme 13 describes a general synthetic route for forming a compound of formula (B), (A), (X), or (I), wherein $R_1$ is

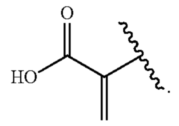

Boc is a tert-butyloxycarbonyl group. Halo refers to any halogen atom, including, for example, chlorine, bromine, or iodine. Any suitable base may be used in step (i) of Scheme 13, including, for example, trimethylamine (TEA). Any suitable base may be used in step (ii) of Scheme 13, including, for example NaH.

SCHEME 14

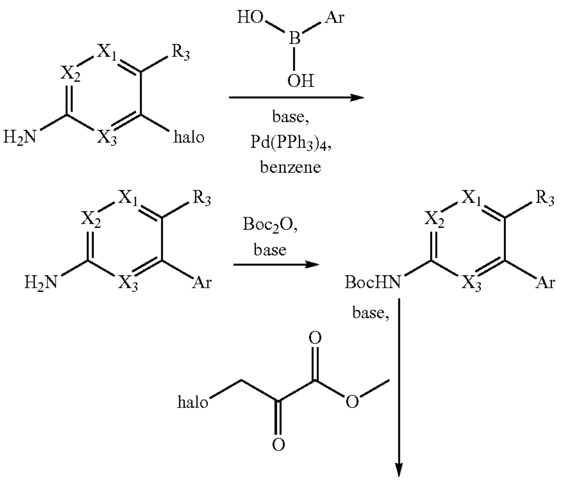

-continued

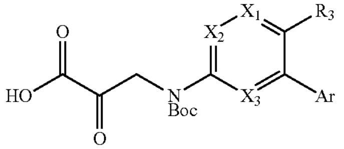

Scheme 14 describes a general synthetic route for forming a compound of formula (B), (A), (X), or (I), wherein $R_1$ is

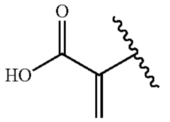

and the -L-$R_2$ moiety is an aromatic moiety. Boc is a tert-butyloxycarbonyl group. Halo refers to any halogen atom, including, for example, chlorine, bromine, or iodine. Ar is any aromatic group, including, for example, substituted or unsubstituted phenyl. Any suitable base may be used for Scheme 14, including, for example, trimethylamine (TEA) or NaH.

Disclosed herein are certain intermediates, including compounds having the structure of formula (II):

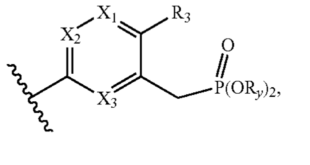

(II)

or a pharmaceutically acceptable salt thereof. $R_y$ is any suitable atom or group, including, for example, $C_{1-8}$ alkyl. In certain variations, $R_y$ is ethyl. The

moiety may be any suitable atom or group, including, for example: a halogen, such a chlorine, bromine, or iodine; the —$N(R_4)CH_2R_1$ moiety as described in formula (B), (A), (X), or (I); or —$NR^sR^t$, wherein $R^s$ and $R^t$ are each independently any suitable atom or group, including, for example, a protecting group. In some variations, $R^s$ and $R^t$ are different. In other variations, $R^s$ and $R^t$ are the same. In one embodiment, —$NR^sR^t$ is —$NO_2$.

In other embodiments, disclosed herein are Intermediates A-E, as described in the Examples below.

EXAMPLES

Intermediate A

Preparation of 7-(4-isopropylphenyl)-2,3-dihydrobenzofuran-5-amine

The general reaction scheme was as follows:

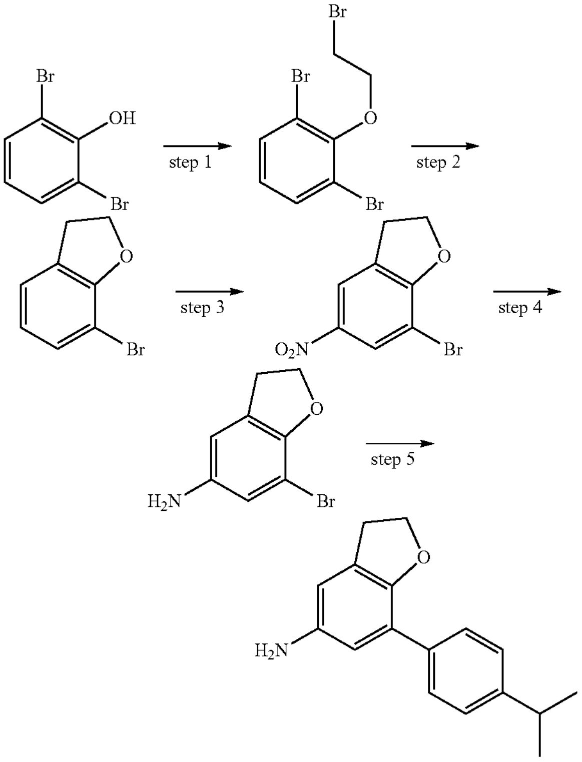

Intermediate A

Step 1: Preparation of 1,3-dibromo-2-(2-bromoethoxy)benzene

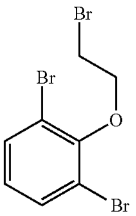 [SMILES: BrCCOc1c(Br)cccc1Br]

A mixture of 2,6-dibromophenol (525 g, 2.08 mol), NaOH (91.7 g, 2.29 mol) and 1,2-dibromoethane (180.43 mL, 2.08 mol) in water (1.5 L) was stirred at 100° C. for 16 hours. After cooling to room temperature, the oil product was separated via a separation funnel, washed with NaOH (1M) (200 mL×2) to remove the starting materials. The product was dissolved in petroleum ether (800 mL), dried over $Na_2SO_4$, filtered and concentrated to afford the title compound (520 g, 69%) as a yellow liquid. $^1$H NMR (400 MHz, DMSO-$d_6$): δ 7.68 (dd, J=8.0, 2.4 Hz, 2H), 7.07 (t, J=8.0 Hz, 1H), 4.28 (t, J=5.6 Hz, 2H), 3.85 (t, J=5.6 Hz, 2H).

Step 2: Preparation of 7-bromo-2,3-dihydrobenzofuran

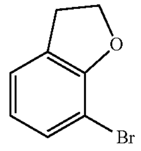

To a mixture of 1,3-dibromo-2-(2-bromoethoxy)benzene (200 g, 557.34 mmol) in THF (1.5 L) was added n-BuLi (227.39 mL, 568.48 mmol, 2.5 mol/L in hexane) at −78° C. dropwise. The mixture was stirred at −78° C. for 1 hour. The reaction was quenched by water (500 mL). The mixture was diluted with water (1 L), extracted with ethyl acetate (1 L×2) and the organic layers were combined. The organic layer was dried over anhydrous sodium sulfate and concentrated under vacuum to afford the title compound (100 g, 90%) as a colorless oil. H NMR (400 MHz, $CDCl_3$): δ 7.30-7.23 (m, 1H), 7.10 (dd, J=7.2, 1.2 Hz, 1H), 6.71 (t, J=7.6 Hz, 1H), 4.65 (t, J=8.8 Hz, 2H), 3.30 (t, J=8.8 Hz, 2H).

Step 3: Preparation of 7-Bromo-5-nitro-2,3-dihydrobenzofuran

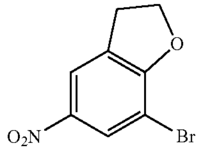

To a mixture of 7-bromo-2,3-dihydrobenzofuran (100 g, 502.41 mmol) in DCM (1 L) at 0° C. was added a mixture solution of con. aq. $H_2SO_4$ (70 mL) and con. aq. $HNO_3$ (68.6 mL). The mixture was stirred at 0° C. for 30 min. The mixture was quenched with water (500 mL), carefully adjusted pH to 9 with 25% NaOH solution and extracted with EtOAc (1 L×3). The organic layer was washed with water (1 L×3), dried over $Na_2SO_4$, filtered and concentrated to afford the tile compound (98 g, 80%) as a yellow solid. $^1$H NMR (400 MHz, $CDCl_3$): δ 8.30 (d, J=2.4 Hz, 1H), 8.04 (d, J=2.4 Hz, 1H), 4.85 (t, J=8.8 Hz, 2H), 3.43 (t, J=8.8 Hz, 1H).

Step 4: Preparation of 7-Bromo-2,3-dihydrobenzofuran-5-amine

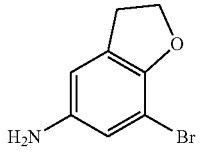

A solution of 7-bromo-5-nitro-2,3-dihydrobenzofuran (100 g, 409.77 mmol), $NH_4Cl$ (110 g, 2.05 mol) and iron powder (115 g, 2.05 mol) in water:ethanol (1:1) (2.5 L) was stirred at 80° C. for 3 hours. After cooling to room temperature, the reaction mixture was filtered and concentrated. Then the mixture was extracted with EtOAc (500 mL×3 and the organic layer was washed with water (500 mL×5). The organics were dried over $Na_2SO_4$, filtered and concentrated. The crude was dissolved in DCM (200 mL) and then petroleum ether (400 mL) was added. The solids where collected to afford the title compound (70.2 g, 80%) as a yellow solid. $^1$H NMR (400 MHz, $CDCl_3$): δ 6.64 (s, 1H), 6.53 (s, 1H), 4.59 (t, J=8.8 Hz, 2H), 3.42 (br s, 2H), 3.23 (t, J=8.8 Hz, 2H).

Step 5: Preparation of 7-(4-Isopropylphenyl)-2,3-dihydrobenzofuran-5-amine

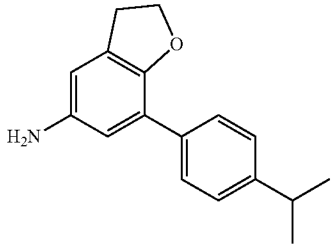 [SMILES: CC(C)c1ccc(-c2cc(N)cc3c2OCC3)cc1]

A mixture of 7-bromo-2,3-dihydrobenzofuran-5-amine (100 g, 467.16 mmol), (4-isopropylphenyl)boronic acid (78.15 g, 476.5 mmol), Pd(dppf)$Cl_2$ (17.09 g, 23.36 mmol), $Na_2CO_3$ (149 g, 1.41 mol) in 1,4-Dioxane (1 L) and water (100 mL) was stirred at 100° C. for 2 hours under a $N_2$ atmosphere. After being cooled to room temperature, the reaction mixture was filtered and the filtrate was concentrated under vacuum. The residue was purified by flash chromatography on silica gel (0-30% ethyl acetate in petroleum ether) to afford the title compound (116 g, 98%) as a yellow solid. $^1$H NMR (400 MHz, $CDCl_3$): δ 7.61 (d, J=8.0 Hz, 2H), 7.29 (d, J=8.0 Hz, 2H), 6.66 (d, J=2.4 Hz, 1H), 6.59 (d, J=2.4 Hz, 1H), 4.56 (t, J=8.8 Hz, 2H), 3.18 (t, J=8.8 Hz, 2H), 3.00-2.92 (m, 1H), 1.30 (d, J=6.8 Hz, 6H); LCMS (ESI): m/z 254.1 $(M+H)^+$.

Intermediate B

Preparation of 4-bromo-7-(4-isopropylphenyl)-2,3-dihydrobenzofuran-5-amine

The general reaction scheme was as follows:

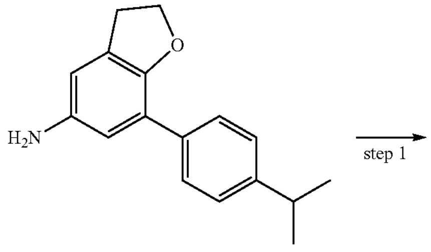

Intermediate A

-continued

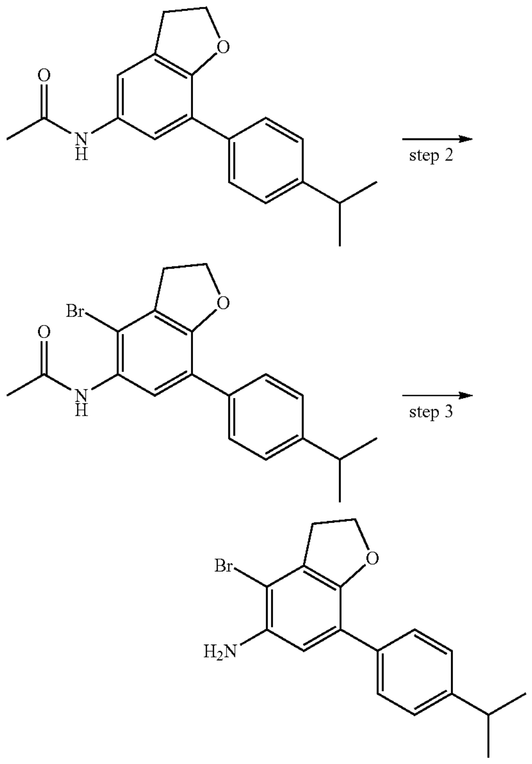

Intermediate B

Step 1: Preparation of N-(7-(4-isopropylphenyl)-2,3-dihydrobenzofuran-5-yl)acetamide

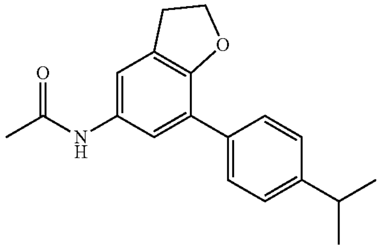

To a solution of 7-(4-isopropylphenyl)-2,3-dihydrobenzofuran-5-amine (150 g, 592.09 mmol) and TEA (99.03 mL, 710.51 mmol) in DCM (1.5 L) was added acetyl chloride (46.31 mL, 651.3 mmol) at −78° C. dropwise. The reaction was stirred at −78° C. for 2 hours. The reaction was quenched with water (200 mL) and extracted with dichloromethane (1 L×2). The combined organic layers were dried over $Na_2SO_4$ and concentrated. The residue was triturated with DCM and hexanes (1:10) and filtered to afford the title compound (222 g, 83%) as a white solid. $^1H$ NMR (400 MHz, $CDCl_3$): δ 7.58 (d, J=8.0 Hz, 2H), 7.48 (s, 1H), 7.25 (d, J=8.0 Hz, 2H), 7.21 (s, 1H), 7.19 (s, 1H), 4.60 (t, J=8.8 Hz, 2H), 3.24 (t, J=8.8 Hz, 2H), 2.96-2.90 (m, 1H), 2.16 (s, 3H), 1.27 (d, J=6.8 Hz, 6H); LCMS (ESI): m/z 296.1 $(M+H)^+$.

Step 2: Preparation of N-(4-bromo-7-(4-isopropylphenyl)-2,3-dihydrobenzofuran-5-yl)acetamide

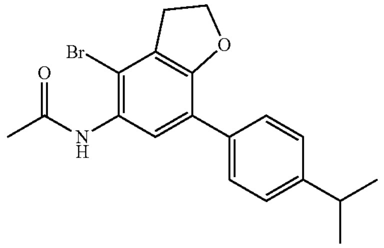

A mixture of N-(7-(4-isopropylphenyl)-2,3-dihydrobenzofuran-5-yl)acetamide (100 g, 338.55 mmol) and bromine (19.08 mL, 372.4 mmol) in Acetic acid (500 mL) was stirred at 50° C. for 10 min. The reaction mixture was diluted with water (1 L) and the pH was adjusted to 7 with a 2M NaOH aqueous solution. The mixture was extracted with EtOAc (1 L×3), the combined organic layers were dried over $Na_2SO_4$ and concentrated. The residue was dissolved in DCM (200 mL) and MTBE was added until a precipitate appears. The heterogenous mixture was cooled to 0° C. for 20 minutes. Then the precipitate was filtered to afford the title compound (38 g, 30%) as a white solid. $^1H$ NMR (400 MHz, $CDCl_3$): δ 8.09 (s, 1H), 7.62 (d, J=8.0 Hz, 2H), 7.27 (d, J=8.0 Hz, 2H), 4.65 (t, J=8.8 Hz, 2H), 3.28 (t, J=8.8 Hz, 2H), 2.93-2.88 (m, 1H), 2.22 (s, 3H), 1.28 (d, J=6.8 Hz, 6H); LCMS (ESI): m/z 374.1 $(M+H)^+$.

Step 3: Preparation of 4-bromo-7-(4-isopropylphenyl)-2,3-dihydrobenzofuran-5-amine

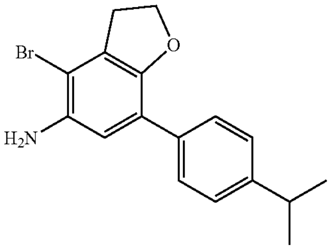 [SMILES: CC(C)c1ccc(-c2cc(N)c(Br)c3c2OCC3)cc1]

A mixture of 12 M aqueous hydrochloric acid (334 mL, 4.01 mol) and N-(4-bromo-7-(4-isopropylphenyl)-2,3-dihydrobenzofuran-5-yl)acetamide (150 g, 400.78 mmol) in ethanol (1.5 L) was stirred at 80° C. for 5 hours. After cooling to room temperature, the solvent was removed under reduced pressure. The residue was diluted with water and the pH was adjusted to 9 with a 2 M NaOH aqueous solution. The mixture was extracted with EtOAc (1 L×3), then the combined organic layers were dried over $Na_2SO_4$ and evaporated to afford the title compound (124 g, 93%) as a brown solid. $^1H$ NMR (400 MHz, $CDCl_3$): δ 7.54 (d, J=8.0 Hz, 2H), 7.25 (d, J=8.0 Hz, 2H), 6.72 (s, 1H), 4.58 (t, J=8.8 Hz, 2H), 3.78 (s, 2H), 3.23 (t, J=8.8 Hz, 2H), 2.93-2.89 (m, 1H), 1.25 (d, J=6.8 Hz, 6H); LCMS (ESI): m/z 332.1 $(M+H)^+$.

Intermediate C

Preparation of 5-amino-7-(4-isopropylphenyl)-2,3-dihydrobenzofuran-4-carbonitrile The general reaction scheme was as follows:

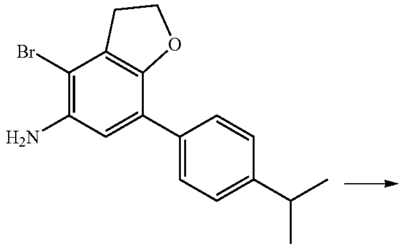

Intermediate B

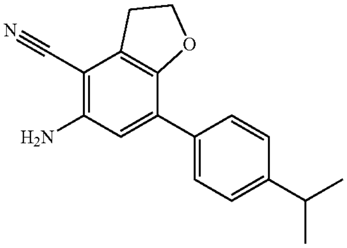

Intermediate C

A mixture of t-BuXPhos Pd G3 (19.0 g, 23.92 mmol), $Zn(CN)_2$ (176.7 g, 1.51 mol) and 4-bromo-7-(4-isopropylphenyl)-2,3-dihydrobenzofuran-5-amine (100 g, 301 mmol) in N,N-dimethylacetamide (1 L) was stirred at 140° C. for 16 hours. After cooling to room temperature, the reaction solution was added into with water (2 L). The mixture solution was filtered and the filter cake was washed with water (2 L). The filter cake was dissolved in EtOAc (2 L), dried over $MgSO_4$, filtered and concentrated. The residue was purified by flash chromatography silica gel (0-50% ethyl acetate in petroleum ether) to afford 80 g crude product. The crude product was triturated with DCM: hexanes (1:10) and filtered to afford the title compound (59 g, 70%) as a yellow solid. $^1H$ NMR (400 MHz, $CDCl_3$): δ 7.59 (dd, J=8.0, 1.6 Hz, 2H), 7.30 (d, J=8.0 Hz, 2H), 6.68 (s, 1H), 4.64 (t, J=8.8 Hz, 2H), 4.08 (br s, 2H), 3.36 (t, J=8.8 Hz, 2H), 2.97-2.95 (m, 1H), 1.28 (d, J=6.8 Hz, 6H); LCMS (ESI): m/z 279.1 $(M+H)^+$.

Intermediate D

Preparation of (5-amino-7-(4-isopropylphenyl)-2,3-dihydrobenzofuran-4-yl)methanol The general reaction scheme was as follows:

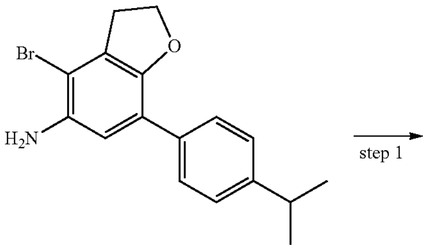

Intermediate B

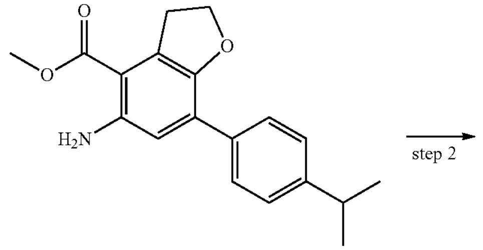

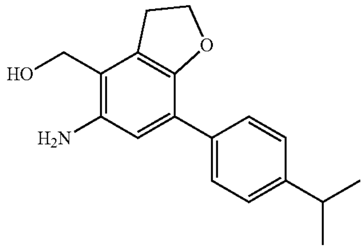

Intermediate D

Step 1: Preparation of methyl 5-amino-7-(4-isopropylphenyl)-2,3-dihydrobenzofuran-4-carboxylate

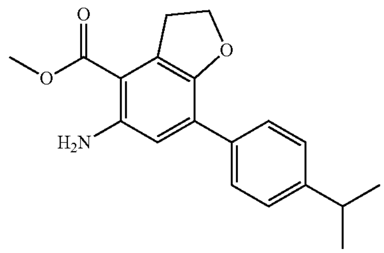 [SMILES: COC(=O)c1c(N)cc(-c2ccc(C(C)C)cc2)c2c1CCO2]

A mixture of 4-bromo-7-(4-isopropylphenyl)-2,3-dihydrobenzofuran-5-amine (5.0 g, 15.1 mmol), $Pd(dppf)Cl_2$ (2.2 g, 3.0 mmol), TEA (10.5 mL, 75.3 mmol) in methanol (25 mL) and DMF (25 mL) was stirred at 100° C. for 16 hours under an atmosphere of CO (15 psi). The solvent was removed under vacuum and the residue was purified by chromatography on silica gel (0-10% EtOAc in petroleum ether) to afford the title (2.3 g, 49%) as a yellow solid. $^1H$ NMR (400 MHz, $CDCl_3$): δ 7.61 (d, J=8.0 Hz, 2H), 7.29 (d, J=8.0 Hz, 2H), 6.65 (s, 1H), 5.38 (s, 2H), 4.54 (t, J=8.8 Hz, 2H), 3.89 (s, 3H), 3.51 (t, J=8.8 Hz, 2H), 2.99-2.88 (m, 1H), 1.28 (d, J=6.8 Hz, 6H).

Step 2: Preparation of (5-Amino-7-(4-isopropylphenyl)-2,3-dihydrobenzofuran-4-yl)methanol

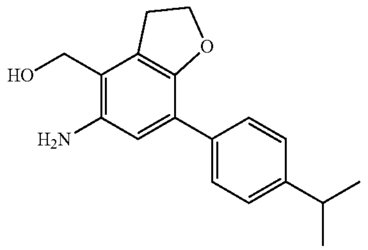 [SMILES: CC(C)c1ccc(-c2cc(N)c(CO)c3c2OCC3)cc1]

To a mixture of methyl 5-amino-7-(4-isopropylphenyl)-2,3-dihydrobenzofuran-4-carboxylate (1.4 g, 4.5 mmol) in THF (20 mL) was added $LiAlH_4$ (170 mg, 4.5 mmol) at 0° C. slowly. The reaction mixture was stirred for 2 hours at 0° C. The reaction mixture was quenched with sat. aq. $KHSO_4$ (1.0 mL). The reaction mixture was dried over $MgSO_4$, filtered and concentrated under vacuum to afford the title compound (1.0 g, 79%) as a yellow solid. $^1$H NMR (400 MHz, DMSO-$d_6$): δ 7.52 (d, J=8.0 Hz, 2H), 7.25 (d, J=8.0 Hz, 2H), 6.62 (s, 1H), 4.92 (t, J=5.2 Hz, 1H), 4.57 (s, 2H), 4.49-4.37 (m, 4H), 3.15 (t, J=8.8 Hz, 2H), 2.93-2.84 (m, 1H), 1.21 (d, J=6.8 Hz, 6H). LCMS (ESI): m/z 284.2 $(M+H)^+$.

Intermediate E

Preparation of 5-amino-7-chloro-2,3-dihydrobenzofuran-4-carbonitrile

The general reaction scheme was as follows:

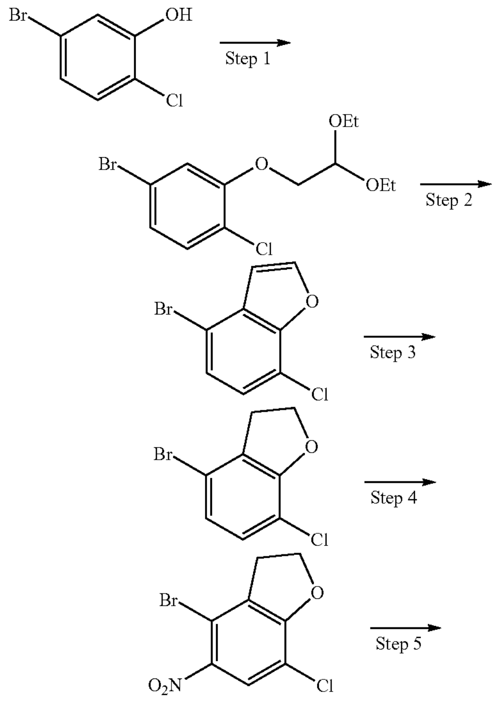

-continued

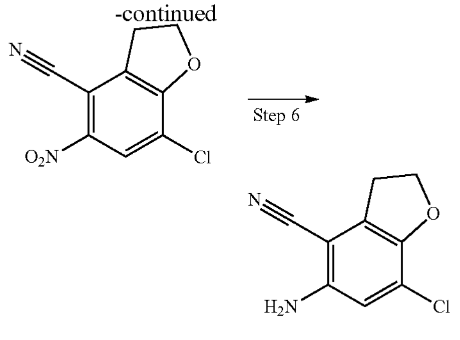

Intermediate E

Step 1: Preparation of 4-bromo-1-chloro-2-(2,2-diethoxyethoxy)benzene

A mixture solution of 5-bromo-2-chloro-phenol (90 g, 433.8 mmol), $K_2CO_3$ (90 g, 650.8 mmol) and 2-bromo-1,1-diethoxyethane (94 g, 477.2 mmol) in DMF (900 mL) was heated at 135° C. for 16 hours. The reaction mixture was concentrated and diluted with EtOAc (600 mL) and washed with brine (500 mL×5). The organic layer was dried over $Na_2SO_4$, filtered and concentrated to afford the title compound (140 g, 99%) as a brown oil. The crude was used for next step without further purification. $^1$H NMR (400 MHz, $CDCl_3$): δ 7.22 (d, J=8.4 Hz, 1H), 7.10 (d, J=2.0 Hz, 1H), 7.04 (dd, J=8.4, 2.0 Hz, 1H), 4.87 (t, J=5.2 Hz, 1H), 4.05 (d, J=5.2 Hz, 2H), 3.87-3.76 (m, 2H), 3.73-3.62 (m, 2H), 1.26 (t, J=7.2 Hz, 6H).

Step 2: Preparation of 4-bromo-7-chlorobenzofuran

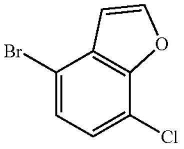 [SMILES: Clc1ccc(Br)c2ccoc12]

The reaction mixture of 4-bromo-1-chloro-2-(2,2-diethoxyethoxy)benzene (140 g, 432.6 mmol) and PPA (140 g) in toluene (1.4 L) was heated at 110° C. for 5 hours. The reaction mixture was quenched with sat. aq. $NaHCO_3$ and extracted with EtOAc (1.0 L×3). The combined organic layers were dried over $Na_2SO_4$, filtered and concentrated under vacuum. The residue was purified by chromatography on silica gel (100% petroleum ether) to afford the title compound (44.0 g, 44%) as a white solid. $^1$H NMR (400 MHz, $CDCl_3$): δ 7.74 (d, J=2.0 Hz, 1H), 7.35 (d, J=8.4 Hz, 1H), 7.20 (d, J=8.4 Hz, 1H), 6.87 (d, J=2.0 Hz, 1H).

Step 3: Preparation of 4-bromo-7-chloro-2,3-dihydrobenzofuran

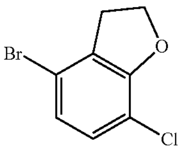 [SMILES: Clc1ccc(Br)c2c1OCC2]

A mixture of Rh/C (10.0 g, 95.0 mmol) and 4-bromo-7-chlorobenzofuran (44.0 g, 190 mmol) in EtOH (440 mL) was stirred at room temperature for 2 hours under atmosphere of $H_2$ (15 psi). The reaction was filtered and the filtrate was concentrated. The residue was purified by chromatography on silica gel (100% petroleum ether) to afford the title compound (33.0 g, 74%) as a white solid. $^1$H NMR (400 MHz, $CDCl_3$): δ 7.01 (d, J=8.8 Hz, 1H), 6.93 (d, J=8.8 Hz, 1H), 4.72 (t, J=8.8 Hz, 2H), 3.30 (t, J=8.8 Hz, 2H).

Step 4: Preparation of 4-bromo-7-chloro-5-nitro-2,3-dihydrobenzofuran

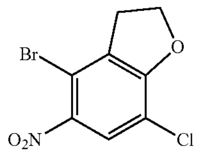 [SMILES: O=[N+]([O-])c1cc(Cl)c2c(c1Br)CCO2]

To the mixture of 4-bromo-7-chloro-2,3-dihydrobenzofuran (30.0 g, 128.5 mmol) in TFA (300 mL) was added $HNO_3$ (11.4 mL, 257.0 mmol) at 0° C. dropwise slowly. The reaction mixture was stirred for 2 hours. At this point, the reaction mixture was quenched with aq. 1M NaOH and the mixture was extracted with EtOAc (1.0 L×3). The combined organic layers were dried over $Na_2SO_4$, filtered and concentrated. The residue was purified by chromatography on silica gel (0-10% EtOAc in petroleum ether) to afford the title compound (27.0 g, 76%) as a white solid. $^1$H NMR (400 MHz, $CDCl_3$): δ 7.97 (s, 1H), 4.88 (t, J=8.8 Hz, 2H), 3.42 (t, J=8.8 Hz, 2H).

Step 5: Preparation of 7-chloro-5-nitro-2,3-dihydrobenzofuran-4-carbonitrile

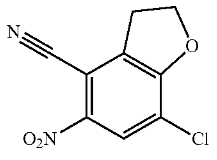 [SMILES: N#Cc1c([N+](=O)[O-])cc(Cl)c2c1CCO2]

To a solution of 4-bromo-7-chloro-5-nitro-2,3-dihydrobenzofuran (12.0 g, 43.1 mmol) in DMF (100 mL) was added CuCN (8.0 g, 86.2 mmol). The mixture was stirred at 80° C. for 16 hours. The reaction mixture was quenched with water (200 mL) and extracted with EtOAC (500 mL×2). The combined organic layers were washed with brine (300 mL×2), dried over $Na_2SO_4$, filtered and concentrated under vacuum. The residue was purified by chromatography on silica gel (0-10% EtOAc in petroleum ether) to afford the title compound (5.3 g, 55%) as a white solid. $^1$H NMR (400 MHz, $CDCl_3$): δ 8.26 (s, 1H), 4.98 (t, J=8.8 Hz, 2H), 3.64 (t, J=8.8 Hz, 2H).

Step 6: 5-amino-7-chloro-2,3-dihydrobenzofuran-4-carbonitrile

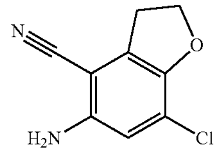

To a mixture of 7-chloro-5-nitro-2,3-dihydrobenzofuran-4-carbonitrile (5.3 g, 23.6 mmol) in HOAc (50 mL) was added Fe (6.6 g, 118.0 mmol). The mixture was stirred at 80° C. for 2 hours. The reaction was adjusted to pH=8 with sat. aq. $NaHCO_3$ and extracted with EtOAc (300 mL×2). The combined organics were dried over $Na_2SO_4$, filtered and concentrated under vacuum. The residue was purified by flash chromatography gel (0-10% EtOAc in petroleum ether) to afford the title compound (4.0 g, 87%) as a yellow solid. $^1$H NMR (400 MHz, $CDCl_3$): δ 6.58 (s, 1H), 4.68 (t, J=8.8 Hz, 2H), 4.10 (s, 2H), 3.38 (t, J=8.8 Hz, 2H). LCMS (ESI): m/z 195.0 $(M+H)^+$.

Example 1

Preparation of 2-(((7-(4-Isopropylphenyl)-2,3-dihydrobenzofuran-5-yl)amino)methyl)acrylic acid The general reaction scheme was as follows:

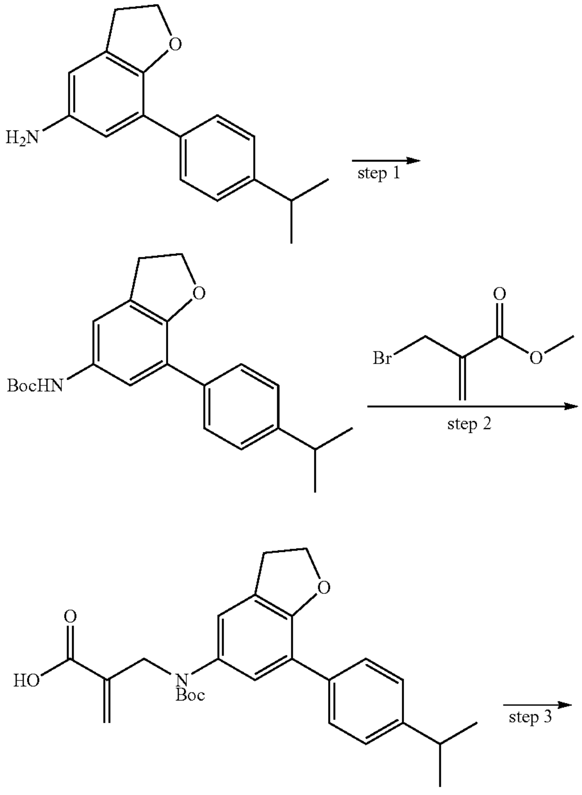

-continued

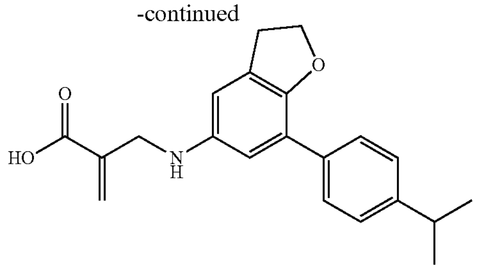

Step 1: Preparation of tert-Butyl (7-(4-isopropylphenyl)-2,3-dihydrobenzofuran-5-yl)carbamate

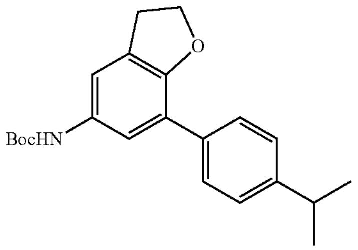 [SMILES: CC(C)c1ccc(-c2cc(NC(=O)OC(C)(C)C)cc3c2OCC3)cc1]

To a solution of 7-(4-isopropylphenyl)-2,3-dihydrobenzofuran-5-amine (500 mg, 1.97 mmol) in THF (6 mL) was added TEA (0.55 mL, 3.95 mmol) and $Boc_2O$ (474 mg, 2.17 mmol). The mixture solution was stirred at room temperature for 16 hours and then the reaction mixture was concentrated in vacuo. The residual was purified by column chromatography on silica gel (0-30% EtOAc in petroleum ether) to afford the title compound (632.5 mg, 91%) as a yellow solid. $^1H$ NMR (400 MHz, $CD_3OD$): δ 7.60 (d, J=8.0 Hz, 2H), 7.25-7.23 (m, 4H), 4.58 (t, J=8.8 Hz, 2H), 3.22 (t, J=8.8 Hz, 2H), 2.95-2.88 (m, 1H), 1.52 (s, 9H), 1.27 (d, J=6.8 Hz, 6H). LCMS (ESI): m/z 376.0 $(M+Na)^+$.

Step 2: Preparation of 2-(((tert-Butoxycarbonyl)(7-(4-isopropylphenyl)-2,3-dihydrobenzofuran-5-yl)amino)methyl)acrylic acid

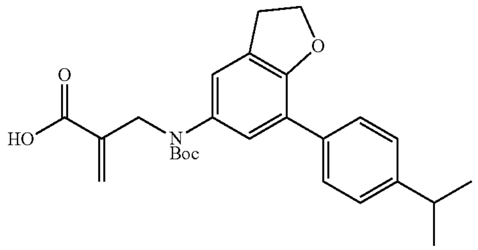

To a solution of tert-butyl (7-(4-isopropylphenyl)-2,3-dihydrobenzofuran-5-yl)carbamate (430.0 mg, 1.22 mmol) in DMF (8 mL) was added NaH (60% in mineral oil, 58.4 mg, 1.46 mmol) and methyl 2-(bromomethyl)acrylate (262 mg, 1.46 mmol) slowly at 0° C. under a $N_2$ atmosphere. The reaction mixture was stirred at room temperature for 16 hours. The reaction mixture was then quenched with water (30 mL) and extracted with ethyl acetate (30 mL×3). The organic layers were combined and washed with brine (45 mL×2), dried over $Na_2SO_4$ and concentrated. The residue was purified by column chromatography on silica gel (0-10% EtOAc in petroleum ether) to afford the title compound (342 mg, 64%) as a yellow oil. LCMS (ESI): m/z 460.1 $(M+Na)^+$.

Step 3: Preparation of 2-(((7-(4-Isopropylphenyl)-2,3-dihydrobenzofuran-5-yl)amino)methyl)acrylic acid

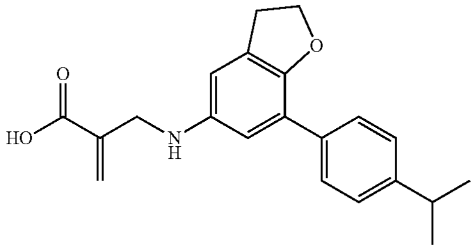

To a mixture of 2-(((tert-butoxycarbonyl)(7-(4-isopropylphenyl)-2,3-dihydrobenzofuran-5-yl)amino)methyl)acrylic acid (340 mg, 0.78 mmol) in DCM (3 mL) was added TFA (1.0 mL, 7.45 mmol) at room temperature. The reaction solution was stirred at room temperature for 2 hours at which point the reaction mixture was concentrated. The residue was purified by prep-HPLC (Boston Green ODS 150*30 mm*5 um; water (0.2% FA)-ACN; 45/75) and prep-TLC (10% methanol in dichloromethane) to afford the title compound (8.4 mg, 3%) as a white solid. $^1H$ NMR (400 MHz, DMSO-$d_6$): δ7.52 (d, J=8.0 Hz, 2H), 7.25 (d, J=8.0 Hz, 2H), 6.47 (s, 1H), 6.44 (s, 1H), 5.88 (s, 1H), 5.43 (s, 1H), 4.41 (t, J=8.4 Hz, 2H), 3.80 (s, 2H), 3.10 (t, J=8.4 Hz, 2H), 2.92-2.86 (m, 1H), 1.22 (d, J=6.4 Hz, 6H); LCMS (ESI): m/z 337.9 $(M+H)^+$.

Example 2

Preparation of 2-(((7-(4-Isopropylphenyl)-2,3-dihydrobenzofuran-5-yl)amino)methyl)acrylamide The general reaction scheme was as follows:

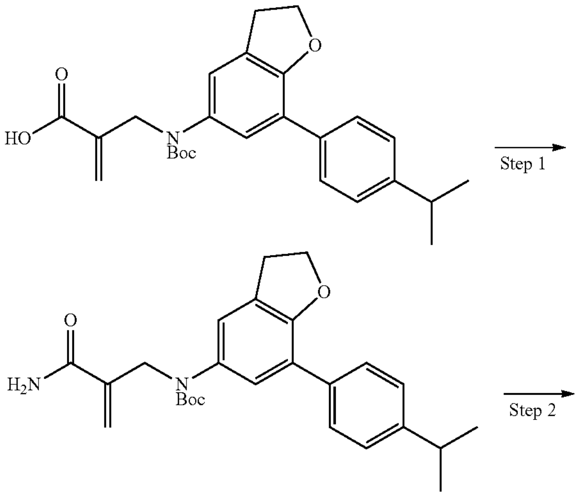

-continued

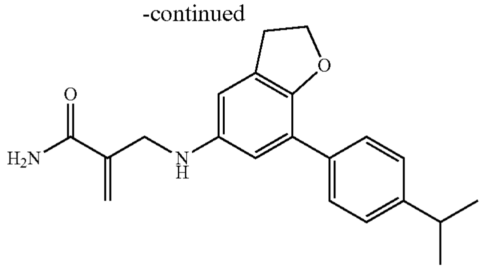

Step 1: Preparation of tert-Butyl (2-carbamoylallyl) (7-(4-isopropylphenyl)-2,3-dihydrobenzofuran-5-yl) carbamate

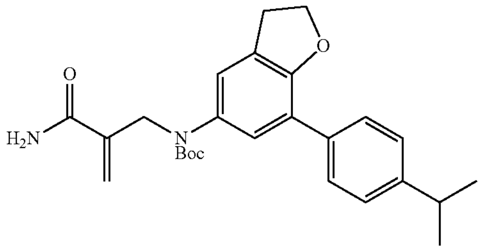

To a mixture of 2-(((tert-butoxycarbonyl)(7-(4-isopropylphenyl)-2,3-dihydrobenzofuran-5-yl)amino)methyl)acrylic acid (342.0 mg, 0.78 mmol), ammonium chloride (47 mg, 0.86 mmol), DIPEA (0.41 mL, 2.35 mmol) in DMF (8 mL) was added HATU (447 mg, 1.18 mmol). The reaction solution was stirred at room temperature for 16 hours. The reaction solution was diluted with ethyl acetate (50 mL), washed with brine (30 mL), dried over $Na_2SO_4$ and concentrated to afford the title compound (549 mg) as a yellow oil crude, which was used for the next step directly. LCMS (ESI): m/z 337.1 $(M\text{-}Boc)^+$.

Step 2: Preparation of 2-(((7-(4-Isopropylphenyl)-2,3-dihydrobenzofuran-5-yl)amino)methyl)acrylamide

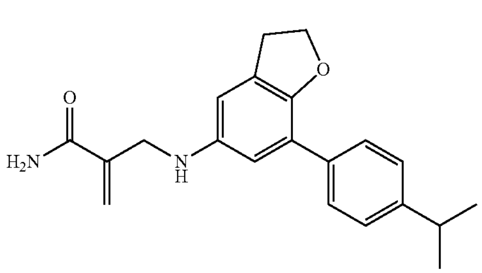 [SMILES: C=C(CNc1cc2c(c(-c3ccc(C(C)C)cc3)c1)OCC2)C(N)=O]

To a mixture of tert-butyl (2-carbamoylallyl)(7-(4-isopropylphenyl)-2,3-dihydrobenzofuran-5-yl)carbamate (340 mg, 0.78 mmol) and TFA (1.0 mL, 7.45 mmol) in dichloromethane (3 mL) was stirred at room temperature for 1 hour at which point the reaction mixture was concentrated. The residue was purified by prep-HPLC (Welch Xtimate C18 150*25 mm*5 um; water (0.2% FA)-CAN; 40/70) and prep-TLC (5% methanol in dichloromethane) to afford the title compound (61.9 mg, 23%) as a yellow solid. $^1H$ NMR (400 MHz, DMSO-$d_6$): δ 7.55 (s, 1H), 7.52 (d, J=8.0 Hz, 2H), 7.25 (d, J=8.0 Hz, 2H), 7.09 (s, 1H), 6.49 (d, J=2.4 Hz, 1H), 6.45 (d, J=2.4 Hz, 1H), 5.79 (s, 1H), 5.48 (s, 1H), 5.46 (s, 1H), 4.41 (t, J=8.4 Hz, 2H), 3.84 (d, J=3.2 Hz, 2H), 3.10 (t, J=8.4 Hz, 2H), 2.93-2.84 (m, 1H), 1.21 (d, J=6.8 Hz, 6H); LCMS (ESI): m/z 336.9 $(M+H)^+$.

Example 3

Preparation of 2-(((4-Cyano-7-(4-isopropylphenyl)-2,3-dihydrobenzofuran-5-yl)amino) methyl)acrylic acid The general reaction scheme was as follows:

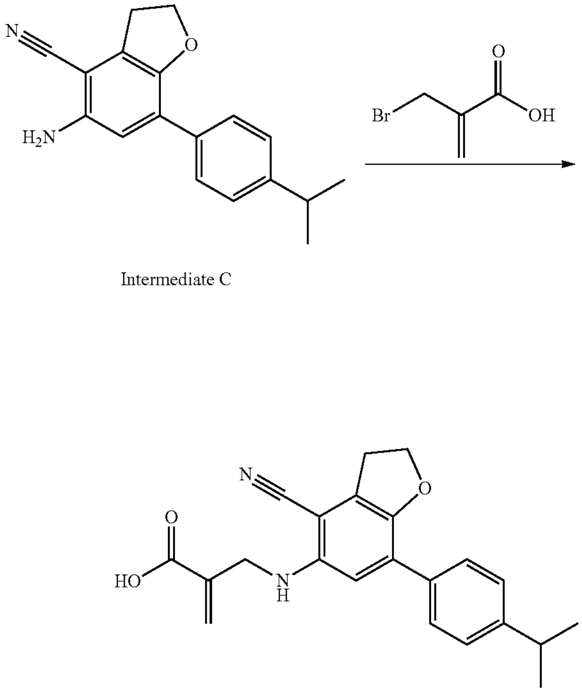

To a mixture of 5-amino-7-(4-isopropylphenyl)-2,3-dihydrobenzofuran-4-carbonitrile (15.0 g, 53.89 mmol) in N,N-Dimethylformamide (150 mL) was added 2-(bromomethyl) acrylic acid (8.89 g, 53.89 mmol). The mixture was stirred at 80° C. for 2 hours at which point the reaction mixture was purified by prep-HPLC (SANPONT C18, 250*80 mm*10 um, 100A, water (0.225% FA)-ACN, 40%-80%) to afford the title compound (8.2 g, 42%) as a yellow solid. $^1H$ NMR (400 MHz, DMSO-$d_6$): δ 12.75 (s, 1H), 7.55 (d, J=8.0 Hz, 2H), 7.31 (d, J=8.0 Hz, 2H), 6.46 (s, 1H), 6.11 (s, 1H), 6.01 (t, J=6.0 Hz, 1H), 5.67 (s, 1H), 4.55 (t, J=8.8 Hz, 2H), 4.05 (d, J=5.2 Hz, 2H), 3.30 (t, J=8.8 Hz, 2H), 2.93-2.90 (m, 1H), 1.22 (d, J=6.8 Hz, 6H); LCMS (ESI): m/z 363.2 $(M+H)^+$.

Example 4

Preparation of 2-(((4-Cyano-7-(4-isopropylphenyl)-2,3-dihydrobenzofuran-5-yl)amino)methyl)acrylamide The general reaction scheme was as follows:

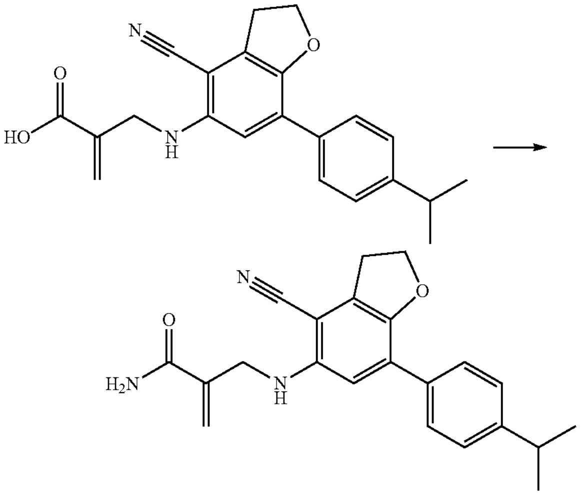

To a mixture of 2-(((4-cyano-7-(4-isopropylphenyl)-2,3-dihydrobenzofuran-5-yl)amino)methyl)acrylic acid (200 mg, 0.49 mmol), $NH_4Cl$ (78 mg, 1.46 mmol), DIPEA (0.34 mL, 1.95 mmol) in N,N-Dimethylformamide (3 mL) was added HATU (370 mg, 0.97 mmol). The resulting mixture was stirred at room temperature for 16 hours at which point the reaction mixture was purified by prep-HPLC (Welch Xtimate C18 150*25 mm*5 um, water (0.2% FA)-ACN, 52%-82%) to afford the title compound (133.93 mg, 76%) as a light yellow solid. $^1$H NMR (400 MHz, DMSO-$d_6$): δ 7.61 (s, 1H), 7.56 (d, J=8.4 Hz, 2H), 7.30 (d, J=8.4 Hz, 2H), 7.15 (s, 1H), 6.48 (s, 1H), 5.98 (t, J=5.6 Hz, 1H), 5.81 (s, 1H), 5.45 (s, 1H), 4.54 (t, J=8.8 Hz, 2H), 4.01 (d, J=5.6 Hz, 2H), 3.29 (d, J=8.8 Hz, 2H), 2.93-2.85 (m, 1H), 1.21 (d, J=6.8 Hz, 6H); LCMS (ESI): m/z 362.2 $(M+H)^+$.

Example 5

Preparation of 2-(((4-cyano-7-(4-isopropylphenyl)-2,3-dihydrobenzofuran-5-yl)amino)methyl)-N-methylacrylamide The general reaction scheme was as follows:

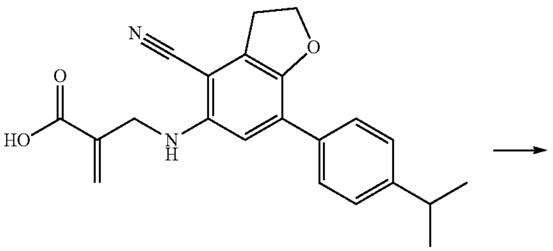

-continued

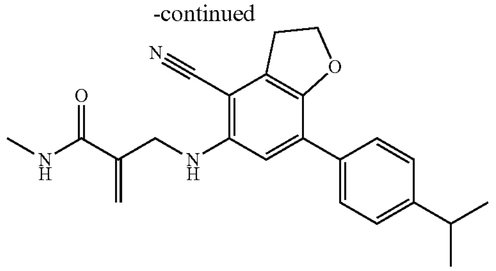

To a mixture of 2-(((4-cyano-7-(4-isopropylphenyl)-2,3-dihydrobenzofuran-5-yl)amino)methyl)acrylic acid (200 mg, 0.49 mmol), DIPEA (0.34 mL, 1.95 mmol), methanamine hydrochloride (99 mg, 1.46 mmol) in DMF (3 mL) was added HATU (370 mg, 0.97 mmol). The resulting mixture was stirred at room temperature for 16 hours at which point the reaction mixture was purified by prep-HPLC (Welch Xtimate C18 150*25 mm*5 um, water (0.2% FA)-ACN, 56%-86%) to afford the title compound (118.56 mg, 67%) as a light yellow solid. $^1$H NMR (400 MHz, DMSO-$d_6$): δ 8.08 (d, J=4.8 Hz, 1H), 7.56 (d, J=8.4 Hz, 2H), 7.30 (d, J=8.4 Hz, 2H), 6.48 (s, 1H), 6.00 (t, J=5.2 Hz, 1H), 5.71 (s, 1H), 5.41 (s, 1H), 4.54 (t, J=8.8 Hz, 2H), 4.03 (d, J=5.2 Hz, 2H), 3.29 (t, J=8.8 Hz, 2H), 2.93-2.83 (m, 1H), 2.65 (d, J=4.8 Hz, 3H), 1.21 (d, J=6.8 Hz, 6H); LCMS (ESI): m/z 376.2 $(M+H)^+$.

Example 6

Preparation of 2-(((4-cyano-7-(4-isopropylphenyl)-2,3-dihydrobenzofuran-5-yl)amino)methyl)-N,N-dimethylacrylamide The general reaction scheme was as follows:

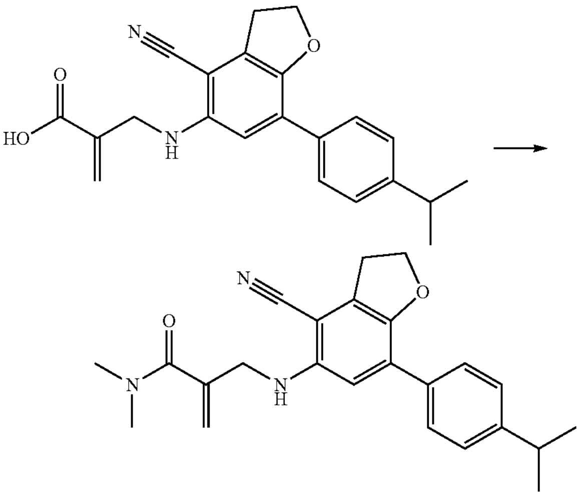

To a mixture of 2-(((4-cyano-7-(4-isopropylphenyl)-2,3-dihydrobenzofuran-5-yl)amino)methyl)acrylic acid (200 mg, 0.49 mmol), N,N-diisopropylethylamine (0.34 mL, 1.95 mmol), dimethylamine hydrochloride (119 mg, 1.46 mmol) in DMF (3 mL) was added HATU (370 mg, 0.97 mmol). The resulting mixture was stirred at room temperature for 16 hours at which point the reaction mixture was purified by prep-HPLC (Welch Xtimate C18 150*25 mm*5 um, water (0.2% FA)-ACN, 60%-90%) to afford the title (110 mg, 63%) as a light yellow solid. $^1$H NMR (400 MHz, DMSO-$d_6$): δ 7.60 (d, J=8.4 Hz, 2H), 7.31 (d, J=8.4 Hz, 2H), 6.64 (s, 1H), 6.15 (t, J=3.6 Hz, 1H), 5.32 (s, 1H), 5.14 (s, 1H), 4.55 (t, J=8.8 Hz, 2H), 3.99 (d, J=3.6 Hz, 2H), 3.29 (t, J=8.8 Hz, 2H), 2.94 (s, 3H), 2.93-2.89 (m, 1H), 2.85 (s, 3H), 1.22 (d, J=6.8 Hz, 6H); LCMS (ESI): m/z 390.3 $(M+H)^+$.

Example 7

Preparation of 2-(((4-cyano-7-(4-isopropylphenyl)-2,3-dihydrobenzofuran-5-yl)(methyl)amino)methyl) acrylic acid The general reaction scheme was as follows:

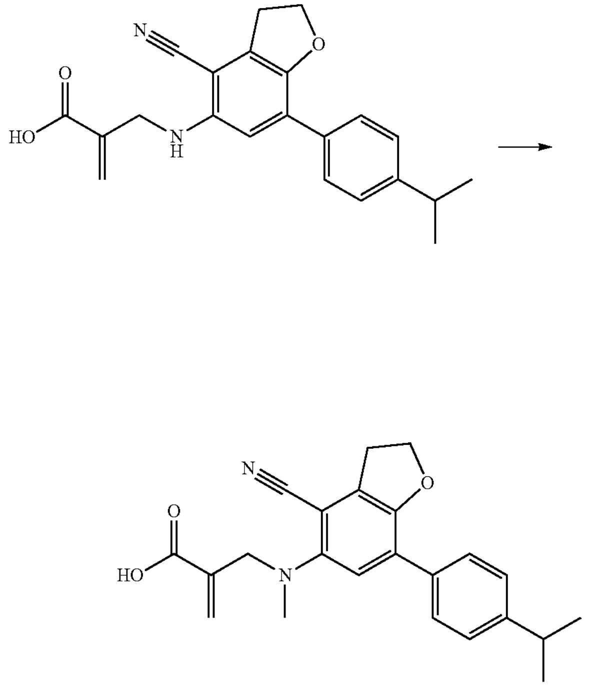

To a mixture of 2-(((4-cyano-7-(4-isopropylphenyl)-2,3-dihydrobenzofuran-5-yl)amino)methyl)acrylic acid (200 mg, 0.55 mmol) and a drop of HOAc in 1,2-dichloroethane (3 mL) was added paraformaldehyde (448 mg, 5.52 mmol) and $NaBH(OAc)_3$ (585 mg, 2.76 mmol). The resulting mixture was stirred at room temperature for 16 hours. The reaction mixture was concentrated and the residue was purified by prep-HPLC (Welch Xtimate C18 150*25 mm*5 um, water (0.2% FA)-ACN, 65%-95%) to afford the title compound (90.46 mg, 44%) as a light yellow solid. $^1$H NMR (400 MHz, DMSO-$d_6$): δ 12.62 (s, 1H), 7.62 (d, J=8.4 Hz, 2H), 7.32 (d, J=8.4 Hz, 2H), 6.98 (s, 1H), 6.20 (s, 1H), 5.77 (s, 1H), 4.62 (t, J=8.8 Hz, 2H), 4.01 (s, 2H), 3.33 (t, J=8.8 Hz, 2H), 2.96-2.86 (m, 1H), 2.83 (s, 3H), 1.22 (d, J=6.8 Hz, 6H); LCMS (ESI): m/z 377.2 $(M+H)^+$.

Example 8

Preparation of methyl 2-(((4-cyano-7-(4-isopropylphenyl)-2,3-dihydrobenzofuran-5-yl)amino) methyl)acrylate The general reaction scheme was as follows:

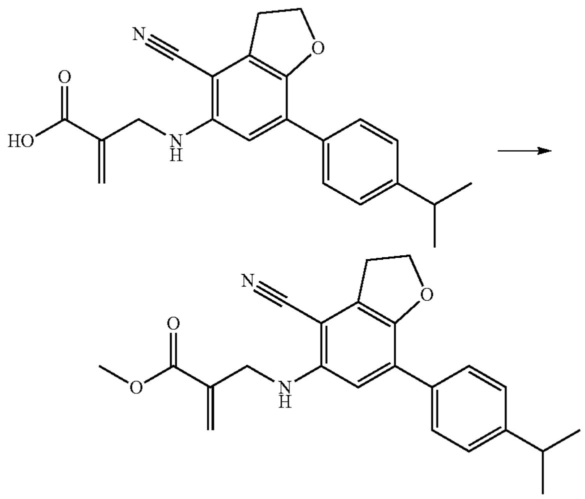

To a mixture of 2-(((4-cyano-7-(4-isopropylphenyl)-2,3-dihydrobenzofuran-5-yl)amino)methyl)acrylic acid (100 mg, 0.28 mmol), methanol (27 mg, 0.83 mmol) in DMF (2 mL) was added HATU (315 mg, 0.83 mmol). The mixture was stirred at room temperature for 2 hours at which point the reaction mixture was purified by prep-HPLC (Welch Xtimate C18 150*25 mm*5 um, water (0.2% FA)-ACN, 65%-95%) to afford the title compound (26 mg, 25%) as a yellow solid. $^1$H NMR (400 MHz, DMSO-$d_6$): δ 7.55 (d, J=8.4 Hz, 2H), 7.31 (d, J=8.4 Hz, 2H), 6.46 (s, 1H), 6.15 (d, J=1.2 Hz, 1H), 6.05 (t, J=6.0 Hz, 1H), 5.71 (s, 1H), 4.55 (t, J=8.8 Hz, 2H), 4.08 (d, J=6.0 Hz, 2H), 3.73 (s, 3H), 3.30 (t, J=8.8 Hz, 2H), 2.94-2.88 (m, 1H), 1.22 (d, J=6.8 Hz, 6H); LCMS (ESI): m/z 377.1 $(M+H)^+$.

Example 9

Preparation of 2-(((4-cyano-7-(4-isopropylphenyl)-2,3-dihydrobenzofuran-5-yl)amino)methyl)-N-hydroxyacrylamide The general reaction scheme was as follows:

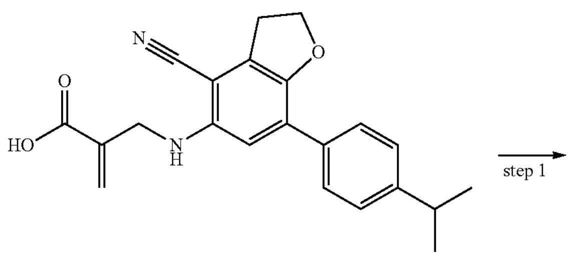

-continued

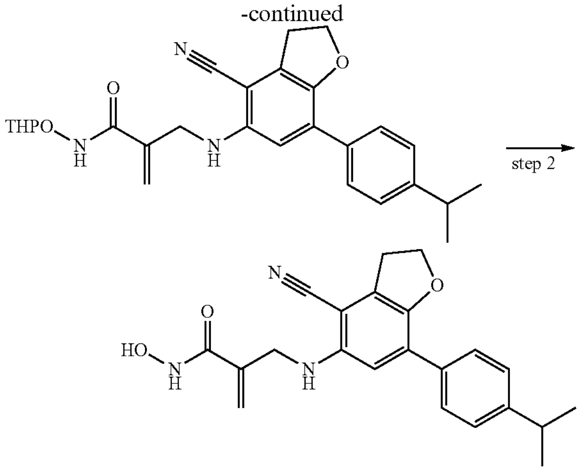

Step 1: Preparation of 2-(((4-Cyano-7-(4-isopropylphenyl)-2,3-dihydrobenzofuran-5-yl)amino)methyl)-N-((tetrahydro-2H-pyran-2-yl)oxy)acrylamide

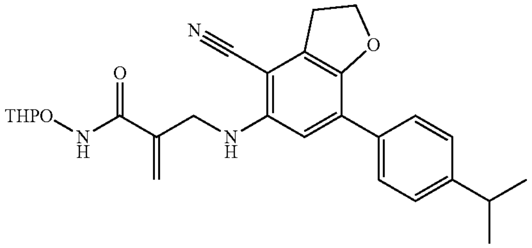

To a mixture of 2-(((4-cyano-7-(4-isopropylphenyl)-2,3-dihydrobenzofuran-5-yl)amino)methyl)acrylic acid (200 mg, 0.49 mmol), triethylamine (0.27 mL, 1.95 mmol), 0-(tetrahydro-2H-pyran-2-yl)hydroxylamine (171 mg, 1.46 mmol) in DMF (3 mL) was added BOP (431 mg, 0.97 mmol). The resulting mixture was stirred at room temperature for 16 hours. At which point, the reaction mixture was quenched with water (20 mL), extracted with EtOAc (20 mL), the organic layer was dried over $Na_2SO_4$, filtered and concentrated. The residue was purified by prep-TLC (40% EtOAc in petroleum ether) to afford the title compound (40 mg, 18%) as light yellow solid. $^1H$ NMR (400 MHz, DMSO-$d_6$): δ 11.34 (s, 1H), 7.58 (d, J=8.0 Hz, 2H), 7.31 (d, J=8.0 Hz, 2H), 6.50 (s, 1H), 6.04 (t, J=6.0 Hz, 1H), 5.67 (s, 1H), 5.47 (s, 1H), 4.88 (s, 1H), 4.55 (t, J=8.8 Hz, 2H), 4.03 (d, J=5.6 Hz, 2H), 3.99 (s, 1H), 3.49-3.45 (m, 1H), 3.31 (d, J=8.8 Hz, 2H), 2.94-2.90 (m, 1H), 1.69-1.65 (m, 3H), 1.54-1.50 (m, 3H), 1.22 (d, J=6.8 Hz, 6H); LCMS (ESI): m/z 484.1 $(M+Na)^+$.

Step 2: Preparation of 2-(((4-cyano-7-(4-isopropylphenyl)-2,3-dihydrobenzofuran-5-yl)amino)methyl)-N-hydroxyacrylamide

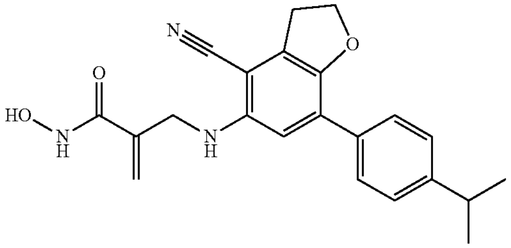 [SMILES: C=C(CNc1cc(-c2ccc(C(C)C)cc2)c2c(c1C#N)CCO2)C(=O)NO]

To a mixture 2-(((4-cyano-7-(4-isopropylphenyl)-2,3-dihydrobenzofuran-5-yl)amino)methyl)-N-((tetrahydro-2H-pyran-2-yl)oxy)acrylamide (40 mg, 0.090 mmol) in methyl alcohol (2 mL) was added 2 M HCl (0.5 mL, 1.0 mmol). The resulting mixture was stirred at room temperature for 2 hours. The reaction mixture was then purified by prep-HPLC (Welch Xtimate C18 150*25 mm*5 um, water (0.2% FA)-ACN, 60%-90%) to afford the title compound (15.3 mg, 47%) as a light yellow solid. $^1H$ NMR (400 MHz, DMSO-$d_6$): δ 10.86 (s, 1H), 8.96 (s, 1H), 7.58 (d, J=8.4 Hz, 2H), 7.31 (d, J=8.4 Hz, 2H), 6.51 (s, 1H), 6.04 (t, J=6.0 Hz, 1H), 5.63 (s, 1H), 5.40 (s, 1H), 4.55 (t, J=8.8 Hz, 2H), 4.03 (d, J=6.0 Hz, 2H), 3.30 (d, J=8.8 Hz, 2H), 2.98-2.83 (m, 1H), 1.22 (d, J=6.8 Hz, 6H); LCMS (ESI): m/z 378.2 $(M+H)^+$.

Example 10

Preparation of (3-((4-cyano-7-(4-isopropylphenyl)-2,3-dihydrobenzofuran-5-yl)amino)prop-1-en-2-yl)boronic acid The general reaction scheme was as follows:

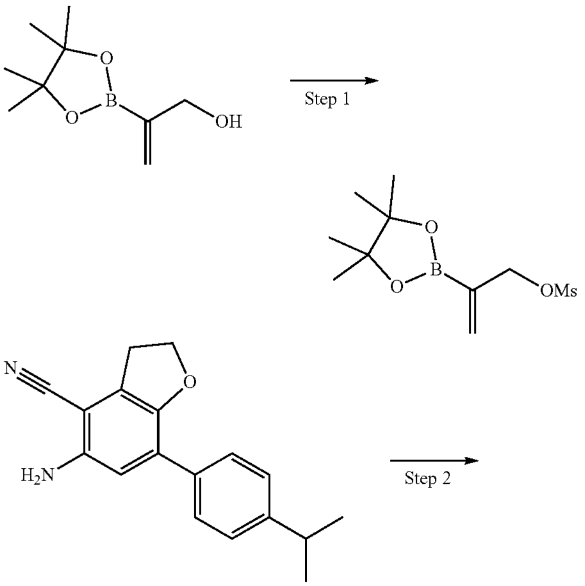

-continued

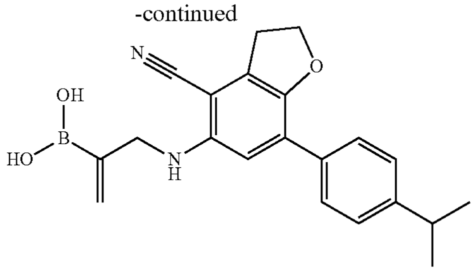

Step 1: Preparation of 2-(4,4,5,5-Tetramethyl-1,3,2-dioxaborolan-2-yl)allyl methanesulfonate

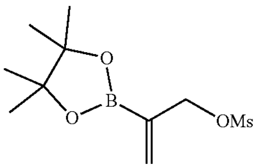 [SMILES: C=C(COS(C)(=O)=O)B1OC(C)(C)C(C)(C)O1]

To a mixture of 2-(4,4,5,5-tetramethyl-1,3,2-dioxaborolan-2-yl)prop-2-en-1-ol (2.0 g, 10.87 mmol) and TEA (2.26 mL, 16.3 mmol) in DCM (20 mL) at 0° C. was added methanesulfonic anhydride (2.84 g, 16.3 mmol). The reaction was stirred at room temperature for 16 hours at which point the reaction was concentrated. The residue was purified by flash chromatography on silica gel (0-25% ethyl acetate in petroleum ether) to afford the title compound (1.2 g, 42%) as a colorless liquid. $^1$H NMR (400 MHz, $CDCl_3$): δ 6.07 (s, 1H), 6.02 (s, 1H), 4.82 (s, 2H), 3.03 (s, 3H), 1.29 (s, 12H).

Step 2: Preparation of (3-((4-Cyano-7-(4-isopropylphenyl)-2,3-dihydrobenzofuran-5-yl)amino)prop-1-en-2-yl)boronic acid

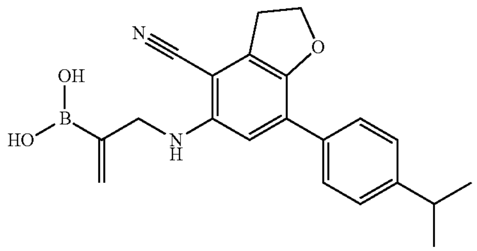 [SMILES: C=C(CNc1cc(-c2ccc(C(C)C)cc2)c2c(c1C#N)CCO2)B(O)O]

A mixture of 5-amino-7-(4-isopropylphenyl)-2,3-dihydrobenzofuran-4-carbonitrile (500 mg, 1.8 mmol) and 2-(4,4,5,5-tetramethyl-1,3,2-dioxaborolan-2-yl)allyl methanesulfonate (704 mg, 2.69 mmol) in DMF (10 mL) was stirred at 80° C. for 2 hours. The reaction mixture was purified by prep-HPLC (Boston Uni C18 40*150*5 um, water (0.225% FA)-ACN, 50-80%) and prep-HPLC (Boston Prime C18 150*30 mm*5 um, water (0.05% NH3H2O)-ACN, 51-81%) to afford the title compound (8.16 mg, 1%) as a yellow solid. $^1$H NMR (400 MHz, $CDCl_3$): δ 7.59 (d, J=8.4 Hz, 2H), 7.31 (d, J=8.4 Hz, 2H), 6.76 (s, 1H), 5.97 (s, 1H), 5.91 (s, 1H), 5.17 (s, 1H), 4.65 (t, J=8.8 Hz, 2H), 4.01 (s, 2H), 3.38 (t, J=8.8 Hz, 2H), 2.99-2.92 (m, 1H), 1.28 (d, J=6.8 Hz, 6H); LCMS (ESI): m/z 363.1 $(M+H)^+$.

Example 11

Preparation of 7-(4-isopropylphenyl)-5-((2-methylene-3-oxobutyl)amino)-2,3-dihydrobenzofuran-4-carbonitrile The general reaction scheme was as follows:

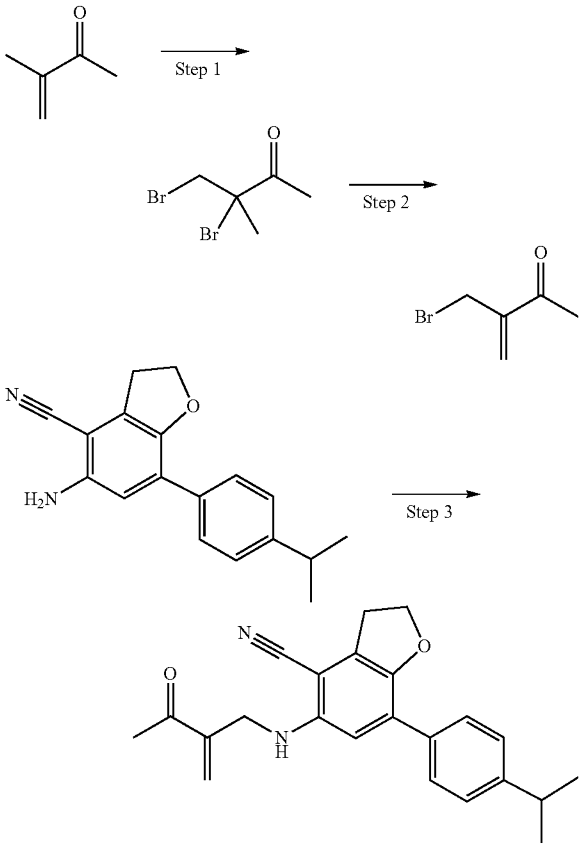

Step 1: Preparation of 3,4-dibromo-3-methylbutan-2-one

To a mixture of 3-methylbut-3-en-2-one (5.0 g, 59.44 mmol) in DCM (50 mL) was added $Br_2$ (3.04 mL, 59.44 mmol). Then the reaction mixture was stirred at 0° C. for 2 hours. Then the reaction was diluted with water (40 mL×3). The organics were dried over $MgSO_4$, filtered and concentrated to afford the title compound (14.3 g, 98%) as a yellow solid. $^1$H NMR (400 MHz, $CDCl_3$): δ 4.55-4.34 (m, 2H), 2.42 (s, 3H), 1.96 (s, 3H).

Step 2: Preparation of 3-(bromomethyl)but-3-en-2-one

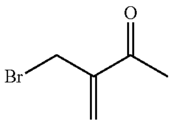

To a mixture of 3,4-dibromo-3-methylbutan-2-one (5.0 g, 59.44 mmol) in DMF (50 mL) was added KBr (11.32 g, 95.10 mmol). Then the reaction mixture was stirred at 80° C. for 12 hours. At which point the reaction was diluted with water (40 mL×3), the organics were dried over $MgSO_4$, filtered and concentrated to afford the title compound (2.2 g, 23%) as a brown liquid. $^1H$ NMR (400 MHz, $CDCl_3$): δ 6.03 (s, 1H), 5.92 (s, 1H), 4.17 (s, 2H), 1.92 (s, 3H).

Step 3: Preparation of 7-(4-isopropylphenyl)-5-((2-methylene-3-oxobutyl)amino)-2,3-dihydrobenzofuran-4-carbonitrile

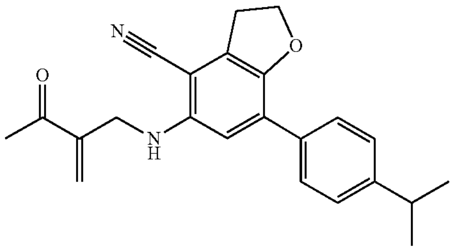 [SMILES: C=C(CNc1cc(-c2ccc(C(C)C)cc2)c2c(c1C#N)CCO2)C(C)=O]

To a mixture of 5-amino-7-(4-isopropylphenyl)-2,3-dihydrobenzofuran-4-carbonitrile (500 mg, 1.8 mmol) in DMF (5 mL) was added 3-(bromomethyl)but-3-en-2-one (585 mg, 3.59 mmol). The reaction mixture was stirred at room temperature for 16 hours. At which point the reaction was diluted with water (20 mL) and extracted with ethyl acetate (40 mL×2). The organics were washed with brine (20 mL×2), dried over $Na_2SO_4$, filtered and concentrated. The residue was purified by prep-TLC (20% ethyl acetate in petroleum ether) and prep-HPLC (Welch Xtimate C18 150*25 mm*5 um, water (0.2% FA)-ACN, 70-100%) to afford the title compound (4.27 mg, 0.66%) as a white solid. $^1H$ NMR (400 MHz, $CDCl_3$): δ 7.60 (d, J=8.4 Hz, 2H), 7.32 (d, J=8.4 Hz, 2H), 6.46 (s, 1H), 6.08 (s, 1H), 5.90 (s, 1H), 5.31-5.23 (m, 1H), 4.63 (t, J=8.8 Hz, 2H), 4.40 (d, J=4.0 Hz, 2H), 3.38 (t, J=8.8 Hz, 2H), 2.99-2.92 (m, 1H), 1.98 (s, 3H), 1.29 (d, J=6.8 Hz, 6H); LCMS (ESI): m/z 361.0 $(M+H)^+$.

Example 12

Preparation of 2-(((4-(hydroxymethyl)-7-(4-isopropylphenyl)-2,3-dihydrobenzofuran-5-yl)amino)methyl)acrylic acid The general reaction scheme was as follows:

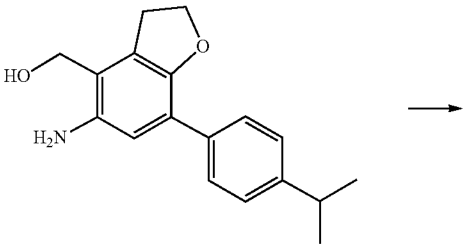

Intermediate D

-continued

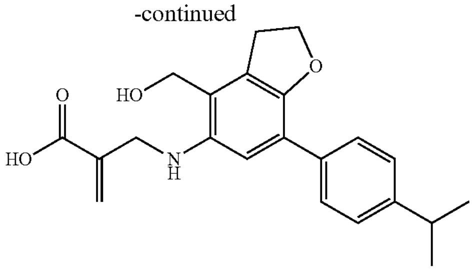

A solution of (5-amino-7-(4-isopropylphenyl)-2,3-dihydrobenzofuran-4-yl)methanol (200 mg, 0.71 mmol, Intermediate D) and 2-(bromomethyl)acrylic acid (105 mg, 0.64 mmol) in DMF (4 mL) was stirred at room temperature for 2 hours. At which point, the reaction solution was diluted with water (20 mL) and extracted with EtOAc (20 mL×3). The combined organic layers were dried over $Na_2SO_4$, filtered and concentrated. The residue was purified by prep-TLC (10% MeOH in DCM) and prep-HPLC (Phenomenex Gemini NX-C18 (75*30 mm*3 um) water (0.05%/NH3H2O+10 mM NH4HCO3)-ACN, 20%-50%) to afford the title compound (14.5 mg, 6%) as a white solid. $^1H$ NMR (400 MHz, DMSO-$d_6$): δ 7.50 (d, J=8.0 Hz, 2H), 7.25 (d, J=8.0 Hz, 2H), 6.35 (s, 1H), 6.04 (s, 1H), 5.64 (s, 1H), 4.46-4.35 (m, 4H), 3.93 (s, 2H), 3.18 (t, J=8.8 Hz, 2H), 2.89-2.85 (m, 1H), 1.21 (d, J=6.8 Hz, 6H); LCMS (ESI): m/z 368.0 $(M+H)^+$.

Example 13

Preparation of 2-(((4-(Hydroxymethyl)-7-(4-isopropylphenyl)-2,3-dihydrobenzofuran-5-yl)amino)methyl)acrylamide The general reaction scheme was as follows:

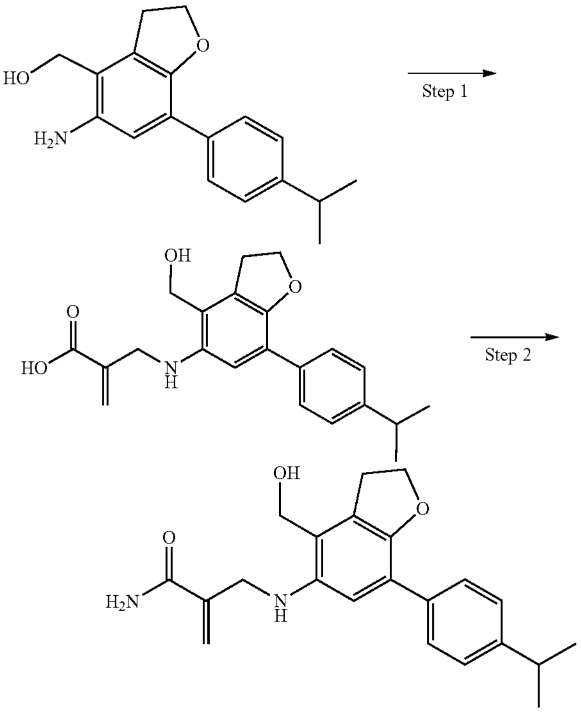

Step 1: Preparation of 2-(((4-(Hydroxymethyl)-7-(4-isopropylphenyl)-2,3-dihydrobenzofuran-5-yl)amino)methyl)acrylic acid

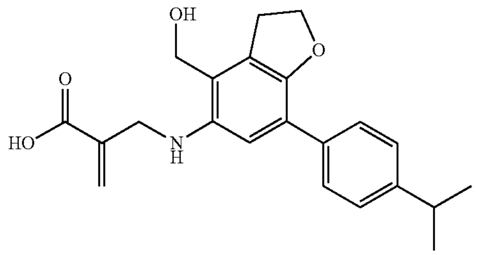 [SMILES: C=C(CNc1cc(-c2ccc(C(C)C)cc2)c2c(c1CO)CCO2)C(=O)O]

A solution of (5-amino-7-(4-isopropylphenyl)-2,3-dihydrobenzofuran-4-yl)methanol (300 mg, 1.1 mmol) and 2-(bromomethyl)acrylic acid (140 mg, 0.90 mmol) in DMF (9 mL) was stirred at 0° C. for 1 hour. The reaction solution was used for next step, without further purification. LCMS (ESI): m/z 368.1 $(M+H)^+$.

Step 2: Preparation of 2-(((4-(Hydroxymethyl)-7-(4-isopropylphenyl)-2,3-dihydrobenzofuran-5-yl)amino)methyl)acrylamide

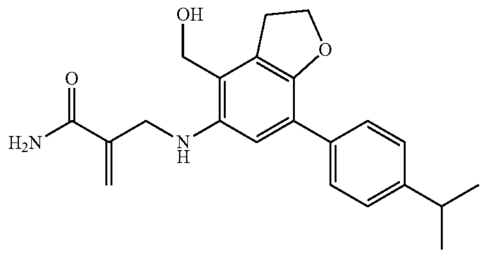 [SMILES: C=C(CNc1cc(-c2ccc(C(C)C)cc2)c2c(c1CO)CCO2)C(N)=O]

To a solution of 2-(((4-(hydroxymethyl)-7-(4-isopropylphenyl)-2,3-dihydrobenzofuran-5-yl)amino)methyl)acrylic acid (200 mg, 0.5 mmol), DIEA (0.5 mL, 2.5 mmol) and $NH_4Cl$ (58 mg, 1.0 mmol) in DMF (1 mL) was added HATU (620 mg, 1.5 mmol) at 25° C., the reaction solution was stirred at 25° C. for 16 hours. The resulting residue was purified by reverse phase chromatography (Phenomenex Gemini-NX 150*30 mm*5 um, acetonitrile 25-55%/water (0.225% FA)-ACN) to get the crude compound (71% of purity) which was purified by preparative SFC (DAICEL CHIRALCEL OJ (250 mm*30 mm, 10 um), 0.1% NH3H2O ETOH) afford the title compound (14.3 mg, 4% two steps) as a yellow solid. $^1H$ NMR (400 MHz, DMSO-$d_6$): δ 7.60 (s, 1H), 7.52 (d, J=8.0 Hz, 2H), 7.24 (d, J=8.0 Hz, 2H), 7.11 (s, 1H), 6.39 (s, 1H), 5.81 (s, 1H), 5.49 (s, 1H), 5.20 (t, J=5.2 Hz, 1H), 5.07 (t, J=5.2 Hz, 1H), 4.67-4.42 (m, 4H), 3.94 (d, J=6.0 Hz, 2H), 3.17 (t, J=8.4 Hz, 2H), 2.90-2.85 (m, 1H), 1.21 (d, J=6.8 Hz, 6H); LCMS (ESI): m/z 367.1 $(M+H)^+$.

Example 14

Preparation of N-hydroxy-2-(((4-(hydroxymethyl)-7-(4-isopropylphenyl)-2,3-dihydrobenzofuran-5-yl)amino)methyl)acrylamide The general reaction scheme was as follows:

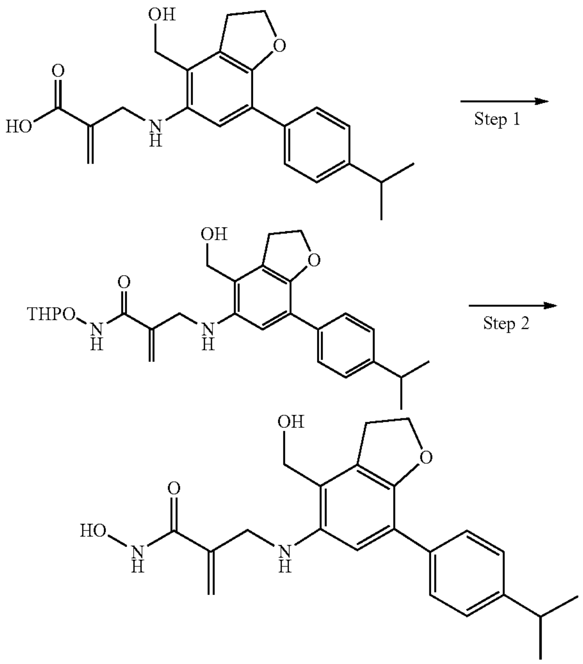

Step 1: Preparation of 2-(((4-cyano-7-(4-isopropylphenyl)-2,3-dihydrobenzofuran-5-yl)amino)methyl)-N-hydroxyacrylamide

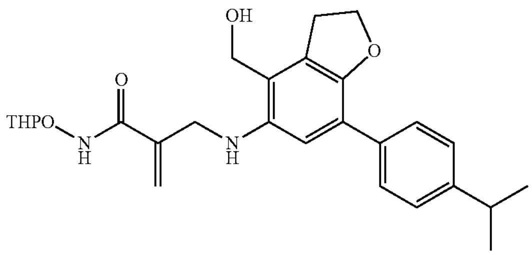

To the mixture of 2-(((4-(hydroxymethyl)-7-(4-isopropylphenyl)-2,3-dihydrobenzofuran-5-yl)amino)methyl)acrylic acid (300 mg, 0.80 mmol), TEA (0.5 mL, 3.30 mmol), O-(tetrahydro-2H-pyran-2-yl)hydroxylamine (287 mg, 2.50 mmol) in DMF (9 mL) was added BOP (722 mg, 1.6 mmol). The resulting mixture was stirred at room temperature for 2 h. The reaction solution was diluted with water (10 mL) and extracted with EtOAc (10 mL×3), the combined organic layers were washed with brine (10 mL×3). The organic was dried over $Na_2SO_4$, filtered and concentrated. The residue was purified by prep-HPLC (Welch Xtimate C18 150*25 mm*5 um, water (0.2% FA)-ACN, 44%-74%) to afford the title compound (50 mg, 13%) product as a white solid. LCMS (ESI): m/z 467.2 $(M+H)^+$.

Step 2: Preparation of N-Hydroxy-2-(((4-(hydroxymethyl)-7-(4-isopropylphenyl)-2,3-dihydrobenzofuran-5-yl)amino)methyl)acrylamide

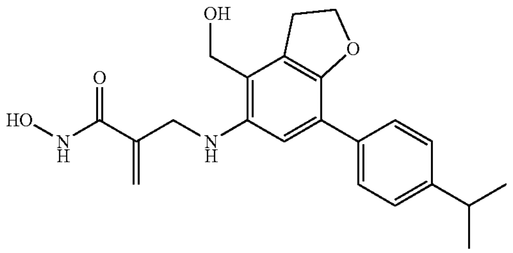 [SMILES: C=C(CNc1cc(-c2ccc(C(C)C)cc2)c2c(c1CO)CCO2)C(=O)NO]

To a mixture of 2-(((4-(hydroxymethyl)-7-(4-isopropylphenyl)-2,3-dihydrobenzofuran-5-yl)amino)methyl)-N-((tetrahydro-2H-pyran-2-yl)oxy)acrylamide (40 mg, 0.090 mmol) in methyl alcohol (2 mL) was added 2M HCl (0.5 mL, 1.0 mmol). The resulting mixture was stirred at room temperature for 2 hours and then the reaction mixture was purified by prep-HPLC (Welch Xtimate C18 150*25 mm*5 um, water (0.2% FA)-ACN, 32%-62%) to afford the title compound (12 mg, 37%) as a white solid. $^{1}H$ NMR (400 MHz, DMSO-$d_6$): δ 10.83 (s, 1H), 8.89 (s, 1H), 7.53 (d, J=8.0 Hz, 2H), 7.25 (d, J=8.0 Hz, 2H), 6.41 (s, 1H), 5.63 (s, 1H), 5.43 (s, 1H), 5.28-5.01 (m, 2H), 4.46-4.40 (m, 4H), 3.95 (s, 2H), 3.17 (t, J=8.8 Hz, 2H), 2.92-2.85 (m, 1H), 1.21 (d, J=6.8 Hz, 6H); LCMS (ESI): m/z 383.3 $(M+H)^+$.

Example 15

Preparation of 2-(((4-Cyano-7-(4-(trifluoromethyl)phenyl)-2,3-dihydrobenzofuran-5-yl)amino)methyl)acrylic acid The general reaction scheme was as follows:

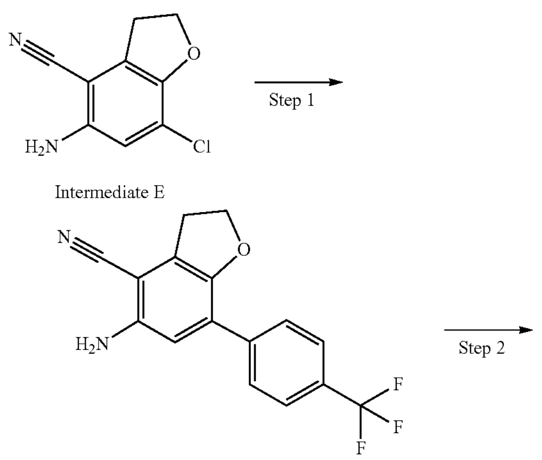

-continued

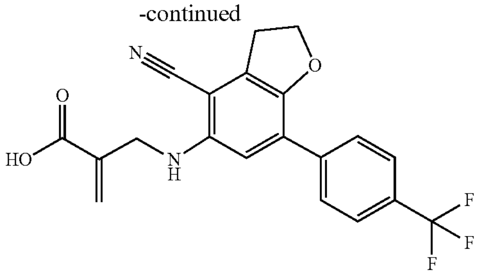

Step 1: Preparation of 5-amino-7-(4-(trifluoromethyl)phenyl)-2,3-dihydrobenzofuran-4-carbonitrile

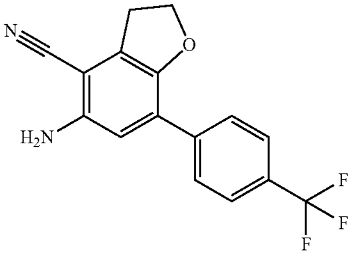 [SMILES: N#Cc1c(N)cc(-c2ccc(C(F)(F)F)cc2)c2c1CCO2]

A solution of 5-amino-7-chloro-2,3-dihydrobenzofuran-4-carbonitrile (200 mg, 1.03 mmol), (4-(trifluoromethyl)phenyl)boronic acid (293 mg, 1.54 mmol), Xphos (49 mg, 0.10 mmol), Xphos Pd $G_2$ (81 mg, 0.10 mmol) and $K_3PO_4$ (202 mg, 2.06 mmol) in 1,4-Dioxane (3 mL) and water (0.3 mL) was stirred at 80° C. under a $N_2$ atmosphere for 4 hours. The mixture was then quenched with water (20 mL) and extracted with EtOAc (20 mL×3). The combined organic layers were dried over $Na_2SO_4$ and concentrated. The residue was purified by prep-TLC (25% ethyl acetate in petroleum ether) which afforded the title compound (160 mg, 51%) as a yellow solid. $^{1}H$ NMR (400 MHz, $CDCl_3$): δ 7.77 (d, J=8.0 Hz, 2H), 7.68 (d, J=8.0 Hz, 2H), 6.69 (s, 1H), 4.66 (t, J=8.8 Hz, 2H), 3.39 (t, J=8.8 Hz, 2H); LCMS (ESI): m/z 304.9 $(M+H)^+$.

Step 2: Preparation of 2-(((4-Cyano-7-(4-(trifluoromethyl)phenyl)-2,3-dihydrobenzofuran-5-yl)amino)methyl)acrylic acid

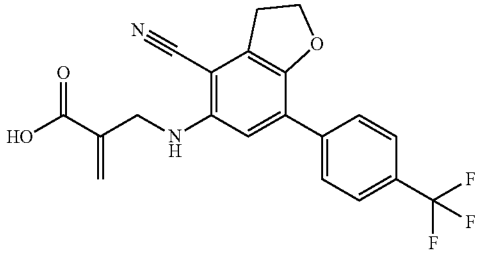 [SMILES: C=C(CNc1cc(-c2ccc(C(F)(F)F)cc2)c2c(c1C#N)CCO2)C(=O)O]

A mixture of 5-amino-7-(4-(trifluoromethyl)phenyl)-2,3-dihydrobenzofuran-4-carbonitrile (80 mg, 0.26 mmol) and 2-(bromomethyl)acrylic acid (50 mg, 0.28 mmol) in DMF (2 mL) was heated at 80° C. for 2 hours. The mixture was purified by prep-HPLC (Phenomenex luna C18 250*80 mm*10 um, water (0.2% FA)-ACN, 40%-80%) to afford the title compound (17 mg, 17%) as a light yellow solid. $^{1}H$ NMR (400 MHz, DMSO-$d_6$): δ 12.89 (s, 1H), 7.86 (d, J=8.4 Hz, 2H), 7.80 (d, J=8.4 Hz, 2H), 6.55 (s, 1H), 6.09 (s, 2H), 5.65 (s, 1H), 4.59 (t, J=8.8 Hz, 2H), 4.06 (s, 2H), 3.31 (t, J=8.8 Hz, 2H); LCMS (ESI): m/z 388.9 $(M+H)^+$.

Example 16
Preparation of (S)-2-(((4-Cyano-7-(4-(1,1,1-trifluoropropan-2-yl)phenyl)-2,3-dihydrobenzofuran-5-yl)amino)methyl)acrylic acid and (R)-2-(((4-cyano-7-(4-(1,1,1-trifluoropropan-2-yl)phenyl)-2,3-dihydrobenzofuran-5-yl)amino)methyl)acrylic acid
The general reaction scheme was as follows:
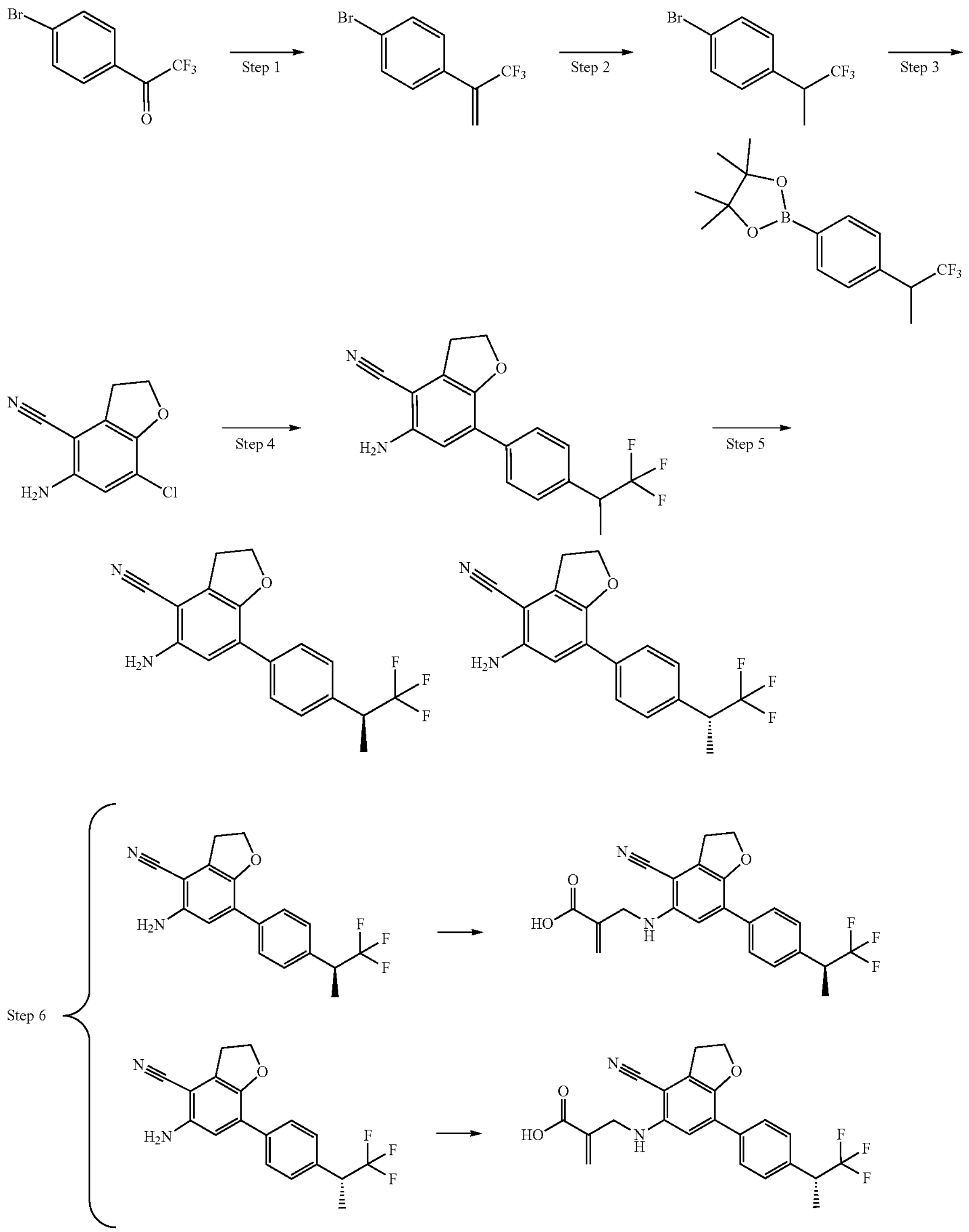

Step 1: Preparation of 1-bromo-4-(3,3,3-trifluoroprop-1-en-2-yl)benzene

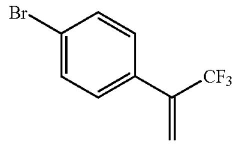

To a mixture of methyltriphenylphosphonium iodide (19.0 g, 47.43 mmol) in THF (100 mL) at 0° C. was added n-BuLi (19 mL, 47.43 mmol, 2.5 mol/L in hexane) dropwise. The mixture was stirred at 0° C. for 1 hour and then 1-(4-bromophenyl)-2,2,2-trifluoroethanone (10.0 g, 39.52 mmol) was added into the mixture, the mixture was stirred for 2 hours at 0° C. The reaction was quenched by saturated aqueous $NH_4Cl$ (20 mL). The mixture was diluted with water (400 mL). The resulting solution was extracted with ethyl acetate (300 mL×2). The organic was dried over $Na_2SO_4$ and concentrated. The residue was purified by column chromatography on silica gel (100% petroleum ether) to afford the title compound (5.3 g, 53%) as a colorless oil. $^1H$ NMR (400 MHz, $CDCl_3$): δ 7.53 (d, J=8.4 Hz, 2H), 7.33 (d, J=8.4 Hz, 2H), 5.99 (d, J=1.6 Hz, 1H), 5.79 (d, J=1.6 Hz, 1H).

Step 2: Preparation of 1-bromo-4-(1,1,1-trifluoropropan-2-yl)benzene

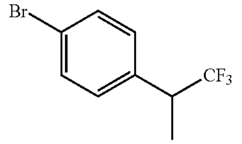

To a mixture of 1-bromo-4-(3,3,3-trifluoroprop-1-en-2-yl)benzene (5.3 g, 21.11 mmol) and $Et_3N$ (5.3 mL, 38.0 mmol) in (1:1) MeOH:EtOAc (106 mL) was added $PtO_2$ (479 mg, 2.11 mmol). The mixture was stirred at room temperature for 4 hours. At which point the mixture was filtered and concentrated. The residue was purified by column chromatography on silica gel (100% petroleum ether) to afford the title compound (4.0 g, 75%) as a colorless oil. $^1H$ NMR (400 MHz, $CDCl_3$): δ 7.50 (d, J=8.4 Hz, 2H), 7.20 (d, J=8.4 Hz, 2H), 3.45-3.34 (m, 1H), 1.50 (d, J=7.2 Hz, 3H).

Step 3: Preparation of 4,4,5,5-Tetramethyl-2-(4-(1,1,1-trifluoropropan-2-yl)phenyl)-1,3,2-dioxaborolane

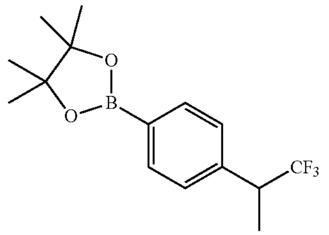 [SMILES: CC(c1ccc(B2OC(C)(C)C(C)(C)O2)cc1)C(F)(F)F]

A mixture of KOAc (1.75 g, 17.78 mmol), 4,4,4',4',5,5,5',5'-octamethyl-2,2'-bi(1,3,2-dioxaborolane) (2.26 g, 8.89 mmol), $Pd(dppf)Cl_2$ (0.44 g, 0.59 mmol) and 1-bromo-4-(1,1,1-trifluoropropan-2-yl)benzene (1.5 g, 5.93 mmol) in 1,4-Dioxane (15 mL) was stirred at 100° C. under a $N_2$ atmosphere for 4 hours. At which point, the mixture was diluted with water (300 mL). The resulting solution was extracted with ethyl acetate (200 mL×2). The combined organics were dried over $Na_2SO_4$ and concentrated. The residue was purified by column chromatography on silica gel (100% petroleum ether) to afford the title compound (500 mg, 28%) as a white solid. $^1H$ NMR (400 MHz, $CDCl_3$): δ 7.81 (d, J=8.0 Hz, 2H), 7.34 (d, J=8.0 Hz, 2H), 3.53-3.35 (m, 1H), 1.52 (d, J=7.2 Hz, 3H), 1.35 (s, 12H).

Step 4: Preparation of 5-amino-7-(4-(1,1,1-trifluoropropan-2-yl)phenyl)-2,3-dihydrobenzofuran-4-carbonitrile

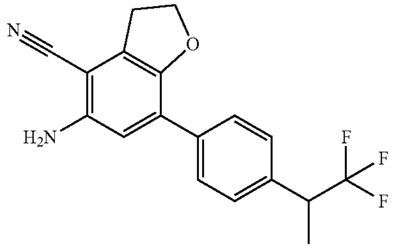 [SMILES: CC(c1ccc(-c2cc(N)c(C#N)c3c2OCC3)cc1)C(F)(F)F]

A mixture of Xphos Pd $G_2$ (136 mg, 0.16 mmol), Xphos Pd (76 mg, 0.16 mmol), 5-amino-7-chloro-2,3-dihydrobenzofuran-4-carbonitrile (300 mg, 1.60 mmol), 4,4,5,5-tetramethyl-2-(4-(1,1,1-trifluoropropan-2-yl)phenyl)-1,3,2-dioxaborolane (576 mg, 1.92 mmol) and $K_3PO_4$ (1.0 g, 4.80 mmol) in 10:1 1,4-dioxane:water (5.5 mL) was stirred at 80° C. for 3 hours. The mixture was diluted with EtOAc (50 mL) and washed with water (100 mL×2). The organic was dried over $Na_2SO_4$ and concentrated. The residue was purified by column chromatography on silica gel (0-30% EtOAc in petroleum ether) to afford the title compound (140 mg, 26%) as a yellow solid. LCMS (ESI): m/z 333.1 $(M+H)^+$.

Step 5: Preparation of (S)-5-Amino-7-(4-(1,1,1-trifluoropropan-2-yl)phenyl)-2,3-dihydrobenzofuran-4-carbonitrile and (R)-5-amino-7-(4-(1,1,1-trifluoropropan-2-yl)phenyl)-2,3-dihydrobenzofuran-4-carbonitrile

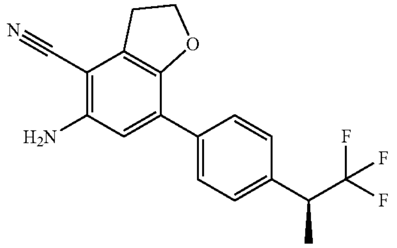

-continued

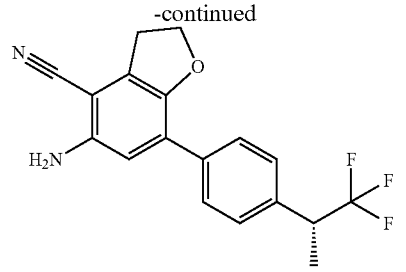

The 5-amino-7-(4-(1,1,1-trifluoropropan-2-yl)phenyl)-2,3-dihydrobenzofuran-4-carbonitrile (180 mg, 0.54 mmol) was separated by SFC (DAICEL CHIRALPAK IG (250 mm*30 mm, 10 um); 0.1% $NH_3H_2O$ MEOH; 30/30%) to afford a first-eluting Enantiomer A (60 mg, 33%) as a white solid and a second-eluting Enantiomer B (65 mg, 36%) as a white solid.

Step 6: Preparation of (S)-2-(((4-cyano-7-(4-(1,1,1-trifluoropropan-2-yl)phenyl)-2,3-dihydrobenzofuran-5-yl)amino)methyl)acrylic acid and (R)-2-(((4-cyano-7-(4-(1,1,1-trifluoropropan-2-yl)phenyl)-2,3-dihydrobenzofuran-5-yl)amino)methyl)acrylic acid

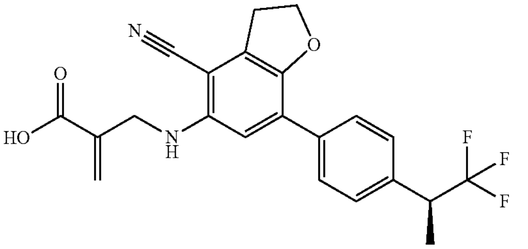

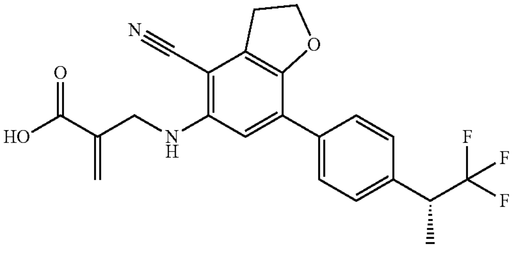

A mixture of Enantiomer A (60 mg, 0.18 mmol) and 2-(bromomethyl)acrylic acid (30 mg, 0.18 mmol) in DMF (3 mL)) was stirred at 80° C. for 16 hours. The reaction mixture was purified by prep-HPLC (Boston Green ODS 150*30 mm*5 um; water (0.2% FA)-ACN; 56/86%) to afford Enantiomer C (31.0 mg, 41%) as a white solid. $^1H$ NMR (400 MHz, DMSO-$d_6$): δ 12.73 (s, 1H), 7.64 (d, J=8.4 Hz, 2H), 7.46 (d, J=8.4 Hz, 2H), 6.49 (s, 1H), 6.10 (s, 1H), 6.01 (t, J=6.0 Hz, 1H), 5.67 (s, 1H), 4.56 (t, J=8.8 Hz, 2H), 4.05 (d, J=5.2 Hz, 2H), 3.94-3.68 (m, 1H), 3.29 (t, J=8.8 Hz, 2H), 1.45 (d, J=7.2 Hz, 3H); LCMS (ESI): m/z 417.0 $(M+H)^+$.

A mixture of Enantiomer B (60 mg, 0.18 mmol) and 2-(bromomethyl)acrylic acid (30 mg, 0.18 mmol) in DMF (3 mL)) was stirred at 80° C. for 16 hours. The reaction mixture was purified by prep-HPLC (Boston Green ODS 150*30 mm*5 um; water (0.2% FA)-ACN; 56/86%) to afford Enantiomer D (37.0 mg, 41%) as a white solid. $^1H$ NMR (400 MHz, DMSO-$d_6$): δ 12.73 (s, 1H), 7.64 (d, J=8.4 Hz, 2H), 7.46 (d, J=8.4 Hz, 2H), 6.49 (s, 1H), 6.10 (s, 1H), 6.01 (t, J=6.0 Hz, 1H), 5.67 (s, 1H), 4.56 (t, J=8.8 Hz, 2H), 4.05 (d, J=5.2 Hz, 2H), 3.94-3.68 (m, 1H), 3.29 (t, J=8.8 Hz, 2H), 1.45 (d, J=7.2 Hz, 3H); LCMS (ESI): m/z 417.0 $(M+H)^+$.

Example 17

Preparation of 2-(((4-cyano-7-(4-(trifluoromethoxy)phenyl)-2,3-dihydrobenzofuran-5-yl)amino)methyl)acrylic acid The general reaction scheme was as follows:

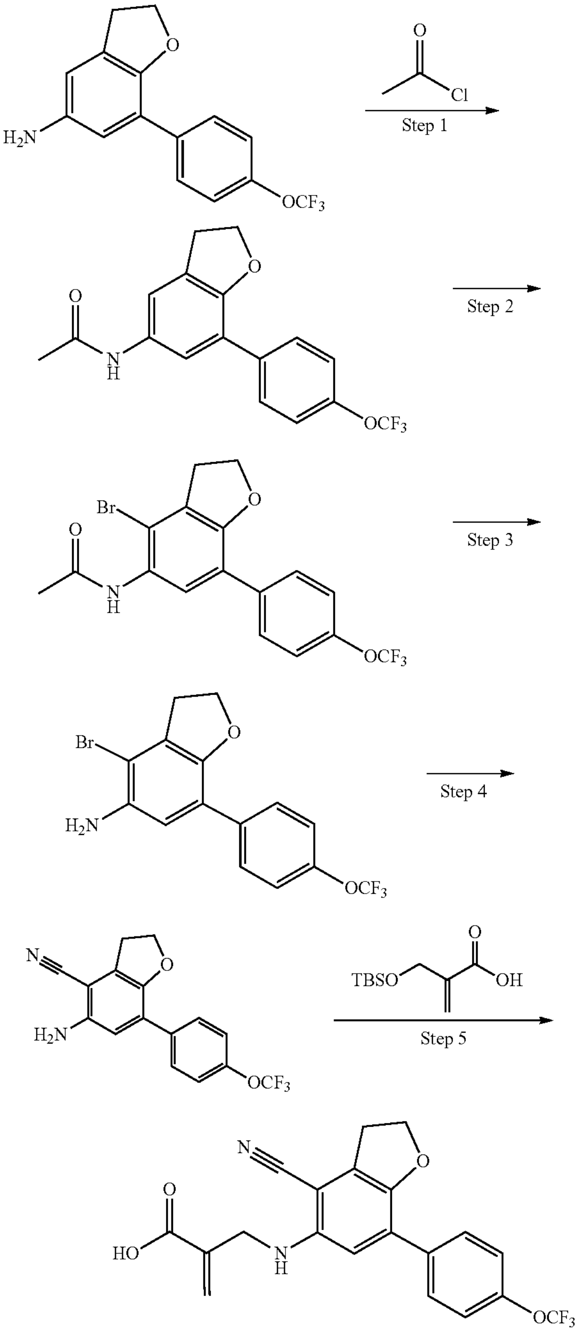

Step 1: Preparation of N-(7-(4-(Trifluoromethoxy) phenyl)-2,3-dihydrobenzofuran-5-yl)acetamide

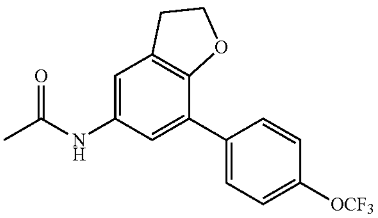 [SMILES: CC(=O)Nc1cc2c(c(-c3ccc(OC(F)(F)F)cc3)c1)OCC2]

To a mixture of 7-(4-(trifluoromethoxy)phenyl)-2,3-dihydrobenzofuran-5-amine (7.6 g, 25.74 mmol) and TEA (4.29 mL, 30.89 mmol) in DCM (70 mL) was added acetyl chloride (2.01 mL, 28.31 mmol) dropwise at −78° C. The reaction solution was stirred for further 1 hour at −78° C. The reaction was diluted with water (50 mL) and extracted with dichloromethane (80 mL×2). The organics were washed with brine (80 mL×2), dried over $Na_2SO_4$, filtered and concentrated. The residue was dissolved with DCM (20 mL) and then petroleum ether was added into it. The heterogenous mixture was filtered and the filter cake was washed with cold petroleum ether to afford the title compound (7.7 g, 89%) as a white solid. $^1$H NMR (400 MHz, $CDCl_3$): δ 7.72-7.65 (m, 2H), 7.44 (s, 1H), 7.35 (s, 1H), 7.27-7.21 (m, 3H), 4.61 (t, J=8.8 Hz, 2H), 3.25 (t, J=8.8 Hz, 2H), 2.17 (s, 3H).

Step 2: Preparation of N-(4-bromo-7-(4-(trifluoromethoxy)phenyl)-2,3-dihydrobenzofuran-5-yl) acetamide

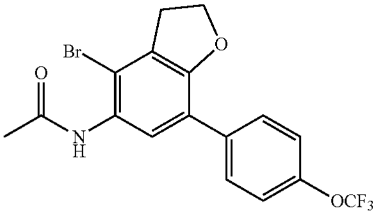 [SMILES: CC(=O)Nc1cc(-c2ccc(OC(F)(F)F)cc2)c2c(c1Br)CCO2]

To a mixture of N-(7-(4-(trifluoromethoxy)phenyl)-2,3-dihydrobenzofuran-5-yl)acetamide (1.0 g, 2.96 mmol) in acetic acid (5 mL) was added bromine (0.15 mL, 2.96 mmol) and the reaction mixture was stirred at 50° C. for 1 hour. The mixture was adjusted to pH=8 with a 2 M aq. NaOH solution. The reaction was diluted with water (20 mL) and extracted with ethyl acetate (40 mL×2). The organics were washed with brine (20 mL×2), dried over $Na_2SO_4$, filtered and concentrated. The residue was purified by flash chromatography silica gel (0-29% EtOAc in petroleum ether) to afford the title compound (273 mg, 22%) as a brown solid. $^1$H NMR (400 MHz, $CDCl_3$): δ 8.15 (s, 1H), 7.75 (d, J=8.8 Hz, 2H), 7.36 (s, 1H), 7.26 (d, J=8.8 Hz, 2H), 4.71 (t, J=8.8 Hz, 2H), 3.33 (t, J=8.8 Hz, 2H), 2.27 (s, 3H); LCMS (ESI): m/z 416.0 $(M+H)^+$.

Step 3: Preparation of 4-bromo-7-(4-(trifluoromethoxy)phenyl)-2,3-dihydrobenzofuran-5-amine

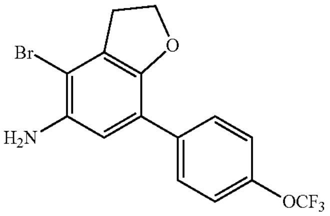 [SMILES: Nc1cc(-c2ccc(OC(F)(F)F)cc2)c2c(c1Br)CCO2]

To a mixture of N-(4-bromo-7-(4-(trifluoromethoxy)phenyl)-2,3-dihydrobenzofuran-5-yl)acetamide (1.2 g, 2.88 mmol) in ethanol (10 mL) was added conc. HCl (2.4 mL, 28.83 mmol). The reaction mixture was stirred at 80° C. for 16 hours. The reaction was diluted with water (30 mL) and extracted with dichloromethane (40 mL×2). The organics were washed with brine (30 mL×2), dried over $Na_2SO_4$, filtered and concentrated. The residue was purified by flash chromatography silica gel (0-20% EtOAc in petroleum ether) to afford the title compound (700 mg, 65%) as a white solid. $^1$H NMR (400 MHz, $CDCl_3$): δ 7.73-7.67 (m, 2H), 7.30-7.27 (m, 2H), 6.74 (s, 1H), 4.65 (t, J=8.8 Hz, 2H), 3.87 (s, 2H), 3.29 (t, J=8.8 Hz, 2H); LCMS (ESI): m/z 373.8 $(M+H)^+$.

Step 4: Preparation of 5-amino-7-(4-(trifluoromethoxy)phenyl)-2,3-dihydrobenzofuran-4-carbonitrile

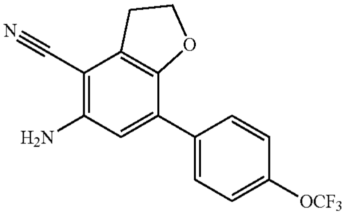 [SMILES: N#Cc1c(N)cc(-c2ccc(OC(F)(F)F)cc2)c2c1CCO2]

A mixture of 4-bromo-7-(4-(trifluoromethoxy)phenyl)-2,3-dihydrobenzofuran-5-amine (200 mg, 0.53 mmol), t-BuXPhos Pd $G_3$ (128 mg, 0.16 mmol) and $Zn(CN)_2$ (314 mg, 2.67 mmol) in DMA (10 mL) was stirred at 135° C. for 16 hours. The reaction solution was quenched with water (50 mL) and extracted with EtOAc (50 mL×2), washed with brine (50 mL×2), dried over $Na_2SO_4$ and concentrated. The residue was purified by flash chromatography silica gel (0-25% EtOAc in petroleum ether) to afford the title compound (100 mg, 58%) as a yellow solid. $^1$H NMR (400 MHz, $CDCl_3$): δ 7.71-7.69 (m, 2H), 7.30-7.27 (m, 2H), 6.66 (s, 1H), 4.96 (t, J=8.8 Hz, 2H), 3.68 (t, J=8.8 Hz, 2H).

Step 5: Preparation of 2-(((4-cyano-7-(4-(trifluoromethoxy)phenyl)-2,3-dihydrobenzofuran-5-yl) amino)methyl)acrylic acid

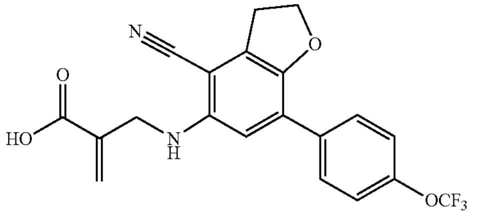 [SMILES: C=C(CNc1cc(-c2ccc(OC(F)(F)F)cc2)c2c(c1C#N)CCO2)C(=O)O]

To a solution of 5-amino-7-(4-(trifluoromethoxy)phenyl)-2,3-dihydrobenzofuran-4-carbonitrile (100 mg, 0.31 mmol), 2-(((tert-butyldimethylsilyl)oxy)methyl)acrylic acid (203 mg, 0.94 mmol), DMAP (4.0 mg, 0.03 mmol) and TEA (0.13 mL, 0.94 mmol) in DMF (5 mL) was added $T_3P$ (597 mg, 0.94 mmol, 50% in ethyl acetate). The reaction solution was stirred at 70° C. for 16 hours. The reaction solution was purified prep-HPLC (Boston Green ODS 150*30 mm*5 um; water (0.2% FA)-ACN; 55/85) to afford the title compound (24.32 mg, 19%) as a yellow solid. $^1H$ NMR (400 MHz, $CDCl_3$): δ 7.67 (d, J=8.8 Hz, 2H), 7.28 (d, J=8.8 Hz, 2H), 6.48 (s, 1H), 6.46 (s, 1H), 5.94 (s, 1H), 4.65 (t, J=8.8 Hz, 2H), 4.16 (s, 2H), 3.39 (t, J=8.8 Hz, 2H); LCMS (ESI): m/z 404.9 $(M+H)^+$.

Example 18

Preparation of 2-(((4-cyano-7-(4-(1,1-difluoroethyl) phenyl)-2,3-dihydrobenzofuran-5-yl)amino)methyl) acrylic acid The general reaction scheme was as follows:

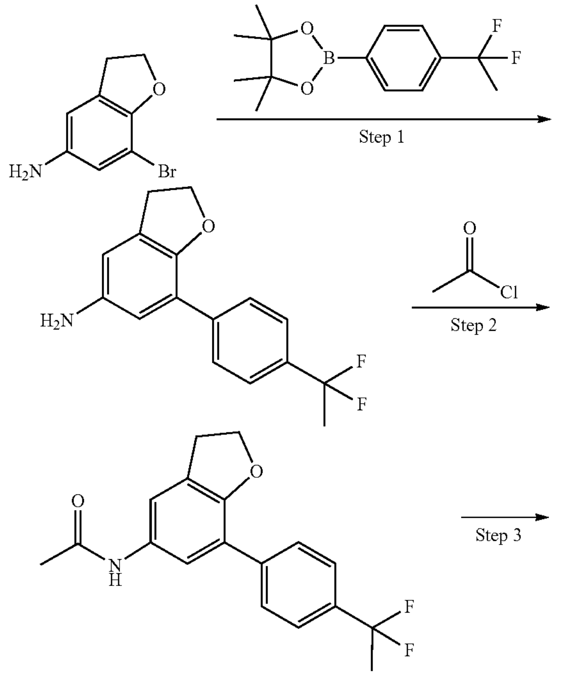

-continued

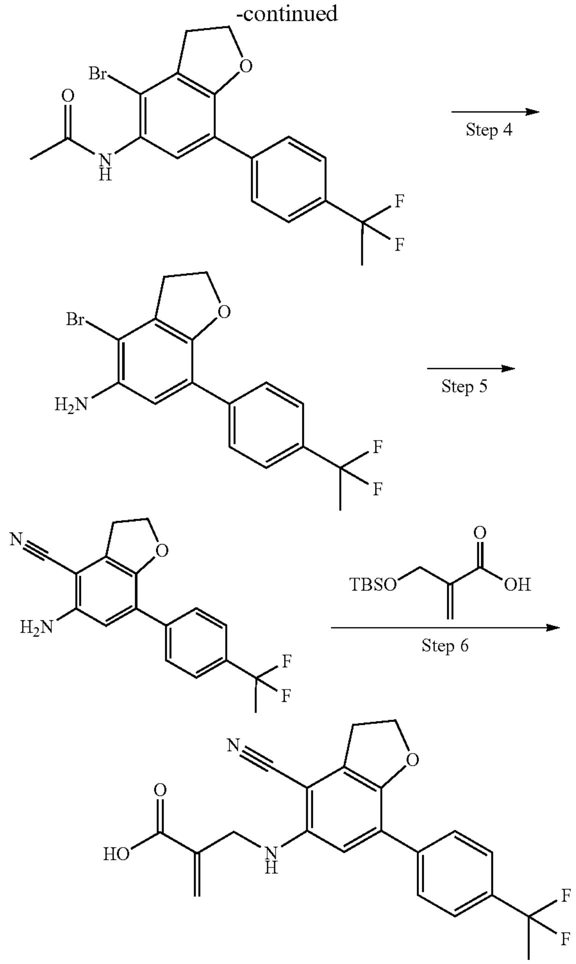

Step 1: Preparation of 7-(4-(1,1-difluoroethyl)phenyl)-2,3-dihydrobenzofuran-5-amine

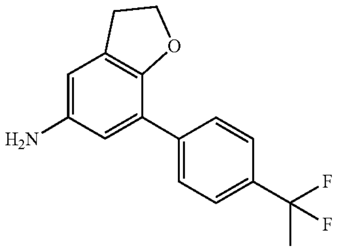 [SMILES: CC(F)(F)c1ccc(-c2cc(N)cc3c2OCC3)cc1]

A mixture of 7-bromo-2,3-dihydrobenzofuran-5-amine (5.0 g, 23.36 mmol), 2-(4-(1,1-difluoroethyl)phenyl)-4,4,5,5-tetramethyl-1,3,2-dioxaborolane (7.51 g, 28.03 mmol), $Na_2CO_3$ (7.43 g, 70.07 mmol), $Pd(dppf)Cl_2$ (1.71 g, 2.34 mmol) in 1,4-Dioxane (52 mL) was stirred at 100° C. for 16 hours under a $N_2$ atmosphere. The solution was then concentrated and the residue was purified by column chromatography on silica gel (0-30% EtOAc in petroleum ether) to afford the title compound (4.0 g, 62%) as a yellowish solid. $^1H$ NMR (400 MHz, $CDCl_3$): δ 7.73 (d, J=8.0 Hz, 2H), 7.55 (d, J=8.0 Hz, 2H), 6.66-6.60 (m, 2H), 4.56 (t, J=8.4 Hz, 2H), 3.47 (s, 2H), 3.18 (t, J=8.4 Hz, 2H), 1.94 (t, J=18.4, 3H); LCMS (ESI): m/z 276.11 $(M+H)^+$.

Step 2: Preparation of N-(7-(4-(1,1-difluoroethyl)phenyl)-2,3-dihydrobenzofuran-5-yl)acetamide

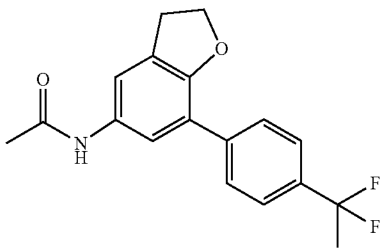 [SMILES: CC(=O)Nc1cc2c(c(-c3ccc(C(C)(F)F)cc3)c1)OCC2]

The mixture of 7-(4-(1,1-difluoroethyl)phenyl)-2,3-dihydrobenzofuran-5-amine (4.0 g, 14.53 mmol) and TEA (2.42 mL, 17.44 mmol) in DCM (40 mL) was added acetyl chloride (1.14 mL, 15.98 mmol) at −75° C. under a $N_2$ atmosphere. The solution was stirred for a further 1 hour at −78° C. The reaction was diluted with water (40 mL) and extracted with dichloromethane (50 mL×2). The organics were washed with brine (50 mL×2), dried over $Na_2SO_4$, filtered and concentrated. The residue was dissolved with DCM (20 mL) then petroleum ether was added into it to create a heterogeneous mixture. The mixture was filtered and the filter cake was washed with petroleum ether to afford the title compound (4.0 g, 86%) as a white solid. $^1H$ NMR (400 MHz, $CDCl_3$): δ 7.72 (d, J=8.0 Hz, 2H), 7.54 (d, J=8.0 Hz, 2H), 7.49 (s, 1H), 7.25 (s, 1H), 7.22 (s, 1H), 4.62 (t, J=8.8 Hz, 2H), 3.26 (t, J=8.8 Hz, 2H), 2.18 (s, 3H), 1.94 (t, J=18.0 Hz, 3H).

Step 3: Preparation of N-(4-Bromo-7-(4-(1,1-difluoroethyl)phenyl)-2,3-dihydrobenzofuran-5-yl)acetamide

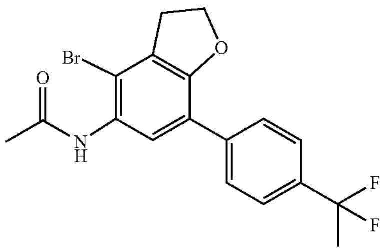 [SMILES: CC(=O)Nc1cc(-c2ccc(C(C)(F)F)cc2)c2c(c1Br)CCO2]

To a mixture of N-(7-(4-(1,1-difluoroethyl)phenyl)-2,3-dihydrobenzofuran-5-yl)acetamide (1.6 g, 5.04 mmol) in HOAc (8.5 mL) was added bromine (0.28 mL, 5.55 mmol). The reaction mixture was stirred at 50° C. for 2 hours. The mixture was adjusted to around pH=8 with 2 M aq. NaOH solution. The reaction was diluted with water (20 mL) and extracted with ethyl acetate (40 mL×2). The organics were washed with brine (20 mL×2), dried over $Na_2SO_4$, filtered and concentrated. The residue was purified by flash chromatography silica gel (0-29% EtOAc in petroleum ether) to afford the title compound (270 mg, 14%) as solid. $^1H$ NMR (400 MHz, $CDCl_3$): δ 8.13 (s, 1H), 7.75 (d, J=8.0 Hz, 2H), 7.55 (d, J=8.0 Hz, 2H), 7.34 (s, 1H), 4.69 (t, J=8.8 Hz, 2H), 3.31 (t, J=8.8 Hz, 2H), 2.25 (s, 3H), 1.94 (t, J=18.0 Hz, 3H).

Step 4: Preparation of 4-bromo-7-(4-(1,1-difluoroethyl)phenyl)-2,3-dihydrobenzofuran-5-amine

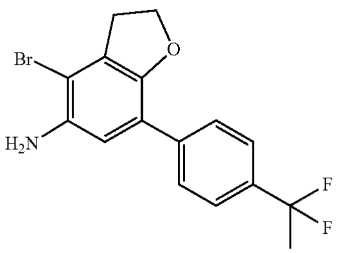 [SMILES: CC(F)(F)c1ccc(-c2cc(N)c(Br)c3c2OCC3)cc1]

The mixture of N-(4-bromo-7-(4-(1,1-difluoroethyl)phenyl)-2,3-dihydrobenzofuran-5-yl)acetamide (270 mg, 0.65 mmol) in EtOH (5 mL) was added hydrogen chloride (0.2 mL, 6.49 mmol). Then the reaction mixture was stirred at 80° C. for 16 hours. At this point, the mixture was adjusted to around pH=8 with 2 M NaOH solution. The reaction was diluted with water (30 mL) and extracted with dichloromethane (40 mL×2). The organics were washed with brine (30 mL×2), dried over $Na_2SO_4$, filtered and concentrated. The residue was purified by flash chromatography silica gel (0-30% EtOAc in petroleum ether) to afford the title compound (125 mg, 52%) as a yellow solid. $^1H$ NMR (400 MHz, $CDCl_3$): δ 7.69 (d, J=8.4 Hz, 2H), 7.55 (d, J=8.4 Hz, 2H), 6.75 (s, 1H), 4.63 (t, J=8.8 Hz, 2H), 3.85 (s, 2H), 3.27 (t, J=8.8 Hz, 2H), 1.94 (t, J=18.4 Hz, 3H); LCMS (ESI): m/z 353.8 $(M+H)^+$.

Step 5: Preparation of 5-amino-7-(4-(1,1-difluoroethyl)phenyl)-2,3-dihydrobenzofuran-4-carbonitrile

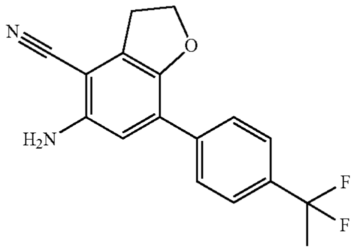 [SMILES: CC(F)(F)c1ccc(-c2cc(N)c(C#N)c3c2OCC3)cc1]

A mixture of 4-bromo-7-(4-(1,1-difluoroethyl)phenyl)-2,3-dihydrobenzofuran-5-amine (200 mg, 0.56 mmol), t-BuXPhos Pd $G_3$ (135 mg, 0.17 mmol) and $Zn(CN)_2$ (312 mg, 2.82 mmol) in DMA (15 mL) was stirred at 135° C. for 16 hours. The reaction solution was quenched with water (50 mL) and extracted with EtOAc (50 mL×2), washed with brine (50 mL×2) and concentrated. The residue was purified by prep-TLC (25% EtOAc in petroleum ether) afford the title compound (80 mg, 47%) as a yellow solid. $^1H$ NMR (400 MHz, $CDCl_3$): δ 7.71 (d, J=8.4 Hz, 2H), 7.57 (d, J=8.4 Hz, 2H), 6.69 (s, 1H), 4.66 (t, J=8.8 Hz, 2H), 4.13 (s, 2H), 3.38 (t, J=8.8 Hz, 2H), 1.95 (t, J=18.4 Hz, 3H).

Step 6: Preparation of 2-(((4-Cyano-7-(4-(1,1-difluoroethyl)phenyl)-2,3-dihydrobenzofuran-5-yl)amino)methyl)acrylic acid

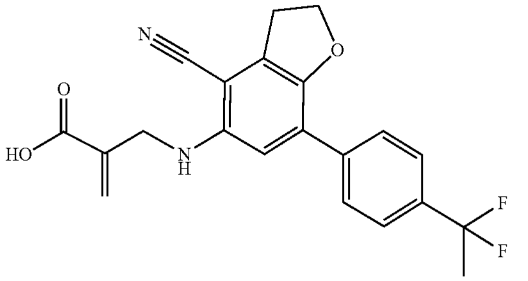 [SMILES: C=C(CNc1cc(-c2ccc(C(C)(F)F)cc2)c2c(c1C#N)CCO2)C(=O)O]

To a solution of 5-amino-7-(4-(1,1-difluoroethyl)phenyl)-2,3-dihydrobenzofuran-4-carbonitrile (80 mg, 0.27 mmol), 2-(((tert-butyldimethylsilyl)oxy)methyl)acrylic acid (173 mg, 0.80 mmol), DMAP (4 mg, 0.03 mmol) and TEA (0.11 mL, 0.80 mmol) in DMF (3 mL) was added $T_3P$ (509 mg, 0.80 mmol, 50% in ethyl acetate). The reaction solution was stirred at 70° C. for 16 hours. The reaction solution was purified prep-HPLC (Boston Green ODS 150*30 mm*5 um; water (0.2% FA)-ACN; 55/85) to afford the title compound (6.09 mg, 5.8%) as a yellow solid. $^1$H NMR (400 MHz, $CDCl_3$): δ 7.68 (d, J=8.0 Hz, 2H), 7.57 (d, J=8.0 Hz, 2H), 6.49 (s, 1H), 6.47 (s, 1H), 5.94 (s, 1H), 4.65 (t, J=8.8 Hz, 2H), 4.16 (s, 2H), 3.39 (t, J=8.8 Hz, 2H), 1.94 (t, J=18.4 Hz, 3H); LCMS (ESI): m/z 385.0 $(M+H)^+$.

Example 19

Preparation of 2-(((4-(4-isopropylphenyl)-6,7-dihydrofuro[3,2-d]pyrimidin-2-yl)amino)methyl)acrylic acid The general reaction scheme was as follows:

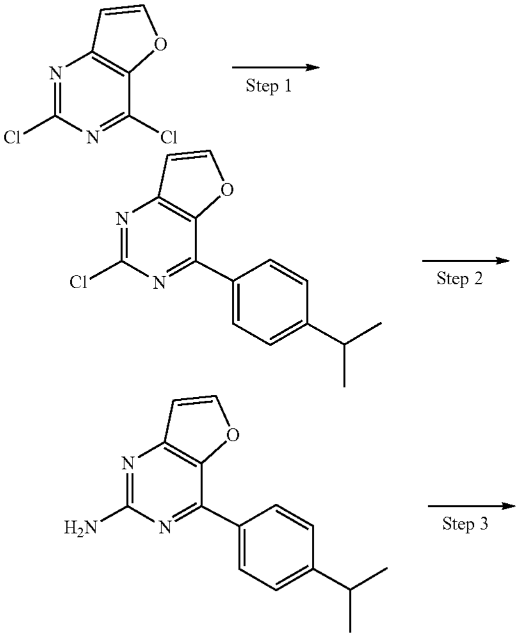

-continued

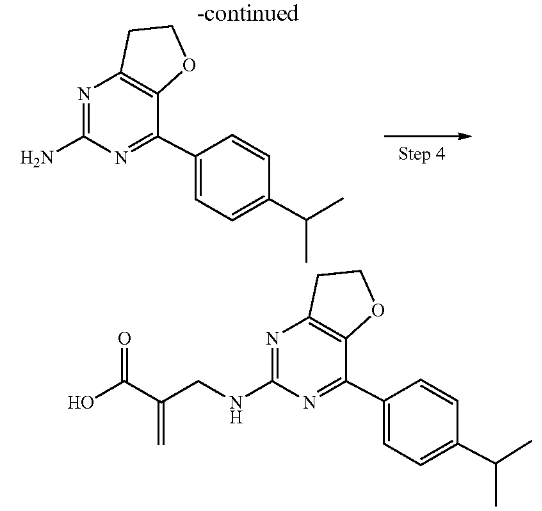

Step 1: Preparation of 2-chloro-4-(4-isopropylphenyl)furo[3,2-d]pyrimidine

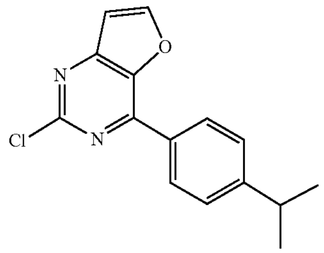 [SMILES: CC(C)c1ccc(-c2nc(Cl)nc3ccoc23)cc1]

A mixture of 2,4-dichlorofuro[3,2-d]pyrimidine (1.0 g, 5.3 mmol), (4-isopropylphenyl)boronic acid (955 mg, 5.8 mmol), $Pd(PPh_3)_2Cl_2$ (371 mg, 0.53 mmol), TEA (1.5 mL, 10.6 mmol) in DMF (10 mL) and $H_2O$ (1 mL) was stirred at 80° C. for 4 hours. At which point, the reaction mixture was diluted by water (20 mL) and extracted with EtOAc (20 mL×3). The combined organic layers were washed with brine (20 mL×3) and dried over $Na_2SO_4$ and concentrated. The residue was purified by chromatography on silica gel (0-10% EtOAc in petroleum ether) to afford the title compound (830 mg, 56%) as a yellow oil. $^1$H NMR (400 MHz, $CDCl_3$): δ δ 8.43 (d, J=8.4 Hz, 2H), 8.08 (d, J=2.0 Hz, 1H), 7.44 (d, J=8.4 Hz, 2H), 6.99 (d, J=2.0 Hz, 1H), 3.15-2.90 (m, 1H), 1.32 (d, J=6.8 Hz, 6H).

Step 2: Preparation of 4-(4-isopropylphenyl)furo[3,2-d]pyrimidin-2-amine

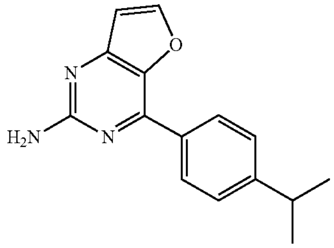 [SMILES: CC(C)c1ccc(-c2nc(N)nc3ccoc23)cc1]

A mixture of $Pd_2(dba)_3$ (100 mg, 0.11 mmol), 2-chloro-4-(4-isopropylphenyl)furo[3,2-d]pyrimidine (300 mg, 1.1 mmol), RockPhos (52 mg, 0.11 mmol), $NH_3$ (0.2 mL) and t-BuOK (317 mg, 3.3 mmol) in 1,4-dioxane (5 mL) was stirred at 100° C. for 2 hours. At which point, the mixture was quenched with water (10 ml) and extracted with EtOAc (10 mL×2). The organic layer was dried over $Na_2SO_4$ and evaporated under vacuum. The residue was purified by chromatography on silica gel (0-25% ethyl acetate in petroleum ether) to afford the title compound (220 mg, 79%) as a yellow solid. $^1H$ NMR (400 MHz, $CDCl_3$): δ 8.33 (d, J=8.4 Hz, 2H), 7.87 (d, J=2.0 Hz, 1H), 7.40 (d, J=8.4 Hz, 2H), 6.73 (d, J=2.0 Hz, 1H), 4.99 (s, 2H), 3.04-2.89 (m, 1H), 1.31 (d, J=6.8 Hz, 6H). LCMS (ESI): m/z 254.1 $(M+H)^+$.

Step 3: Preparation of 4-(4-isopropylphenyl)-6,7-dihydrofuro[3,2-d]pyrimidin-2-amine

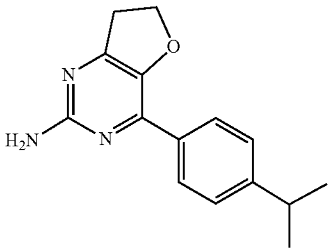 [SMILES: CC(C)c1ccc(-c2nc(N)nc3c2OCC3)cc1]

A mixture of Rh/C (45 mg, 0.45 mmol) and 4-(4-isopropylphenyl)furo[3,2-d]pyrimidin-2-amine (220 mg, 0.9 mmol) in EtOH (5 mL) was stirred at room temperature for 2 hours under an atmosphere of $H_2$ (15 psi). The mixture was then filtered and the filtrate was concentrated under reduced pressure to afford the title compound (0.22 g, 99%) as a yellow oil. The crude was used for next step without further purification. LCMS (ESI): m/z 256.2 $(M+H)^+$.

Step 4: Preparation of 2-(((4-(4-isopropylphenyl)-6,7-dihydrofuro[3,2-d]pyrimidin-2-yl)amino)methyl)acrylic acid

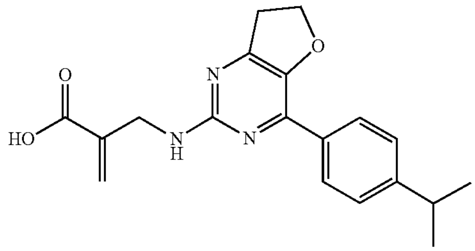

To a solution of 4-(4-isopropylphenyl)-6,7-dihydrofuro[3,2-d]pyrimidin-2-amine (80 mg, 0.30 mmol), 2-(((tert-butyldimethylsilyl)oxy)methyl)acrylic acid (203 mg, 0.90 mmol), DMAP (4 mg, 0.030 mmol) and TEA (0.13 mL, 0.90 mmol) in DMF (2 mL) was added $T_3P$ (598 mg, 0.90 mmol, 50% in ethyl acetate). The reaction solution was stirred at 100° C. for 16 hours. At which point, the reaction was diluted by EtOAc (5 mL), washed with water (5 mL×3). The combined organics were dried over $Na_2SO_4$ and concentrated. The residue was purified by reverse phase chromatography (3_Phenomenex Luna C18 75*30 mm*3 um 50-80%/water (0.2% FA)-ACN) to afford the title compound (8.02 mg, 8%) as a white solid. $^1H$ NMR (400 MHz, DMSO-$d_6$): δ 8.12 (d, J=8.4 Hz, 2H), 7.35 (d, J=8.4 Hz, 2H), 6.96-6.85 (m, 1H), 6.05 (s, 1H), 5.65 (s, 1H), 4.59 (t, J=8.8 Hz, 2H), 4.18-4.06 (m, 2H), 3.17 (t, J=8.8 Hz, 2H), 2.98-2.85 (m, 1H), 1.22 (d, J=6.8 Hz, 6H). LCMS (ESI): m/z 340.0 $(M+H)^+$.

Example 20

Preparation of 2-(((4-fluoro-7-(4-isopropylphenyl)-2,3-dihydrobenzofuran-5-yl)amino)methyl)acrylic acid The general reaction scheme was as follows:

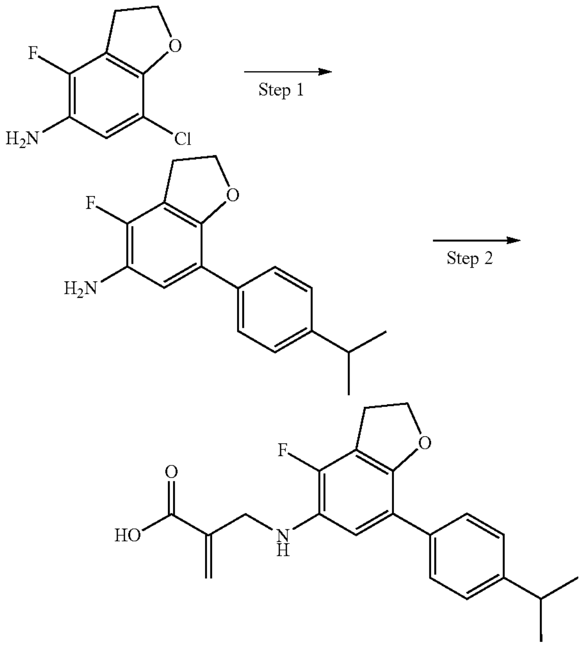

Step 1: Preparation of 4-fluoro-7-(4-isopropylphenyl)-2,3-dihydrobenzofuran-5-amine

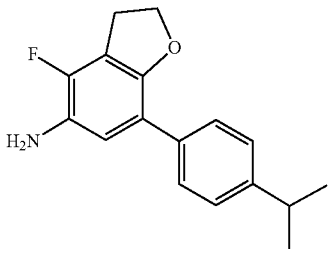 [SMILES: CC(C)c1ccc(-c2cc(N)c(F)c3c2OCC3)cc1]

A mixture of XPhos Pd $G_3$ (136 mg, 0.16 mmol), XPhos (76 mg, 0.16 mmol), 7-chloro-4-fluoro-2,3-dihydrobenzofuran-5-amine (300 mg, 1.6 mmol), (4-isopropylphenyl)boronic acid (314 mg, 1.92 mmol) and $Na_2CO_3$ (508 mg, 4.8 mmol) in 1,4-dioxane:$H_2O$ (6 mL, 5:1) was stirred at 100° C. for 3 hours. The mixture was then diluted with EtOAc (50 mL) and washed with water (30 mL×3). The organics were dried over $Na_2SO_4$ and concentrated. The residue was purified by column chromatography on silica gel (0-30% EtOAc in petroleum ether) to afford the title compound (300 mg, 69%) as a yellow solid. $^1$H NMR (400 MHz, $CDCl_3$): δ 7.54 (d, J=8.0 Hz, 2H), 7.26 (d, J=8.0 Hz, 2H), 6.74 (d, J=8.8 Hz, 1H), 4.61 (t, J=8.4 Hz, 2H), 3.46 (s, 2H), 3.27 (t, J=8.4 Hz, 2H), 2.94-2.88 (m, 1H), 1.27 (d, J=6.8 Hz, 6H).

Step 2: Preparation of 2-(((4-fluoro-7-(4-isopropylphenyl)-2,3-dihydrobenzofuran-5-yl)amino)methyl) acrylic acid

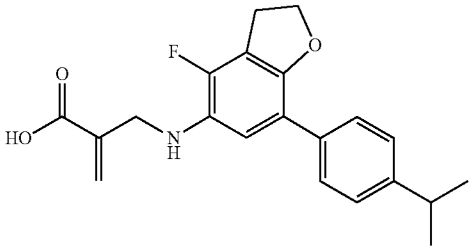 [SMILES: C=C(CNc1cc(-c2ccc(C(C)C)cc2)c2c(c1F)CCO2)C(=O)O]

To a mixture of 4-fluoro-7-(4-isopropylphenyl)-2,3-dihydrobenzofuran-5-amine (260 mg, 0.96 mmol) in DMF (3 mL) was added 2-(bromomethyl)acrylic acid (158 mg, 0.96 mmol). The mixture was stirred at 50° C. for 2 hours. Then the mixture was diluted with EtOAc (50 mL) and washed with water (30 mL×3). The organics were dried over $Na_2SO_4$ and concentrated. The residue was purified by prep-TLC (10% MeOH in DCM) and prep-HPLC (Phenomenex Gemini-NX 80*30 mm*3 um; water (10 mM NH4HCO3)-ACN; 10/80%) to afford the title compound (80 mg, 22%) as a white solid. $^1$H NMR (400 MHz, DMSO-$d_6$): δ 7.48 (d, J=8.0 Hz, 2H), 7.25 (d, J=8.0 Hz, 2H), 6.48 (d, J=8.8 Hz, 1H), 5.79 (s, 1H), 5.31 (s, 1H), 4.51 (t, J=8.8 Hz, 2H), 3.84 (s, 2H), 3.21 (t, J=8.8 Hz, 2H), 2.91-2.84 (m, 1H), 1.21 (d, J=6.8 Hz, 6H); LCMS (ESI): m/z 355.9 $(M+H)^+$.

Example 21

Preparation of 2-(((4-cyano-7-(4-isopropylphenyl)-2,3-dihydrofuro[2,3-c]pyridin-5-yl)amino)methyl) acrylic acid The general reaction scheme was as follows:

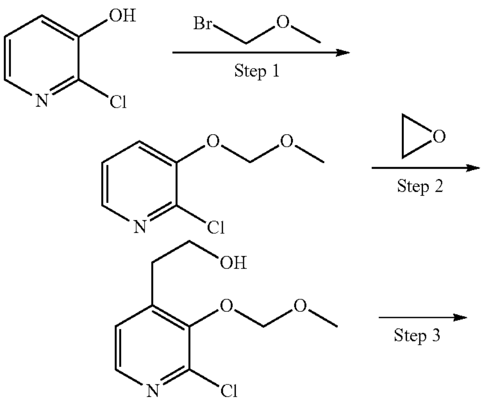

-continued

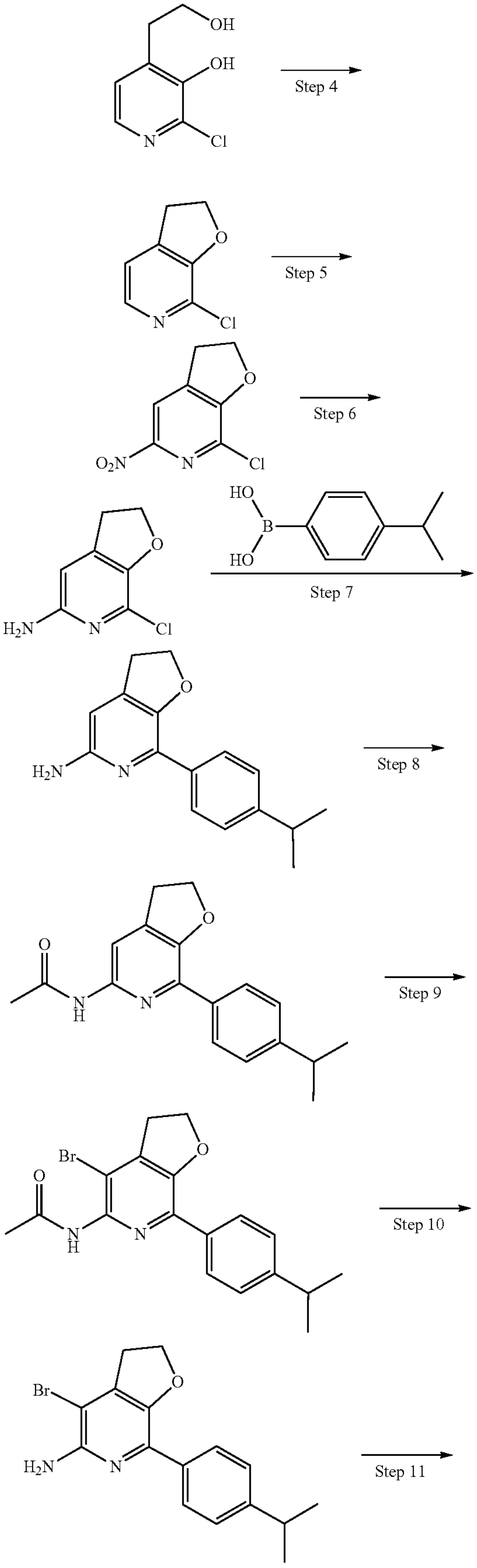

-continued

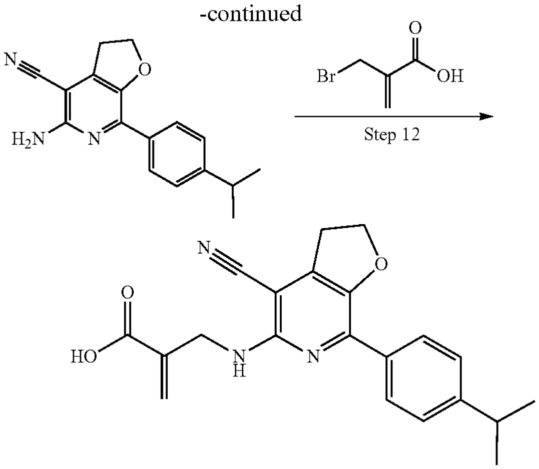

Step 1: Preparation of 2-chloro-3-(methoxymethoxy)pyridine

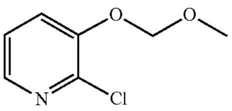

To a mixture of 2-chloropyridin-3-ol (25.0 g, 193 mmol), DMAP (3.78 g, 30.88 mmol) in DCM (250 mL) was added bromo(methoxy)methane (28.9 g, 232 mmol) and DIPEA (64 mL, 384 mmol) at 0° C. The mixture was stirred at room temperature for 16 hours. At which point, the reaction mixture was washed with water (300 mL×3), dried over $Na_2SO_4$, filtered and concentrated. The crude was purified by chromatography on silica gel (0-15% ethyl acetate in petroleum ether) to afford the title compound (30 g, 90%) as a colorless oil. $^1$H NMR (400 MHz, $CDCl_3$): δ 8.06 (dd, J=3.2 Hz, 1H), 7.49 (dd, J=8.4, 1.6 Hz, 1H), 7.22-7.17 (m, 1H), 5.28 (s, 2H), 3.53 (s, 3H).

Step 2: Preparation of 2-(2-chloro-3-(methoxymethoxy)pyridin-4-yl)ethanol

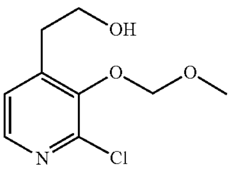

To a solution of 2-chloro-3-(methoxymethoxy)pyridine (5.0 g, 28.8 mmol) in THF (50 mL) was added n-BuLi (17.28 mL, 43.2 mmol, 2.5 mol/L in hexane) at −78° C. dropwise. Then the reaction was stirred at −78° C. for 30 minutes. Oxirane (6.34 g, 144.01 mmol) was then added the reaction mixture at −78° C. and the reaction was stirred at room temperature for 16 hours. The reaction mixture was quenched with $NH_4Cl$ solution (50 mL), extracted with EtOAc (100 mL×3), washed with water (100 mL×3), dried over $Na_2SO_4$, filtered and concentrated. The residue was purified by chromatography on silica gel (0-50% ethyl acetate in petroleum ether) to afford the title compound (3.6 g, 57%) as a colorless oil. $^1$H NMR (400 MHz, $CDCl_3$): δ 8.11 (d, J=4.8 Hz, 1H), 7.18 (d, J=4.8 Hz, 1H), 5.16 (s, 2H), 3.97-3.92 (m, 2H), 3.66 (s, 3H), 3.02 (t, J=6.4 Hz, 2H), 1.89 (t, J=5.6 Hz, 1H).

Step 3: Preparation of 2-chloro-4-(2-hydroxyethyl)pyridin-3-ol

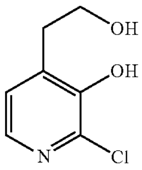 [SMILES: OCCc1ccnc(Cl)c1O]

To a solution of 2-(2-chloro-3-(methoxymethoxy)pyridin-4-yl)ethanol (3.6 g, 16.54 mmol) in MeOH (60 mL) was added conc. hydrochloric acid (15 mL). The reaction was stirred at room temperature for 3 hours. At which point, the reaction mixture was diluted with water (50 mL), adjusted pH to 4 with a sat. aq. $NaHCO_3$ solution (50 mL), extracted with EtOAc (100 mL×3), dried over $Na_2SO_4$, filtered and concentrated. The residue was purified by chromatography on silica gel (0-50% ethyl acetate in petroleum ether) to afford the title compound (2.5 g, 87%) as a white solid. $^1$H NMR (400 MHz, DMSO-$d_6$): δ 7.79 (d, J=4.8 Hz, 1H), 7.17 (d, J=4.8 Hz, 1H), 3.64 (t, J=6.4 Hz, 2H), 2.79 (t, J=6.4 Hz, 2H).

Step 4: Preparation of 7-chloro-2,3-dihydrofuro[2,3-c]pyridine

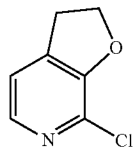

To a solution of 2-chloro-4-(2-hydroxyethyl)pyridin-3-ol (2.0 g, 11.52 mmol) and $PPh_3$ (3.32 g, 12.67 mmol) in THF (20 mL) was added DIAD (2.56 g, 12.67 mmol) dropwise at ° C. The reaction mixture was stirred at room temperature for 16 hours. At which point, the reaction mixture was extracted with EtOAc (300 mL×3), washed with water (300 mL×3), dried over $Na_2SO_4$, filtered and concentrated. The residue was purified by chromatography on silica gel (0-20% ethyl acetate in petroleum ether) to afford the title compound (1.6 g, 89%) as a white solid. $^1$H NMR (400 MHz, $CDCl_3$): δ 7.94 (d, J=4.4 Hz, 1H), 7.12 (d, J=4.4 Hz, 1H), 4.72 (t, J=8.8 Hz, 2H), 3.34 (t, J=8.8 Hz, 2H).

Step 5: Preparation of 7-chloro-5-nitro-2,3-dihydrofuro[2,3-c]pyridine

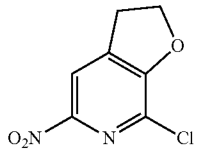

To a solution of 7-chloro-2,3-dihydrofuro[2,3-c]pyridine (6.0 g, 38.57 mmol) in $H_2SO_4$ (30 mL, 38.57 mmol) was added a mixture of $HNO_3$ (5 mL, 38.57 mmol) and $H_2SO_4$ (5 mL) dropwise at 0° C. Then mixture was slowly heated to 50° C. and stirred for 3 additional hours. The mixture was then quenched with water (200 mL), adjusted pH to 9 with sat. aq. $NaHCO_3$ solution and extracted with EtOAC (500 mL×3). The organic layer was washed with water (500 mL×3), dried over $Na_2SO_4$, filtered and concentrated to afford the title compound (5.0 g, 64%) as a yellow solid.

Step 6: Preparation of 7-chloro-2,3-dihydrofuro[2,3-c]pyridin-5-amine

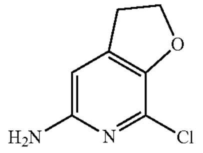 [SMILES: O=[N+]([O-])c1cc2c(c(Cl)n1)OCC2]

A mixture of 7-chloro-5-nitro-2,3-dihydrofuro[2,3-c]pyridine (5.0 g, 24.93 mmol), $NH_4Cl$ (13.3 g, 249.3 mmol) and Fe (13.9 g, 249.3 mmol) in ethanol:water (60 mL, 6:1) was stirred at 80° C. for 3 hours. At which point. the reaction mixture was filtered and concentrated. Then the mixture was extracted with EtOAc (100 mL×3), washed with water (100 mL×3), dried over $Na_2SO_4$, filtered and concentrated. The residue was purified by chromatography on silica gel (0-50% EtOAc in petroleum ether) to afford the title compound (1.0 g, 24%) as a yellow solid. $^1H$ NMR (400 MHz, $CDCl_3$): δ 6.38 (s, 1H), 4.62 (t, J=8.4 Hz, 2H), 4.27 (s, 2H), 3.23 (t, J=8.4 Hz, 2H).

Step 7: Preparation of 7-(4-isopropylphenyl)-2,3-dihydrofuro[2,3-c]pyridin-5-amine

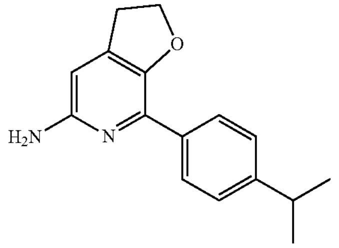 [SMILES: CC(C)c1ccc(-c2nc(N)cc3c2OCC3)cc1]

A solution of 7-chloro-2,3-dihydrofuro[2,3-c]pyridin-5-amine (500 mg, 2.93 mmol), Xphos (139 mg, 0.29 mmol), Xphos Pd $G_3$ (248 mg, 0.29 mmol), $K_3PO_4$ (1.87 g, 8.79 mmol) and (4-isopropylphenyl)boronic acid (721 mg, 4.4 mmol) in 1,4-dioxane (10 mL) and water (2 mL) was stirred at 100° C. for 3 hours. The mixture extracted with EtOAc (100 mL×3), washed with water (100 mL×3), dried over $Na_2SO_4$, filtered and concentrated. The residue was purified by chromatography on silica gel (0-50% EtOAc in petroleum ether) to afford the title compound (700 mg, 94%) as a yellow solid.

Step 8: Preparation of N-(7-(4-isopropylphenyl)-2,3-dihydrofuro[2,3-c]pyridin-5-yl)acetamide

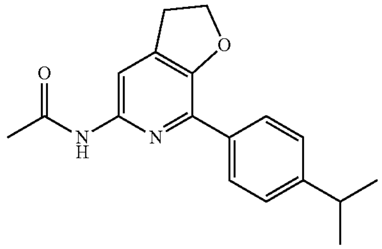 [SMILES: CC(=O)Nc1cc2c(c(-c3ccc(C(C)C)cc3)n1)OCC2]

To a mixture of 7-(4-isopropylphenyl)-2,3-dihydrofuro[2,3-c]pyridin-5-amine (700 mg, 2.75 mmol) and TEA (278 mg, 2.75 mmol) in DCM (10 mL) was added acetyl chloride (216 mg, 2.75 mmol) at −78° C. The mixture was stirred at −78° C. for 30 minutes. Then the mixture was quenched with water (1 mL). The organic layer was separated, dried over $Na_2SO_4$ and evaporated. The residue was purified by chromatography on silica gel (0-50% ethyl acetate in petroleum ether) to afford the title compound (700 mg, 86%) as a yellow solid. LCMS (ESI): m/z 297.1 $(M+H)^+$.

Step 9: Preparation of N-(4-Bromo-7-(4-isopropylphenyl)-2,3-dihydrofuro[2,3-c]pyridin-5-yl)acetamide

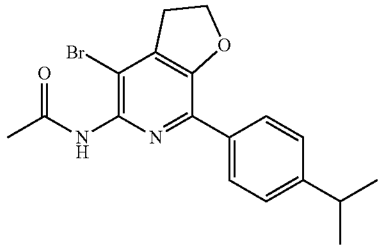 [SMILES: CC(=O)Nc1nc(-c2ccc(C(C)C)cc2)c2c(c1Br)CCO2]

To a solution of N-(7-(4-isopropylphenyl)-2,3-dihydrofuro[2,3-c]pyridin-5-yl)acetamide (700 mg, 2.36 mmol) in DCM (20 mL) was added NBS (630 mg, 3.54 mmol) at 0° C. Then the reaction was stirred at room temperature for 16 hours. At which point, the mixture was washed with water (50 mL×2), the organic layer was dried over $Na_2SO_4$ and evaporated. The residue was purified by chromatography on silica gel (0-50% ethyl acetate in petroleum ether) to afford the title compound (350 mg, 39%) as a yellow solid. LCMS (ESI): m/z 374.9 $(M+H)^+$.

Step 10: 4-bromo-7-(4-isopropylphenyl)-2,3-dihydrofuro[2,3-c]pyridin-5-amine

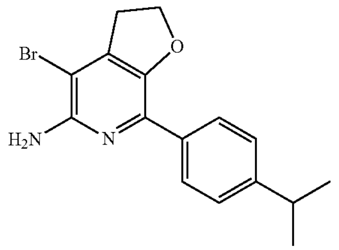 [SMILES: CC(C)c1ccc(-c2nc(N)c(Br)c3c2OCC3)cc1]

A solution of N-(4-bromo-7-(4-isopropylphenyl)-2,3-dihydrofuro[2,3-c]pyridin-5-yl)acetamide (350 mg, 0.93 mmol) and conc. hydrochloric acid (1 mL) in EtOH (10 mL) was stirred at 80° C. for 2 hours. At which point, the mixture was adjusted pH to 9 with 2 M aq. NaOH solution, extracted with EtOAc (200 mL×3), washed with water (200 mL×3), dried over $Na_2SO_4$, filtered and concentrated. The residue was purified by chromatography on silica gel (0-25% EtOAc in petroleum ether) to afford the title compound (280 mg, 90%) as a yellow oil. $^1$H NMR (400 MHz, $CDCl_3$): δ 8.00 (d, J=8.4 Hz, 2H), 7.26 (d, J=8.4 Hz, 2H), 4.65 (t, J=8.8 Hz, 2H), 4.59 (s, 2H), 3.21 (t, J=8.8 Hz, 2H), 2.97-2.87 (m, 1H), 1.26 (d, J=6.8 Hz, 6H).

Step 11: Preparation of 5-amino-7-(4-isopropylphenyl)-2,3-dihydrofuro[2,3-c]pyridine-4-carbonitrile

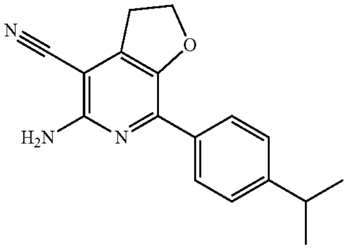 [SMILES: CC(C)c1ccc(-c2nc(N)c(C#N)c3c2OCC3)cc1]

A mixture of 4-bromo-7-(4-isopropylphenyl)-2,3-dihydrofuro[2,3-c]pyridin-5-amine (260 mg, 0.78 mmol), t-BuXphos Pd $G_3$ (62 mg, 0.08 mmol) and $Zn(CN)_2$ (458 mg, 3.9 mmol) in DMA (5 mL) was stirred at 135° C. for 16 hours. The reaction solution was quenched with the addition of water (20 mL), extracted with EtOAc (200 mL×3), washed with water (200 mL×3), dried over $Na_2SO_4$, filtered and concentrated. The residue was purified by chromatography on silica gel (solvent gradient: 0-20% ethyl acetate in petroleum ether) to afford the title compound (200 mg, 92%) as a yellow solid. $^1$H NMR (400 MHz, $CDCl_3$): δ 8.11 (d, J=8.0 Hz, 2H), 7.32 (d, J=8.0 Hz, 2H), 4.87 (s, 2H), 4.70 (t, J=8.8 Hz, 2H), 3.36 (t, J=8.8 Hz, 2H), 3.01-2.85 (m, 1H), 1.28 (d, J=6.8 Hz, 6H).

Step 12: Preparation of 2-(((4-Cyano-7-(4-isopropylphenyl)-2,3-dihydrofuro[2,3-c]pyridin-5-yl)amino)methyl)acrylic acid

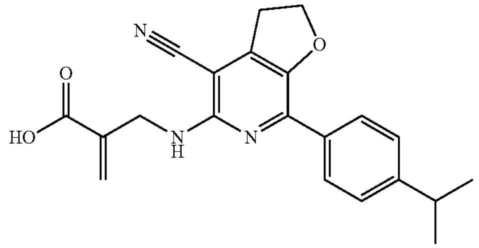 [SMILES: C=C(CNc1nc(-c2ccc(C(C)C)cc2)c2c(c1C#N)CCO2)C(=O)O]

A solution of 5-amino-7-(4-isopropylphenyl)-2,3-dihydrofuro[2,3-c]pyridine-4-carbonitrile (100 mg, 0.36 mmol) and 2-(bromomethyl)acrylic acid (59 mg, 0.36 mmol) in DMF (10 mL) was stirred at 100° C. for 16 hours. The reaction solution was purified by prep-HPLC (Welch Xtimate C18 150*25 mm*5 um, water (0.2% FA)-ACN, 62-92%) to afford the title compound (29.21 mg, 22%) as a yellow solid. $^1$H NMR (400 MHz, DMSO-$d_6$): δ 12.65 (s, 1H), 8.06 (d, J=8.4 Hz, 2H), 7.32 (d, J=8.4 Hz, 2H), 6.99 (t, J=5.6 Hz, 1H), 6.05 (s, 1H), 5.60 (s, 1H), 4.64 (t, J=8.4 Hz, 2H), 4.21 (d, J=5.6 Hz, 2H), 3.33-3.32 (m, 2H), 2.96-2.86 (m, 1H), 1.21 (d, J=6.8 Hz, 6H); LCMS (ESI): m/z 364.0 $(M+H)^+$.

Example 22

Preparation of 2-(((7-(4-Isopropylphenyl)-2,3-dihydrofuro[3,2-b]pyridin-5-yl)amino)methyl)acrylic acid The general reaction scheme was as follows:

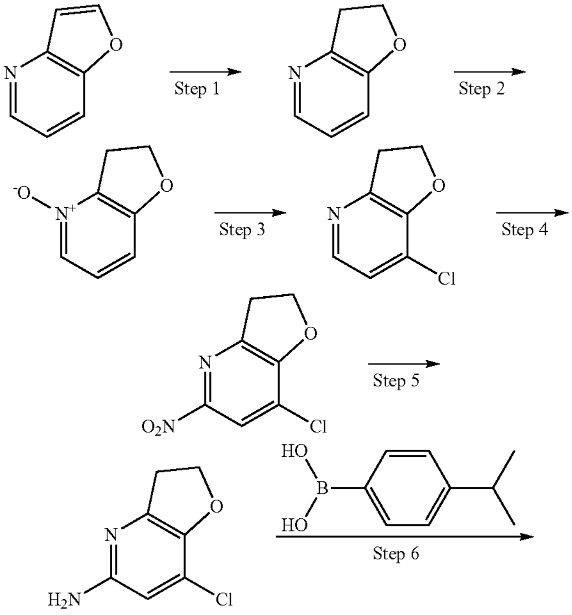

-continued

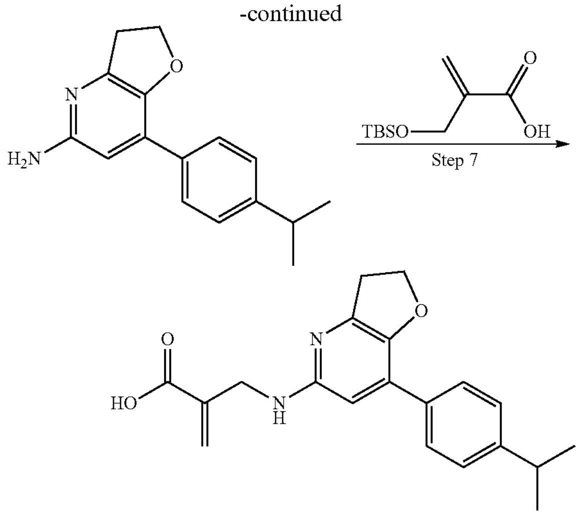

Step 1: Preparation of 2,3-dihydrofuro[3,2-b]pyridine

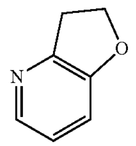

To a mixture of furo[3,2-b]pyridine (19.0 g, 159.5 mmol) in MeOH (200 mL) and HOAc (50 mL) was added 10% Pd on carbon (8.49 g, 7.98 mmol). The mixture was stirred at 50° C. under an atmosphere of $H_2$ (30 psi) for 16 hours. At which point, the reaction mixture was filtered and evaporated. Then the mixture was diluted with EtOAc (1 L), washed with water (300 mL) and brine (500 mlx3). The organic layer was dried over $Na_2SO_4$ and evaporated to afford the title compound (18 g, 93%) as a yellow liquid. $^1H$ NMR (400 MHz, $CDCl_3$): δ 8.05-8.00 (m, 1H), 7.09-6.92 (m, 2H), 4.67-4.62 (m, 2H), 3.35-3.30 (m, 2H).

Step 2: Preparation of 2,3-dihydrofuro[3,2-b]pyridine 4-oxide

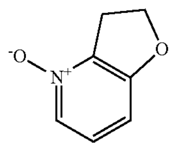

To a solution of 2,3-dihydrofuro[3,2-b]pyridine (16.0 g, 132.08 mmol) in DCM (300 mL) was added m-CPBA (32.18 g, 158.49 mmol, 85% purity) at 0° C. Then the mixture was stirred at room temperature for 3 hours. At which point, the reaction mixture was purified by chromatography on silica gel (0-10% $CH_3OH$ in DCM) to afford the title compound (15.0 g, 82%) as a white solid. $^1H$ NMR (400 MHz, $CDCl_3$): δ 7.78 (d, J=6.4 Hz, 1H), 7.05-7.01 (m, 1H), 6.70 (d, J=8.4 Hz, 1H), 4.74 (t, J=8.8 Hz, 2H), 3.48 (t, J=8.8 Hz, 2H).

Step 3: Preparation of 7-chloro-2,3-dihydrofuro[3,2-b]pyridine

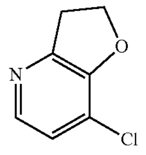

To a solution of 2,3-dihydrofuro[3,2-b]pyridine 4-oxide (24.0 g, 175 mmol) in toluene (100 mL) was added $POCl_3$ (80 mL) dropwise at room temperature. The mixture was stirred at 90° C. for 3 hours. At which point, the mixture was quenched with water (100 mL) and extracted with EtOAc (500 mL×3). The organic layer was washed with water (500 mL×3), dried over $Na_2SO_4$, filtered and concentrated. The residue was purified by chromatography on silica gel (0-15% EtOAc in petroleum ether) to afford the title compound (3.0 g, 11%) as a colorless liquid. $^1H$ NMR (400 MHz, $CDCl_3$): δ 7.95 (d, J=5.4 Hz, 1H), 7.06 (d, J=5.4 Hz, 1H), 4.77 (t, J=8.8 Hz, 2H), 3.42 (t, J=8.8 Hz, 2H); LCMS (ESI): m/z 155.8 $(M+H)^+$.

Step 4: Preparation of 7-chloro-5-nitro-2,3-dihydrofuro[3,2-b]pyridine

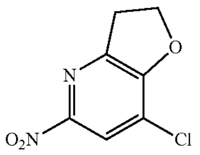 [SMILES: O=[N+]([O-])c1cc(Cl)c2c(n1)CCO2]

To a solution of 7-chloro-2,3-dihydrofuro[3,2-b]pyridine (500 mg, 3.21 mmol) in conc. $H_2SO_4$ (5 mL, 6.43 mmol) was added a mixture of conc. $HNO_3$ (1 mL, 6.43 mmol) and conc. $H_2SO_4$ (1 mL) dropwise at 0° C. Then the mixture was slowly heated to 50° C. and maintained at this temperature for 3 hours. The mixture was then quenched with water (100 mL), extracted with EtOAC (300 mL×3), the combined organics were washed with water (300 mL×3), dried over $Na_2SO_4$, filtered and concentrated. The residue was purified by chromatography on silica gel (0-15% EtOAc in petroleum ether) to afford the title compound (500 mg, 78%) as a yellow solid. $^1H$ NMR (400 MHz, $CDCl_3$): δ 8.19 (s, 1H), 4.96 (t, J=8.8 Hz, 2H), 3.54 (t, J=8.8 Hz, 2H).

Step 5: Preparation of 7-chloro-2,3-dihydrofuro[3,2-b]pyridin-5-amine

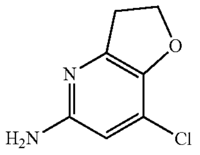

A solution of 7-chloro-5-nitro-2,3-dihydrofuro[3,2-b]pyridine (1.0 g, 4.99 mmol), $NH_4Cl$ (2.67 g, 49.86 mmol) and iron (2.78 g, 49.86 mmol) in water (2 mL) and EtOH (10 mL) was stirred at 80° C. for 3 hours. At which point, the reaction mixture was filtered and concentrated. The mixture was extracted with EtOAc (100 mL×3), washed with water (100 mL×3), dried over $Na_2SO_4$, filtered and concentrated to afford the title compound (800 mg, 94.1%) as a yellow solid. $^1H$ NMR (400 MHz, $CDCl_3$): δ 7.27 (s, 1H), 6.32 (s, 1H), 4.66 (t, J=8.8 Hz, 2H), 4.42-3.79 (m, 2H), 3.26 (t, J=8.8 Hz, 2H).

Step 6: Preparation of 7-(4-isopropylphenyl)-2,3-dihydrofuro[3,2-b]pyridin-5-amine

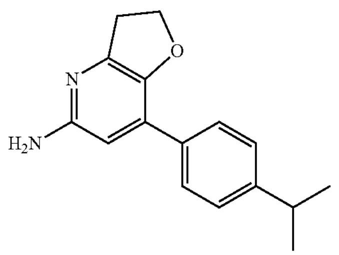 [SMILES: CC(C)c1ccc(-c2cc(N)nc3c2OCC3)cc1]

A solution of 7-chloro-2,3-dihydrofuro[3,2-b]pyridin-5-amine (800 mg, 4.69 mmol), Xphos (224 mg, 0.47 mmol), Xphos Pd $G_3$ (396 mg, 0.47 mmol), $K_3PO_4$ (2.98 g, 14.07 mmol) and (4-isopropylphenyl)boronic acid (1.15 g, 7.03 mmol) in 1,4-dioxane (15 mL) and water (3 mL) was stirred at 100° C. for 3 hours. The mixture was then extracted with EtOAc (100 mL×3), the combined organics were washed with water (100 mL×3), dried over $Na_2SO_4$, filtered and concentrated. The residue was purified by flash chromatography on silica gel (0-100% EtOAc in petroleum ether) to afford the title compound (700 mg, 58%) as a yellow solid. $^1H$ NMR (400 MHz, $CDCl_3$): δ 7.67 (d, J=8.4 Hz, 2H), 7.31 (d, J=8.4 Hz, 2H), 6.46 (s, 1H), 4.63 (t, J=8.8 Hz, 2H), 4.14 (s, 2H), 3.25 (t, J=8.8 Hz, 2H), 3.00-2.90 (m, 1H), 1.28 (d, J=7.2 Hz, 6H); LCMS (ESI): m/z 255.0 $(M+H)^+$.

Step 7: Preparation of 2-(((7-(4-isopropylphenyl)-2,3-dihydrofuro[3,2-b]pyridin-5-yl)amino)methyl)acrylic acid

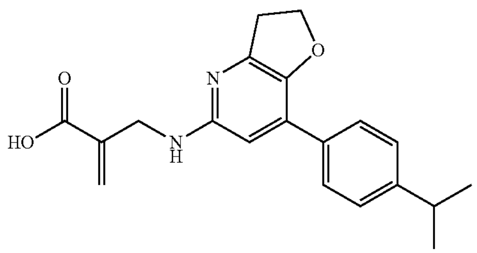 [SMILES: C=C(CNc1cc(-c2ccc(C(C)C)cc2)c2c(n1)CCO2)C(=O)O]

A solution of 7-(4-isopropylphenyl)-2,3-dihydrofuro[3,2-b]pyridin-5-amine (200 mg, 0.79 mmol), DMAP (9 mg, 0.08 mmol), 2-(((tert-butyldimethylsilyl)oxy)methyl)acrylic acid (510 mg, 2.36 mmol), TEA (0.33 mL, 2.36 mmol) and $T_3P$ (1.5 g, 2.36 mmol, 50% in ethyl acetate) in DMF (4 mL) was stirred at 70° C. for 16 hours. The reaction mixture was purified by prep-HPLC (3_Phenomenex Luna C18 75*30 mm*3 um, water (0.2% FA)-ACN, 26-56%) to afford the title compound (2.05 mg, 1%) as a yellow solid. $^1H$ NMR (400 MHz, $CDCl_3$): δ 7.66 (d, J=8.4 Hz, 2H), 7.33 (d, J=8.4 Hz, 2H), 6.40 (s, 1H), 6.33 (s, 1H), 5.78 (s, 1H), 4.64 (t, J=8.8 Hz, 2H), 4.12 (s, 2H), 3.33 (t, J=8.8 Hz, 2H), 3.00-2.93 (m, 1H), 1.28 (d, J=6.8 Hz, 6H); LCMS (ESI): m/z 339.0 $(M+H)^+$.

Example 23

Preparation of 2-(((7-cyano-4-(4-(1,1-difluoroethyl)phenyl)benzo[d]thiazol-6-yl)amino)methyl)acrylic acid The general reaction scheme was as follows:

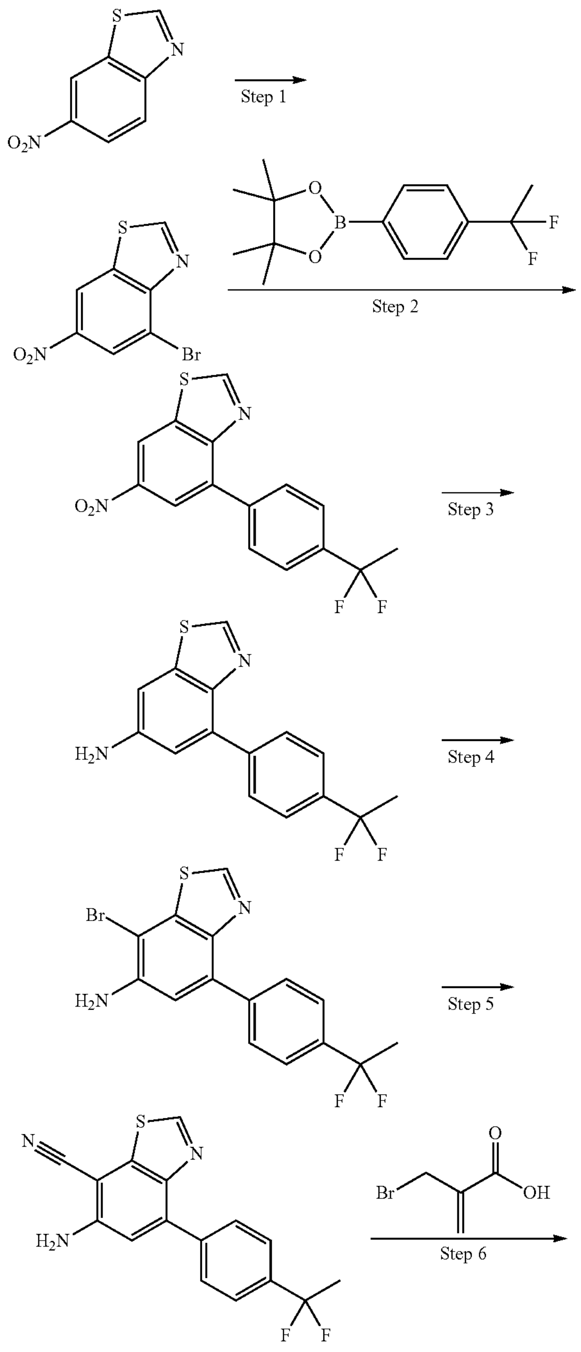

-continued

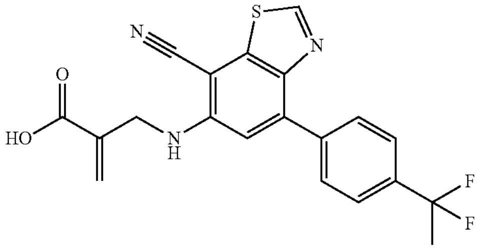

Step 1: Preparation of 4-bromo-6-nitrobenzo[d]thiazole

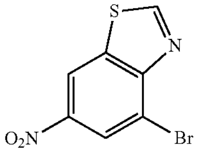

To a solution of 6-nitrobenzo[d]thiazole (10.0 g, 55.5 mmol) in conc. $H_2SO_4$ (50 mL) was added NBS (10.87 g, 61.05 mmol) at 0° C. Then the mixture was stirred at 60° C. for 5 hours. At which point, the mixture was quenched with water (100 mL) and extracted with EtOAc (1 L×3). The organic layer was washed with water (500 mL×3), dried over $Na_2SO_4$, filtered and concentrated. The residue was triturated with EtOAc (50 mL) and filtered. The filter cake was washed with EtOAc and concentrated to afford the title compound (10 g, 69%) as a white solid. $^1H$ NMR (400 MHz, $CDCl_3$): δ 9.37 (s, 1H), 8.89 (d, J=2.0 Hz, 1H), 8.64 (d, J=2.0 Hz, 1H).

Step 2: Preparation of 4-(4-(1,1-Difluoroethyl)phenyl)-6-nitrobenzo[d]thiazole

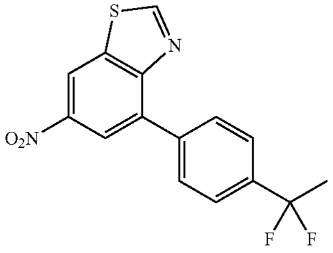 [SMILES: CC(F)(F)c1ccc(-c2cc([N+](=O)[O-])cc3scnc23)cc1]

A mixture of 4-bromo-6-nitrobenzo[d]thiazole (5.0 g, 19.3 mmol), 2-(4-(1,1-difluoroethyl)phenyl)-4,4,5,5-tetramethyl-1,3,2-dioxaborolane (6.21 g, 23.16 mmol), Pd(dppf)$Cl_2$ (1.41 g, 1.93 mmol), $K_2CO_3$ (8.0 g, 57.9 mmol) in 1,4-dioxane (50 mL) and water (5 mL) was stirred at 100° C. for 2 hours under a $N_2$ atmosphere. The reaction mixture was concentrated under vacuum. The residue was purified by flash chromatography on silica gel (0-25% ethyl acetate in petroleum ether) to afford the title compound (5.5 g, 89%) as a yellow solid.

Step 3: Preparation of 4-(4-(1,1-difluoroethyl)phenyl)benzo[d]thiazol-6-amine

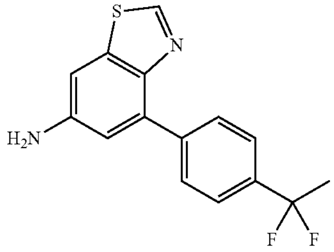 [SMILES: CC(F)(F)c1ccc(-c2cc(N)cc3scnc23)cc1]

A solution of 4-(4-(1,1-difluoroethyl)phenyl)-6-nitrobenzo[d]thiazole (5.5 g, 17.17 mmol), 10% Pd on carbon (1.83 g, 17.17 mmol) in EtOH (100 mL) under a $H_2$ atmosphere (15 Psi) was stirred at room temperature for 3 hours. The reaction mixture was filtered and concentrated. The residue was purified by flash chromatography on silica gel (0-50% EtOAc in petroleum ether) to afford the title compound (3.0 g, 60%) as a yellow solid. LCMS (ESI): m/z 290.9 $(M+H)^+$.

Step 4: Preparation of 7-bromo-4-(4-(1,1-difluoroethyl)phenyl)benzo[d]thiazol-6-amine

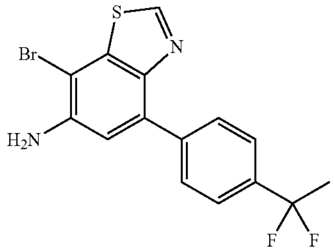 [SMILES: CC(F)(F)c1ccc(-c2cc(N)c(Br)c3scnc23)cc1]

A solution of 4-(4-(1,1-difluoroethyl)phenyl)benzo[d]thiazol-6-amine (500 mg, 1.72 mmol) and NBS (306 mg, 1.72 mmol) in DCM (10 mL) was stirred at 0° C. for 1 hour. The residue was purified by flash chromatography on silica gel (0-25% EtOAc in petroleum ether) to afford the title compound (400 mg, 63%) as a yellow solid. $^1H$ NMR (400 MHz, $CDCl_3$): δ 8.79 (s, 1H), 7.82 (d, J=8.0 Hz, 2H), 7.63 (d, J=8.0 Hz, 2H), 7.03 (s, 1H), 4.32 (s, 2H), 1.97 (t, J=18.0 Hz, 3H); LCMS (ESI): m/z 369.0 $(M+H)^+$.

Step 5: Preparation of 6-amino-4-(4-(1,1-difluoroethyl)phenyl)benzo[d]thiazole-7-carbonitrile

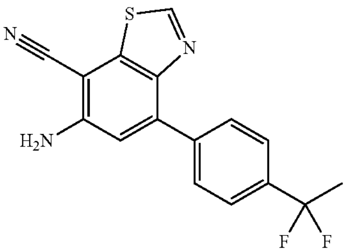 [SMILES: CC(F)(F)c1ccc(-c2cc(N)c(C#N)c3scnc23)cc1]

A mixture of 7-bromo-4-(4-(1,1-difluoroethyl)phenyl)benzo[d]thiazol-6-amine (350 mg, 0.95 mmol), t-BuXphos Pd G3 (75 mg, 0.09 mmol) and $Zn(CN)_2$ (556 mg, 4.74 mmol) in DMA (7 mL) was stirred at 135° C. for 2 hours. At which time, the reaction solution was quenched with water (100 mL), extracted with EtOAc (200 mL×2) dried over $MgSO_4$, filtered and concentrated. The residue was purified by flash chromatography on silica gel (0-25% ethyl acetate in petroleum ether) to afford the title compound (250 mg, 83%) as a yellow solid. LCMS (ESI): m/z 316.1 $(M+H)^+$.

Step 6: Preparation of 2-(((7-cyano-4-(4-(1,1-difluoroethyl)phenyl)benzo[d]thiazol-6-yl)amino)methyl)acrylic acid

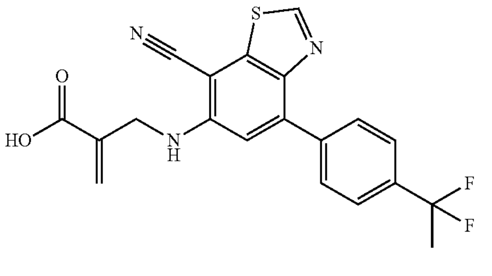 [SMILES: C=C(CNc1cc(-c2ccc(C(C)(F)F)cc2)c2ncsc2c1C#N)C(=O)O]

A solution of 6-amino-4-(4-(1,1-difluoroethyl)phenyl)benzo[d]thiazole-7-carbonitrile (100 mg, 0.32 mmol) and 2-(bromomethyl)acrylic acid (52 mg, 0.32 mmol) in DMF (1 mL) was stirred at 90° C. for 16 hours. The reaction solution was purified by prep-HPLC (Welch Xtimate C18 150*25 mm*5 um, water (0.2% FA)-ACN, 58-88%) to afford the title compound (28.37 mg, 21%) as a white solid. $^1H$ NMR (400 MHz, DMSO-$d_6$): δ 12.80 (s, 1H), 9.14 (s, 1H), 7.88 (d, J=8.4 Hz, 2H), 7.69 (d, J=8.4 Hz, 2H), 7.14 (t, J=6.0 Hz, 1H), 6.91 (s, 1H), 6.13 (s, 1H), 5.67 (s, 1H), 4.23 (d, J=5.6 Hz, 2H), 2.02 (t, J=19.2 Hz, 3H); LCMS (ESI): m/z 400.0 $(M+H)^+$.

Example 24

Preparation of 2-(((6-methoxy-5-((E)-2-(trans-4-(trifluoromethyl)cyclohexyl)vinyl)pyridin-3-yl)amino)methyl)acrylic acid The general reaction scheme was as follows:

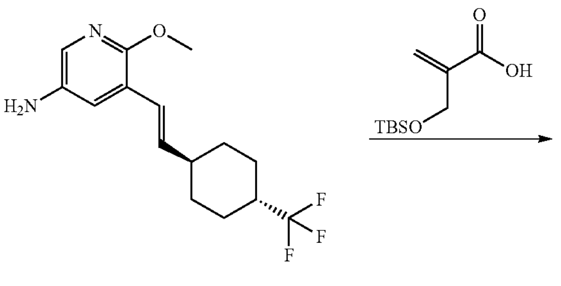

-continued

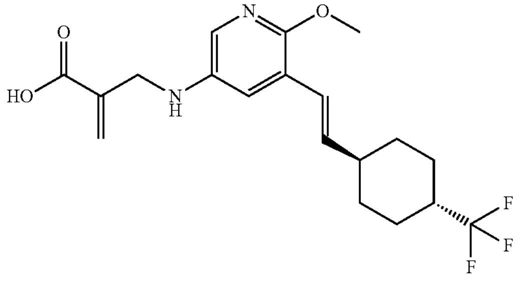

To a solution of DIPEA (0.42 mL, 2.5 mmol), 6-methoxy-5-((E)-2-(trans-4-(trifluoromethyl)cyclohexyl)vinyl)pyridin-3-amine (500 mg, 1.66 mmol) and 2-(((tert-butyldimethylsilyl)oxy)methyl)acrylic acid (1.0 g, 4.5 mmol) in DCM (20 mL) was added HATU (696 mg, 1.83 mmol) at room temperature. The reaction mixture was stirred for 30 minutes. The reaction mixture was quenched with water (50 mL), extracted with EtOAc (30 mL×2). The organic layers were combined, dried over $Na_2SO_4$ and concentrated. The resulting residue was purified by prep-HPLC (Boston Green ODS 150*30 mm*5 um, water (0.2% FA)-ACN, 52%-82%) to afford 30 mg crude product. The crude product was further purified by pre-TLC (10% MeOH in DCM) to afford the title compound (9.6 mg, 2%) as a white solid. $^1H$ NMR (400 MHz, DMSO-$d_6$): δ 7.35 (d, J=2.8 Hz, 1H), 7.09 (d, J=2.8 Hz, 1H), 6.40 (d, J=16.0 Hz, 1H), 6.16 (dd, J=16.0, 6.8 Hz, 1H), 5.89 (s, 1H), 5.38 (s, 1H), 3.82 (s, 2H), 3.74 (s, 3H), 2.24-2.20 (m, 1H), 2.14-2.10 (m, 1H), 1.90-1.80 (m, 4H), 1.33-1.20 (m, 4H). LCMS (ESI): m/z 385.2 $(M+H)^+$.

Example 25

Preparation of 2-(((6-Cyano-5-((E)-2-(trans-4-(trifluoromethyl)cyclohexyl)vinyl)pyridin-3-yl)amino)methyl)acrylic acid The general reaction scheme was as follows:

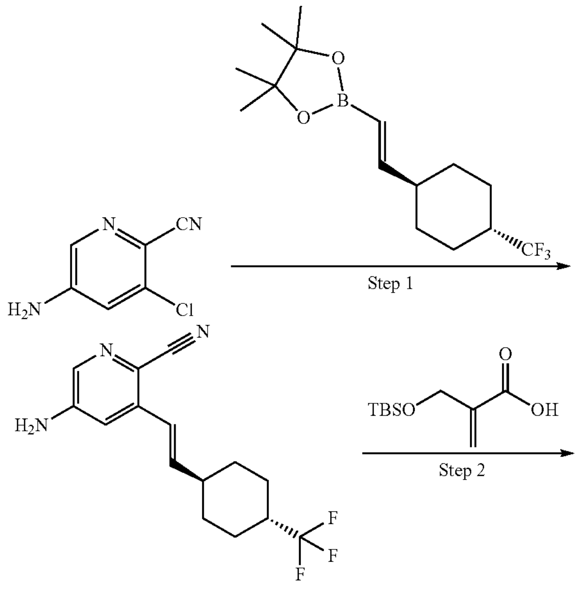

-continued

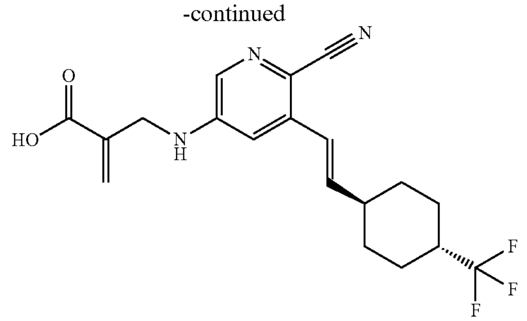

Step 1: Preparation of 5-Amino-3-((E)-2-(trans-4 (trifluoromethyl)cyclohexyl)vinyl)picolinonitrile

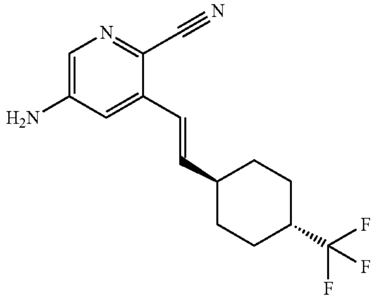 [SMILES: N#Cc1ncc(N)cc1/C=C/[C@H]1CC[C@H](C(F)(F)F)CC1]

A mixture of 4,4,5,5-tetramethyl-2-((E)-2-(trans-4-(trifluoromethyl)cyclohexyl)vinyl)-1,3,2-dioxaborolane (396 mg, 1.3 mmol), $K_3PO_4$ (829 mg, 3.91 mmol), Xphos Pd $G_3$ (55 mg, 0.07 mmol), Xphos (31 mg, 0.07 mmol), 5-amino-3-chloropicolinonitrile (200 mg, 1.3 mmol) and in 1,4-dioxane (6 mL) and water (1 mL) was stirred at 100° C. for 3 hours. The mixture was diluted with EtOAc (50 mL) and washed with water (30 mL). The organic layer was dried over $Na_2SO_4$ and concentrated. The residue was purified by column chromatography on silica gel (0-30% EtOAc in petroleum ether) to afford the title compound (350 mg, 91%) as a yellow solid. LCMS (ESI): m/z 296.1 $(M+H)^+$.

Step 2: Preparation of 2-(((6-cyano-5-((E)-2-(trans-4-(trifluoromethyl)cyclohexyl)vinyl)pyridin-3-yl) amino)methyl)acrylic acid

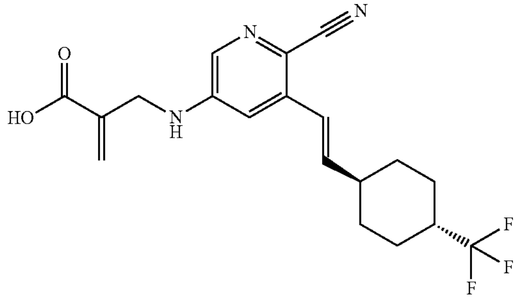 [SMILES: C=C(CNc1cnc(C#N)c(/C=C/[C@H]2CC[C@H](C(F)(F)F)CC2)c1)C(=O)O]

A mixture of DMAP (8 mg, 0.07 mmol), 5-amino-3-((E)-2-(trans-4-(trifluoromethyl)cyclohexyl)vinyl)picolinonitrile (200 mg, 0.68 mmol), 2-(((tert-butyldimethylsilyl)oxy)methyl)acrylic acid (439 mg, 2.03 mmol) and $T_3P$ (1.29 g, 2.03 mmol, 50% in ethyl acetate) in ethyl acetate (3 mL) was stirred at 80° C. for 16 hours. The mixture was quenched with water (100 mL) and extracted with EtOAc (100 mL×2). The organic layer was washed with water (100 mL×3), dried over $Na_2SO_4$, filtered and concentrated. The residue was purified by column chromatography on silica gel (0-15% EtOAc in petroleum ether) to afford 100 mg crude product. The crude product was further purified by pre-HPLC (3_Phenomenex Luna C18 75*30 mm*3 um, water (0.2% FA)-ACN, 60%-90%) to afford the title compound (27.5 mg, 11%) as a white solid. $^1H$ NMR (400 MHz, $CDCl_3$): δ 7.95 (d, J=2.4 Hz, 1H), 6.88 (d, J=2.4 Hz, 1H), 6.63 (d, J=16.0 Hz, 1H), 6.49 (s, 1H), 6.29 (dd, J=16.0, 7.2 Hz, 1H), 5.92 (s, 1H), 4.73 (s, 1H), 4.14 (s, 2H), 2.28-2.18 (m, 1H), 2.10-1.97 (m, 5H), 1.51-1.34 (m, 2H), 1.32-1.14 (m, 2H). LCMS (ESI): m/z 380.2 $(M+H)^+$.

Example 26

Preparation of 2-(((4-(Hydroxymethyl)-7-(4-(trifluoromethoxy)phenyl)-2,3-dihydrobenzofuran-5-yl) amino)methyl)acrylamide The general reaction scheme was as follows:

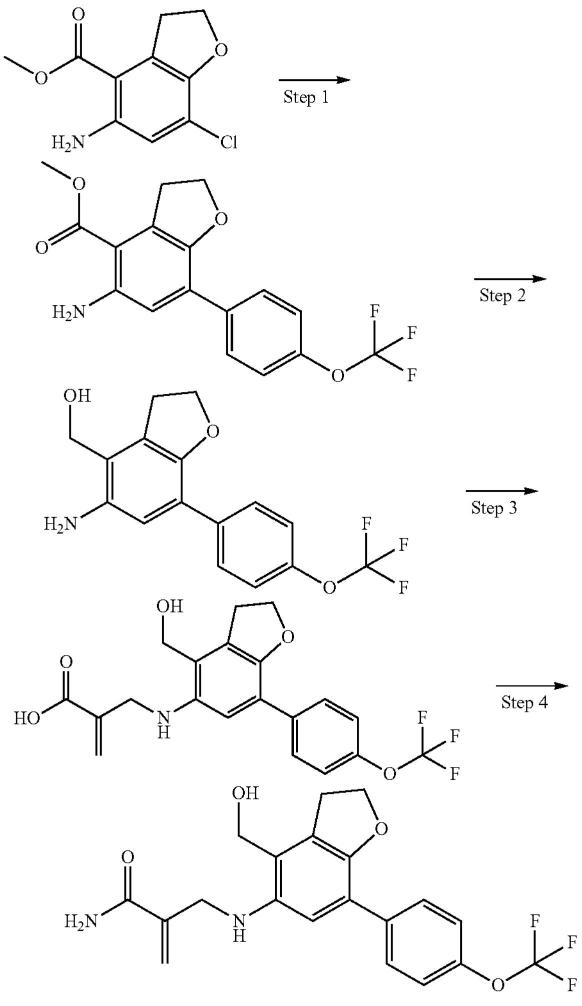

Step 1: Preparation of methyl 5-amino-7-(4-(trifluoromethoxy)phenyl)-2,3-dihydrobenzofuran-4-carboxylate

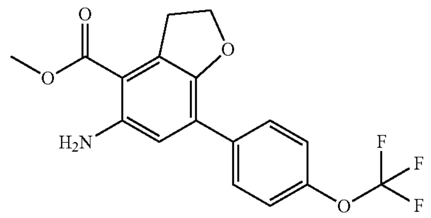 [SMILES: COC(=O)c1c(N)cc(-c2ccc(OC(F)(F)F)cc2)c2c1CCO2]

A mixture of (4-(trifluoromethoxy)phenyl)boronic acid (1.1 g, 5.3 mmol), methyl 5-amino-7-chloro-2,3-dihydrobenzofuran-4-carboxylate (1.0 g, 4.4 mmol), KOAc (860 mg, 8.8 mmol), Xphos (210 mg, 0.44 mmol) and Xphos Pd $G_2$ (345 mg, 0.44 mmol) in 1,4-Dioxane (20 mL) and Water (2 mL) was stirred at 100° C. for 2 hours under a nitrogen atmosphere. The reaction was quenched with water (50 mL) and extracted with ethyl acetate (30 mL×2), the combined organic layers were dried over $Na_2SO_4$ and concentrated. The residue was purified by chromatography on silica gel (0-10% ethyl acetate in petroleum ether) to afford the title compound (1.4 g, 90%) as a yellow solid. $^1$H NMR (400 MHz, $CDCl_3$): δ 7.71 (d, J=8.0 Hz, 2H), 7.27 (d, J=8.0 Hz, 2H), 6.63 (s, 1H), 5.42 (s, 2H), 4.55 (t, J=8.8 Hz, 2H), 3.90 (s, 3H), 3.52 (t, J=8.8 Hz, 2H); LCMS (ESI): m/z 353.9 $(M+H)^+$.

Step 2: Preparation of (5-Amino-7-(4-(trifluoromethoxy)phenyl)-2,3-dihydrobenzofuran-4-yl)methanol

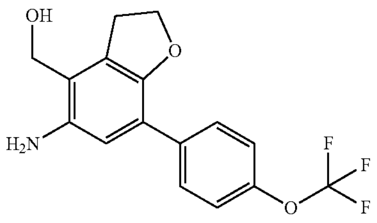 [SMILES: Nc1cc(-c2ccc(OC(F)(F)F)cc2)c2c(c1CO)CCO2]

To a solution of methyl 5-amino-7-(4-(trifluoromethoxy)phenyl)-2,3-dihydrobenzofuran-4-carboxylate (1.6 g, 3.62 mmol) in THF (20 mL) was added $LiAlH_4$ (412 mg, 10.87 mmol) slowly at 0° C. Then the reaction mixture was stirred at 0° C. for 1 hour. The mixture was quenched by water (0.5 mL), 1 M aq. NaOH (0.5 mL) and water (0.5 mL). To the solution was added anhydrous $MgSO_4$, the mixture was filtered and washed with ethyl acetate (50 mL). The filtrate was concentrated to afford the title compound (1.1 g, 93%) as a brown solid. $^1$H NMR (400 MHz, $CDCl_3$): δ 7.95 (d, J=8.4 Hz, 2H), 7.52 (d, J=8.4 Hz, 2H), 6.92 (s, 1H), 4.97 (s, 2H), 4.85 (t, J=8.8 Hz, 2H), 3.50 (t, J=8.8 Hz, 2H); LCMS (ESI): m/z 325.8 $(M+H)^+$.

Step 3: Preparation of 2-(((4-(Hydroxymethyl)-7-(4-(trifluoromethoxy)phenyl)-2,3-dihydrobenzofuran-5-yl)amino)methyl)acrylic acid

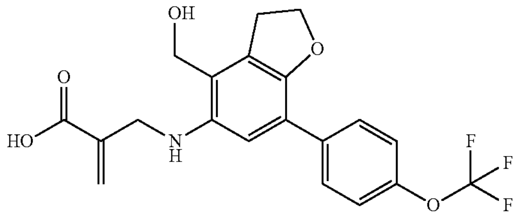 [SMILES: C=C(CNc1cc(-c2ccc(OC(F)(F)F)cc2)c2c(c1CO)CCO2)C(=O)O]

To a solution of (5-amino-7-(4-(trifluoromethoxy)phenyl)-2,3-dihydrobenzofuran-4-yl)methanol (200 mg, 0.61 mmol) in DMF (2 mL) was added 2-(bromomethyl)acrylic acid (81 mg, 0.49 mmol). The mixture was stirred at room temperature for 1 hour. The reaction mixture was used directly for next step directly. LCMS (ESI): m/z 410.2 $(M+H)^+$.

Step 4: Preparation of 2-(((4-(Hydroxymethyl)-7-(4-(trifluoromethoxy)phenyl)-2,3-dihydrobenzofuran-5-yl)amino)methyl)acrylamide

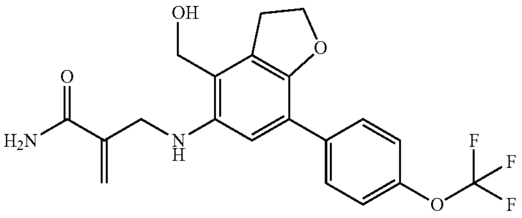 [SMILES: C=C(CNc1cc(-c2ccc(OC(F)(F)F)cc2)c2c(c1CO)CCO2)C(N)=O]

To a solution of 2-(((4-(hydroxymethyl)-7-(4-(trifluoromethoxy)phenyl)-2,3-dihydrobenzofuran-5-yl)amino)methyl)acrylic acid (200 mg, 0.54 mmol), DIPEA (0.48 mL, 2.72 mmol) and $NH_4Cl$ (59 mg, 1.09 mmol) in DMF (1 mL) was added HATU (621 mg, 1.63 mmol) at room temperature, the reaction solution was stirred at room temperature for 2 hours. The resulting residue was purified by reverse phase chromatography (Welch Xtimate C18 150*25 mm*5 um, water (0.2% FA)-CAN, 32%-62%) to afford 40 mg crude product. The crude product was further purified by Prep-TLC (petroleum ether:ethyl acetate:ethyl alcohol=8:3:1) to afford the title compound (24 mg, 12%) as a white solid. $^1$H NMR (400 MHz, DMSO-$d_6$): δ 7.74 (d, J=8.8 Hz, 2H), 7.58 (s, 1H), 7.38 (d, J=8.8 Hz, 2H), 7.11 (s, 1H), 6.44 (s, 1H), 5.81 (s, 1H), 5.50 (s, 1H), 5.24 (t, J=6.0 Hz, 1H), 5.11 (t, J=5.2 Hz, 1H), 4.54-4.40 (m, 4H), 3.95 (d, J=5.2 Hz, 2H), 3.19 (t, J=8.8 Hz, 2H); LCMS (ESI): m/z 409.2 $(M+H)^+$.

Example 27

Preparation of N-Hydroxy-2-(((4-(hydroxymethyl)-7-(4-(trifluoromethoxy)phenyl)-2,3-dihydrobenzofuran-5-yl)amino)methyl)acrylamide

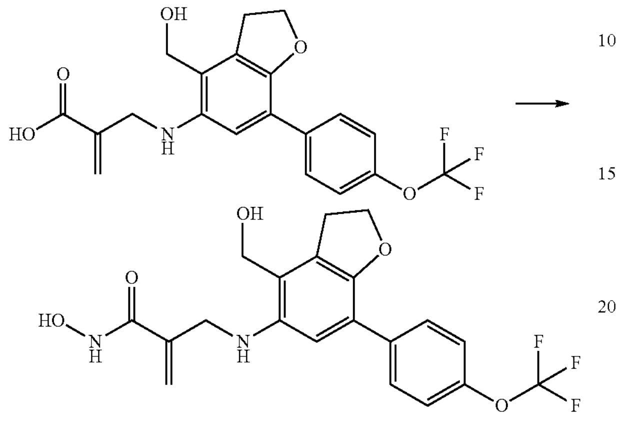

To a solution of 2-(((4-(hydroxymethyl)-7-(4-(trifluoromethoxy)phenyl)-2,3-dihydrobenzofuran-5-yl)amino) methyl)acrylic acid (200 mg, 0.49 mmol), TEA (0.22 mL, 1.56 mmol) in DMF (2 mL) was added PyBop (280 mg, 0.54 mmol). The reaction was stirred for 20 minutes then hydroxylamine hydrochloride (38 mg, 0.54 mmol) was added into the reaction mixture. The resulting mixture was stirred at room temperature for 2 hours. The combined mixture was purified by Prep-HPLC (Welch Xtimate C18 150*25 mm*5 um, water (0.2% FA)-CAN, 26%-56%) to afford 30 mg crude product. The crude product was further purified by Prep-TLC (petroleum ether:ethyl acetate:ethyl alcohol=4:3:1) to afford 20 mg product. The product was further purified by Prep-HPLC (Welch Xtimate C18 150*25 mm*5 um, water (0.2% FA)-CAN, 26%-56%) to afford the title compound (3.79 mg, 2%) as a white solid. $^1$H NMR (400 MHz, DMSO-$d_6$): δ 10.83 (s, 1H), 8.92 (s, 1H), 7.74 (d, J=8.8 Hz, 2H), 7.39 (d, J=8.8 Hz, 2H), 6.44 (s, 1H), 5.63 (s, 1H), 5.43 (s, 1H), 5.26 (s, 1H), 5.13 (s, 1H), 4.53-4.40 (m, 4H), 3.96 (d, J=4.4 Hz, 2H), 3.19 (t, J=8.4 Hz, 2H); LCMS (ESI): m/z 425.2 $(M+H)^+$.

Example 28

Preparation of 2-(((4-Cyano-7-(2-fluoro-4-isopropylphenyl)-2,3-dihydrobenzofuran-5-yl)amino)methyl) acrylic acid The general reaction scheme was as follows:

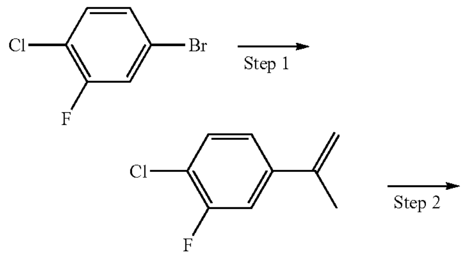

-continued

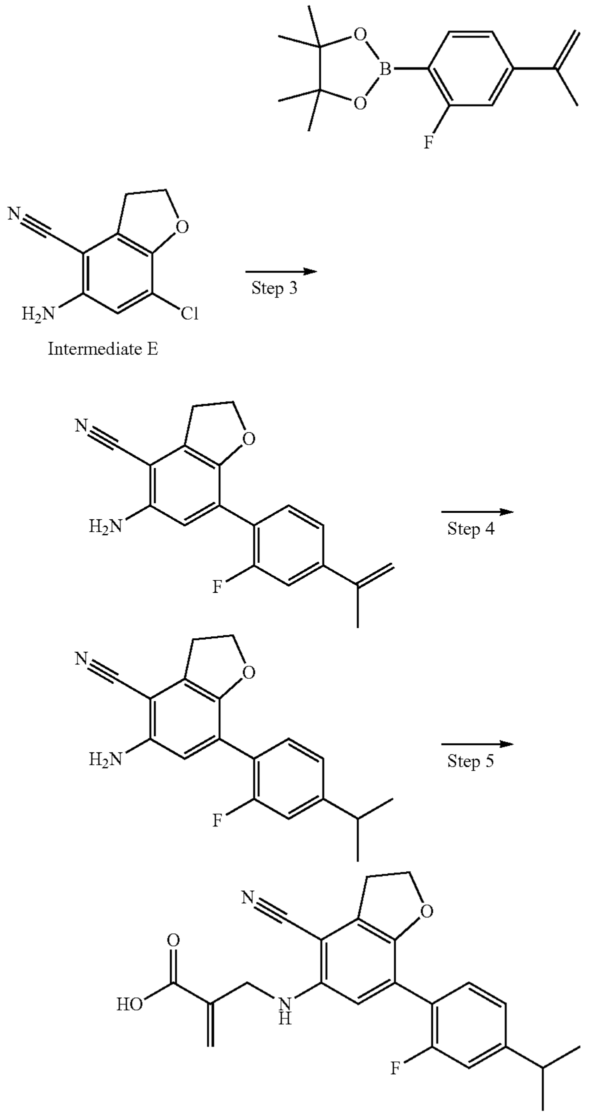

Step 1: Preparation of 1-Chloro-2-fluoro-4-(prop-1-en-2-yl)benzene

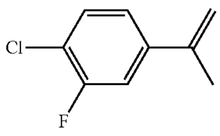

A mixture of 4-bromo-1-chloro-2-fluorobenzene (2.0 g, 9.55 mmol), 4,4,5,5-tetramethyl-2-(prop-1-en-2-yl)-1,3,2-dioxaborolane (2.41 g, 14.32 mmol), $Pd(dppf)Cl_2$ (700 mg, 0.95 mmol), $K_2CO_3$ (3.96 g, 28.65 mmol) in 1,4-dioxane (20 mL) and water (2 mL) was stirred at 100° C. for 2 hours under a nitrogen atmosphere. The reaction mixture was concentrated under vacuum. The residue was purified by flash chromatography on silica gel (100% petroleum ether) to afford the title compound (1.4 g, 57%) as a colorless oil.

Step 2: Preparation of 2-(2-Fluoro-4-(prop-1-en-2-yl)phenyl)-4,4,5,5-tetramethyl-1,3,2-dioxaborolane

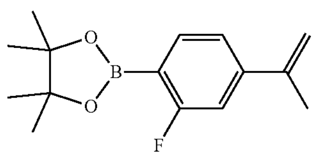 [SMILES: C=C(C)c1ccc(B2OC(C)(C)C(C)(C)O2)c(F)c1]

A mixture of 1-chloro-2-fluoro-4-(prop-1-en-2-yl)benzene (1.4 g, 4.92 mmol), 4,4,4',4',5,5,5',5'-octamethyl-2,2'-bi(1,3,2-dioxaborolane) (1.25 g, 4.92 mmol), Pd(dppf)$Cl_2$ (360 mg, 0.49 mmol), KOAc (0.97 g, 9.85 mmol) in 1,4-dioxane (20 mL) was stirred at 100° C. for 16 hours under a nitrogen atmosphere. The reaction mixture was concentrated under vacuum. The residue was purified by flash chromatography on silica gel (0-4% DCM in petroleum ether) to afford the title compound the title compound (800 mg, 62%) as a colorless oil. $^1H$ NMR (400 MHz, $CDCl_3$): δ 7.75-7.63 (m, 1H), 7.27-7.24 (m, 1H), 7.12 (d, J=7.2 Hz, 1H), 5.45 (s, 1H), 5.17 (s, 1H), 2.14 (s, 3H), 1.37 (s, 12H).

Step 3: Preparation of 5-Amino-7-(2-fluoro-4-(prop-1-en-2-yl)phenyl)-2,3-dihydrobenzofuran-4-carbonitrile

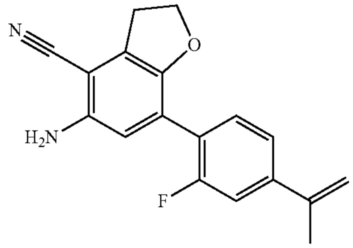 [SMILES: C=C(C)c1ccc(-c2cc(N)c(C#N)c3c2OCC3)c(F)c1]

A mixture of Xphos Pd $G_2$ (218 mg, 0.26 mmol), Xphos (123 mg, 0.26 mmol), 5-amino-7-chloro-2,3-dihydrobenzofuran-4-carbonitrile (500 mg, 2.57 mmol), 2-(2-fluoro-4-(prop-1-en-2-yl)phenyl)-4,4,5,5-tetramethyl-1,3,2-dioxaborolane (800 mg, 3.05 mmol), 1,4-dioxane (10 mL) and water (2 mL) was stirred at 80° C. for 4 hours under a nitrogen atmosphere. The mixture was diluted with ethyl acetate (50 mL) and washed with water (30 mL×3). The organics were combined, dried over $Na_2SO_4$ and concentrated. The residue was purified by flash chromatography on silica gel (0-30% ethyl acetate in petroleum ether) to afford the title compound (600 mg, 79%) as a yellow solid. $^1H$ NMR (400 MHz, $CDCl_3$): δ 7.48-7.41 (m, 1H), 7.33-7.30 (m, 1H), 7.26-7.23 (m, 1H), 6.66 (s, 1H), 5.44 (s, 1H), 5.17 (s, 1H), 4.63 (t, J=8.8 Hz, 2H), 4.09 (s, 2H), 3.38 (t, J=8.8 Hz, 2H), 2.16 (s, 3H); LCMS (ESI): m/z 294.9 $(M+H)^+$.

Step 4: Preparation of 5-Amino-7-(2-fluoro-4-isopropylphenyl)-2,3-dihydrobenzofuran-4-carbonitrile

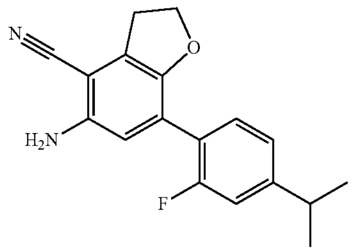 [SMILES: CC(C)c1ccc(-c2cc(N)c(C#N)c3c2OCC3)c(F)c1]

To a solution of 5-amino-7-(2-fluoro-4-(prop-1-en-2-yl)phenyl)-2,3-dihydrobenzofuran-4-carbonitrile (500 mg, 1.7 mmol) in ethyl acetate (15 mL) and MeOH (3 mL) was added 10% Pd/C (100 mg, 1.7 mmol). The reaction was stirred at room temperature for 2 hours under a $H_2$ atmosphere (15 psi). The solution was filtered and concentrated to afford the title compound (400 mg, 80%) as a yellow oil. LCMS (ESI): m/z 297.0 $(M+H)^+$.

Step 5: Preparation of 2-(((4-Cyano-7-(2-fluoro-4-isopropylphenyl)-2,3-dihydrobenzofuran-5-yl)amino)methyl)acrylic acid

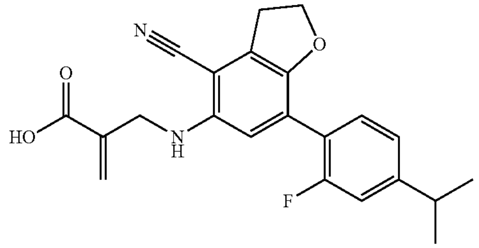 [SMILES: C=C(CNc1cc(-c2ccc(C(C)C)cc2F)c2c(c1C#N)CCO2)C(=O)O]

The mixture of 5-amino-7-(2-fluoro-4-isopropylphenyl)-2,3-dihydrobenzofuran-4-carbonitrile (200 mg, 0.67 mmol), 2-(bromomethyl)acrylic acid (112 mg, 0.67 mmol) in DMF (5 mL) was stirred at room temperature for 24 hours. The solution was purified by reverse phase chromatography (Boston Green ODS 150*30 mm*5 um, water (0.225% FA)-ACN acetonitrile 58-88/0.1% FA in water) to afford the title compound (48.98 mg, 19%) as a light yellow solid. $^1H$ NMR (400 MHz, DMSO-$d_6$): δ 7.31-7.26 (m, 1H), 7.18-7.08 (m, 2H), 6.34 (s, 1H), 6.10 (s, 1H), 6.02 (s, 1H), 5.61 (s, 1H), 4.51 (t, J=8.8 Hz, 2H), 3.98 (s, 2H), 3.29 (t, J=8.8 Hz, 2H), 2.96-2.89 (m, 1H), 1.21 (d, J=6.8 Hz, 6H); LCMS (ESI): m/z 381.0 $(M+H)^+$.

Example 29

Preparation of 2-(((4-Cyano-7-(2,6-difluoro-4-isopropylphenyl)-2,3-dihydrobenzofuran-5-yl)amino)methyl)acrylic acid The general reaction scheme was as follows:

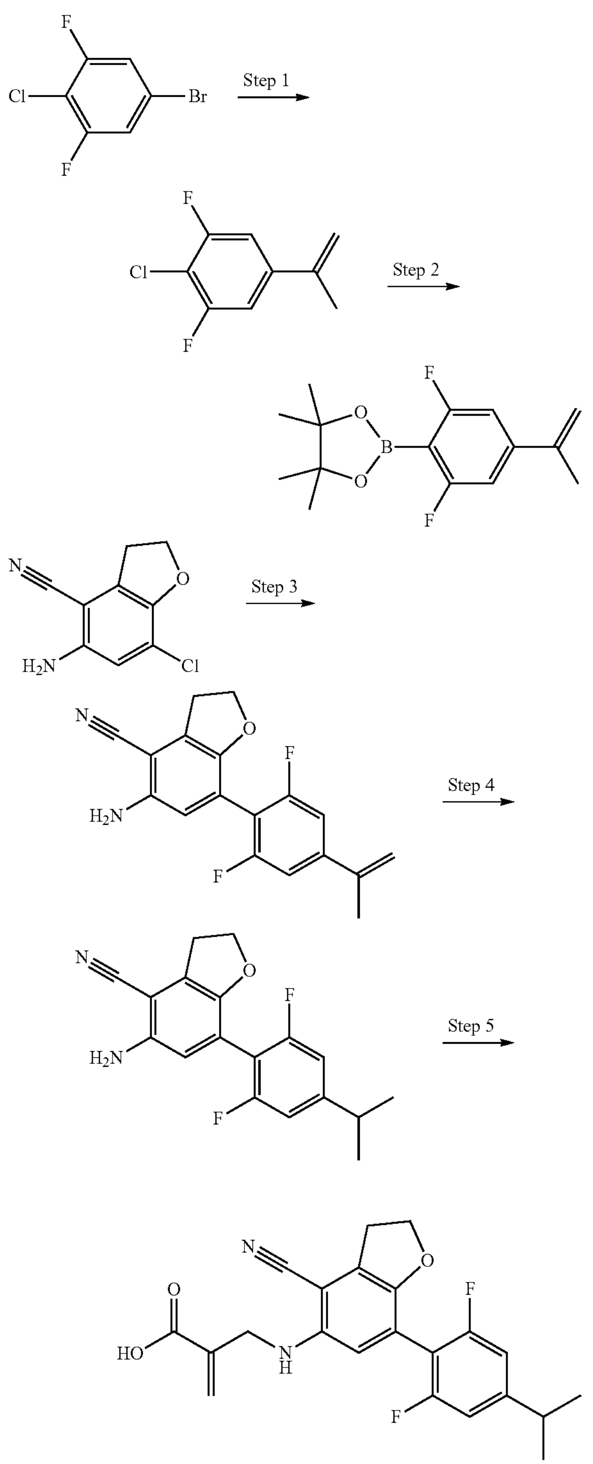

Step 1: Preparation of 2-Chloro-1,3-difluoro-5-(prop-1-en-2-yl)benzene

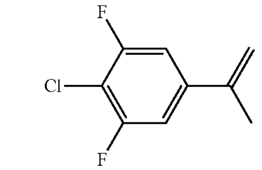

A mixture of 5-bromo-2-chloro-1,3-difluorobenzene (2.0 g, 8.8 mmol), 4,4,5,5-tetramethyl-2-(prop-1-en-2-yl)-1,3,2-dioxaborolane (1.6 g, 9.2 mmol), Pd(dppf)$Cl_2$ (0.6 g, 0.90 mmol), $K_2CO_3$ (3.7 g, 26.4 mmol) in 1,4-dioxane (20 mL) and $H_2O$ (5 mL) was stirred at 90° C. for 2 hours under a nitrogen atmosphere. The reaction mixture was concentrated under vacuum. The residue was purified by flash chromatography on silica gel (100% petroleum ether) to afford the title compound (1.4 g, 84%) as a colorless oil. $^1$H NMR (400 MHz, $CDCl_3$): δ 7.07 (dd, J=12.8, 4.4 Hz, 2H), 5.41 (s, 1H), 5.20 (s, 1H), 2.11 (s, 3H).

Step 2: Preparation of 2-(2,6-Difluoro-4-(prop-1-en-2-yl)phenyl)-4,4,5,5-tetramethyl-1,3,2-dioxaborolane

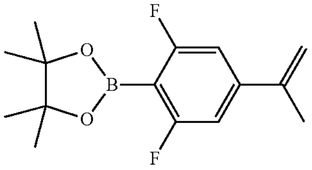 [SMILES: C=C(C)c1cc(F)c(B2OC(C)(C)C(C)(C)O2)c(F)c1]

A mixture of 2-chloro-1,3-difluoro-5-(prop-1-en-2-yl)benzene (1.2 g, 6.4 mmol), KOAc (1.2 g, 12.7 mmol), 4,4,4',4',5,5,5',5'-octamethyl-2,2'-bi(1,3,2-dioxaborolane) (2.4 g, 9.5 mmol) and Pd(dppf)$Cl_2$ (0.5 g, 0.6 mmol) in 1,4-dioxane (10 mL) was stirred at 100° C. for 16 hours under a nitrogen atmosphere. The solution was concentrated under vacuum. The residue was purified by flash chromatography on silica gel (0-2% ethyl acetate in petroleum ether) to afford the title compound (580 mg, 33%) as a light yellow oil. $^1$H NMR (400 MHz, $CDCl_3$): δ 7.01-6.92 (m, 2H), 5.45 (s, 1H), 5.19 (s, 1H), 2.11 (s, 3H), 1.39 (s, 12H).

Step 3: Preparation of 5-Amino-7-(2,6-difluoro-4-(prop-1-en-2-yl)phenyl)-2,3-dihydrobenzofuran-4-carbonitrile

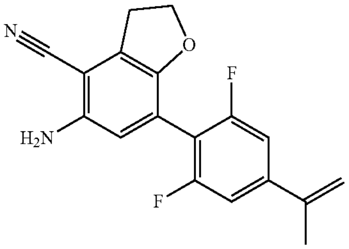 [SMILES: C=C(C)c1cc(F)c(-c2cc(N)c(C#N)c3c2OCC3)c(F)c1]

A mixture of Xphos Pd $G_2$ (130 mg, 0.15 mmol), Xphos (73 mg, 0.15 mmol), 5-amino-7-chloro-2,3-dihydrobenzofuran-4-carbonitrile (300 mg, 1.54 mmol), 2-(2,6-difluoro-4-(prop-1-en-2-yl)phenyl)-4,4,5,5-tetramethyl-1,3,2-dioxaborolane (0.56 g, 2.00 mmol) in 1,4-dioxane (5 mL) and $H_2O$ (0.5 mL) was stirred at 80° C. for 4 hours under a nitrogen atmosphere. The mixture was diluted with ethyl acetate (50 mL) and washed with water (30 mLx3). The organics were combined, dried over $Na_2SO_4$ and concentrated. The residue was purified by flash chromatography on silica gel (0-10% ethyl acetate in petroleum ether) to afford the title compound (150 mg, 31%) as a yellow solid. $^1H$ NMR (400 MHz, $CDCl_3$): δ 7.08 (d, J=8.8 Hz, 2H), 6.57 (s, 1H), 5.45 (s, 1H), 5.21 (s, 1H), 4.63 (t, J=8.8 Hz, 2H), 4.09 (s, 2H), 3.39 (t, J=8.8 Hz, 2H), 2.14 (s, 3H); LCMS (ESI): m/z 313.1 $(M+H)^+$.

Step 4: Preparation of 5-Amino-7-(2,6-difluoro-4-isopropylphenyl)-2,3-dihydrobenzofuran-4-carbonitrile

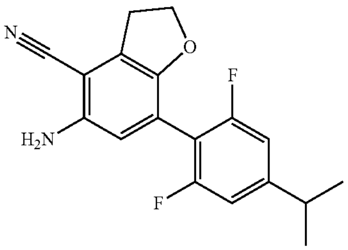 [SMILES: CC(C)c1cc(F)c(-c2cc(N)c(C#N)c3c2OCC3)c(F)c1]

A mixture of 5-amino-7-(2,6-difluoro-4-(prop-1-en-2-yl)phenyl)-2,3-dihydrobenzofuran-4-carbonitrile (150 mg, 0.48 mmol) and 10% Pd/C (10 mg, 0.1 mmol) in MeOH (2 mL) was stirred at room temperature for 2 hours under $H_2$ (15 psi). The reaction mixture was filtered and the filtrate was concentrated under vacuum to afford the title compound (120 mg, 80%) as a yellow solid. The crude product was used for next step directly without further purification. $^1H$ NMR (400 MHz, $CDCl_3$): δ 6.85 (d, J=8.8 Hz, 2H), 6.56 (s, 1H), 4.62 (t, J=8.8 Hz, 2H), 4.09 (s, 2H), 3.39 (t, J=8.8 Hz, 2H), 2.97-2.87 (m, 1H), 1.26 (d, J=7.2 Hz, 6H); LCMS (ESI): m/z 314.9 $(M+H)^+$.

Step 5: Preparation of 2-(((4-Cyano-7-(2,6-difluoro-4-isopropylphenyl)-2,3-dihydrobenzofuran-5-yl)amino)methyl)acrylic acid

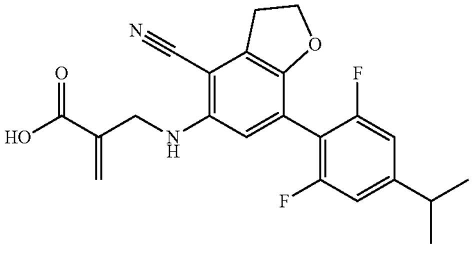 [SMILES: C=C(CNc1cc(-c2c(F)cc(C(C)C)cc2F)c2c(c1C#N)CCO2)C(=O)O]

A mixture of 5-amino-7-(2,6-difluoro-4-isopropylphenyl)-2,3-dihydrobenzofuran-4-carbonitrile (120 mg, 0.38 mmol) and 2-(bromomethyl)acrylic acid (57 mg, 0.34 mmol) in DMF (3 mL) was stirred at room temperature for 16 hours. The resulting solution was purified by reverse phase chromatography (Welch Xtimate C18 150*25 mm*5 um, acetonitrile 49-79%/water (0.2% FA)-ACN) to afford the title compound (49.32 mg, 32%) as a yellow solid. $^1H$ NMR (400 MHz, DMSO-$d_6$): δ 7.07 (d J=9.2 Hz, 2H), 6.34 (s, 1H), 6.08 (s, 1H), 6.01 (s, 1H), 5.63 (s, 1H), 4.50 (t, J=8.8 Hz, 2H), 3.95 (s, 2H), 3.30 (t, J=8.8 Hz, 2H), 2.99-2.86 (m, 1H), 1.21 (d, J=6.8 Hz, 6H); LCMS (ESI): m/z 399.0 $(M+H)^+$.

Example 30

Preparation of 2-(((4-Cyano-7-(5-isopropylpyridine-2-yl)-2,3-dihydrobenzofuran-5-yl)amino)methyl) acrylic acid The general reaction scheme was as follows:

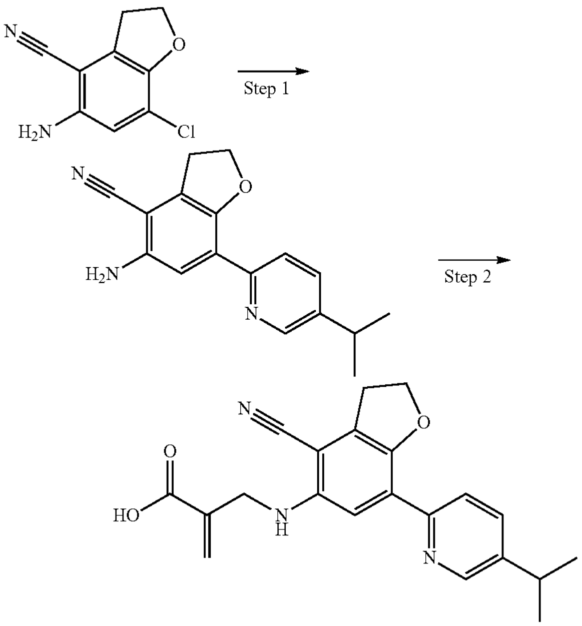

Step 1: Preparation of 5-Amino-7-(5-isopropylpyridine-2-yl)-2,3-dihydrobenzofuran-4-carbonitrile

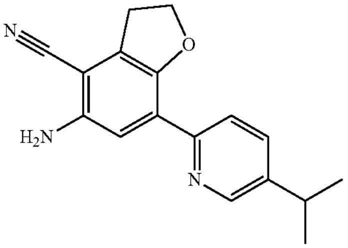 [SMILES: CC(C)c1ccc(-c2cc(N)c(C#N)c3c2OCC3)nc1]

A mixture of 5-amino-7-chloro-2,3-dihydrobenzofuran-4-carbonitrile (500 mg, 2.8 mmol), 4,4,4',4',5,5,5',5'-octamethyl-2,2'-bi(1,3,2-dioxaborolane) (800 mg, 3.1 mmol), Pd(dppf)$Cl_2$ (200 mg, 0.26 mmol), KOAc (800 mg, 7.7 mmol) in 1,4-dioxane (5 mL) was stirred at 80° C. for 2 hours under a nitrogen atmosphere. The solution was cooled to room temperature, then 2-bromo-5-isopropylpyridine (620 mg, 3.1 mmol), Pd(dppf)$Cl_2$ (200 mg, 0.26 mmol), $Na_2CO_3$ (800 mg, 7.7 mmol) and $H_2O$ (1 mL) was added into the reaction solution. Then the solution was stirred at 80° C. for 2 hours under a nitrogen atmosphere. The reaction mixture was diluted with water (20 mL) and extracted with ethyl acetate (10 mL×3). Combined organic layers were dried over $Na_2SO_4$ and concentrated under vacuum. The residue was purified by flash chromatography on silica gel (0-10% ethyl acetate in petroleum ether) to afford the crude product. The resulting residue was purified by reverse phase chromatography (Welch Xtimate C18 150*25 mm*5 um, acetonitrile 41-71%/water (0.2% FA)-ACN) to afford the title compound (60 mg, 8%) as a yellow solid. $^1$H NMR (400 MHz, $CDCl_3$): δ 8.56 (d, J=2.4 Hz, 1H), 8.05 (d, J=8.4 Hz, 1H), 7.61 (dd, J=8.4, 2.4 Hz, 1H), 7.41 (s, 1H), 4.70 (t, J=8.8 Hz, 2H), 4.13 (s, 2H), 3.37 (t, J=8.8 Hz, 2H), 3.03-2.93 (m, 1H), 1.31 (d, J=6.8 Hz, 6H); LCMS (ESI): m/z 280.1 $(M+H)^+$.

Step 2: Preparation of 2-(((4-Cyano-7-(5-isopropylpyridin-2-yl)-2,3-dihydrobenzofuran-5-yl)amino) methyl)acrylic acid

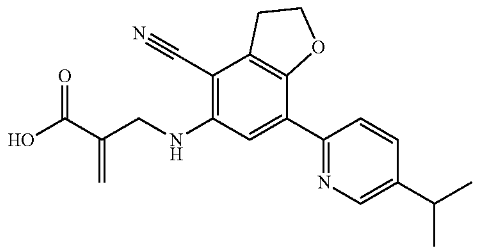

A mixture of 5-amino-7-(5-isopropylpyridin-2-yl)-2,3-dihydrobenzofuran-4-carbonitrile (60 mg, 0.21 mmol) and 2-(bromomethyl)acrylic acid (32 mg, 0.19 mmol) in DMF (3 mL) was stirred at room temperature for 4 hours. The resulting solution was purified by reverse phase chromatography (Welch Xtimate C18 150*25 mm*5 um, acetonitrile 28-58%/water (0.2% FA)-ACN) to afford the title compound (10.93 mg, 14%) as a yellow solid. $^1$H NMR (400 MHz, DMSO-$d_6$): δ 8.58 (s, 1H), 8.03 (d, J=8.0 Hz, 1H), 7.74 (dd, J=8.0, 2.0 Hz, 1H), 7.15 (s, 1H), 6.10 (s, 1H), 6.04 (s, 1H), 5.61 (s, 1H), 4.64 (t, J=8.8 Hz, 2H), 4.00 (s, 2H), 3.31 (t, J=8.8 Hz, 2H), 2.98-2.90 (m, 1H), 1.24 (d, J=6.8 Hz, 6H); LCMS (ESI): m/z 364.0 $(M+H)^+$.

Example 31

Preparation of 2-(((4-Cyano-7-(4-isopropylthiophen-2-yl)-2,3-dihydrobenzofuran-5-yl)amino)methyl) acrylic acid The general reaction scheme was as follows:

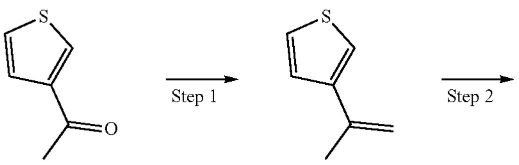

-continued

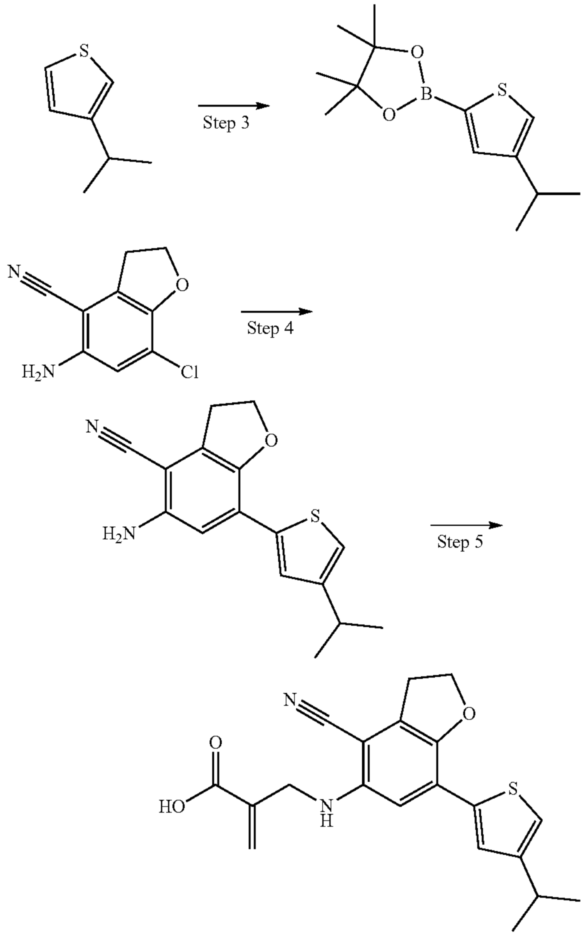

Step 1: Preparation of 3-(Prop-1-en-2-yl)thiophene

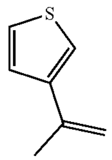

To a mixture of methyltriphenyl phosphonium bromide (27.0 g, 76.1 mmol) in THF (300 mL) was added n-BuLi (30 mL, 76.1 mmol, 2.5 M in hexane) slowly at 0° C. After the addition, the mixture was stirred at the same temperature for 2 hours. Then the solution of 1-(thiophen-3-yl)ethanone (8.0 g, 63.4 mmol) in THF (50 mL) was added at 0° C. dropwise. And the reaction mixture was stirred at 0° C. for 16 hours. The reaction was quenched with sat. aq. $NH_4Cl$ solution (500 mL) and extracted with ethyl acetate (500 mL×2). The combined organic layers were dried over $Na_2SO_4$ and concentrated under vacuum. The residue was purified by flash chromatography on silica gel (100% petroleum ether) to afford the title compound (5.7 g, 72%) as a colorless liquid. $^1$H NMR (400 MHz, $CDCl_3$): δ 7.31-7.26 (m, 2H), 7.23-7.19 (m, 1H), 5.37 (s, 1H), 5.04 (s, 1H), 2.14 (s, 3H).

Step 2: Preparation of 3-Isopropylthiophene

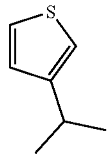

A mixture of 3-(prop-1-en-2-yl)thiophene (2.0 g, 16.1 mmol) and 10% Pd/C (250 mg, 2.4 mmol) in THF (20 mL) was stirred at room temperature for 16 hours under a $H_2$ atmosphere (50 psi). The reaction mixture was filtered and the filtrate was concentrated under vacuum to afford the title compound (2.0 g, 98%) as a brown liquid. The crude product was used for next step directly without further purification. $^1$H NMR (400 MHz, $CDCl_3$): δ 7.08 (dd, J=4.8, 2.8 Hz, 1H), 6.88-6.81 (m, 1H), 6.80-6.72 (m, 1H), 2.91-2.76 (m, 1H), 1.11 (d, J=6.8 Hz, 6H).

Step 3: Preparation of 2-(4-Isopropylthiophen-2-yl)-4,4,5,5-tetramethyl-1,3,2-dioxaborolane

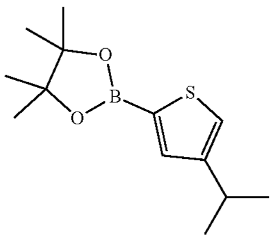 [SMILES: CC(C)c1csc(B2OC(C)(C)C(C)(C)O2)c1]

Inside a glove box, a solution of 3-isopropylthiophene (200 mg, 1.58 mmol), $(Ir(cod)OMe)_2$ (2.6 mg, 0.004 mmol), 4,4,4',4',5,5,5',5'-octamethyl-2,2'-bi(1,3,2-dioxaborolane) (201 mg, 0.79 mmol), 4,4,5,5-tetramethyl-1,3,2-dioxaborolane (223 mg, 1.74 mmol) and 4,4'-di-tert-butyl-2,2'-bipyridine (2.1 mg, 0.008 mmol) in THF (2 mL) was stirred at 80° C. for 16 hours. The reaction was concentrated under reduced pressure. The residue was purified by flash chromatography on silica gel (0-2% ethyl acetate in petroleum ether) to afford the title compound (350 mg, 70%) as a colorless oil. $^1$H NMR (400 MHz, $CDCl_3$): δ 7.59 (s, 1H), 7.25 (s, 1H), 3.61-3.52 (m, 1H), 1.31 (s, 12H), 1.21 (d, J=6.8 Hz, 6H).

Step 4: Preparation of 5-Amino-7-(4-isopropylthiophen-2-yl)-2,3-dihydrobenzofuran-4-carbonitrile

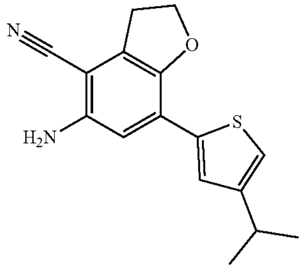 [SMILES: CC(C)c1csc(-c2cc(N)c(C#N)c3c2OCC3)c1]

A mixture of Xphos Pd $G_2$ (87 mg, 0.1 mmol), Xphos (49 mg, 0.1 mmol), 5-amino-7-chloro-2,3-dihydrobenzofuran-4-carbonitrile (200 mg, 1.03 mmol) and 2-(4-isopropylthiophen-2-yl)-4,4,5,5-tetramethyl-1,3,2-dioxaborolane (337 mg, 1.34 mmol) in 1,4-dioxane (5 mL) and $H_2O$ (0.5 mL) was stirred at 80° C. for 4 hours. The mixture was diluted with ethyl acetate (20 mL) and washed with water (30 mL×3). The combined organics were dried over $Na_2SO_4$ and concentrated. The residue was purified by flash chromatography on silica gel (0-10% ethyl acetate in petroleum ether) to afford the title compound (150 mg, 51%) as a yellow solid. $^1$H NMR (400 MHz, $CDCl_3$): δ 7.57 (d, J=1.6 Hz, 1H), 6.99 (d, J=1.6 Hz, 1H), 6.80 (s, 1H), 4.72 (t, J=8.8 Hz, 2H), 4.06 (s, 2H), 3.35 (t, J=8.8 Hz, 2H), 3.01-2.94 (m, 1H), 1.28 (d, J=7.2 Hz, 6H); LCMS (ESI): m/z 285.1 $(M+H)^+$.

Step 5: Preparation of 2-(((4-Cyano-7-(4-isopropylthiophen-2-yl)-2,3-dihydrobenzofuran-5-yl)amino)methyl)acrylic acid

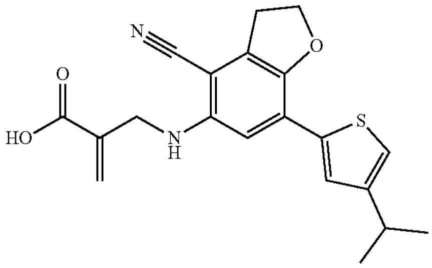 [SMILES: C=C(CNc1cc(-c2cc(C(C)C)cs2)c2c(c1C#N)CCO2)C(=O)O]

A mixture of 5-amino-7-(4-isopropylthiophen-2-yl)-2,3-dihydrobenzofuran-4-carbonitrile (150 mg, 0.53 mmol), 2-(bromomethyl)acrylic acid (78 mg, 0.47 mmol) in DMF (3 mL) and was stirred at room temperature for 4 hours. The resulting residue was purified by reverse phase chromatography (Welch Xtimate C18 150*25 mm*5 um, acetonitrile 50-80%/water (0.2% FA)-ACN) to afford the title compound (52.06 mg, 27%) as a yellow solid. $^1$H NMR (400 MHz, DMSO-$d_6$): δ 7.57 (s, 1H), 7.23 (s, 1H), 6.58 (s, 1H), 6.12 (s, 1H), 5.96 (s, 1H), 5.70 (s, 1H), 4.65 (t, J=8.8 Hz, 2H), 4.04 (s, 2H), 3.28 (t, J=8.8 Hz, 2H), 3.00-2.84 (m, 1H), 1.21 (d, J=6.8 Hz, 6H); LCMS (ESI): m/z 369.0 $(M+H)^+$.

Example 32

Preparation of 2-(((4-Cyano-7-(5-isopropylthiazol-2-yl)-2,3-dihydrobenzofuran-5-yl)amino)methyl) acrylic acid The general reaction scheme was as follows:

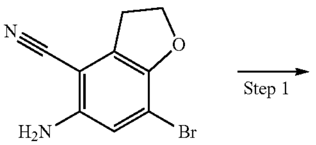

-continued

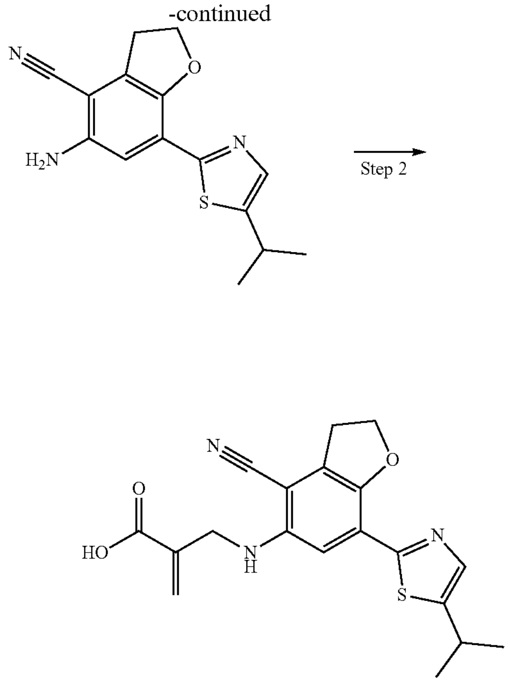

Step 1: Preparation of 5-Amino-7-(5-isopropylthiazol-2-yl)-2,3-dihydrobenzofuran-4-carbonitrile

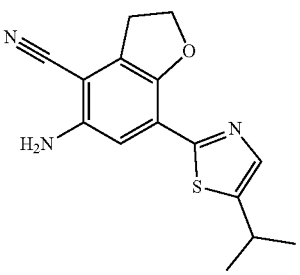 [SMILES: CC(C)c1cnc(-c2cc(N)c(C#N)c3c2OCC3)s1]

A mixture of 5-amino-7-bromo-2,3-dihydrobenzofuran-4-carbonitrile (200 mg, 0.84 mmol), 4,4,4',4',5,5,5',5'-octamethyl-2,2'-bi(1,3,2-dioxaborolane) (233 mg, 0.92 mmol), KOAc (246 mg, 2.51 mmol), Pd(dppf)$Cl_2$ (61 mg, 0.08 mmol) in 1,4-dioxane (5 mL) was stirred at 100° C. for 4 hours under a nitrogen atmosphere. The solution was cooled to the room temperature. Then 2-bromo-5-isopropylthiazole (158 mg, 0.77 mmol), $Na_2CO_3$ (222 mg, 2.1 mmol), Pd(dppf)$Cl_2$ (51 mg, 0.07 mmol) and water (1 mL) was added into the reaction mixture. The solution was stirred at 100° C. for 4 hours under a nitrogen atmosphere again. The mixture was diluted with $H_2O$ (100 mL), extracted with ethyl acetate (150 mL×3) and washed with water (150 mL×3). The organic layer was dried over $Na_2SO_4$ and concentrated. The residue was purified by flash chromatography on silica gel (0-25% ethyl acetate in petroleum ether) to afford the title compound (80 mg, 40%) as a yellow solid. $^1H$ NMR (400 MHz, $CDCl_3$): δ 7.61 (s, 1H), 7.43 (s, 1H), 4.80 (t, J=8.8 Hz, 2H), 4.12 (s, 2H), 3.40 (t, J=8.8 Hz, 2H), 3.32-3.19 (m, 1H), 1.39 (d, J=6.8 Hz, 6H); LCMS (ESI): m/z 286.1 $(M+H)^+$.

Step 2: Preparation of 2-(((4-Cyano-7-(5-isopropylthiazol-2-yl)-2,3-dihydrobenzofuran-5-yl)amino)methyl)acrylic acid

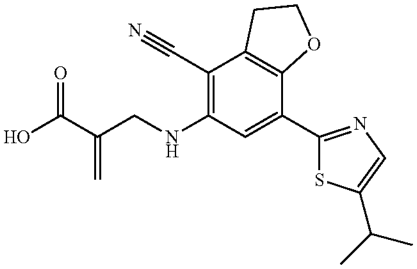 [SMILES: C=C(CNc1cc(-c2ncc(C(C)C)s2)c2c(c1C#N)CCO2)C(=O)O]

To a mixture of 5-amino-7-(5-isopropylthiazol-2-yl)-2,3-dihydrobenzofuran-4-carbonitrile (80 mg, 0.28 mmol) in DMF (2 mL) was added 2-(bromomethyl)acrylic acid (46 mg, 0.28 mmol). The resulting mixture was stirred at room temperature for 16 hours. The reaction mixture was purified by Prep-HPLC (Welch Xtimate C18 150*25 mm*5 um, water (0.2% FA)-ACN, 51%-81%) to afford the title compound (20.92 mg, 19%) as a light yellow solid. $^1H$ NMR (400 MHz, DMSO-$d_6$): δ 7.71 (s, 1H), 7.05 (s, 1H), 6.16 (s, 1H), 6.10 (s, 1H), 5.60 (s, 1H), 4.74 (t, J=8.8 Hz, 2H), 3.99 (s, 2H), 3.30-3.20 (m, 3H), 1.30 (d, J=6.8 Hz, 6H); LCMS (ESI): m/z 370.0 $(M+H)^+$.

Example 33

Preparation of 2-(((4-Cyano-7-(4-isopropylthiazol-2-yl)-2,3-dihydrobenzofuran-5-yl)amino)methyl)-N-hydroxyacrylamide The general reaction scheme was as follows:

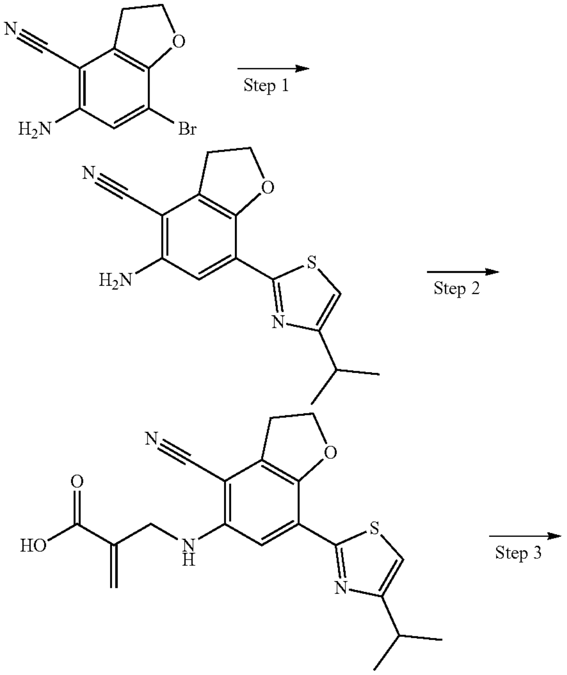

-continued

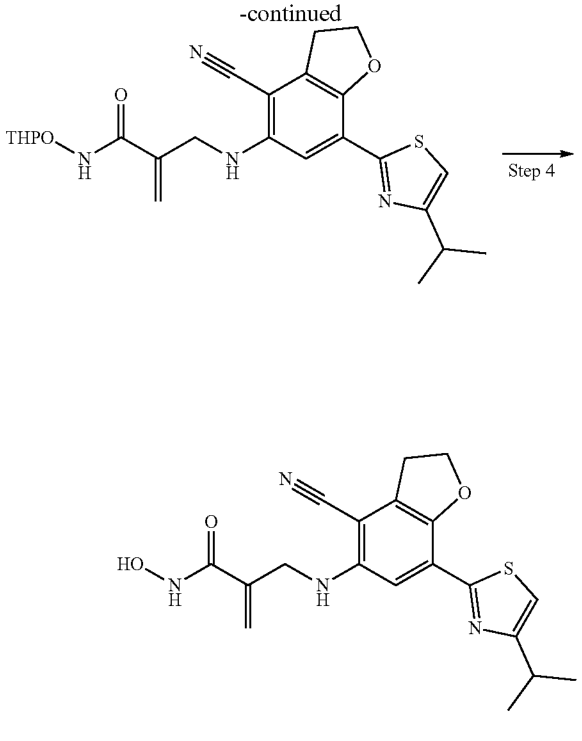

Step 1: Preparation of 5-Amino-7-(4-isopropylthiazol-2-yl)-2,3-dihydrobenzofuran-4-carbonitrile

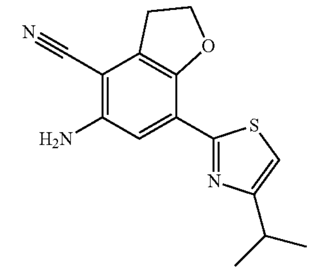 [SMILES: CC(C)c1csc(-c2cc(N)c(C#N)c3c2OCC3)n1]

A mixture of 5-amino-7-bromo-2,3-dihydrobenzofuran-4-carbonitrile (300 mg, 1.25 mmol), 4,4,4',4',5,5,5',5'-octamethyl-2,2'-bi(1,3,2-dioxaborolane) (350 mg, 1.38 mmol), KOAc (369 mg, 3.76 mmol), Pd(dppf)$Cl_2$ (92 mg, 0.13 mmol) in 1,4-dioxane (5 mL) was stirred at 100° C. for 4 hours under atmosphere. After being cooled to room temperature, 2-bromo-4-isopropylthiazole (182 mg, 0.88 mmol), $Na_2CO_3$ (255 mg, 2.41 mmol), Pd(dppf)$Cl_2$ (58 mg, 0.08 mmol) and water (1 mL) were added into the reaction mixture. Then the solution was stirred at 100° C. for 2 hours. The mixture was diluted with ethyl acetate (50 mL) and washed with water (30 mL×3). The organic was dried over $Na_2SO_4$ and concentrated. The residue was purified by flash chromatography on silica gel (0-15% ethyl acetate in petroleum ether) to afford the title compound (130 mg, 57%) as a yellow solid. $^1$H NMR (400 MHz, $CDCl_3$): δ 7.52 (s, 1H), 7.04 (s, 1H), 4.79 (t, J=8.8 Hz, 2H), 4.15 (s, 2H), 3.40 (t, J=8.8 Hz, 2H), 3.23-3.08 (m, 1H), 1.36 (d, J=6.8 Hz, 6H); LCMS (ESI): m/z 285.9 $(M+H)^+$.

Step 2: Preparation of 2-(((4-Cyano-7-(4-isopropylthiazol-2-yl)-2,3-dihydrobenzofuran-5-yl)amino)methyl)acrylic acid

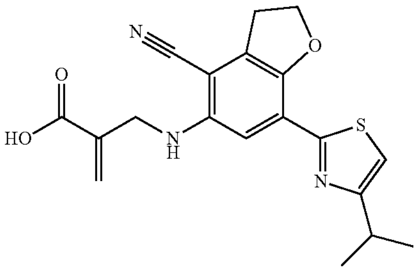 [SMILES: C=C(CNc1cc(-c2nc(C(C)C)cs2)c2c(c1C#N)CCO2)C(=O)O]

To a mixture of 5-amino-7-(4-isopropylthiazol-2-yl)-2,3-dihydrobenzofuran-4-carbonitrile (130 mg, 0.46 mmol) in DMF (3 mL) was added 2-(bromomethyl)acrylic acid (75 mg, 0.46 mmol). The resulting mixture was stirred at 100° C. for 16 hours. The reaction mixture was purified by Prep-HPLC (Welch Xtimate C18 150*25 mm*5 um, water (0.2% FA)-CAN, 51%-81%) to afford the title compound (44.98 mg, 25%) as a light yellow solid. $^1$H NMR (400 MHz, DMSO-$d_6$): δ 12.76 (s, 1H), 7.44 (s, 1H), 7.14 (s, 1H), 6.16 (s, 1H), 6.13 (s, 1H), 5.66 (s, 1H), 4.74 (t, J=8.8 Hz, 2H), 4.02 (s, 2H), 3.37 (t, J=8.8 Hz, 2H), 3.13-3.03 (m, 1H), 1.27 (d, J=6.8 Hz, 6H); LCMS (ESI): m/z 370.0 $(M+H)^+$.

Step 3: Preparation of 2-(((4-Cyano-7-(4-isopropylthiazol-2-yl)-2,3-dihydrobenzofuran-5-yl)amino)methyl)-N-((tetrahydro-2H-pyran-2-yl)oxy)acrylamide

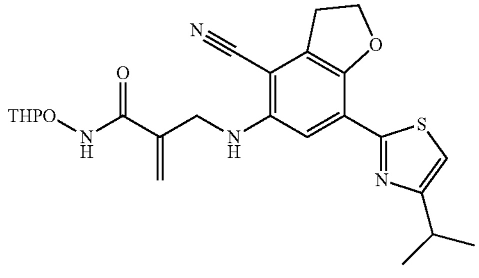

To a mixture of 2-(((4-cyano-7-(4-isopropylthiazol-2-yl)-2,3-dihydrobenzofuran-5-yl)amino)methyl)acrylic acid (160 mg, 0.43 mmol), TEA (0.24 mL, 1.73 mmol), 0-(tetrahydro-2H-pyran-2-yl)hydroxylamine (152 mg, 1.3 mmol) in DMF (3 mL) was added BOP (383 mg, 0.87 mmol). The resulting mixture was stirred at room temperature for 16 hours. The reaction mixture was quenched with water (100 mL), extracted with ethyl acetate (200 mL). The organic layer was dried over $Na_2SO_4$, filtered and concentrated. The residue was purified by flash chromatography on silica gel (0-30% ethyl acetate in petroleum ether) to afford the title compound (60 mg, 30%) as a yellow solid. LCMS (ESI): m/z 469.3 $(M+H)^+$.

Step 4: Preparation of 2-(((4-Cyano-7-(4-isopropylthiazol-2-yl)-2,3-dihydrobenzofuran-5-yl)amino)methyl)-N-hydroxyacrylamide

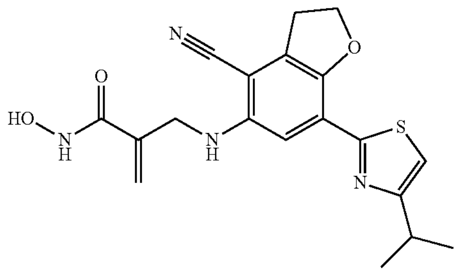 [SMILES: C=C(CNc1cc(-c2nc(C(C)C)cs2)c2c(c1C#N)CCO2)C(=O)NO]

To a mixture of 2-(((4-cyano-7-(4-isopropylthiazol-2-yl)-2,3-dihydrobenzofuran-5-yl)amino)methyl)-N-((tetrahydro-2H-pyran-2-yl)oxy)acrylamide (60 mg, 0.13 mmol) in methyl alcohol (3 mL) was added aq. HCl (1 mL, 2 N). The resulting mixture was stirred at room temperature for 2 hours. The reaction mixture was purified by Prep-HPLC (Welch Xtimate C18 150*25 mm*5 um, water (0.2% FA)-ACN, 44%-74%) to afford the title compound (47.83 mg, 93%) as a light yellow solid. $^1$H NMR (400 MHz, DMSO-$d_6$): δ 10.85 (s, 1H), 8.94 (s, 1H), 7.44 (s, 1H), 7.21 (s, 1H), 6.05 (t, J=5.6 Hz, 1H), 5.71 (s, 1H), 5.42 (s, 1H), 4.74 (t, J=8.8 Hz, 2H), 4.03 (d, J=5.6 Hz, 2H), 3.37 (t, J=8.8 Hz, 2H), 3.14-3.04 (m, 1H), 1.29 (d, J=6.8 Hz, 6H); LCMS (ESI): m/z 385.1 $(M+H)^+$.

Example 34

Preparation of 2-(((4-Cyano-7-(5-isopropylthiazol-2-yl)-2,3-dihydrobenzofuran-5-yl)amino)methyl)-N-hydroxyacrylamide The general reaction scheme was as follows:

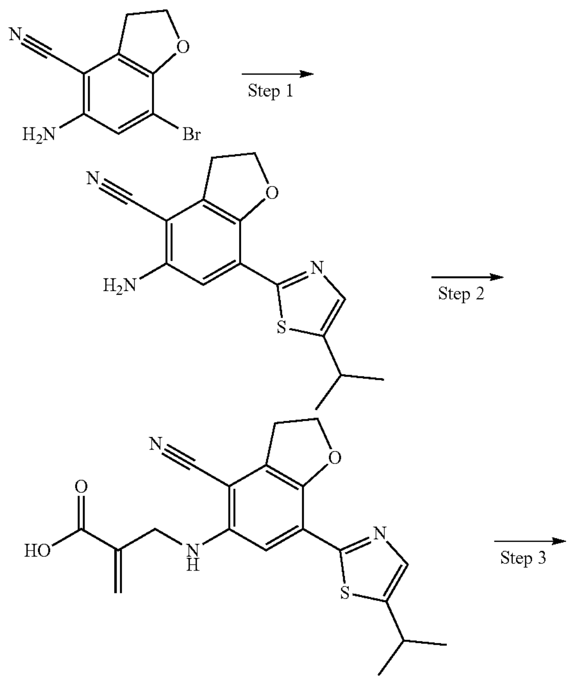

-continued

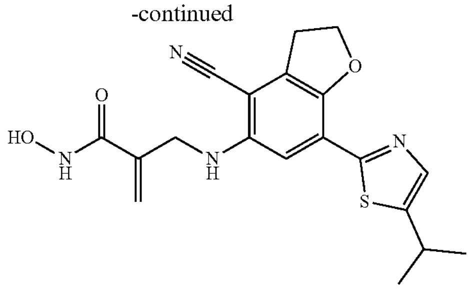

Step 1: Preparation of 5-Amino-7-(5-isopropylthiazol-2-yl)-2,3-dihydrobenzofuran-4-carbonitrile

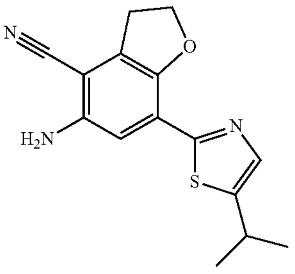 [SMILES: CC(C)c1cnc(-c2cc(N)c(C#N)c3c2OCC3)s1]

A mixture of 5-amino-7-bromo-2,3-dihydrobenzofuran-4-carbonitrile (500 mg, 2.09 mmol), 4,4,4',4',5,5,5',5'-octamethyl-2,2'-bi(1,3,2-dioxaborolane) (584 mg, 2.3 mmol), KOAc (615 mg, 6.27 mmol), Pd(dppf)$Cl_2$ (153 mg, 0.21 mmol) in 1,4-dioxane (6 mL) was stirred at 100° C. for 4 hours under a nitrogen atmosphere. The solution was cooled to room temperature. Then 2-bromo-5-isopropylthiazole (637 mg, 3.09 mmol), $Na_2CO_3$ (655 mg, 6.19 mmol), Pd(dppf)$Cl_2$ (150 mg, 0.21 mmol) and water (1 mL) was added into the solution. The reaction solution was stirred at 100° C. for 4 hours again. The reaction mixture was diluted with water (20 mL), extracted with ethyl acetate (20 mL×2). The organic layer was washed with brine (40 mL), dried over $Na_2SO_4$, filtered and concentrated. The residue was purified by flash chromatography on silica gel (0-10% ethyl acetate in petroleum ether) to afford the title compound (460 mg, 78%) as a yellow solid. $^1$H NMR (400 MHz, $CDCl_3$): δ 7.60 (s, 1H), 7.43 (s, 1H), 4.79 (t, J=8.8 Hz, 2H), 4.13 (s, 2H), 3.39 (t, J=8.8 Hz, 2H), 3.30-3.23 (m, 1H), 1.39 (d, J=6.8 Hz, 6H); LCMS (ESI): m/z 286.1 $[M+H]^+$.

Step 2: Preparation of 2-(((4-Cyano-7-(5-isopropylthiazol-2-yl)-2,3-dihydrobenzofuran-5-yl)amino)methyl)acrylic acid

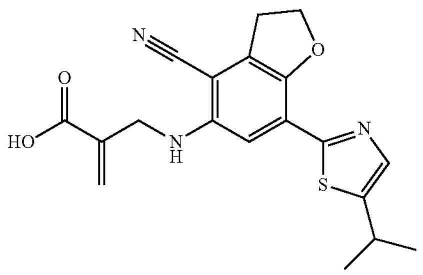 [SMILES: C=C(CNc1cc(-c2ncc(C(C)C)s2)c2c(c1C#N)CCO2)C(=O)O]

To a mixture of 5-amino-7-(5-isopropylthiazol-2-yl)-2,3-dihydrobenzofuran-4-carbonitrile (610 mg, 2.14 mmol) in DMF (8 mL) was added 2-(bromomethyl)acrylic acid (352 mg, 2.14 mmol). The resulting mixture was stirred at 100° C. for 16 hours. The reaction mixture was diluted with water (100 mL), extracted with ethyl acetate (100 mL×2). The organic layer was washed with brine (100 mL×5), dried over $Na_2SO_4$, filtered and concentrated to afford the title compound (590 mg, 75%) as yellow solid. The crude product was used for the next step without purification. LCMS (ESI): m/z 370.0 [M+H]+.

Step 3: Preparation of 2-(((4-Cyano-7-(5-isopropylthiazol-2-yl)-2,3-dihydrobenzofuran-5-yl)amino)methyl)-N-hydroxyacrylamide

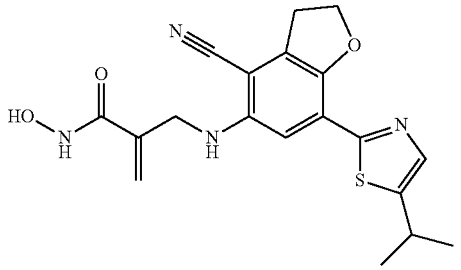 [SMILES: C=C(CNc1cc(-c2ncc(C(C)C)s2)c2c(c1C#N)CCO2)C(=O)NO]

To a solution of PyBop (155 mg, 0.30 mmol) and 2-(((4-cyano-7-(5-isopropylthiazol-2-yl)-2,3-dihydrobenzofuran-5-yl)amino)methyl)acrylic acid (100 mg, 0.27 mmol) in DMF (2 mL) was added TEA (0.12 mL, 0.87 mmol). The resulting mixture was stirred at room temperature for 15 min. Then the mixture was added hydroxylamine hydrochloride (20 mg, 0.30 mmol). The resulting mixture was stirred at room temperature for 1 hour. The reaction mixture was purified by reverse phase chromatography (acetonitrile 45-75%/(0.2% FA) in water) to afford the title compound (31.72 mg, 310%) as a yellow solid. $^1H$ NMR (400 MHz, DMSO-$d_6$): δ 10.90 (s, 1H), 7.72 (s, 1H), 7.10 (s, 1H), 6.11 (s, 1H), 5.68 (s, 1H), 5.34 (s, 1H), 4.73 (t, J=8.8 Hz, 2H), 4.01 (s, 2H), 3.28 (t, J=8.8 Hz, 2H), 3.07-2.95 (m, 1H), 1.31 (d, J=6.8 Hz, 6H); LCMS (ESI): m/z 385.0 [M+H]+.

Example 35

Preparation of 2-(((4-Cyano-7-(3-isopropyl-1H-pyrazol-1-yl)-2,3-dihydrobenzofuran-5-yl)amino)methyl)-N-hydroxyacrylamide The general reaction scheme was as follows:

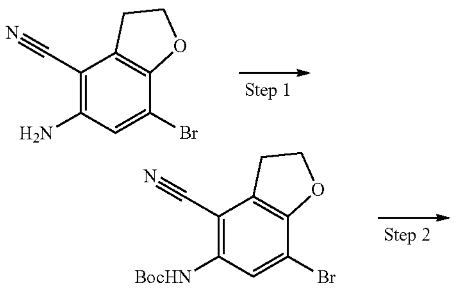

-continued

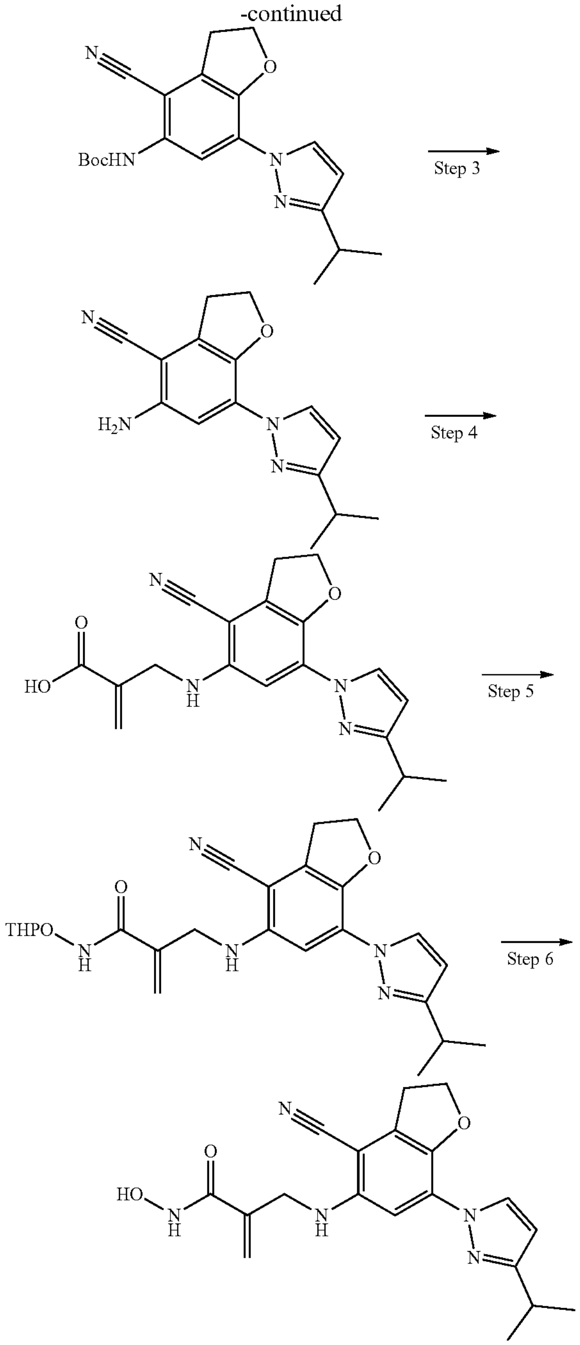

Step 1: Preparation of tert-Butyl (7-bromo-4-cyano-2,3-dihydrobenzofuran-5-yl)carbamate

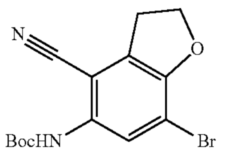 [SMILES: CC(C)(C)OC(=O)Nc1cc(Br)c2c(c1C#N)CCO2]

To a solution of 5-amino-7-bromo-2,3-dihydrobenzofuran-4-carbonitrile (2.0 g, 8.37 mmol), DMAP (101 mg, 0.84 mmol) and TEA (3.5 mL, 25.1 mmol) in DCM (10 mL) was added di-tert-butyl dicarbonate (2.74 g, 12.55 mmol), then the mixture was stirred at room temperature for 16 hours. The solvents were evaporated to dryness in vacuum to afford crude product, which was purified by flash chromatography on silica gel (0-20% ethyl acetate in petroleum ether) to afford the title compound (1.9 g, 67%) as a white solid. $^1$H NMR (400 MHz, $CDCl_3$): δ 7.24 (s, 1H), 4.82 (t, J=8.8 Hz, 2H), 3.52 (t, J=8.8 Hz, 2H), 1.49 (s, 9H).

Step 2: Preparation of tert-Butyl (4-cyano-7-(3-isopropyl-1H-pyrazol-1-yl)-2,3-dihydrobenzofuran-5-yl)carbamate

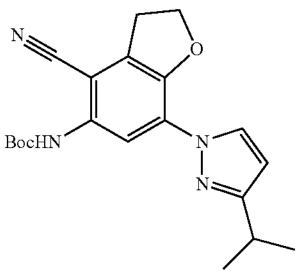 [SMILES: CC(C)c1ccn(-c2cc(NC(=O)OC(C)(C)C)c(C#N)c3c2OCC3)n1]

A solution of tert-butyl (7-bromo-4-cyano-2,3-dihydrobenzofuran-5-yl)carbamate (400 mg, 1.18 mmol), 3-isopropyl-1H-pyrazole (195 mg, 1.77 mmol), Brettphos Pd $G_3$ (106 mg, 0.12 mmol) and $K_3PO_4$ (751 mg, 3.53 mmol) in 1,4-dioxane (5 mL) was stirred at 90° C. for 16 hours under a nitrogen atmosphere. The reaction solution was quenched with water (200 mL), dissolved in ethyl acetate (200 mL), dried over $MgSO_4$, filtered and concentrated. The residue was purified by flash chromatography on silica gel (0-50% ethyl acetate in petroleum ether) to afford the title compound (300 mg, 69%) as a white solid. $^1$H NMR (400 MHz, $CDCl_3$): δ 8.46 (s, 1H), 8.25 (d, J=2.4 Hz, 1H), 6.72 (s, 1H), 6.28 (d, J=2.4 Hz, 1H), 4.78 (t, J=8.8 Hz, 2H), 3.45 (t, J=8.8 Hz, 2H), 3.15-3.03 (m, 1H), 1.55 (s, 9H), 1.31 (d, J=6.8 Hz, 6H); LCMS (ESI): m/z 369.1 $(M+H)^+$.

Step 3: Preparation of 5-Amino-7-(3-isopropyl-1H-pyrazol-1-yl)-2,3-dihydrobenzofuran-4-carbonitrile

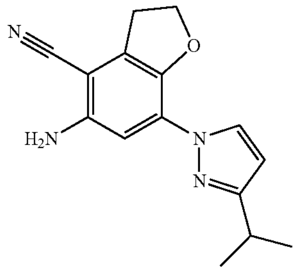 [SMILES: CC(C)c1ccn(-c2cc(N)c(C#N)c3c2OCC3)n1]

A solution of tert-butyl (4-cyano-7-(3-isopropyl-1H-pyrazol-1-yl)-2,3-dihydrobenzofuran-5-yl)carbamate (300 mg, 0.88 mmol) in 5% TFA in HFIP (10 mL) was stirred at room temperature for 16 hours. The reaction solution was quenched with water (20 mL), adjusted pH to 8 with sat. aq. $NaHCO_3$, dissolved in ethyl acetate (200 mL), dried over $MgSO_4$, filtered and concentrated. The residue was purified by flash chromatography on silica gel (0-50% ethyl acetate in petroleum ether) to afford the title compound (130 mg, 55%) as a yellow solid. $^1$H NMR (400 MHz, $CDCl_3$): δ 8.31 (d, J=2.4 Hz, 1H), 7.31 (s, 1H), 6.28 (d, J=2.4 Hz, 1H), 4.71 (t, J=8.8 Hz, 2H), 4.17 (s, 2H), 3.37 (t, J=8.8 Hz, 2H), 3.13-3.00 (m, 1H), 1.31 (d, J=7.2 Hz, 6H).

Step 4: Preparation of 2-(((4-Cyano-7-(3-isopropyl-1H-pyrazol-1-yl)-2,3-dihydrobenzofuran-5-yl)amino)methyl)acrylic acid

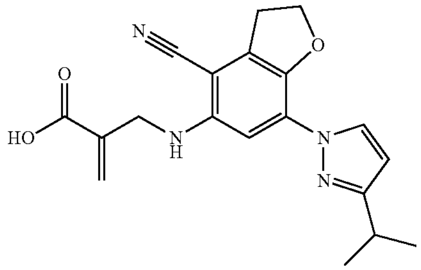 [SMILES: C=C(CNc1cc(-n2ccc(C(C)C)n2)c2c(c1C#N)CCO2)C(=O)O]

A solution of 5-amino-7-(3-isopropyl-1H-pyrazol-1-yl)-2,3-dihydrobenzofuran-4-carbonitrile (130 mg, 0.48 mmol) and 2-(bromomethyl)acrylic acid (80 mg, 0.48 mmol) in DMF (5 mL) was stirred at 100° C. for 16 hours. The reaction solution was quenched with water (200 mL), dissolved in ethyl acetate (200 mL), dried over $MgSO_4$, filtered and concentrated to afford the title compound (100 mg, 57%) as a brown liquid. The crude product was used for the next step without purification. LCMS (ESI): m/z 353.1 $(M+H)^+$.

Step 5: Preparation of 2-(((4-Cyano-7-(3-isopropyl-1H-pyrazol-1-yl)-2,3-dihydrobenzofuran-5-yl)amino)methyl)-N-((tetrahydro-2H-pyran-2-yl)oxy)acrylamide

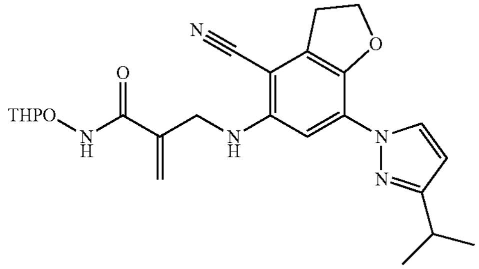

To a mixture of 2-(((4-cyano-7-(3-isopropyl-1H-pyrazol-1-yl)-2,3-dihydrobenzofuran-5-yl)amino)methyl)acrylic acid (100 mg, 0.28 mmol), 0-(tetrahydro-2H-pyran-2-yl)hydroxylamine (50 mg, 0.43 mmol), DIPEA (110 mg, 0.85 mmol) in DMF (3 mL) was added HATU (162 mg, 0.43 mmol). The mixture was stirred at room temperature for 16 hours. Then the reaction was diluted with water (20 mL) and extracted with ethyl acetate (100 mL×3). The organics were washed with brine (100 mL×2), dried over sodium sulfate, filtered and concentrated. The residue was purified by flash chromatography on silica gel (0-30% ethyl acetate/EtOH=3:1 in petroleum ether) to afford the title compound (50 mg, 39%) as a brown liquid. LCMS (ESI): m/z 452.2 $(M+H)^+$.

Step 6: Preparation of 2-(((4-Cyano-7-(3-isopropyl-1H-pyrazol-1-yl)-2,3-dihydrobenzofuran-5-yl)amino)methyl)-N-hydroxyacrylamide

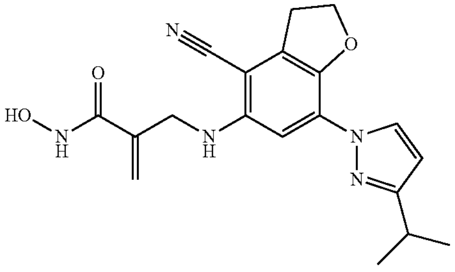 [SMILES: C=C(CNc1cc(-n2ccc(C(C)C)n2)c2c(c1C#N)CCO2)C(=O)NO]

To the mixture of 2-(((4-cyano-7-(3-isopropyl-1H-pyrazol-1-yl)-2,3-dihydrobenzofuran-5-yl)amino)methyl)-N-((tetrahydro-2H-pyran-2-yl)oxy)acrylamide (50 mg, 0.11 mmol) in methyl alcohol (3 mL) was added aq. HCl (2 mL, 2M). The resulting mixture was stirred at room temperature for 2 hours. The reaction mixture was purified by Prep-HPLC (Welch Xtimate C18 150*25 mm*5 um, water (0.2% FA)-ACN, 50%-80%) to afford the title compound (18.16 mg, 44%) as a white solid. $^1$H NMR (400 MHz, DMSO-$d_6$): δ 10.85 (s, 1H), 8.94 (s, 1H), 8.26 (d, J=2.4 Hz, 1H), 6.98 (s, 1H), 6.41 (d, J=2.4 Hz, 1H), 6.14 (t, J=5.6 Hz, 1H), 5.70 (s, 1H), 5.40 (s, 1H), 4.67 (t, J=8.8 Hz, 2H), 4.00 (d, J=5.6 Hz, 2H), 3.31 (t, J=8.8 Hz, 2H), 3.02-2.92 (m, 1H), 1.23 (d, J=6.8 Hz, 6H); LCMS (ESI): m/z 368.2 $(M+H)^+$.

Example 36

Preparation of 2-(((4-Cyano-7-(4-(trifluoromethoxy)phenyl)-2,3-dihydrobenzofuran-5-yl)amino)methyl)-N-hydroxyacrylamide The general reaction scheme was as follows:

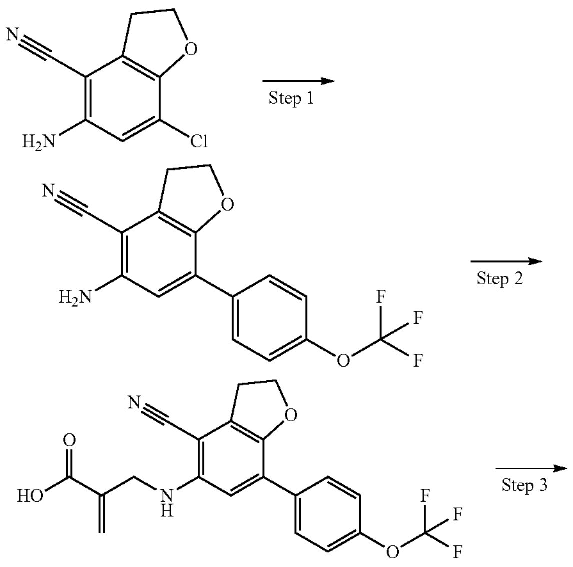

-continued

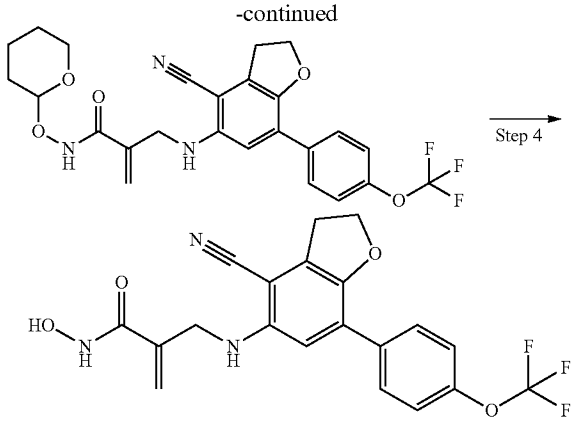

Step 1: Preparation of 5-Amino-7-(4-(trifluoromethoxy)phenyl)-2,3-dihydrobenzofuran-4-carbonitrile

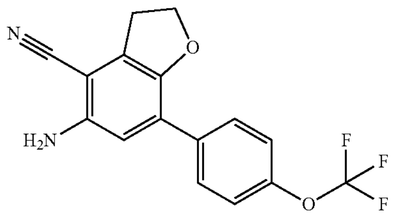 [SMILES: N#Cc1c(N)cc(-c2ccc(OC(F)(F)F)cc2)c2c1CCO2]

A solution of 5-amino-7-chloro-2,3-dihydrobenzofuran-4-carbonitrile (500 mg, 2.57 mmol), (4-(trifluoromethoxy)phenyl)boronic acid (794 mg, 3.85 mmol), Xphos (123 mg, 0.26 mmol), Xphos Pd $G_2$ (202 mg, 0.26 mmol) and KOAc (505 mg, 5.14 mmol) in 1,4-dioxane (15 mL) and water (1.5 mL) was stirred at 80° C. for 4 hours under a nitrogen atmosphere. The reaction was diluted with water (20 mL) and extracted with ethyl acetate (20 mL×2). The combined organic lawyers were washed with brine (50 mL), dried over anhydrous $Na_2SO_4$, filtered and concentrated. The residue was purified by flash chromatography on silica gel (0-20% ethyl acetate in petroleum ether) to afford the title compound (560 mg, 68%) as a yellow solid. LCMS (ESI): m/z 321.1 $(M+H)^+$.

Step 2: Preparation of 2-(((4-Cyano-7-(4-(trifluoromethoxy)phenyl)-2,3-dihydrobenzofuran-5-yl)amino)methyl)acrylic acid

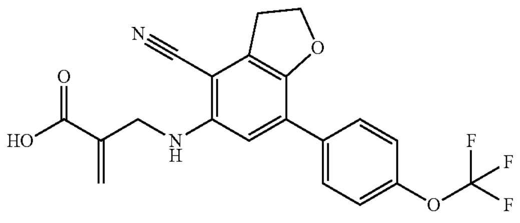 [SMILES: C=C(CNc1cc(-c2ccc(OC(F)(F)F)cc2)c2c(c1C#N)CCO2)C(=O)O]

A solution of 5-amino-7-(4-(trifluoromethoxy)phenyl)-2,3-dihydrobenzofuran-4-carbonitrile (560 mg, 1.75 mmol) and 2-(bromomethyl)acrylic acid (288 mg, 1.75 mmol) in DMF (10 mL) was stirred at 80° C. for 2 hours. The reaction mixture was purified by prep-HPLC (Boston Uni C18 40*150*5 um, water (0.225% FA)-ACN, 50-80%) to afford the title compound (390 mg, 55%) as a yellow solid. LCMS (ESI): m/z 405.1 $[M+H]^+$.

Step 3: Preparation of 2-(((4-Cyano-7-(4-(trifluoromethoxy)phenyl)-2,3-dihydrobenzofuran-5-yl)amino)methyl)-N-((tetrahydro-2H-pyran-2-yl)oxy)acrylamide

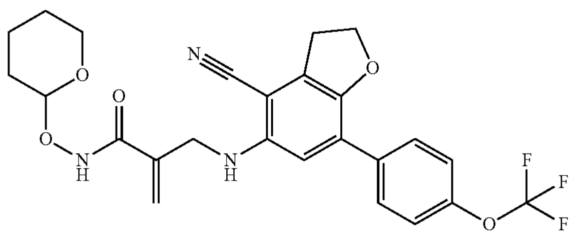 [SMILES: C=C(CNc1cc(-c2ccc(OC(F)(F)F)cc2)c2c(c1C#N)CCO2)C(=O)NOC1CCCCO1]

A solution of 2-(((4-cyano-7-(4-(trifluoromethoxy)phenyl)-2,3-dihydrobenzofuran-5-yl)amino)methyl)acrylic acid (290 mg, 0.72 mmol), TEA (0.4 mL, 2.87 mmol), O-(tetrahydro-2H-pyran-2-yl)hydroxylamine (252 mg, 2.15 mmol) and BOP (634 mg, 1.43 mmol) in DMF (3 mL) was stirred at room temperature for 16 hours. The reaction was diluted with water (20 mL) and extracted with ethyl acetate (20 mL×2). The combined organic lawyers were washed with brine (50 mL), dried over anhydrous $Na_2SO_4$, filtered and concentrated. The residue was purified by flash chromatography on silica gel (0-30% ethyl acetate in petroleum ether) to afford the title compound (170 mg, 47%) as a yellow solid. LCMS (ESI): m/z: 526.2 $[M+Na]^+$.

Step 4: Preparation of 2-(((4-Cyano-7-(4-(trifluoromethoxy)phenyl)-2,3-dihydrobenzofuran-5-yl)amino)methyl)-N-hydroxyacrylamide

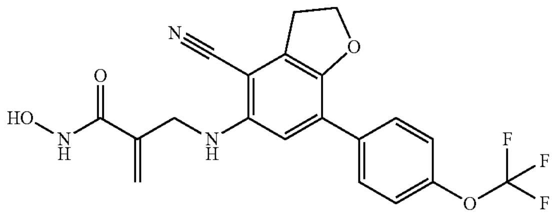 [SMILES: C=C(CNc1cc(-c2ccc(OC(F)(F)F)cc2)c2c(c1C#N)CCO2)C(=O)NO]

To the mixture of 2-(((4-cyano-7-(4-(trifluoromethoxy)phenyl)-2,3-dihydrobenzofuran-5-yl)amino)methyl)-N-((tetrahydro-2H-pyran-2-yl)oxy)acrylamide (80 mg, 0.16 mmol) in MeOH (3 mL) was added 2 M HCl (0.9 mL, 1.88 mmol). The resulting mixture was stirred at room temperature for 2 hours. The reaction mixture was purified by prep-HPLC (Welch Xtimate C18 150*25 mm*5 um, water (0.2% FA)-ACN, 50%-80%) to afford the title compound (35.4 mg, 53%) as a yellow solid. $^1H$ NMR (400 MHz, DMSO-$d_6$): δ 10.86 (s, 1H), 8.94 (s, 1H), 7.78 (d, J=8.0 Hz, 2H), 7.44 (d, J=8.0 Hz, 2H), 6.55 (s, 1H), 6.08 (t, J=6.0 Hz, 1H), 5.62 (s, 1H), 5.40 (s, 1H), 4.57 (t, J=8.8 Hz, 2H), 4.03 (d, J=6.0 Hz, 2H), 3.29 (t, J=8.8 Hz, 2H); LCMS (ESI): m/z 420.0 $[M+H]^+$.

Example 37

Preparation of 2-(((4-Cyano-7-(4-(trifluoromethoxy)phenyl)-2,3-dihydrobenzofuran-5-yl)amino)methyl)-N-hydroxy-N-methylacrylamide The general reaction scheme was as follows:

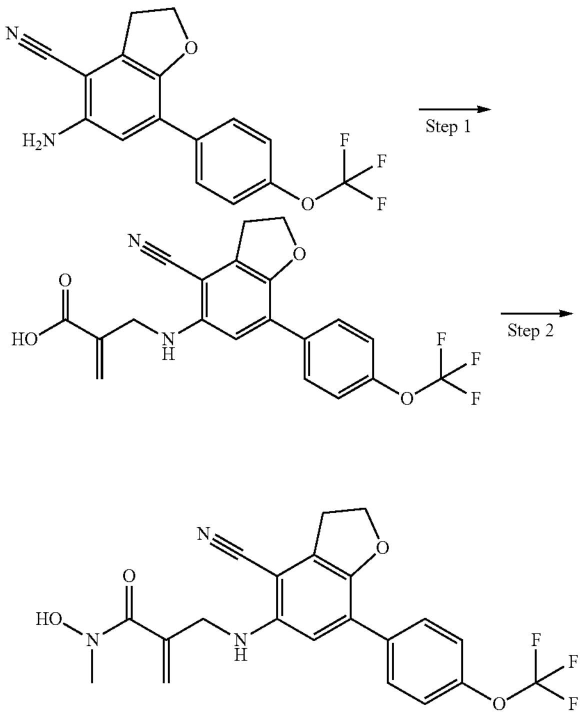

Step 1: Preparation of 2-(((4-Cyano-7-(4-(trifluoromethoxy)phenyl)-2,3-dihydrobenzofuran-5-yl)amino)methyl)acrylic acid

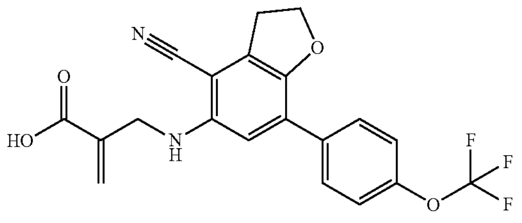 [SMILES: C=C(CNc1cc(-c2ccc(OC(F)(F)F)cc2)c2c(c1C#N)CCO2)C(=O)O]

A solution of 5-amino-7-(4-(trifluoromethoxy)phenyl)-2,3-dihydrobenzofuran-4-carbonitrile (780 mg, 2.44 mmol), 2-(bromomethyl)acrylic acid (402 mg, 2.44 mmol) in DMF (12 mL) was stirred at 80° C. for 2 hours. The reaction mixture was diluted with water (50 mL), extracted with ethyl acetate (50 mL×2). The organic layer was washed with brine (100 mL×5), dried over $Na_2SO_4$, filtered and concentrated. The residue was purified by flash chromatography on silica gel (0-60% ethyl acetate in petroleum ether) to afford the title compound (600 mg, 61%) as a yellow solid. LCMS (ESI): m/z 405.0 $[M+H]^+$.

Step 2: Preparation of 2-(((4-Cyano-7-(4-(trifluoromethoxy)phenyl)-2,3-dihydrobenzofuran-5-yl)amino)methyl)-N-hydroxy-N-methylacrylamide

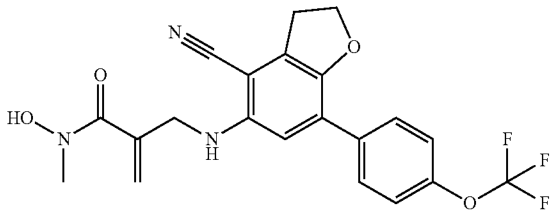 [SMILES: C=C(CNc1cc(-c2ccc(OC(F)(F)F)cc2)c2c(c1C#N)CCO2)C(=O)N(C)O]

To a solution of N-methyl hydroxylamine hydrochloride (62 mg, 0.74 mmol), 2-(((4-cyano-7-(4-(trifluoromethoxy)phenyl)-2,3-dihydrobenzofuran-5-yl)amino)methyl)acrylic acid (300 mg, 0.74 mmol), DIEA (0.26 mL, 1.48 mmol) in DCM (4 mL) was added HATU (339 mg, 0.89 mmol). The resulting mixture was stirred at room temperature for 1 hour. The reaction mixture was purified by prep-HPLC (Welch Xtimate C18 150*25 mm*5 um, water (0.2% FA)-ACN, 61-91%) to afford the title compound (58.85 mg, 18%) as a yellow solid. $^1$H NMR (400 MHz, $CDCl_3$): δ 7.72 (d, J=8.8 Hz, 2H), 7.28 (d, J=8.8 Hz, 2H), 6.64 (s, 1H), 5.68 (s, 1H), 5.47 (s, 1H), 4.65 (t, J=8.8 Hz, 2H), 4.18 (s, 2H), 3.40 (s, 3H), 3.38 (t, J=8.8 Hz, 2H). LCMS (ESI): m/z 434.0 $[M+H]^+$.

Example 38

Preparation of 2-(((4-Cyano-7-(4-(trifluoromethoxy)phenyl)-2,3-dihydrobenzofuran-5-yl)amino)methyl)acrylamide The general reaction scheme was as follows:

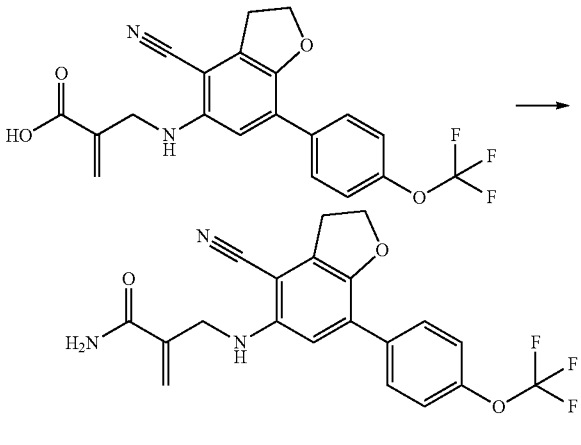

To a mixture of 2-(((4-cyano-7-(4-(trifluoromethoxy)phenyl)-2,3-dihydrobenzofuran-5-yl)amino)methyl)acrylic acid (100 mg, 0.25 mmol), $NH_4Cl$ (66 mg, 1.24 mmol) and DIPEA (224 mg, 1.73 mmol) in DMF (3 mL) was added HATU (141 mg, 0.37 mmol). Then the mixture was stirred at room temperature for 16 hours. The reaction solution was purified by prep-HPLC (Welch Xtimate C18 150*25 mm*5 um, water (0.2% FA)-ACN, 50-80%) to afford the title compound (77.39 mg, 77%) as a yellow solid. $^1$H NMR (400 MHz, DMSO-$d_6$): δ 7.77 (d, J=8.0 Hz, 2H), 7.62 (s, 1H), 7.44 (d, J=8.0 Hz, 2H), 7.16 (s, 1H), 6.54 (s, 1H), 6.03 (s, 1H), 5.81 (s, 1H), 5.46 (s, 1H), 4.57 (t, J=8.8 Hz, 2H), 4.03 (s, 2H), 3.31 (t, J=8.8 Hz, 2H); LCMS (ESI): m/z 404.0 $(M+H)^+$.

Example 39

Preparation of 2-(((4-Cyano-7-(4-(pentafluoro-16-sulfanyl)phenyl)-2,3-dihydrobenzofuran-5-yl)amino)methyl)acrylic acid The general reaction scheme was as follows:

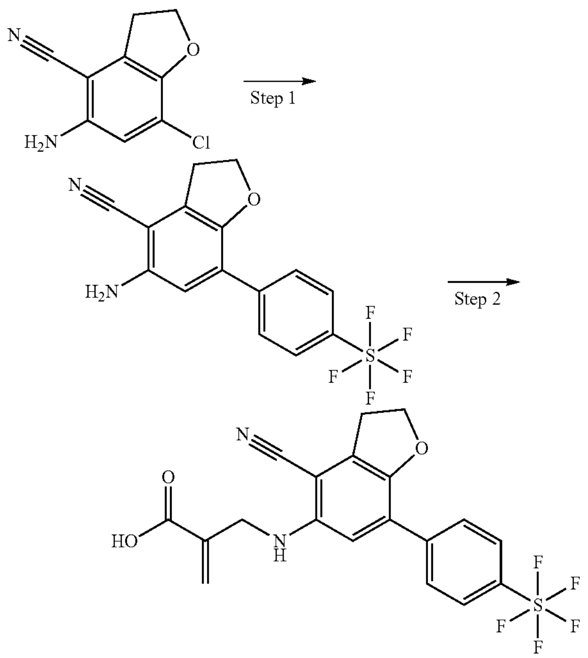

Step 1: Preparation of 5-Amino-7-(4-(pentafluoro-16-sulfanyl)phenyl)-2,3-dihydrobenzofuran-4-carbonitrile

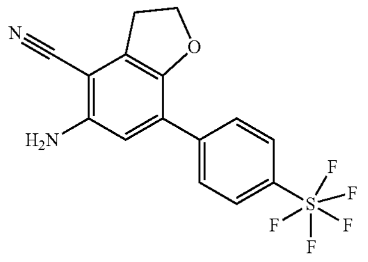 [SMILES: N#Cc1c(N)cc(-c2ccc(S(F)(F)(F)(F)F)cc2)c2c1CCO2]

A mixture of 5-amino-7-chloro-2,3-dihydrobenzofuran-4-carbonitrile (500 mg, 2.57 mmol), 4,4,5,5-tetramethyl-2-(4-(pentafluoro-16-sulfanyl)phenyl)-1,3,2-dioxaborolane (1.02 g, 3.08 mmol), Xphos (122 mg, 0.26 mmol), Xphos Pd $G_2$ (202 mg, 0.26 mmol) and KOAc (756 mg, 7.71 mmol) in 1,4-dioxane (10 mL) and water (1 mL) was stirred at 80° C. under the protection of a nitrogen atmosphere for 4 hours. The reaction was diluted with water (50 mL) and extracted with ethyl acetate (50 mL×2). The combined organic lawyers were washed with brine (50 mL), dried over anhydrous $Na_2SO_4$, filtered and concentrated. The residue was purified by flash chromatography on silica gel (0-14% ethyl acetate in petroleum ether) to afford the title compound (560 mg, 60%) as a yellow solid. LCMS (ESI): m/z 363.1 $(M+H)^+$.

Step 2: Preparation of 2-(((4-Cyano-7-(4-(pentafluoro-16-sulfanyl)phenyl)-2,3-dihydrobenzofuran-5-yl)amino)methyl)acrylic acid

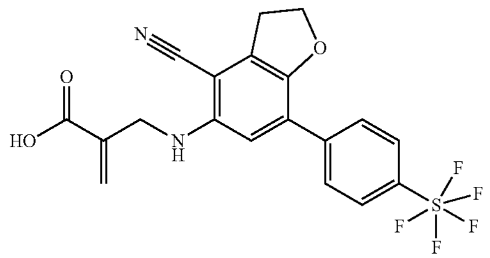 [SMILES: C=C(CNc1cc(-c2ccc(S(F)(F)(F)(F)F)cc2)c2c(c1C#N)CCO2)C(=O)O]

A mixture of 5-amino-7-(4-(pentafluoro-16-sulfanyl)phenyl)-2,3-dihydrobenzofuran-4-carbonitrile (510 mg, 1.41 mmol), 2-(bromomethyl)acrylic acid (232 mg, 1.41 mmol) in DMF (6 mL) was stirred at 100° C. for 2 hours. The mixture was diluted with water (60 mL) and extracted with ethyl acetate (60 mL×2). The combined organic lawyers were washed with brine (100 mL), dried over anhydrous $Na_2SO_4$, filtered and concentrated. The residue was purified by flash chromatography on silica gel (0-50% ethyl acetate in petroleum ether) to afford to afford the title compound (280 mg, 45%) as a yellow solid. $^1H$ NMR (400 MHz, DMSO-$d_6$): δ 7.97 (d, J=8.8 Hz, 2H), 7.87 (d, J=8.8 Hz, 2H), 6.58 (s, 1H), 6.00 (s, 1H), 5.51 (s, 1H), 4.59 (t, J=8.8 Hz, 2H), 4.04 (s, 2H), 3.32 (t, J=8.8 Hz, 2H); LCMS (ESI): m/z 447.1 $[M+H]^+$.

Example 40

Preparation of 2-(((4-Cyano-7-(4-(pentafluoro-16-sulfanyl)phenyl)-2,3-dihydrobenzofuran-5-yl)amino)methyl)-N-hydroxyacrylamide The general reaction scheme was as follows:

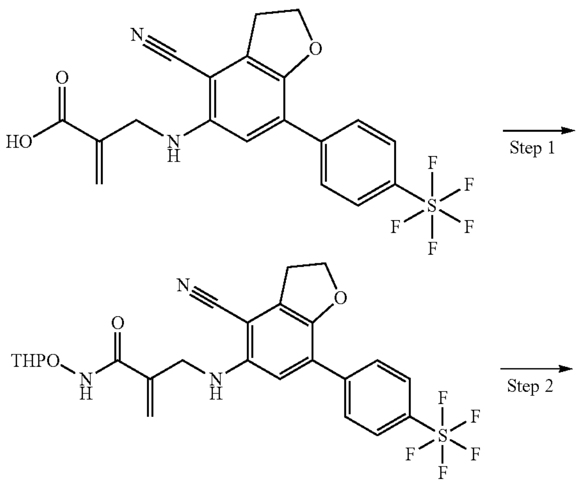

-continued

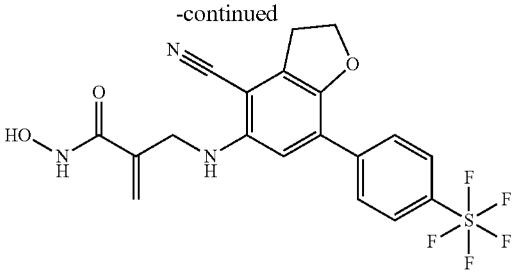

Step 1: Preparation of 2-(((4-Cyano-7-(4-(pentafluoro-16-sulfanyl)phenyl)-2,3-dihydrobenzofuran-5-yl)amino)methyl)-N-((tetrahydro-2H-pyran-2-yl)oxy)acrylamide

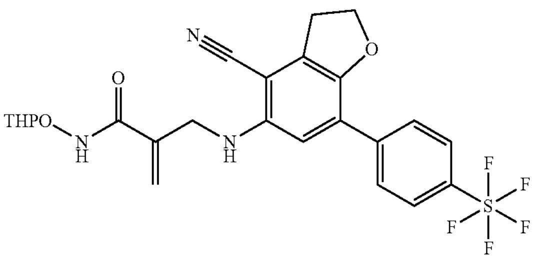

A solution of BOP (555 mg, 1.25 mmol), 0-(tetrahydro-2H-pyran-2-yl)hydroxylamine (220 mg, 1.88 mmol), TEA (0.35 mL, 2.51 mmol) and 2-(((4-cyano-7-(4-(pentafluoro-16-sulfanyl)phenyl)-2,3-dihydrobenzofuran-5-yl)amino)methyl)acrylic acid (280 mg, 0.63 mmol) in DMF (3 mL) was stirred at room temperature for 16 hours. The reaction was diluted with water (20 mL) and extracted with ethyl acetate (20 mL×2). The combined organic lawyers were washed with brine (50 mL), dried over anhydrous $Na_2SO_4$, filtered and concentrated. The residue was purified by flash chromatography on silica gel (0-30% ethyl acetate in petroleum ether) to afford the title compound (90 mg, 26%) as a yellow solid. LCMS (ESI): m/z 462.1 $[M-THP+H]^+$.

Step 2: Preparation of 2-(((4-Cyano-7-(4-(pentafluoro-16-sulfanyl)phenyl)-2,3-dihydrobenzofuran-5-yl)amino)methyl)-N-hydroxyacrylamide

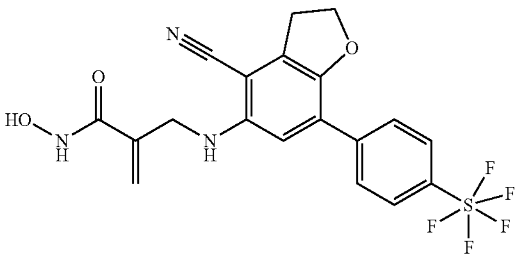 [SMILES: C=C(CNc1cc(-c2ccc(S(F)(F)(F)(F)F)cc2)c2c(c1C#N)CCO2)C(=O)NO]

To the mixture of 2-(((4-cyano-7-(4-(pentafluoro-16-sulfanyl)phenyl)-2,3-dihydrobenzofuran-5-yl)amino)methyl)-N-((tetrahydro-2H-pyran-2-yl)oxy)acrylamide (80 mg, 0.15 mmol) in MeOH (3 mL) was added HCl (0.9 mL, 1.74 mmol). The resulting mixture was stirred at room temperature for 1 hour. The reaction mixture was purified by Prep-TLC (petroleum ether:ethyl acetate:EtOH=6:3:1) to afford the title compound (10.64 mg, 16%) as a white solid. $^1$H NMR (400 MHz, DMSO-$d_6$): δ 10.85 (s, 1H), 8.92 (s, 1H), 7.97 (d, J=8.8 Hz, 2H), 7.87 (d, J=8.8 Hz, 2H), 6.60 (s, 1H), 6.12 (t, J=5.6 Hz, 1H), 5.62 (s, 1H), 5.41 (s, 1H), 4.59 (t, J=8.8 Hz, 2H), 4.04 (d, J=5.6 Hz, 2H), 3.29 (t, J=8.8 Hz, 2H); LCMS (ESI): m/z 462.0 $[M+H]^+$.

Example 41

Preparation of 2-(((4-Cyano-7-(4-(pentafluoro-16-sulfanyl)phenyl)-2,3-dihydrobenzofuran-5-yl)amino)methyl)acrylamide The general reaction scheme was as follows:

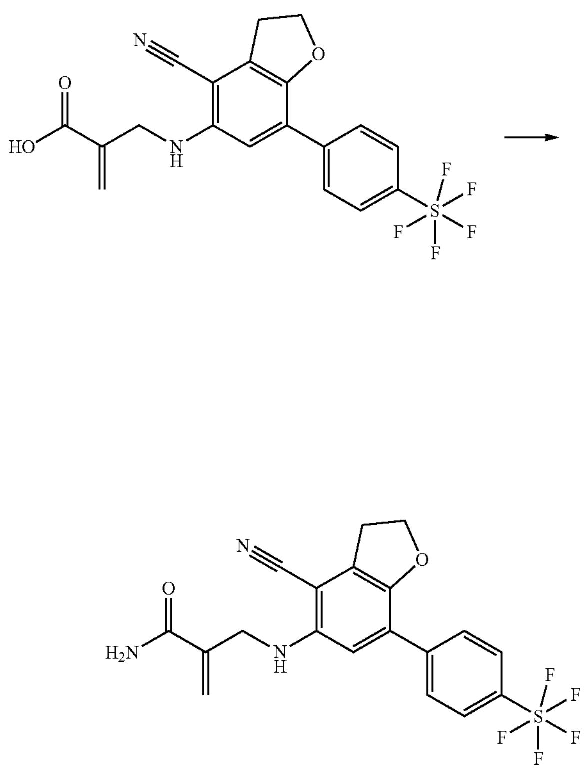

To a mixture of 2-(((4-cyano-7-(4-(pentafluoro-16-sulfanyl)phenyl)-2,3-dihydrobenzofuran-5-yl)amino)methyl)acrylic acid (50 mg, 0.11 mmol), $NH_4Cl$ (18 mg, 0.34 mmol), DIPEA (0.078 mL, 0.45 mmol) in DMF (3 mL) was added HATU (85 mg, 0.22 mmol). The resulting mixture was stirred at room temperature for 2 hours. The reaction mixture was diluted with ethyl acetate (20 mL), washed with water (20 mL×2). The organic layer was dried over $Na_2SO_4$, filtered and concentrated. The residue was purified by Prep-TLC (petroleum ether:ethyl acetate:EtOH=6:3:1) to afford the title compound (35.3 mg, 71%) as a light yellow solid. $^1$H NMR (400 MHz, DMSO-$d_6$): δ 8.00-7.93 (m, 2H), 7.86 (d, J=8.8 Hz, 2H), 7.61 (s, 1H), 7.16 (s, 1H), 6.58 (s, 1H), 6.08 (t, J=5.6 Hz, 1H), 5.81 (s, 1H), 5.47 (s, 1H), 4.59 (t, J=8.8 Hz, 2H), 4.03 (d, J=5.6 Hz, 2H), 3.32 (t, J=8.8 Hz, 2H); LCMS (ESI): m/z 446.1 $[M+H]^+$.

Example 42

Preparation of 2-(((4-Carbamoyl-7-(4-isopropylphenyl)-2,3-dihydrobenzofuran-5-yl)amino)methyl)acrylic acid The general reaction scheme was as follows:

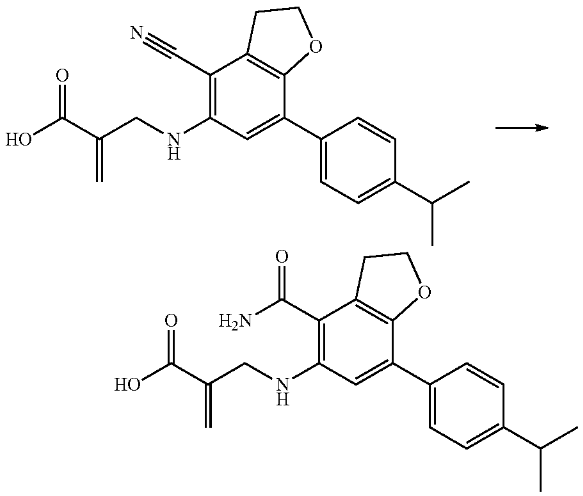

To a solution of 2-(((4-cyano-7-(4-isopropylphenyl)-2,3-dihydrobenzofuran-5-yl)amino)methyl)acrylic acid (200 mg, 0.55 mmol) in THF (3 mL) and $H_2O$ (1 mL) was added KOH (93 mg, 1.66 mmol). The mixture was stirred at 90° C. for 16 hours. After cooling to room temperature, the reaction solution was quenched with 1 N HCl and adjusted to pH with 7. The solution was extracted with ethyl acetate (30 mL×3) and washed with water (30 mL). The organic was dried over $Na_2SO_4$ and concentrated. The residue was purified by reverse phase chromatography (Welch Xtimate C18 150*25 mm*5umv, water (0.2% FA)-CAN, 55%-85%) to afford the title compound (40.09 mg, 17%) as a yellow solid. $^1$H NMR (400 MHz, DMSO-$d_6$): δ 7.55 (s, 2H), 7.53 (d, J=8.4 Hz, 2H), 7.28 (d, J=8.4 Hz, 2H), 6.41 (s, 1H), 6.08 (s, 1H), 5.67 (s, 1H), 4.43 (t, J=8.4 Hz, 2H), 3.95 (s, 2H), 3.31 (t, J=8.4 Hz, 2H), 2.90-2.87 (m, 1H), 1.22 (d, J=6.8 Hz, 6H); LCMS (ESI): m/z 381.2 $(M+H)^+$.

Example 43

Preparation of 2-(((7-(4-Isopropylphenyl)-4-(methylsulfonyl)-2,3-dihydrobenzofuran-5-yl)amino)methyl)acrylic acid The general reaction scheme was as follows:

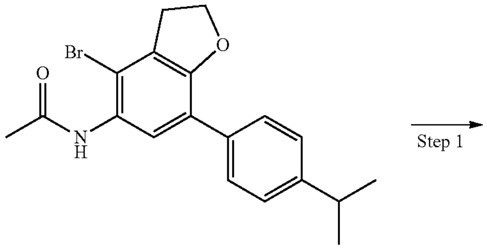

-continued

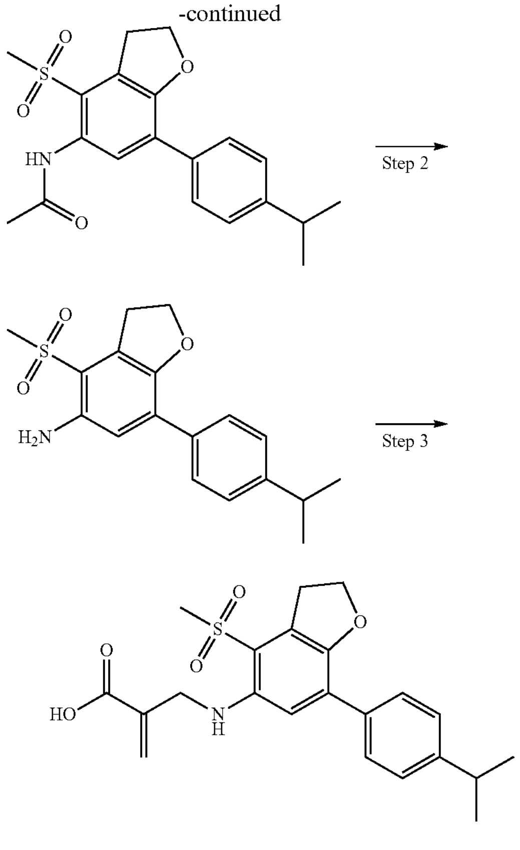

Step 1: Preparation of N-(7-(4-Isopropylphenyl)-4-(methylsulfonyl)-2,3-dihydrobenzofuran-5-yl)acetamide

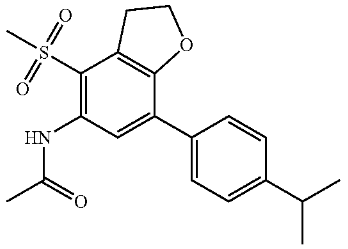 [SMILES: CC(=O)Nc1cc(-c2ccc(C(C)C)cc2)c2c(c1S(C)(=O)=O)CCO2]

To a solution of N-(4-bromo-7-(4-isopropylphenyl)-2,3-dihydrobenzofuran-5-yl)acetamide (500 mg, 1.34 mmol), CuI (127 mg, 0.67 mmol), KOH (75 mg, 1.34 mmol), pyrrolidine-2-carboxylic acid (77 mg, 0.67 mmol) in DMF (20 mL) was added sodium methane sulfinate (273 mg, 2.67 mmol). The reaction mixture was stirred at 120° C. for 16 hours. The reaction was diluted with water (30 mL) and extracted with ethyl acetate (30 mL×2). The combined organic lawyers were washed with brine (50 mL), dried over anhydrous $Na_2SO_4$, filtered and concentrated. The residue was purified by flash chromatography on silica gel (0-14% ethyl acetate in petroleum ether) to afford the title compound (310 mg, 62%) as a yellow solid. LCMS (ESI): m/z 374.2 $[M+H]^+$.

Step 2: Preparation of 7-(4-Isopropylphenyl)-4-(methylsulfonyl)-2,3-dihydrobenzofuran-5-amine

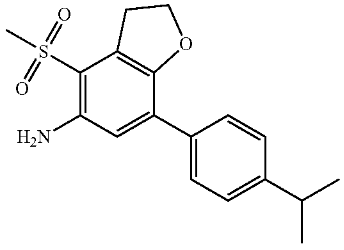 [SMILES: CC(C)c1ccc(-c2cc(N)c(S(C)(=O)=O)c3c2OCC3)cc1]

To a solution of 6N aq. HCl (0.7 mL, 8.3 mmol) in ethanol (8 mL) was added N-(7-(4-isopropylphenyl)-4-(methylsulfonyl)-2,3-dihydrobenzofuran-5-yl)acetamide (310 mg, 0.83 mmol). The reaction mixture was stirred at 80° C. for 16 hours. The reaction mixture was concentrated, diluted with $H_2O$ (20 mL), basified with 2M aq. NaOH to pH 8, extracted with ethyl acetate (20 mL×2). The combined organic layer was dried over $Na_2SO_4$, filtered and concentrated to afford the title compound (240 mg, 87%) as a yellow solid. LCMS (ESI): m/z 332.1 $[M+H]^+$.

Step 3: Preparation of 2-(((7-(4-Isopropylphenyl)-4-(methylsulfonyl)-2,3-dihydrobenzofuran-5-yl)amino)methyl)acrylic acid

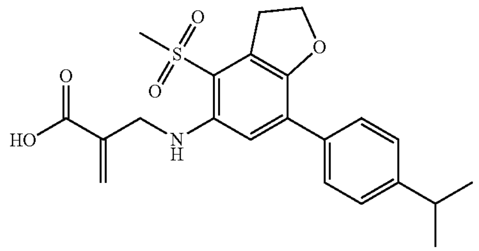 [SMILES: C=C(CNc1cc(-c2ccc(C(C)C)cc2)c2c(c1S(C)(=O)=O)CCO2)C(=O)O]

A solution of 7-(4-isopropylphenyl)-4-methylsulfonyl-2,3-dihydrobenzofuran-5-amine (100 mg, 0.30 mmol), 2-(bromomethyl)acrylic acid (50 mg, 0.30 mmol) in DMF (2 mL) was stirred at room temperature for 2 hours. The reaction mixture was purified by prep-HPLC (Welch Xtimate C18 150*25 mm*5 um, 150*25 mm*5 um, water (0.2% FA)-ACN, 55-85%) to afford the title compound (52.97 mg, 42%) as a yellow solid. $^1H$ NMR (400 MHz, DMSO-$d_6$): δ 7.55 (d, J=8.4 Hz, 2H), 7.31 (d, J=8.4 Hz, 2H), 6.59 (s, 1H), 6.34 (s, 1H), 6.03 (s, 1H), 5.57 (s, 1H), 4.48 (t, J=8.8 Hz, 2H), 4.05 (s, 2H), 3.48 (t, J=8.8 Hz, 2H), 3.21 (s, 3H), 2.95-2.87 (m, 1H), 1.22 (d, J=6.8 Hz, 6H); LCMS (ESI): m/z 416.0 $[M+H]^+$.

Example 44

Preparation of 2-[[[4-Cyano-3,3-dideuterio-7-(4-isopropylphenyl)-2H-benzofuran-5-yl]amino]methyl]prop-2-enoic acid The general reaction scheme was as follows:

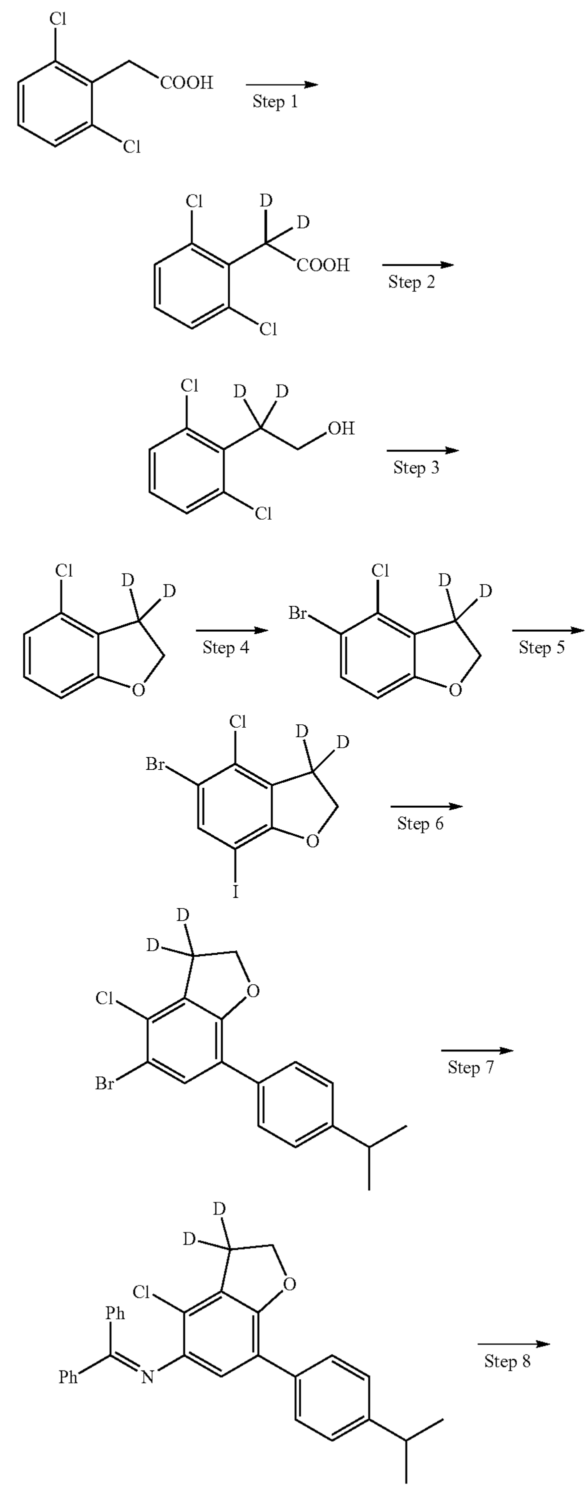

-continued

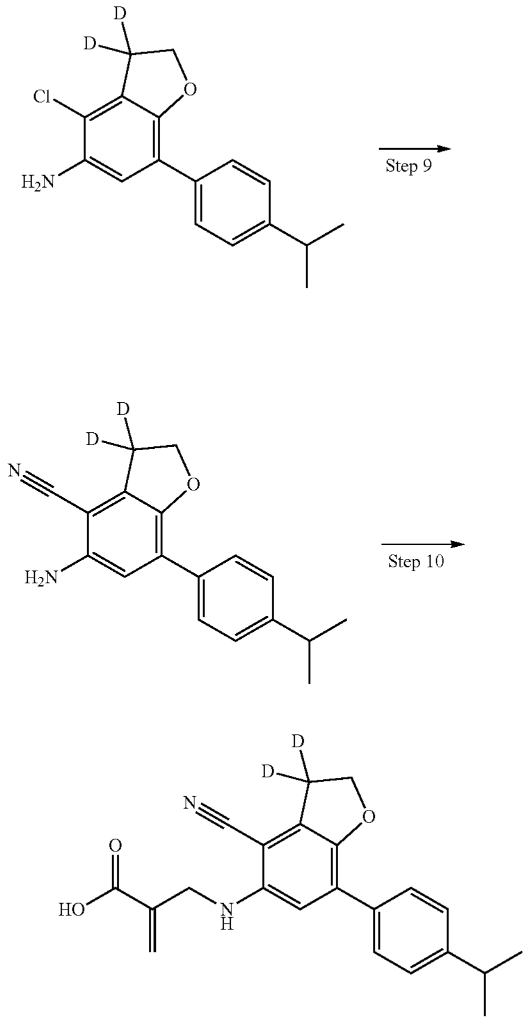

Step 1: Preparation of 2,2-Dideuterio-2-(2,6-dichlorophenyl)acetic acid

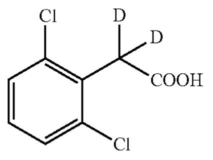 [SMILES: [2H]C([2H])(C(=O)O)c1c(Cl)cccc1Cl]

A solution of 2-(2,6-dichlorophenyl)acetic acid (25.0 g, 121.93 mmol), TBAB (0.39 g, 1.22 mmol) and NaOD (15.62 g, 152.41 mmol, 40 wt % in $D_2O$) in $D_2O$ (130.mL) was stirred at 100° C. for 40 hours. The reaction solution was cooled to 0° C. by ice water, adjusted pH to 3-4 with aq. HCl solution (2 M) and extracted with ethyl acetate (500 mL) and washed with water (1 L×5). The organic was dried over $Na_2SO_4$ and filtered and concentrated to afford the title compound (24.0 g, 95%) as a white solid. $^1H$ NMR (400 MHz, $CDCl_3$): δ 7.34 (d, J=8.0 Hz, 2H), 7.22-7.16 (m, 1H).

Step 2: Preparation of 2,2-Dideuterio-2-(2,6-dichlorophenyl)ethanol

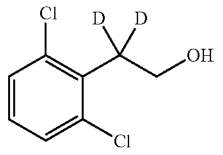 [SMILES: [2H]C([2H])(CO)c1c(Cl)cccc1Cl]

To a solution of 2,2-dideuterio-2-(2,6-dichlorophenyl) acetic acid (24.0 g, 115.91 mmol) in THF (60 mL) was added $B_2H_6$ (231.83 mL, 231.83 mmol, 1.0 mmol/L in THF) dropwise at 0° C. After addition, the reaction solution was stirred at room temperature for 16 hours. The reaction was quenched with ice water (500 mL) and extracted with ethyl acetate (500 mL), washed with brine (500 mL×2), dried over $Na_2SO_4$ and filtered. The filtrate was concentrated to afford the title compound (20.0 g, 89%) as a white solid. $^1$H NMR (400 MHz, DMSO-$d_6$): δ 7.48-7.39 (m, 2H), 7.30-7.22 (m, 1H), 4.88 (s, 1H), 3.53 (d, J=3.2 Hz, 2H).

Step 3: Preparation of 4-Chloro-3,3-dideuterio-2H-benzofuran

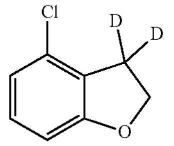

To a mixture of 2,2-dideuterio-2-(2,6-dichlorophenyl) ethanol (20.0 g, 103.59 mmol) in pyridine (200 mL) was added NaH (5.18 g, 129.49 mmol, 60% in mineral oil) at 0° C. The mixture was stirred at 0° C. for 1 hour. Then CuCl (0.51 g, 5.18 mmol) was added into the reaction mixture. The reaction solution was stirred at 115° C. for 16 hours. The reaction mixture was quenched with water (300 mL), adjusted pH to 3 with HCl solution (2 M), diluted with petroleum ether (1 L) and washed with water (500 mL×2). The organic layer was dried over $Na_2SO_4$ and filtered and concentrated. The residue was purified by flash chromatography on silica gel (100% petroleum ether) to afford the title compound (6.0 g, 37%) as a colorless liquid. $^1$H NMR (400 MHz, $CDCl_3$): δ 7.05 (t, J=8.0 Hz, 1H), 6.83 (d, J=8.0 Hz, 1H), 6.68 (d, J=8.0 Hz, 1H), 4.60 (s, 2H).cc Step 4: Preparation of 5-Bromo-4-chloro-3,3-dideuterio-2H-benzofuran

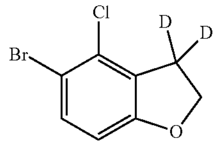 [SMILES: [2H]C1([2H])COc2ccc(Br)c(Cl)c21]

To a solution of 4-chloro-3,3-dideuterio-2H-benzofuran (3.8 g, 24.26 mmol) in acetonitrile (60 mL) was added NBS (4.75 g, 26.69 mmol) and the mixture was stirred at room temperature for 16 hours. The mixture was quenched with water (300 mL) and diluted with ethyl acetate (300 mL), washed with brine (150 mL×2), dried over $Na_2SO_4$, filtered and concentrated to afford the title compound (4.8 g, 84%) as a white solid. $^1$H NMR (400 MHz, $CDCl_3$): δ 7.34 (d, J=8.8 Hz, 1H), 6.58 (d, J=8.8 Hz, 1H), 4.64 (s, 2H).

Step 5: Preparation of 5-Bromo-4-chloro-3,3-dideuterio-7-iodo-2H-benzofuran

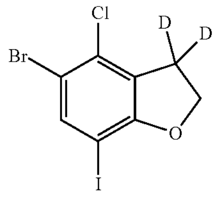 [SMILES: [2H]C1([2H])COc2c(I)cc(Br)c(Cl)c21]

To a solution of 5-bromo-4-chloro-3,3-dideuterio-2H-benzofuran (4.8 g, 20.38 mmol) in methyl alcohol (60 mL) was added $Ag_2SO_4$ (3.18 g, 10.19 mmol) and $I_2$ (5.69 g, 22.42 mmol) and the mixture was stirred at room temperature for 4 hours. The mixture was quenched with sat. aq. $NaHSO_3$ solution (300 mL) and diluted with ethyl acetate (500 mL), washed with brine (150 mL×2). The organic layer was dried over $Na_2SO_4$ and filtered and concentrated. The residue was purified by flash chromatography on silica gel (100% petroleum ether) to afford the title compound (6.2 g, 84%) as a white solid. $^1$H NMR (400 MHz, $CDCl_3$): δ 7.70 (s, 1H), 4.72 (s, 2H).

Step 6: Preparation of 5-Bromo-4-chloro-3,3-dideuterio-7-(4-isopropylphenyl)-2H-benzofuran

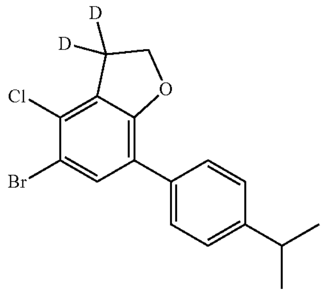 [SMILES: [2H]C1([2H])COc2c(-c3ccc(C(C)C)cc3)cc(Br)c(Cl)c21]

A mixture of 5-bromo-4-chloro-3,3-dideuterio-7-iodo-2H-benzofuran (200 mg, 0.55 mmol), (4-isopropylphenyl) boronic acid (86 mg, 0.53 mmol), Pd(dppf)$Cl_2$ (40 mg, 0.06 mmol) and $Na_2CO_3$ (176 mg, 1.66 mmol) in 1,4-dioxane (10 mL) and water (1 mL) was stirred at 80° C. for 3 hours under a nitrogen atmosphere. The reaction mixture was concentrated under vacuum. The residue was purified by flash chromatography on silica gel (100% petroleum ether) to afford the title compound (150 mg, 77%) as a colorless liquid. $^1$H NMR (400 MHz, $CDCl_3$): δ 7.56 (d, J=8.0 Hz, 2H), 7.53 (s, 1H), 7.29 (d, J=8.0 Hz, 2H), 4.69 (s, 2H), 3.03-2.84 (m, 1H), 1.28 (d, J=7.2 Hz, 6H).

Step 7: Preparation of N-[4-Chloro-3,3-dideuterio-7-(4-isopropylphenyl)-2H-benzofuran-5-yl]-1,1-diphenyl-methanimine

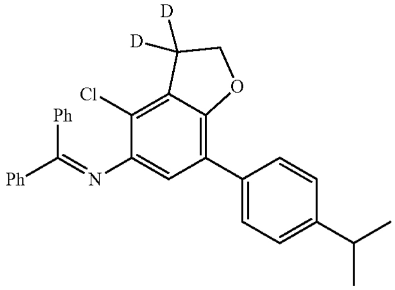 [SMILES: [2H]C1([2H])COc2c(-c3ccc(C(C)C)cc3)cc(N=C(c3ccccc3)c3ccccc3)c(Cl)c21]

A mixture of 5-bromo-4-chloro-3,3-dideuterio-7-(4-isopropylphenyl)-2H-benzofuran (1.2 g, 3.39 mmol), t-BuXphos (144 mg, 0.34 mmol), $Pd_2(dba)_3$ (310 mg, 0.34 mmol), t-BuONa (978 mg, 10.18 mmol) and diphenylmethanimine (1.23 g, 6.79 mmol) in 1,4-dioxane (20 mL) was stirred at 110° C. for 16 hour under a nitrogen atmosphere. The reaction mixture was concentrated under vacuum. The residue was purified by flash chromatography on silica gel (0-10% ethyl acetate in petroleum ether) to afford the title compound (1.4 g, crude) as a yellow liquid.

Step 8: Preparation of 4-Chloro-3,3-dideuterio-7-(4-isopropylphenyl)-2H-benzofuran-5-amine

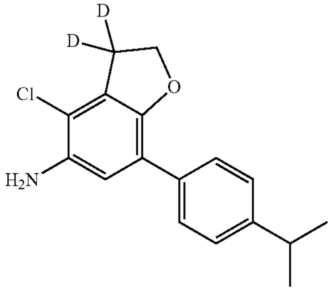 [SMILES: [2H]C1([2H])COc2c(-c3ccc(C(C)C)cc3)cc(N)c(Cl)c21]

To a mixture of N-[4-chloro-3,3-dideuterio-7-(4-isopropylphenyl)-2H-benzofuran-5-yl]-1,1-diphenyl-methanimine (1.3 g, 2.86 mmol) in THF (10 mL) was added aq. HCl (10 mL, 2 M). Then the reaction was stirred at room temperature for 1 hour. The mixture was adjusted pH to 8 with aq. NaOH solution (2 M), diluted with ethyl acetate (300 mL), washed with brine (150 mL×2), dried over $Na_2SO_4$ and filtered. The filtrate was concentrated and purified by flash chromatography on silica gel (0-25% ethyl acetate in petroleum ether) afford the title compound (400 mg, 48%) as a yellow liquid. $^1$H NMR (400 MHz, $CDCl_3$): δ 7.56 (d, J=8.0 Hz, 2H), 7.28 (d, J=8.0 Hz, 2H), 6.75 (s, 1H), 4.61 (s, 2H), 3.77 (s, 2H), 3.00-2.90 (m, 1H), 1.27 (d, J=6.8 Hz, 6H).

Step 9: Preparation of 5-Amino-3,3-dideuterio-7-(4-isopropylphenyl)-2H-benzofuran-4-carbonitrile

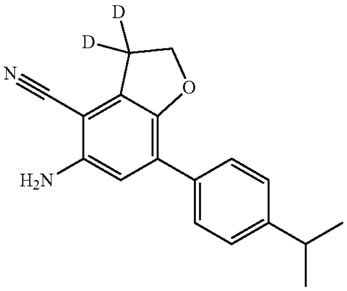 [SMILES: [2H]C1([2H])COc2c(-c3ccc(C(C)C)cc3)cc(N)c(C#N)c21]

A mixture of 4-chloro-3,3-dideuterio-7-(4-isopropylphenyl)-2H-benzofuran-5-amine (630 mg, 2.17 mmol), t-BuXphos Pd $G_3$ (173 mg, 0.22 mmol), $Zn(CN)_2$ (510 mg, 4.35 mmol) and Zn (142 mg, 2.17 mmol) in DMA (10 mL) was stirred at 120° C. for 16 hours under a nitrogen atmosphere. The reaction solution was quenched with water (200 mL), dissolved in ethyl acetate (300 mL), dried over $MgSO_4$, filtered and concentrated. The residue was purified by flash chromatography on silica gel (0-20% ethyl acetate in petroleum ether) to afford the title compound (480 mg, 79%) as a yellow solid. $^1$H NMR (400 MHz, $CDCl_3$): δ 7.59 (d, J=8.0 Hz, 2H), 7.30 (d, J=8.0 Hz, 2H), 6.68 (s, 1H), 4.63 (s, 2H), 4.09 (s, 2H), 3.00-2.90 (m, 1H), 1.28 (d, J=6.8 Hz, 6H).

Step 10: Preparation of 2-[[[4-Cyano-3,3-dideuterio-7-(4-isopropylphenyl)-2H-benzofuran-5-yl]amino]methyl]prop-2-enoic acid

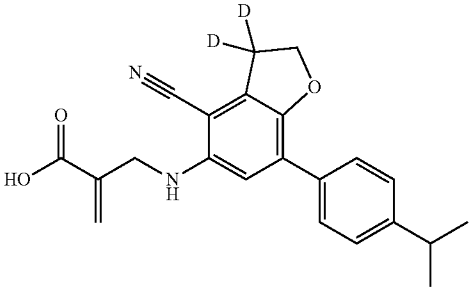 [SMILES: [2H]C1([2H])COc2c(-c3ccc(C(C)C)cc3)cc(NCC(=C)C(=O)O)c(C#N)c21]

A solution of 5-amino-3,3-dideuterio-7-(4-isopropylphenyl)-2H-benzofuran-4-carbonitrile (80 mg, 0.29 mmol), 2-(bromomethyl)acrylic acid (47 mg, 0.29 mmol) in DMF (2 mL) was stirred at 80° C. for 2 hours. The reaction mixture was purified by prep-HPLC (Welch Xtimate C18 150*25 mm*5 um, water (0.2% FA)-ACN, 50-80%) to afford the title compound (40.6 mg, 39%) as a yellow solid. $^1$H NMR (400 MHz, DMSO-$d_6$): δ 12.73 (s, 1H), 7.56 (d, J=8.4 Hz, 2H), 7.30 (d, J=8.4 Hz, 2H), 6.46 (s, 1H), 6.11 (s, 1H), 5.98 (s, 1H), 5.66 (s, 1H), 4.54 (s, 2H), 4.04 (s, 2H), 2.95-2.85 (m, 1H), 1.21 (d, J=6.8 Hz, 6H); LCMS (ESI): m/z 365.1 $(M+H)^+$.

Example 45

Preparation of 2-[[[4-Cyano-3,3-dideuterio-7-(4-isopropylphenyl)-2H-benzofuran-5-yl]amino] methyl]prop-2-enehydroxamic acid The general reaction scheme was as follows:

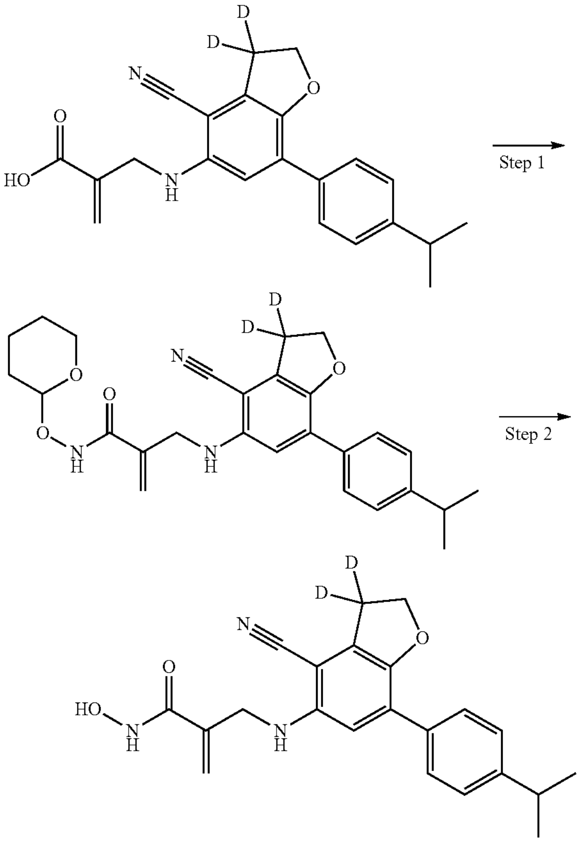

Step 1: Preparation of 2-[[[4-Cyano-3,3-dideuterio-7-(4-isopropylphenyl)-2H-benzofuran-5-yl]amino] methyl]-N-tetrahydropyran-2-yloxy-prop-2-enamide

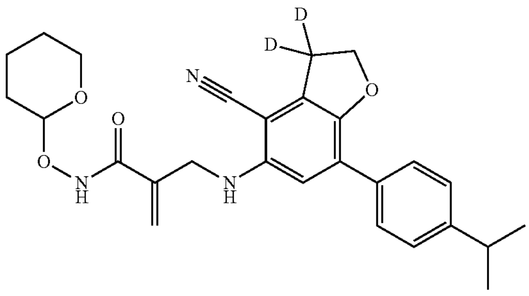 [SMILES: [2H]C1([2H])COc2c(-c3ccc(C(C)C)cc3)cc(NCC(=C)C(=O)NOC3CCCCO3)c(C#N)c21]

To a mixture of 2-[[[4-cyano-3,3-dideuterio-7-(4-isopropylphenyl)-2H-benzofuran-5-yl]amino]methyl]prop-2-enoic acid (250 mg, 0.69 mmol), TEA (0.37 mL, 2.74 mmol), O-(tetrahydro-2H-pyran-2-yl)hydroxylamine (241 mg, 2.06 mmol) in DMF (3 mL) was added BOP (606 mg, 1.37 mmol). The resulting mixture was stirred at room temperature for 16 hours. The reaction mixture was quenched with water (20 mL), extracted with ethyl acetate (20 mL). The organic layer was dried over $Na_2SO_4$, filtered and concentrated. The residue was purified by flash chromatography on silica gel (0-30% ethyl acetate in petroleum ether) to afford the title compound (100 mg, 31%) as light yellow solid. LCMS (ESI): m/z 464.3 $(M+H)^+$.

Step 2: Preparation of 2-[[[4-Cyano-3,3-dideuterio-7-(4-isopropylphenyl)-2H-benzofuran-5-yl]amino] methyl]prop-2-enehydroxamic acid

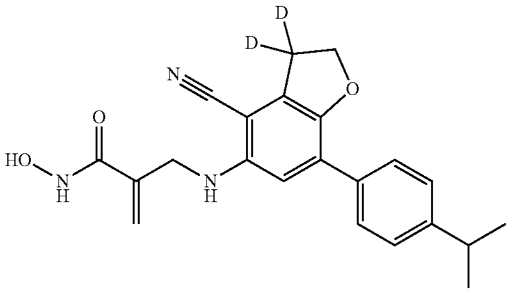 [SMILES: [2H]C1([2H])COc2c(-c3ccc(C(C)C)cc3)cc(NCC(=C)C(=O)NO)c(C#N)c21]

To a mixture of 2-[[[4-cyano-3,3-dideuterio-7-(4-isopropylphenyl)-2H-benzofuran-5-yl]amino]methyl]-N-tetrahydropyran-2-yloxy-prop-2-enamide (100 mg, 0.22 mmol) in methyl alcohol (5 mL) was added aq. HCl (2.0 mL, 2 M). The resulting mixture was stirred at room temperature for 2 hours. The reaction mixture was purified by Prep-HPLC (Welch Xtimate C18 150*25 mm*5 um, water (0.2% FA)-ACN, 47%-77%) to afford the title compound (63.04 mg, 75%) as a light yellow solid. $^1H$ NMR (400 MHz, DMSO-$d_6$): δ 10.87 (s, 1H), 8.94 (s, 1H), 7.57 (d, J=8.0 Hz, 2H), 7.30 (d, J=8.0 Hz, 2H), 6.50 (s, 1H), 6.03 (t, J=5.6 Hz, 1H), 5.62 (s, 1H), 5.39 (s, 1H), 4.53 (s, 2H), 4.02 (d, J=5.6 Hz, 2H), 2.95-2.85 (m, 1H), 1.21 (d, J=6.8 Hz, 6H); LCMS (ESI): m/z 380.1 $(M+H)^+$.

Example 46

Preparation of 2-[[[4-Cyano-3,3-dideuterio-7-(4-isopropylphenyl)-2H-benzofuran-5-yl]amino] methyl]prop-2-enamide The general reaction scheme was as follows:

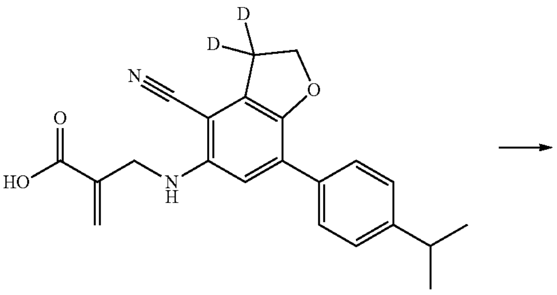

-continued

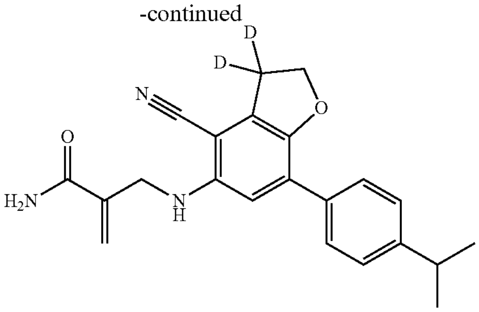

To a mixture of 2-[[[4-cyano-3,3-dideuterio-7-(4-isopropylphenyl)-2H-benzofuran-5-yl]amino]methyl]prop-2-enoic acid (50 mg, 0.14 mmol), $NH_4Cl$ (36 mg, 0.69 mmol), DIPEA (124 mg, 0.96 mmol) in DMF (3 mL) was added HATU (78 mg, 0.21 mmol), then the mixture was stirred at room temperature for 16 hours. The reaction solution was purified by prep-HPLC (Welch Xtimate C18 150*25 mm*5 um, water (0.2% FA)-ACN, 50-80%) to afford the title compound (37.47 mg, 74%) as a yellow solid. $^1H$ NMR (400 MHz, DMSO-$d_6$): δ 7.61 (s, 1H), 7.56 (d, J=8.0 Hz, 2H), 7.30 (d, J=8.0 Hz, 2H), 7.14 (s, 1H), 6.49 (s, 1H), 5.94 (s, 1H), 5.81 (s, 1H), 5.46 (s, 1H), 4.53 (s, 2H), 4.02 (s, 2H), 2.95-2.85 (m, 1H), 1.21 (d, J=6.8 Hz, 6H); LCMS (ESI): m/z 364.0 $(M+H)^+$.

Example 47

Preparation of 2-[[[4-Cyano-2,2-dideuterio-7-[4-(trifluoromethoxy)phenyl]-3H-benzofuran-5-yl]amino]methyl]prop-2-enehydroxamic acid The general reaction scheme was as follows:

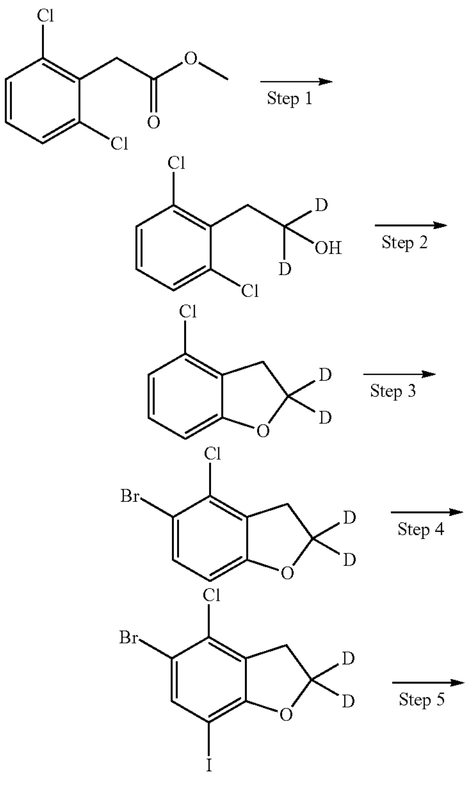

-continued

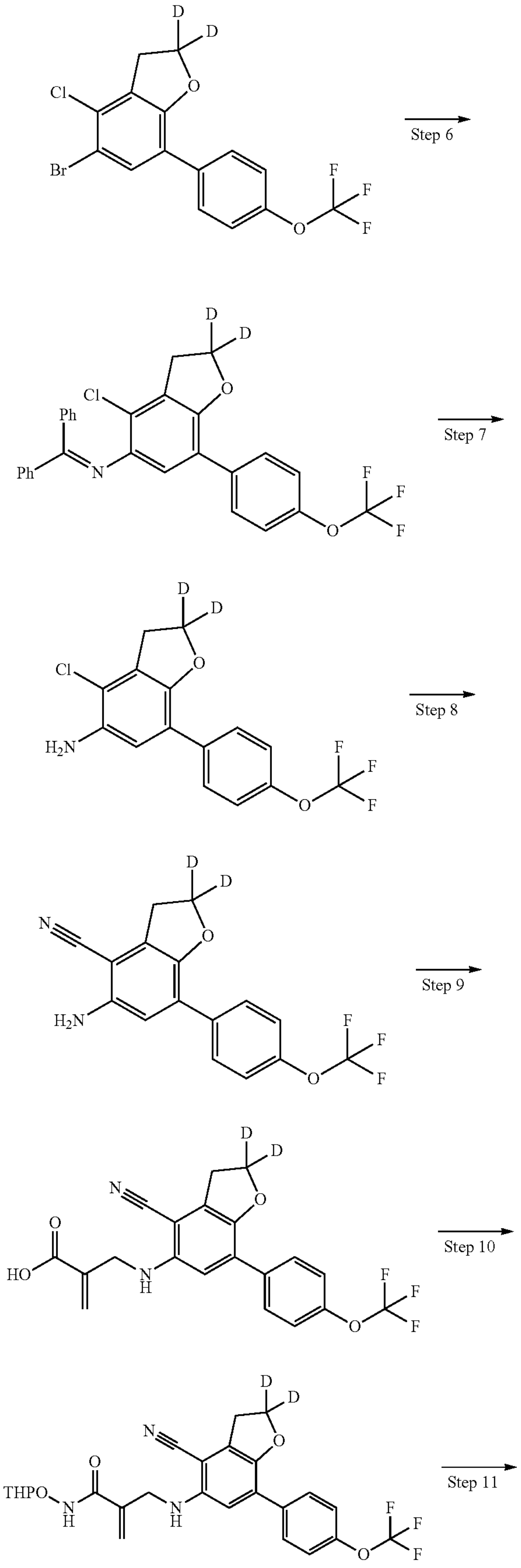

-continued

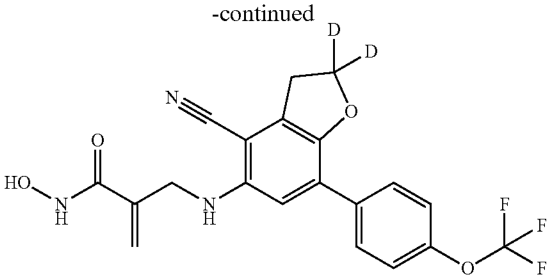

Step 1: Preparation of 1,1-Dideuterio-2-(2,6-dichlorophenyl)ethanol

To a mixture of methyl 2-(2,6-dichlorophenyl)acetate (10.0 g, 45.65 mmol) in THF (100 mL) was added $LiAlD_4$ (4.02 g, 95.86 mmol) at 0° C. Then the reaction was stirred at 0° C. for 2 hours. The reaction was quenched with water (4 mL) and aq. NaOH solution (4 mL, 2 M). The organic was dried over $MgSO_4$ and concentrated. The residue was purified by flash chromatography on silica gel (0-14% ethyl acetate in petroleum ether) to afford the title compound (6.0 g, 68%) as a white solid. $^1$H NMR (400 MHz, $CDCl_3$): δ 7.32-7.30 (m, 2H), 7.14-7.07 (m, 1H), 3.26 (s, 2H), 1.49 (s, 1H).

Step 2: Preparation of 4-Chloro-2,2-dideuterio-3H-benzofuran

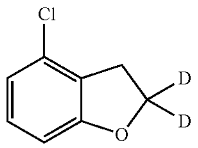 [SMILES: [2H]C1([2H])Cc2c(Cl)cccc2O1]

To a mixture of 1,1-dideuterio-2-(2,6-dichlorophenyl) ethanol (6.0 g, 31.08 mmol) in pyridine (60 mL) was added NaH (1.55 g, 38.85 mmol, 60% in mineral oil) at 0° C. The mixture was stirred at 0° C. for 1 hour. Then CuCl (0.15 g, 1.55 mmol) was added the reaction mixture and the reaction mixture was stirred at 115° C. for 16 hours. The reaction mixture was quenched by water (300 mL), adjusted pH to 3 with aq. HCl solution (2 M), diluted with petroleum ether (1 L), and washed with water (500 mL×2). The organic layer was dried over $Na_2SO_4$, filtered and concentrated. The residue was purified by flash chromatography on silica gel (100% petroleum ether) to afford the title compound (2.5 g, 51%) as a colorless liquid. $^1$H NMR (400 MHz, $CDCl_3$) δ 7.07-7.03 (m, 1H), 6.83 (d, J=8.4 Hz, 1H), 6.68 (d, J=8.4 Hz, 1H), 3.25 (s, 2H).

Step 3: Preparation of 5-Bromo-4-chloro-2,2-dideuterio-3H-benzofuran

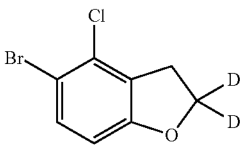 [SMILES: [2H]C1([2H])Cc2c(ccc(Br)c2Cl)O1]

To a solution of 4-chloro-2,2-dideuterio-3H-benzofuran (2.5 g, 15.96 mmol) in acetonitrile (60 mL) was added NBS (2.84 g, 15.96 mmol) and the mixture was stirred at room temperature for 16 hours. The mixture was quenched with water (30 mL) and diluted with ethyl acetate (300 mL), washed with brine (150 mL×2), dried over $Na_2SO_4$ and filtered. The filtrate was concentrated afford the title compound (3.7 g, 98%) as a white solid. $^1$H NMR (400 MHz, $CDCl_3$): δ 7.33 (d, J=8.4 Hz, 1H), 6.58 (d, J=8.4 Hz, 1H), 3.27 (s, 2H).

Step 4: Preparation of 5-Bromo-4-chloro-2,2-dideuterio-7-iodo-3H-benzofuran

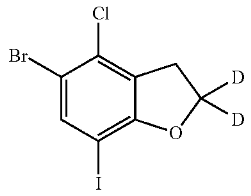 [SMILES: [2H]C1([2H])Cc2c(Cl)c(Br)cc(I)c2O1]

To a solution of 5-bromo-4-chloro-2,2-dideuterio-3H-benzofuran (3.7 g, 15.71 mmol) in methyl alcohol (60 mL) was added $Ag_2SO_4$ (2.45 g, 7.86 mmol) and $I_2$ (4.38 g, 17.28 mmol). The mixture was stirred at room temperature for 4 hours. The reaction was quenched with sat. aq. $NaHSO_3$ solution (300 mL), diluted with ethyl acetate (500 mL), washed with brine (150 mL×2), dried over $Na_2SO_4$, filtered and concentrated. The residue was purified by flash chromatography on silica gel (100% petroleum ether) to afford the title compound (4.5 g, 79%) as a white solid. $^1$H NMR (400 MHz, $CDCl_3$): δ 7.70 (s, 1H), 3.40 (s, 2H).

Step 5: Preparation of 5-Bromo-4-chloro-2,2-dideuterio-7-[4-(trifluoromethoxy)phenyl]-3H-benzofuran

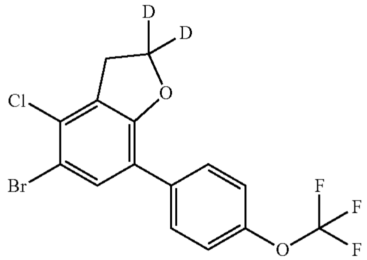 [SMILES: [2H]C1([2H])Cc2c(Cl)c(Br)cc(-c3ccc(OC(F)(F)F)cc3)c2O1]

A mixture of 5-bromo-4-chloro-2,2-dideuterio-7-iodo-3H-benzofuran (1.5 g, 4.15 mmol), (4-(trifluoromethoxy) phenyl)boronic acid (811 mg, 3.94 mmol), $Pd(dppf)Cl_2$ (303 mg, 0.42 mmol), $Na_2CO_3$ (1.32 g, 12.45 mmol) in 1,4-dioxane (30 mL) and water (3 mL). The reaction was stirred at 80° C. for 4 hours under a nitrogen atmosphere. The reaction mixture was concentrated under vacuum. The residue was purified by flash chromatography on silica gel (100% petroleum ether) to afford the title compound (1.2 g, 73%) as a colorless liquid. $^1$H NMR (400 MHz, $CDCl_3$): δ 7.66 (d, J=8.8 Hz, 2H), 7.52 (s, 1H), 7.27 (d, J=8.8 Hz, 2H), 3.35 (s, 2H).

Step 6: Preparation of N-[4-Chloro-2,2-dideuterio-7-(4-isopropylphenyl)-3H-benzofuran-5-yl]-1,1-diphenyl-methanimine

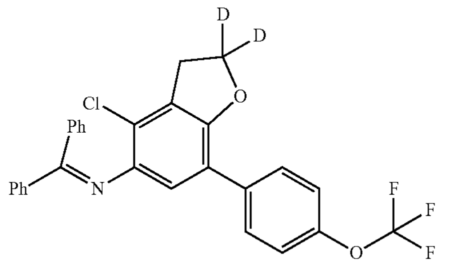 [SMILES: [2H]C1([2H])Cc2c(Cl)c(N=C(c3ccccc3)c3ccccc3)cc(-c3ccc(OC(F)(F)F)cc3)c2O1]

A mixture of 5-bromo-4-chloro-2,2-dideuterio-7-(4-isopropylphenyl)-3H-benzofuran (1.2 g, 3.39 mmol), t-BuXphos (144 mg, 0.34 mmol), $Pd_2(dba)_3$ (310 mg, 0.34 mmol), t-BuONa (978 mg, 10.18 mmol), diphenylmethanimine (1.23 g, 6.79 mmol) in 1,4-dioxane (20 mL) was stirred at 110° C. for 16 hours under a nitrogen atmosphere. The reaction mixture was concentrated under vacuum. The residue was purified by flash chromatography on silica gel (0-10% ethyl acetate in petroleum ether) to afford the title compound (1 g, crude) as a yellow liquid. LCMS (ESI): m/z 496.1 $(M+H)^+$.

Step 7: Preparation of 4-Chloro-2,2-dideuterio-7-(4-isopropylphenyl)-3H-benzofuran-5-amine

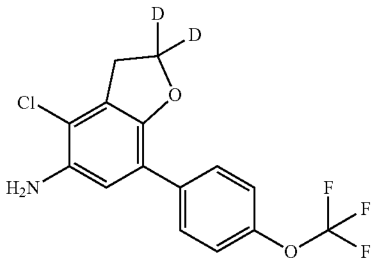 [SMILES: [2H]C1([2H])Cc2c(Cl)c(N)cc(-c3ccc(OC(F)(F)F)cc3)c2O1]

To a mixture of N-[4-chloro-2,2-dideuterio-7-(4-isopropylphenyl)-3H-benzofuran-5-yl]-1,1-diphenyl-methanimine (1.0 g, 2.2 mmol) in THF (10 mL) was added aq. HCl (5 mL, 2N) and the reaction was stirred at room temperature for 1 hour. The mixture was adjusted pH to 8 with aq. NaOH solution (2 M) and diluted with ethyl acetate (300 mL), washed with brine (150 mL×2), dried over $Na_2SO_4$ and filtered. The filtrate was concentrated. The residue was purified by flash chromatography on silica gel (0-10% ethyl acetate in petroleum ether) afford the title compound (500 mg, 78%) as a yellow liquid. $^1H$ NMR (400 MHz, $CDCl_3$): δ 7.70-7.62 (m, 2H), 7.27-7.23 (m, 2H), 6.72 (s, 1H), 3.79 (s, 2H), 3.27 (s, 2H).

Step 8: Preparation of 5-Amino-2,2-dideuterio-7-[4-(trifluoromethoxy)phenyl]-3H-benzofuran-4-carbonitrile

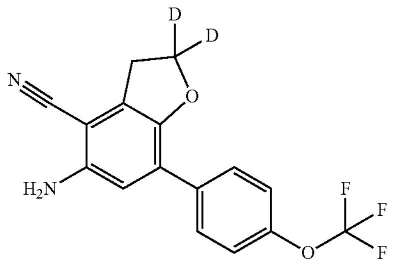 [SMILES: [2H]C1([2H])Cc2c(C#N)c(N)cc(-c3ccc(OC(F)(F)F)cc3)c2O1]

A mixture of 4-chloro-2,2-dideuterio-7-[4-(trifluoromethoxy)phenyl]-3H-benzofuran-5-amine (500 mg, 1.51 mmol), t-BuXphos (119 mg, 0.15 mmol), $Zn(CN)_2$ (354 mg, 3.01 mmol) and Zn (98 mg, 1.51 mmol) in DMA (10 mL) was stirred at 120° C. for 16 hours under a nitrogen atmosphere. The reaction solution was quenched with water (200 mL), dissolved in ethyl acetate (300 mL), dried over $MgSO_4$, filtered and concentrated. The residue was purified by flash chromatography on silica gel (0-20% ethyl acetate in petroleum ether) to afford the title compound (400 mg, 82%) as a yellow solid. $^1H$ NMR (400 MHz, $CDCl_3$): δ 7.69 (d, J=8.8 Hz, 2H), 7.28 (d, J=8.8 Hz, 2H), 6.66 (s, 1H), 4.12 (s, 2H), 3.36 (s, 2H).

Step 9: Preparation of 2-[[[4-Cyano-7-(4-isopropylphenyl)-2,3-dihydrobenzofuran-5-yl]amino]methyl]prop-2-enoic acid

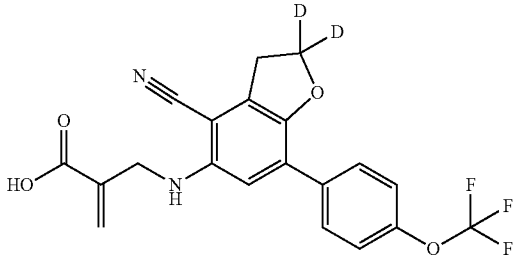 [SMILES: [2H]C1([2H])Cc2c(C#N)c(NCC(=C)C(=O)O)cc(-c3ccc(OC(F)(F)F)cc3)c2O1]

A solution of 5-amino-2,2-dideuterio-7-[4-(trifluoromethoxy)phenyl]-3H-benzofuran-4-carbonitrile (400 mg, 1.24 mmol), 2-(bromomethyl)acrylic acid (204 mg, 1.24 mmol) in DMF (5 mL) was stirred at 80° C. for 2 hours. The reaction solution was quenched with water (200 mL), dissolved in ethyl acetate (200 mL), dried over $MgSO_4$, filtered and concentrated. The residue was purified by flash chromatography on silica gel (0-50% ethyl acetate in petroleum ether) to afford the title compound (300 mg, 60%) as a yellow solid. LCMS (ESI): m/z 407.1 $(M+H)^+$.

Step 10: 2-[[[4-Cyano-2,2-dideuterio-7-[4-(trifluoromethoxy)phenyl]-3H-benzofuran-5-yl]amino]methyl]-N-tetrahydropyran-2-yloxy-prop-2-enamide

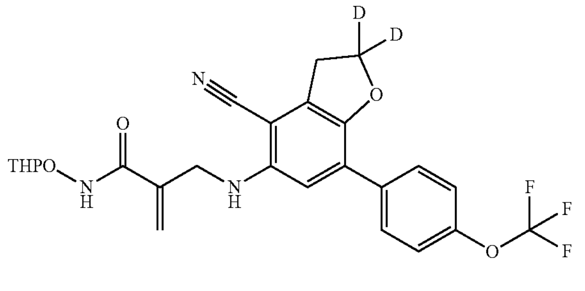

To the mixture of 2-[[[4-cyano-2,2-dideuterio-7-[4-(trifluoromethoxy)phenyl]-3H-benzofuran-5-yl]amino]methyl]prop-2-enoic acid (300 mg, 0.74 mmol), TEA (0.4 mL, 2.95 mmol), O-tetrahydro-2H-pyran-2-ylhydroxylamine (259 mg, 2.21 mmol) in DMF (3 mL) was added BOP (653 mg, 1.48 mmol). The resulting mixture was stirred at room temperature for 16 hours. The reaction mixture was quenched with water (20 mL), extracted with ethyl acetate (200 mL). The organic layer was dried over $Na_2SO_4$, filtered and concentrated. The residue was purified by flash chromatography on silica gel (0-30% ethyl acetate in petroleum ether) to afford the title compound (200 mg, 54%) as a light yellow solid. LCMS (ESI): m/z 528.3 $(M+Na)^+$.

Step 11: Preparation of 2-[[[4-Cyano-2,2-dideuterio-7-[4-(trifluoromethoxy)phenyl]-3H-benzofuran-5-yl]amino]methyl]prop-2-enehydroxamic acid

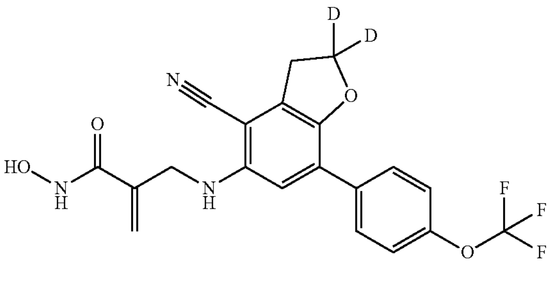 [SMILES: [2H]C1([2H])Cc2c(C#N)c(NCC(=C)C(=O)NO)cc(-c3ccc(OC(F)(F)F)cc3)c2O1]

To the mixture of 2-[[[4-cyano-2,2-dideuterio-7-[4-(trifluoromethoxy)phenyl]-3H-benzofuran-5-yl]amino]methyl]-N-tetrahydropyran-2-yloxy-prop-2-enamide (200 mg, 0.40 mmol) in methyl alcohol (5 mL) was added aq. HCl (3 mL, 2N). The resulting mixture was stirred at room temperature for 2 hours. The reaction mixture was purified by Prep-HPLC (Welch Xtimate C18 150*25 mm*5 um, water (0.2% FA)-ACN, 45%-75%) to afford the title compound (37.13 mg, 22%) as a light yellow solid. $^1H$ NMR (400 MHz, DMSO-$d_6$): δ 10.86 (s, 1H), 8.94 (s, 1H), 7.78 (d, J=8.4 Hz, 2H), 7.44 (d, J=8.4 Hz, 2H), 6.55 (s, 1H), 6.08 (t, J=5.6 Hz, 1H), 5.62 (s, 1H), 5.40 (s, 1H), 4.03 (d, J=5.6 Hz, 2H), 3.30 (s, 2H); LCMS (ESI): m/z 422.0 $(M+H)^+$.

Example 48

Preparation of 2-(((7-Cyano-4-(4-(trifluoromethoxy)phenyl)benzo[d]thiazol-6-yl)amino)methyl)acrylamide The general reaction scheme was as follows:

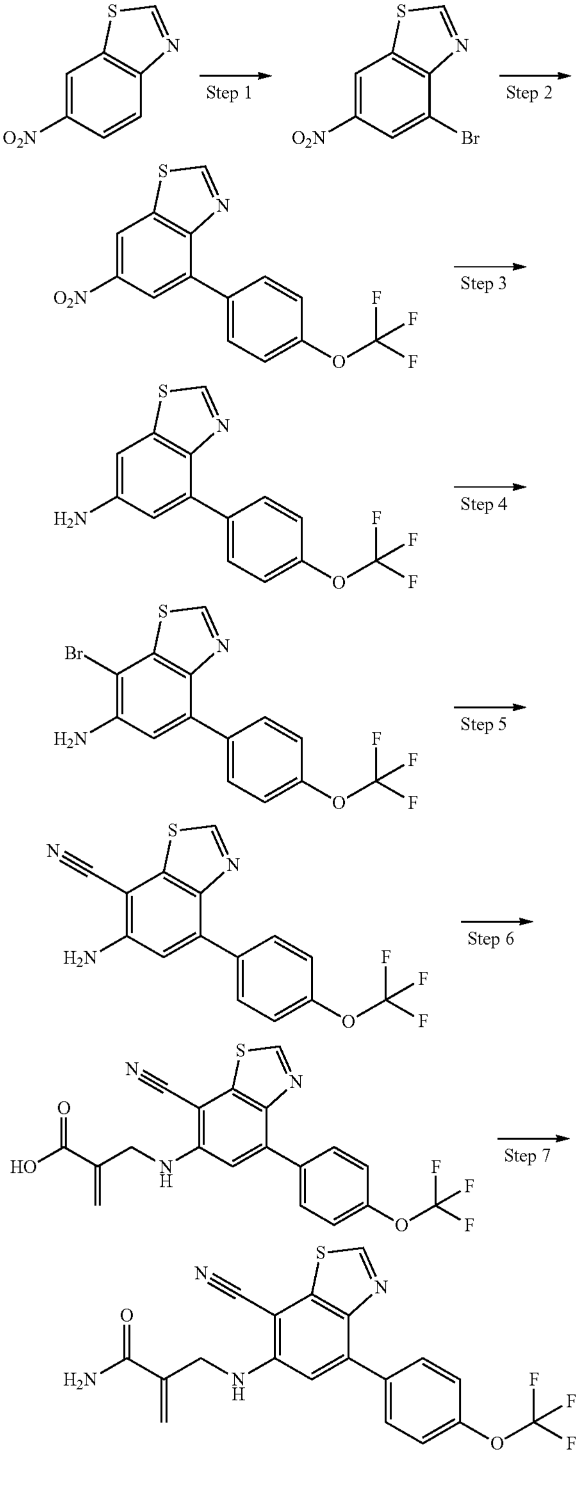

Step 1: Preparation of 4-Bromo-6-nitrobenzo[d]thiazole

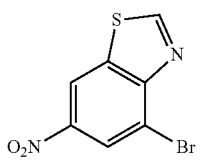

To a solution of 6-nitrobenzo[d]thiazole (10.0 g, 55.5 mmol) in $H_2SO_4$ (50 mL) was added NBS (10.87 g, 61.05 mmol) at 0° C. Then the mixture was stirred at 60° C. for 5 hours. The mixture was quenched with water (500 mL) and extracted with ethyl acetate (1 L×3). The organic layer was washed with water (500 mL×3), dried over $Na_2SO_4$, filtered and concentrated. The residue was washed by ethyl acetate (50 mL) to afford the title compound (10.0 g, 69%) as a white solid. $^1H$ NMR (400 MHz, $CDCl_3$): δ 9.37 (s, 1H), 8.89 (d, J=2.0 Hz, 1H), 8.64 (d, J=2.0 Hz, 1H).

Step 2: Preparation of 6-Nitro-4-(4-(trifluoromethoxy)phenyl)benzo[d]thiazole

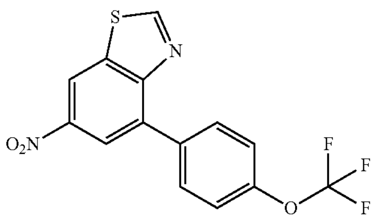 [SMILES: O=[N+]([O-])c1cc(-c2ccc(OC(F)(F)F)cc2)c2ncsc2c1]

A mixture of 4-bromo-6-nitrobenzo[d]thiazole (4.90 g, 18.91 mmol), (4-(trifluoromethoxy)phenyl)boronic acid (4.67 g, 22.7 mmol), $Pd(dppf)Cl_2$ (1.38 g, 1.89 mmol), $K_2CO_3$ (7.84 g, 56.74 mmol) in 1,4-dioxane (50 mL) and water (5 mL) was stirred at 100° C. for 2 hours under a nitrogen atmosphere. The reaction mixture was concentrated under vacuum. The residue was purified by flash chromatography on silica gel (0-25% ethyl acetate in petroleum ether) to afford the title compound (5.0 g, 78%) as a yellow solid. $^1H$ NMR (400 MHz, $CDCl_3$): δ 9.32 (s, 1H), 8.92 (d, J=2.4 Hz, 1H), 8.48 (d, J=2.4 Hz, 1H), 7.94-7.13 (m, 2H), 7.41 (d, J=8.0 Hz, 2H); LCMS (ESI): m/z 340.9 $(M+H)^+$.

Step 3: Preparation of 4-(4-(Trifluoromethoxy)phenyl)benzo[d]thiazol-6-amine

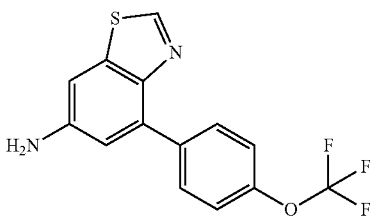

A solution of 6-nitro-4-(4-(trifluoromethoxy)phenyl)benzo[d]thiazole (5.0 g, 14.69 mmol) and 10% Pd/C (1.56 g, 14.69 mmol) in ethanol (100 mL) was stirred at room temperature for 16 hours under $H_2$ (15 psi). The reaction mixture was filtered and concentrated to afford the title compound (4.2 g, 92%) as a yellow solid. $^1H$ NMR (400 MHz, $CDCl_3$): δ 8.75 (s, 1H), 7.84-7.81 (m, 2H), 7.34 (d, J=8.0 Hz, 2H), 7.20 (d, J=2.4 Hz, 1H), 6.93 (d, J=2.4 Hz, 1H), 3.93 (s, 2H); LCMS (ESI): m/z 310.9 $(M+H)^+$.

Step 4: Preparation of 7-Bromo-4-(4-(trifluoromethoxy)phenyl)benzo[d]thiazol-6-amine

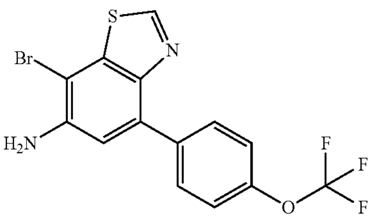 [SMILES: Nc1cc(-c2ccc(OC(F)(F)F)cc2)c2ncsc2c1Br]

A solution of 4-(4-(trifluoromethoxy)phenyl)benzo[d]thiazol-6-amine (4.2 g, 13.54 mmol) and NBS (2.41 g, 13.54 mmol) in DCM (50 mL) was stirred at 0° C. for 1 hour. The mixture was diluted with $H_2O$ (100 mL), and extracted with DCM (100 mL×2), dried over $Na_2SO_4$, filtered and concentrated. The residue was purified by flash chromatography on silica gel (0-25% ethyl acetate in petroleum ether) to afford the title compound (3.8 g, 72%) as a yellow solid. $^1H$ NMR (400 MHz, $CDCl_3$): δ 8.79 (s, 1H), 7.79 (d, J=8.4 Hz, 2H), 7.34 (d, J=8.4 Hz, 2H), 7.00 (s, 1H), 4.31 (s, 2H); LCMS (ESI): m/z 389.0 $(M+H)^+$.

Step 5: Preparation of 6-Amino-4-(4-(trifluoromethoxy)phenyl)benzo[d]thiazole-7-carbonitrile

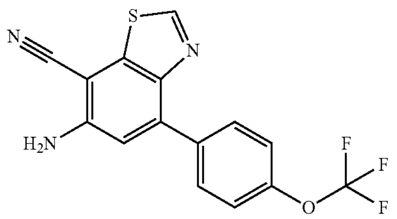 [SMILES: N#Cc1c(N)cc(-c2ccc(OC(F)(F)F)cc2)c2ncsc12]

A mixture of 7-bromo-4-(4-(trifluoromethoxy)phenyl)benzo[d]thiazol-6-amine (2.0 g, 5.14 mmol), t-BuXphos Pd $G_3$ (408 mg, 0.51 mmol) and $Zn(CN)_2$ (3.02 g, 25.69 mmol) in DMA (20 mL) was stirred at 135° C. for 16 hours under a nitrogen atmosphere. The reaction solution was quenched with water (200 mL), extracted with ethyl acetate (200 mL), dried over $Na_2SO_4$, filtered and concentrated. The residue was purified by flash chromatography on silica gel (0-25% ethyl acetate in petroleum ether) to afford the title compound (1.3 g, 75%) as a yellow solid. $^1H$ NMR (400 MHz, $CDCl_3$): δ 8.82 (s, 1H), 7.85-7.78 (m, 2H), 7.36 (d, J=8.4 Hz, 2H), 6.93 (s, 1H), 4.74 (s, 2H); LCMS (ESI): m/z 335.9 $(M+H)^+$.

Step 6: Preparation of 2-(((7-Cyano-4-(4-(trifluoromethoxy)phenyl)benzo[d]thiazol-6-yl)amino)methyl)acrylic acid

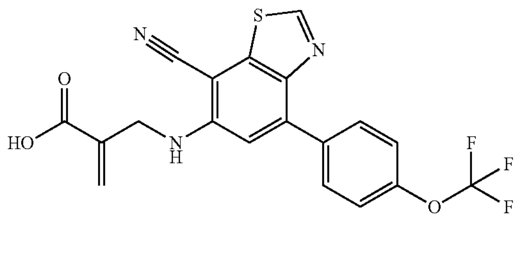 [SMILES: C=C(CNc1cc(-c2ccc(OC(F)(F)F)cc2)c2ncsc2c1C#N)C(=O)O]

A solution of 6-amino-4-(4-(trifluoromethoxy)phenyl)benzo[d]thiazole-7-carbonitrile (500 mg, 1.49 mmol), 2-(bromomethyl)acrylic acid (246 mg, 1.49 mmol) in DMF (5 mL) was stirred at 100° C. for 16 hours. The reaction solution was quenched with water (200 mL), dissolved in ethyl acetate (200 mL), dried over $MgSO_4$, filtered and concentrated. The residue was purified by flash chromatography on silica gel (0-50% ethyl acetate in petroleum ether) to afford the title compound (400 mg, 64%) as a white solid. LCMS (ESI): m/z 420.2 $(M+H)^+$.

Step 7: Preparation of 2-(((7-Cyano-4-(4-(trifluoromethoxy)phenyl)benzo[d]thiazol-6-yl)amino)methyl)acrylamide

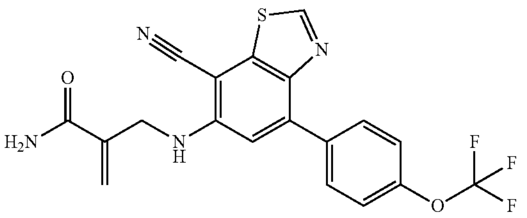 [SMILES: C=C(CNc1cc(-c2ccc(OC(F)(F)F)cc2)c2ncsc2c1C#N)C(N)=O]

To a mixture of 2-(((7-cyano-4-(4-(trifluoromethoxy)phenyl)benzo[d]thiazol-6-yl)amino)methyl)acrylic acid (100 mg, 0.24 mmol), $NH_4Cl$ (63.77 mg, 1.19 mmol) and DIPEA (215 mg, 1.67 mmol) in DMF (3 mL) was added HATU (136 mg, 0.36 mmol) at room temperature, the mixture was stirred at room temperature for 16 hours. The reaction solution was purified by prep-HPLC (Welch Xtimate C18 150*25 mm*5 um, water (0.2% FA)-ACN, 47-77%) to afford the title compound (51.08 mg, 51%) as a white solid. $^1H$ NMR (400 MHz, DMSO-$d_6$): δ 9.13 (s, 1H), 7.93 (d, J=8.0 Hz, 2H), 7.65 (s, 1H), 7.50 (d, J=8.0 Hz, 2H), 7.18 (s, 1H), 7.08 (t, J=5.6 Hz, 1H), 6.93 (s, 1H), 5.83 (s, 1H), 5.47 (s, 1H), 4.21 (d, J=5.6 Hz, 2H); LCMS (ESI): m/z 419.0 $(M+H)^+$.

Example 49

Preparation of 2-(((7-Cyano-4-(4-(trifluoromethoxy)phenyl)benzo[d]thiazol-6-yl)amino)methyl)-N-hydroxyacrylamide The general reaction scheme was as follows:

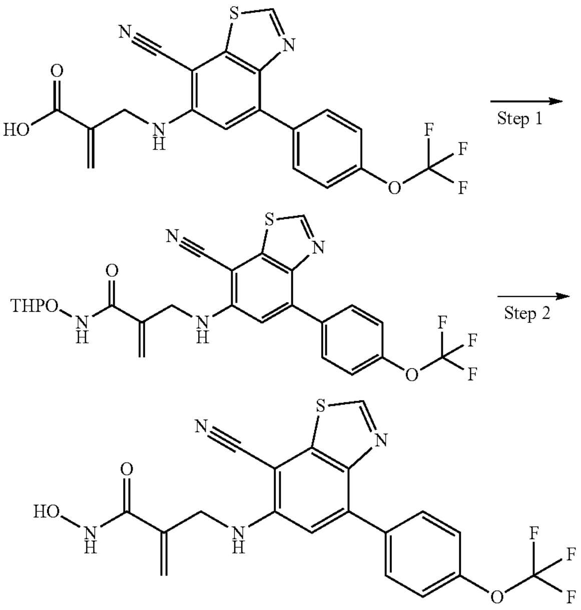

Step 1: Preparation of 2-(((7-Cyano-4-(4-(trifluoromethoxy)phenyl)benzo[d]thiazol-6-yl)amino)methyl)-N-((tetrahydro-2H-pyran-2-yl)oxy)acrylamide

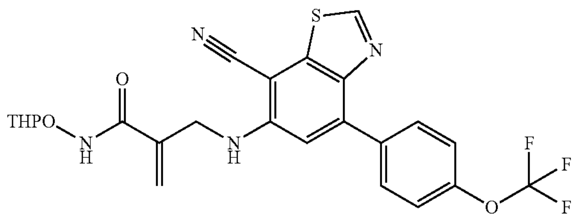

To the mixture of 2-(((7-cyano-4-(4-(trifluoromethoxy)phenyl)benzo[d]thiazol-6-yl)amino)methyl)acrylic acid (300 mg, 0.72 mmol), TEA (0.39 mL, 2.86 mmol), O-(tetrahydro-2H-pyran-2-yl)hydroxylamine (251 mg, 2.15 mmol) in DMF (3 mL) was added BOP (633 mg, 1.43 mmol). Then the resulting mixture was stirred at room temperature for 16 hours. The reaction mixture was quenched with water (200 mL), extracted with ethyl acetate (200 mL). The organic layer was dried over $Na_2SO_4$, filtered and concentrated. The residue was purified by flash chromatography on silica gel (0-30% ethyl acetate in petroleum ether) to afford the title compound (100 mg, 27%) as light yellow solid. LCMS (ESI): m/z 519.1 $(M+H)^+$.

Step 2: Preparation of 2-(((7-Cyano-4-(4-(trifluoromethoxy)phenyl)benzo[d]thiazol-6-yl)amino)methyl)-N-hydroxyacrylamide

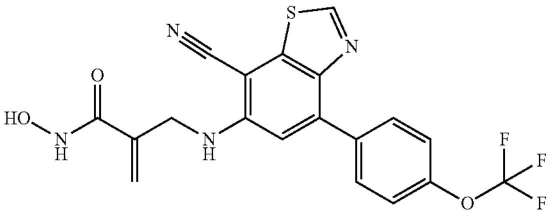 [SMILES: C=C(CNc1cc(-c2ccc(OC(F)(F)F)cc2)c2ncsc2c1C#N)C(=O)NO]

To the mixture of 2-(((7-cyano-4-(4-(trifluoromethoxy)phenyl)benzo[d]thiazol-6-yl)amino)methyl)-N-((tetrahydro-2H-pyran-2-yl)oxy)acrylamide (100 mg, 0.19 mmol) in methyl alcohol (5 mL) was added aq. HCl (2 mL, 2 N). The resulting mixture was stirred at room temperature for 2 hours. The reaction mixture was purified by Prep-HPLC (Welch Xtimate C18 150*25 mm*5 um, water (0.2% FA)-ACN, 45%-75%) to afford the title compound (48.9 mg, 56%) as a white solid. $^1H$ NMR (400 MHz, DMSO-$d_6$): δ 10.91 (s, 1H), 9.15 (s, 1H), 8.97 (s, 1H), 7.94 (d, J=8.4 Hz, 2H), 7.51 (d, J=8.4 Hz, 2H), 7.15 (t, J=5.6 Hz, 1H), 6.94 (s, 1H), 5.64 (s, 1H), 5.41 (s, 1H), 4.21 (d, J=5.6 Hz, 2H); LCMS (ESI): m/z 435.0 $(M+H)^+$.

Example 50

Preparation of 2-(((7-Cyano-4-(4-(pentafluoro-16-sulfanyl)phenyl)benzo[d]thiazol-6-yl)amino)methyl)-N-hydroxyacrylamide The general reaction scheme was as follows:

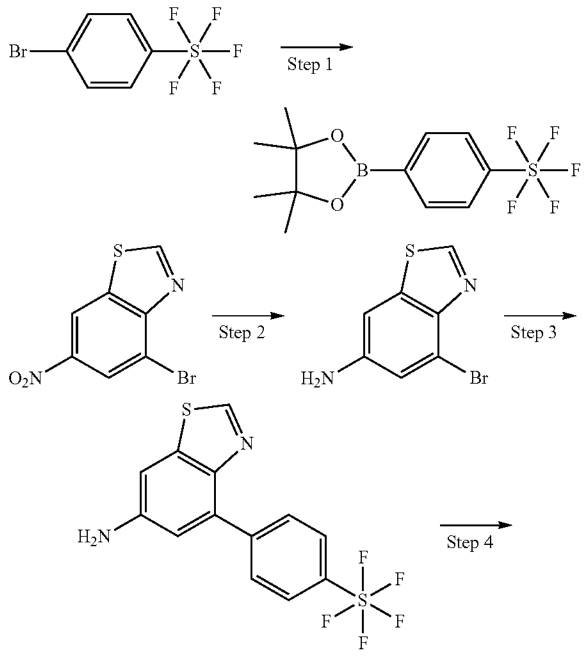

-continued

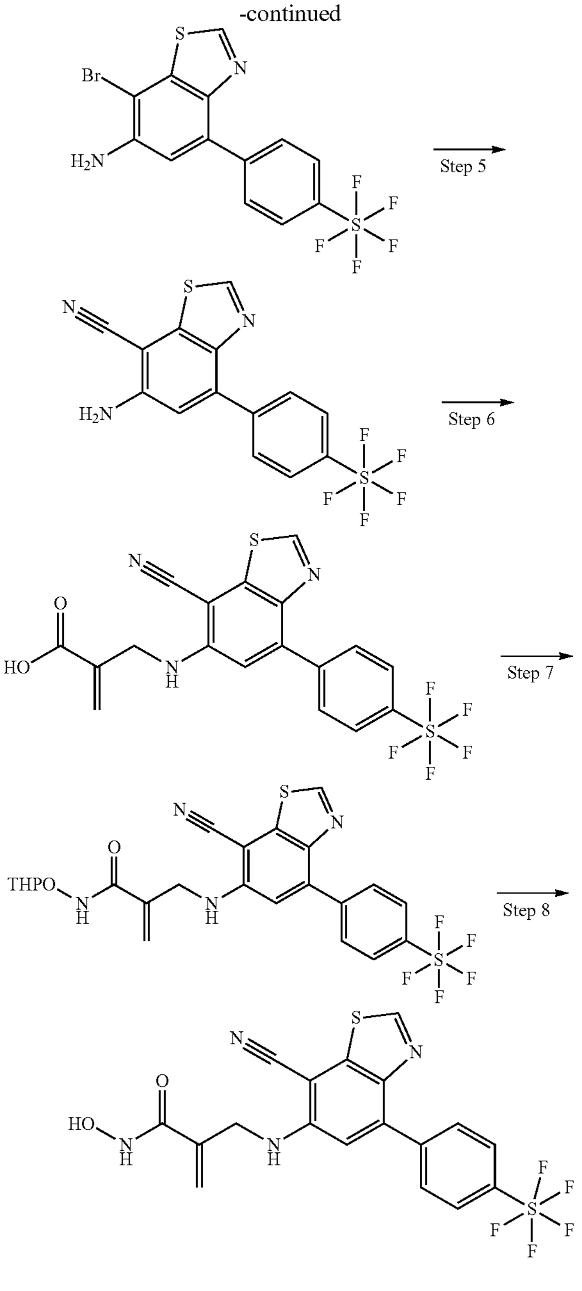

Step 1: Preparation of 4,4,5,5-Tetramethyl-2-(4-(pentafluoro-16-sulfanyl)phenyl)-1,3,2-dioxaborolane

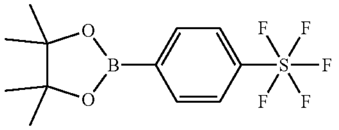 [SMILES: CC1(C)OB(c2ccc(S(F)(F)(F)(F)F)cc2)OC1(C)C]

A mixture of 1-bromo-4-(pentafluorosulfanyl)benzene (1.0 g, 3.53 mmol), 4,4,4',4',5,5,5',5'-octamethyl-2,2'-bi(1,3,2-dioxaborolane) (897 mg, 3.53 mmol), Pd(dppf)$Cl_2$ (256 mg, 0.35 mmol) and KOAc (1.04 g, 10.6 mmol) in 1,4-dioxane (20 mL) was stirred at 100° C. for 16 hours under a nitrogen atmosphere. The mixture was quenched with water (30 mL), extracted with ethyl acetate (100 mL×2) and washed with brine (100 mL×3). The organic layers were dried over anhydrous sodium sulfate and concentrated. The residue was purified by flash chromatography on silica gel (0-20% ethyl acetate in petroleum ether) to afford the title compound (820 mg, 70%) as a white solid. $^1$H NMR (400 MHz, $CDCl_3$): δ 7.91-7.87 (m, 2H), 7.76-7.68 (m, 2H), 1.36 (s, 12H).

Step 2: Preparation of 4-Bromobenzo[d]thiazol-6-amine

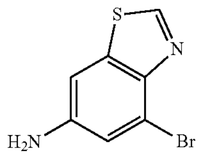

To a mixture of 4-bromo-6-nitrobenzo[d]thiazole (1.0 g, 3.86 mmol) in ethanol (10 mL) was added iron (1.08 g, 19.3 mmol) and $NH_4Cl$ (0.61 g, 11.58 mmol). The mixture was stirred at 60° C. for 2 hours. The reaction mixture was filtered and concentrated. The mixture was added water (50 mL) and extracted with ethyl acetate (100 mL) and washed with brine (30 mL×3). The organic layers were dried over anhydrous sodium sulfate and concentrated under reduced pressure to afford the title compound (720 mg, 81%) as a yellow solid. $^1$H NMR (400 MHz, $CDCl_3$): δ 8.77 (s, 1H), 7.13-7.10 (m, 2H), 3.89 (s, 2H); LCMS (ESI): m/z 228.9 $(M+H)^+$.

Step 3: Preparation of 4-(4-(Pentafluoro-16-sulfanyl)phenyl)benzo[d]thiazol-6-amine

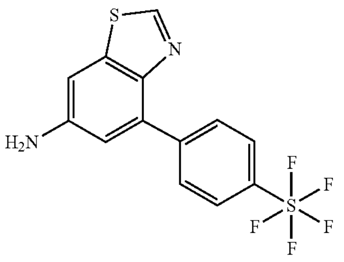 [SMILES: Nc1cc(-c2ccc(S(F)(F)(F)(F)F)cc2)c2ncsc2c1]

A mixture of 4-bromobenzo[d]thiazol-6-amine (400 mg, 1.75 mmol), 4,4,5,5-tetramethyl-2-(4-(pentafluoro-16-sulfanyl)phenyl)-1,3,2-dioxaborolane (634 mg, 1.92 mmol), $Na_2CO_3$ (555 mg, 5.24 mmol), Pd(dppf)$Cl_2$ (128 mg, 0.17 mmol) in 1,4-dioxane (5 mL) and water (1 mL) was stirred at 100° C. for 4 hours under a nitrogen atmosphere. The mixture was extracted with ethyl acetate (250 mL) and washed with water (200 mL×3). The organic was dried over $Na_2SO_4$ and concentrated. The residue was purified by flash chromatography on silica gel (0-15% ethyl acetate in petroleum ether) to afford the title compound (580 mg, 94%) as a yellow solid. $^1$H NMR (400 MHz, $CDCl_3$): δ 8.76 (s, 1H), 7.93-7.85 (m, 4H), 7.23 (d, J=2.0 Hz, 1H), 6.93 (d, J=2.0 Hz, 1H), 3.98 (s, 2H).

Step 4: Preparation of 7-Bromo-4-(4-(pentafluoro-16-sulfanyl)phenyl)benzo[d]thiazol-6-amine

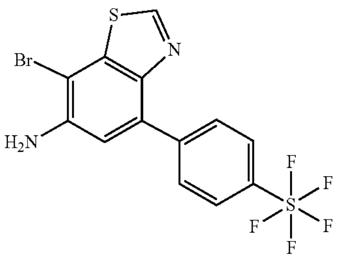 [SMILES: Nc1cc(-c2ccc(S(F)(F)(F)(F)F)cc2)c2ncsc2c1Br]

To a solution of 4-(4-(pentafluoro-16-sulfanyl)phenyl)benzo[d]thiazol-6-amine (580 mg, 1.65 mmol) in DCM (10 mL) was added NBS (293 mg, 1.65 mmol) at 0° C. Then the reaction was stirred at 0° C. for 1 hour. The mixture was diluted with $H_2O$ (100 mL), extracted with DCM (100 mL×2), dried over $Na_2SO_4$, filtered and concentrated. The residue was purified by flash chromatography on silica gel (0-15% ethyl acetate in petroleum ether) to afford the title compound (550 mg, 78%) as a yellow solid. $^1$H NMR (400 MHz, $CDCl_3$): δ 8.80 (s, 1H), 7.89-7.84 (m, 4H), 7.02 (s, 1H), 4.35 (s, 2H).

Step 5: Preparation of 6-Amino-4-(4-(pentafluoro-16-sulfanyl)phenyl)benzo[d]thiazole-7-carbonitrile

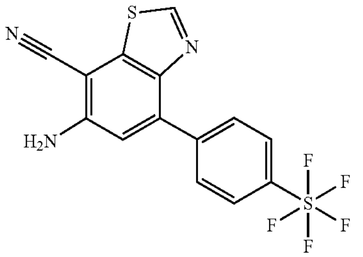 [SMILES: N#Cc1c(N)cc(-c2ccc(S(F)(F)(F)(F)F)cc2)c2ncsc12]

A mixture of 7-bromo-4-(4-(pentafluoro-16-sulfanyl)phenyl)benzo[d]thiazol-6-amine (500 mg, 1.16 mmol), t-BuXphos Pd $G_3$ (92 mg, 0.12 mmol) and $Zn(CN)_2$ (740 mg, 6.3 mmol) in DMF (10 mL) was stirred at 135° C. for 16 hours. The reaction solution was quenched with water (200 mL). The mixture was extracted with ethyl acetate (250 mL) and washed with water (200 mL×3). The organic layer was dried over $Na_2SO_4$ and concentrated. The residue was purified by flash chromatography on silica gel (0-20% ethyl acetate in petroleum ether) to afford the title compound (350 mg, 80%) as a yellow solid. $^1$H NMR (400 MHz, $CDCl_3$): δ 8.83 (s, 1H), 7.93-7.84 (m, 4H), 6.95 (s, 1H), 4.78 (s, 2H); LCMS (ESI): m/z 378.0 $(M+H)^+$.

Step 6: Preparation of 2-(((7-Cyano-4-(4-(pentafluoro-16-sulfanyl)phenyl)benzo[d]thiazol-6-yl)amino)methyl)acrylic acid

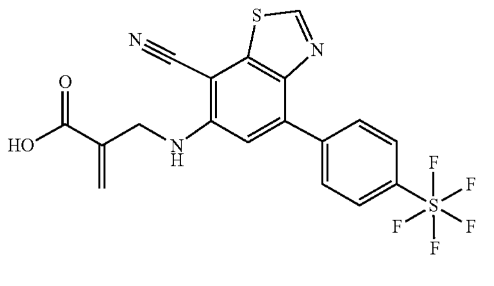 [SMILES: C=C(CNc1cc(-c2ccc(S(F)(F)(F)(F)F)cc2)c2ncsc2c1C#N)C(=O)O]

A solution of 6-amino-4-(4-(pentafluoro-16-sulfanyl)phenyl)benzo[d]thiazole-7-carbonitrile (300 mg, 0.79 mmol), 2-(bromomethyl)acrylic acid (131 mg, 0.79 mmol) in DMF (5 mL) was stirred at 100° C. for 16 hours. The reaction solution was quenched with water (200 mL), dissolved in ethyl acetate (200 mL), dried over $MgSO_4$, filtered and concentrated. The residue was purified by flash chromatography on silica gel (0-50% ethyl acetate in petroleum ether) to afford the title compound (200 mg, 55%) as a white solid. LCMS (ESI): m/z 462.1 $(M+H)^+$.

Step 7: Preparation of 2-(((7-Cyano-4-(4-(pentafluoro-16-sulfanyl)phenyl)benzo[d]thiazol-6-yl)amino)methyl)-N-((tetrahydro-2H-pyran-2-yl)oxy)acrylamide

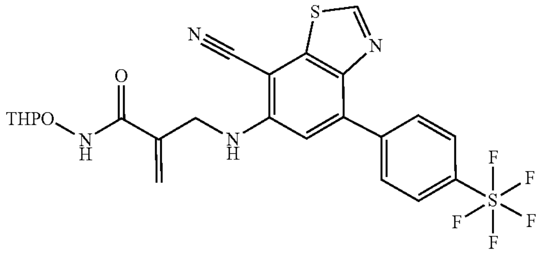

To the mixture of 2-(((7-cyano-4-(4-(pentafluoro-16-sulfanyl)phenyl)benzo[d]thiazol-6-yl)amino)methyl)acrylic acid (200 mg, 0.43 mmol), TEA (0.24 mL, 1.73 mmol), O-(tetrahydro-2H-pyran-2-yl)hydroxylamine (152 mg, 1.3 mmol) in DMF (3 mL) was added BOP (383 mg, 0.87 mmol). The resulting mixture was stirred at room temperature for 16 hours. The reaction mixture was quenched with water (100 mL), extracted with ethyl acetate (100 mL). The organic layer was dried over $Na_2SO_4$, filtered and concentrated. The residue was purified by flash chromatography on silica gel (0-30% ethyl acetate in petroleum ether) to afford the title compound (100 mg, 41%) as a light yellow solid. LCMS (ESI): m/z 583.1 $(M+Na)^+$.

Step 8: Preparation of 2-(((7-Cyano-4-(4-(pentafluoro-16-sulfanyl)phenyl)benzo[d]thiazol-6-yl)amino)methyl)-N-hydroxyacrylamide

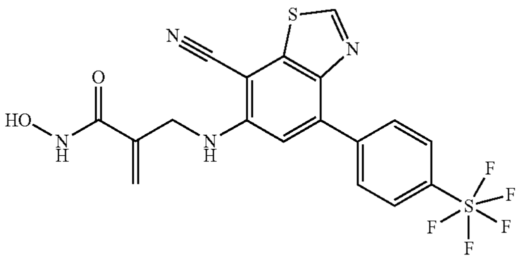 [SMILES: C=C(CNc1cc(-c2ccc(S(F)(F)(F)(F)F)cc2)c2ncsc2c1C#N)C(=O)NO]

To the mixture of 2-(((7-cyano-4-(4-(pentafluoro-16-sulfanyl)phenyl)benzo[d]thiazol-6-yl)amino)methyl)-N-((tetrahydro-2H-pyran-2-yl)oxy)acrylamide (100 mg, 0.18 mmol) in methyl alcohol (5 mL) was added aq. HCl (2 mL, 2 N). The resulting mixture was stirred at room temperature for 2 hours. The reaction mixture was quenched with water (20 mL), extracted with ethyl acetate (100 mL). The organic layer was dried over $Na_2SO_4$, filtered and concentrated. The residue was purified by prep-TLC (ethyl acetate:petroleum ether:EtOH=3:4:1) to afford the title compound (33.99 mg, 38%) as a white solid. $^1H$ NMR (400 MHz, DMSO-$d_6$): δ 10.90 (s, 1H), 9.17 (s, 1H), 8.96 (s, 1H), 8.09-7.95 (m, 4H), 7.20 (t, J=5.6 Hz, 1H), 7.00 (s, 1H), 5.64 (s, 1H), 5.42 (s, 1H), 4.21 (d, J=5.6 Hz, 2H); LCMS (ESI): m/z 477.0 $(M+H)^+$.

Example 51

His-tagged TEAD proteins are pre-incubated with TEAD project compounds for 30 minutes or 4 hours at room temperature. Biotinylated lipid pocket probes are then added to the TEAD/Compound mixture and incubated for 60 minutes at room temperature. The lipid pocket probe competes with the test compound for the TEAD lipid pocket until equilibrium is reached. After 60 minutes, Europium labelled anti-His (Perkin Elmer #AD0110) and XL665 labelled streptavidin (CIS Bio 610SAXAC) are added to the TEAD/test compound/lipid pocket mixture and incubated for 30 minutes or 4 hours. TR-FRET values are then measured using an EnVision multi-label plate reader (Perkin Elmer Cat #2104-0010A.) If the lipid pocket probe binds to TEAD as expected, a TR-FRET signal results from the proximity of anti-His Eu and XL665. If a TEAD lipid pocket binder such as binds and displaces the lipid pocket probe, the disruption of the TEAD:probe interaction results in a decrease in TR-FRET signal. The potency of compounds as TEAD lipid pocket binders is determined by $IC_{50}$ value generated using a non-linear 4 parameter curve fit. This assay format enables more sensitive determinations of lipid pocket affinity than the aforementioned TEAD lipid pocket FP assay due to the decreased concentration of TEAD protein required for the TR-FRET assay format.

The $IC_{50}$ data for selected compounds are presented in Table 2 (30 mins) and Table 3 (4 hours) below. Note that the “Compound Number” in Table 2 and Table 3 corresponds to the “Compound Number” in Table 1.

TABLE 2

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 1 | 0.22 | 0.22 | 8.40 | 0.04 |
| 2 | 0.59 | 0.08 | 18.00 | 0.03 |
| 3 | 0.02 | 0.06 | 2.88 | 0.02 |
| 4 | 0.32 | 0.10 | 10.00 | 0.08 |
| 5 | 1.60 | 2.00 | >50.00 | 1.30 |
| 6 | 1.10 | 3.50 | >50.00 | 0.50 |
| 7 | 0.54 | 0.23 | 14.00 | 0.16 |
| 8 | 0.07 | 0.04 | 0.24 | 0.02 |
| 9 | 0.28 | 0.11 | 2.40 | 0.12 |
| 10 | 6.30 | 2.70 | >50.00 | 1.30 |
| 11 | 0.18 | 0.08 | 0.13 | 0.04 |
| 12 | 1.50 | 0.93 | 47.00 | 0.47 |
| 13 | 0.78 | 0.22 | 11.00 | 0.18 |
| 14 | 0.52 | 0.12 | 2.40 | 0.42 |
| 15 | 0.05 | 0.53 | 3.40 | 0.11 |
| Enantiomer C from Example 16 | 0.02 | 0.04 | 3.00 | 0.01 |
| Enantiomer D from Example 16 | 0.08 | 0.16 | 6.10 | 0.03 |
| 18 | 0.03 | 0.14 | 2.50 | 0.03 |
| 19 | 0.05 | 0.35 | 6.40 | 0.11 |
| 20 | 0.20 | 0.07 | 3.80 | 0.02 |
| 21 | 0.06 | 0.07 | 4.00 | 0.02 |
| 22 | 0.09 | 0.10 | 15.00 | 0.05 |
| 24 | 0.16 | 0.74 | 20.00 | 0.37 |
| 25 | 0.58 | 0.27 | 1.25 | 0.14 |
| 26 | 4.80 | 1.70 | 0.97 | 1.50 |
| 28 | 0.69 | 0.35 | 16.00 | 0.32 |
| 30 | 0.05 | 0.10 | 5.90 | 0.03 |
| 34 | 1.80 | 0.97 | >50.00 | 0.33 |
| 42 | 0.37 | 0.14 | >50.00 | 0.26 |
| 47 | 2.20 | 2.70 | >50.00 | 1.50 |
| 50 | 0.74 | 0.10 | 44.5 | 0.59 |

TABLE 3

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 27 | 0.31 | 0.11 | >50.00 | 0.17 |
| 29 | 0.06 | 0.01 | 0.43 | 0.04 |
| 31 | >50.00 | 0.86 | >50.00 | 36.00 |
| 32 | 0.01 | 0.04 | 0.43 | 0.01 |
| 33 | 0.18 | 0.06 | 1.40 | 0.08 |
| 35 | 0.16 | 0.03 | 1.70 | 0.25 |
| 36 | >50.00 | 0.71 | >50.00 | >50.00 |
| 37 | 0.05 | 0.01 | 0.42 | 0.05 |
| 38 | 0.09 | 0.03 | 0.71 | 0.08 |
| 39 | 0.04 | 0.01 | 0.40 | 0.06 |
| 40 | 0.02 | 0.04 | 0.68 | 0.02 |
| 41 | 0.08 | 0.01 | 0.66 | 0.04 |
| 43 | 0.40 | 1.70 | 18.00 | 0.52 |
| 44 | 0.11 | 0.04 | 1.20 | 0.14 |
| 45 | 0.03 | 0.17 | 0.92 | 0.08 |
| 46 | 0.05 | 0.01 | 0.44 | 0.06 |
| 48 | 0.25 | 0.22 | 2.60 | 0.26 |
| 49 | 0.31 | 0.24 | 2.80 | 0.09 |
| 51 | 0.20 | 0.03 | 1.20 | 0.06 |

Example 52

Purified His-tagged TEAD protein (YAP Binding Domain, amino acids 217-447) is pre-incubated with Europium labelled anti-His antibody tracer (Perkin Elmer Cat #AD0110). Small molecule Inhibitors are then incubated with the TEAD-Eu protein complex for 30 minutes or 4 hours to allow for binding to TEAD protein. Biotinylated YAP peptide for TEAD-YAP assays (AA's 50-100) or biotinylated TAZ peptide for TEAD-TAZ assays (AA's 13-57) that has been pre-incubated with streptavidin-xl665 acceptor (CIS-Bio Cat #610SAXAC) or is added to the compound-TEAD mix. The TEAD-YAP-inhibitor mixture is then incubated for 60 minutes at room temperature. All reactions are carried out in a polystyrene plate. After 60 minutes, the plate is read on a plate reader using TR-FRET mode with wavelengths of 665 nm/615 nm. If YAP or TAZ binds to TEAD as expected, a TR-FRET signal results from the proximity of YAP or TAZ and TEAD after binding. If an inhibitor such as peptide 17 (Selleckchem Cat #S8164) interferes with YAP-TEAD or TAZ-TEAD binding, the disruption of the YAP or TAZ:TEAD interaction results in a decrease in TR-FRET signal. The potency of compounds as YAP:TEAD or TAZ:TEAD protein-protein interaction (PPi) inhibitors is determined by an $IC_{50}$ or $EC_{50}$ value generated using anon-linear four parameter curve fit. The extent to which representative examples of the disclosed compounds are able to inhibit interaction between TEAD1, TEAD2, TEAD3 or TEAD4 and YAP truncated from amino acids 50-100 or TAZ truncated from amino acids 13-57 as measured by Homogeneous Time Resolved Fluorescence (HTRF) to generate $EC_{50}$ and $C_{50}$ data.

The $EC_{50}$ data (30 mins) for selected compounds are presented in Table 4 below. Note that the "Compound Number" in Table 4 corresponds to the "Compound Number" in Table 1.

TABLE 4

| Compound Number | TEAD1 YAP50-100 HTRF combined $EC_{50}$ [uM] | TEAD2 YAP50-100 HTRF combined $EC_{50}$ [uM] | TEAD3 YAP50-100 HTRF combined $EC_{50}$ [uM] | TEAD4 YAP50-100 HTRF combined $EC_{50}$ [uM] |
|---|---|---|---|---|
| 1 | 0.17 | 0.10 | >50.00 | 0.05 |
| 2 | 0.46 | 0.07 | 18.00 | 0.09 |
| 3 | 0.02 | 0.03 | 6.22 | 0.03 |
| 4 | 0.23 | 0.05 | 13.00 | 0.16 |
| 5 | >50.00 | >50.00 | >50.00 | >50.00 |
| 6 | 0.97 | 2.80 | >50.00 | 1.00 |
| 7 | 0.51 | 0.18 | >50.00 | 0.43 |
| 8 | >50.00 | >50.00 | >50.00 | >50.00 |
| 9 | 0.19 | 0.05 | 2.20 | 0.28 |
| 10 | 5.70 | 2.10 | >50.00 | 2.10 |
| 11 | 0.32 | 0.13 | 0.20 | 0.08 |
| 12 | 0.78 | 0.30 | >50.00 | 0.75 |
| 13 | 0.33 | 0.04 | 22.00 | 0.18 |
| 14 | 0.28 | 0.07 | 3.40 | 0.89 |
| 15 | 0.04 | 0.38 | 11.00 | 0.25 |
| Enantiomer C from Example 16 | 0.01 | 0.02 | 5.90 | 0.01 |
| Enantiomer D from Example 16 | 0.04 | 0.07 | >50.00 | 0.10 |
| 18 | 0.02 | 0.09 | 7.80 | 0.06 |
| 19 | 0.04 | 0.19 | 15.00 | 0.23 |
| 20 | 0.15 | 0.04 | >50.00 | 0.04 |
| 21 | 0.04 | <0.01 | >50.00 | 0.03 |
| 22 | 0.06 | 0.06 | >50.00 | 0.10 |
| 24 | 0.08 | 0.26 | 15.00 | >50.00 |
| 25 | >50.00 | >50.00 | >50.00 | >50.00 |
| 28 | >50.00 | >50.00 | >50.00 | >50.00 |
| 30 | 0.03 | 0.04 | 8.20 | 0.04 |
| 34 | 1.00 | 0.58 | >50.00 | 0.70 |
| 42 | >50.00 | >50.00 | >50.00 | >50.00 |
| 47 | 1.90 | 1.90 | >50.00 | 3.40 |
| 50 | 0.53 | 0.08 | 17.00 | 2.00 |

The $IC_{50}$ data (4 hours) for selected compounds are presented in Table 5 below. Note that the "Compound Number" in Table 5 corresponds to the "Compound Number" in Table 1.

TABLE 5

| Compound Number | TEAD1 YAP50-100 HTRF combined $IC_{50}$ [uM] | TEAD2 YAP50-100 HTRF combined $IC_{50}$ [uM] | TEAD3 YAP50-100 HTRF combined $IC_{50}$ [uM] | TEAD4 YAP50-100 HTRF combined $IC_{50}$ [uM] |
|---|---|---|---|---|
| 27 | >50.00 | >50.00 | >50.00 | >50.00 |
| 29 | 0.06 | 0.01 | 0.85 | 0.10 |
| 31 | >50.00 | >50.00 | >50.00 | >50.00 |
| 32 | 0.01 | 0.01 | 1.00 | 0.01 |
| 33 | 0.22 | 0.05 | 3.20 | 0.20 |
| 35 | 0.41 | 0.06 | 3.30 | 0.59 |
| 36 | >50.00 | >50.00 | >50.00 | >50.00 |
| 37 | 0.06 | 0.01 | 0.71 | 0.14 |
| 38 | 0.10 | 0.05 | 0.97 | 0.16 |
| 39 | 0.07 | 0.01 | 0.70 | 0.18 |
| 40 | 0.02 | 0.02 | 1.90 | 0.03 |
| 41 | 0.14 | 0.01 | 1.40 | 0.08 |
| 43 | 0.28 | 0.35 | 8.50 | 0.49 |
| 44 | 0.24 | 0.07 | 1.60 | 0.32 |
| 45 | 0.03 | 0.08 | 1.40 | 0.12 |
| 46 | 0.05 | 0.01 | 0.52 | 0.24 |
| 48 | 0.35 | 0.29 | 5.20 | 0.58 |
| 49 | 0.30 | 0.13 | 36.00 | 0.20 |
| 51 | 0.21 | 0.03 | 1.70 | >50.00 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A method for treating cancer in a mammal, comprising administering a compound of formula (X), or a stereoisomer, tautomer, or pharmaceutically acceptable salt thereof, to the mammal, (X)

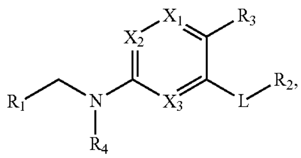

or a stereoisomer, tautomer, or pharmaceutically acceptable salt thereof, wherein:

$X_1$ is C—$R_5$, wherein the $R_5$ of $X_1$ is taken together with $R_3$, and the atoms to which they are attached, to form a 5-membered heterocyclyl or a 5-membered heteroaryl, wherein the 5-membered heterocyclyl or 5-membered heteroaryl is optionally substituted with one or more D;

$X_2$ is N or C—$R_5$, wherein each $R_5$ is independently selected from the group consisting of H, cyano, halo, $C(O)NH_2$, $N(R^e)(R^f)$, $C_{3-10}$cycloalkyl, $C_{1-6}$alkoxy, $C_{6-20}$aryl, $S(O)_2$—$C_{1-6}$alkyl, and $C_{1-6}$alkyl, wherein the $C_{1-6}$alkyl of $R_5$ is optionally substituted with hydroxyl or $N(R^e)(R^f)$;

$X_3$ is N or C—H;

$R_1$ is:

(i) a 3-5 membered saturated heterocyclyl comprising at least one annular oxygen atom, wherein the 3-5 membered saturated heterocyclyl is optionally substituted with one or more $C_{1-6}$alkyl, or (ii) $N(R^e)(R^f)$, or (iii)

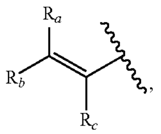

wherein $R_a$, $R_b$, and $R_c$ are each independently selected from the group consisting of H, halo, cyano, hydroxyl, $B(OH)_2$, C(O)—OH, C(O)—$N(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl, or (iv)

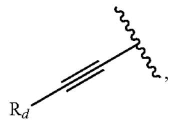

wherein $R_d$ is selected from the group consisting of H, halo, cyano, hydroxyl, $B(OH)_2$, C(O)—OH, C(O)—N$(R^e)(R^f)$, C(O)—$C_{1-6}$alkoxy, C(O)—$C_{1-6}$alkyl, $C_{1-6}$alkyl, $C_{3-10}$cycloalkyl, $C_{6-20}$aryl, 3-10 membered heterocyclyl, $C_{5-13}$spirocyclyl, and 5-20 membered heteroaryl, wherein the $C_{1-6}$alkyl is further optionally substituted with hydroxyl;

L is absent or is selected from the group consisting of —O—, *—$CH_2$—O—**, *—O—$CH_2$—, —CH═CH—, and —C≡C—, wherein  indicates the attachment point to the $R_2$ moiety and * indicates the attachment point to the remainder of the molecule;

$R_2$ is $C_{1-12}$alkyl, $C_{3-10}$cycloalkyl, 3-10 membered heterocyclyl, $C_{5-13}$spirocyclyl, $C_{6-20}$aryl, or 5-20 membered heteroaryl, wherein the $C_{1-12}$alkyl, $C_{3-10}$cycloalkyl, 3-10 membered saturated heterocyclyl, $C_{5-13}$spirocyclyl, $C_{6-20}$aryl, or 5-20 membered heteroaryl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$, provided that, when $R_2$ is $C_{1-12}$alkyl, wherein the $C_{1-12}$alkyl of $R_2$ is independently optionally substituted with one or more substituents selected from the group consisting of cyano, halo, $C_{1-6}$alkyl, $C_{1-6}$haloalkyl, $C_{3-10}$cycloalkyl, $NO_2$, $N(R^e)(R^f)$, $O(R^e)$, and $S(R^g)_5$ then L is —CH═CH— or —C≡C—;

$R_4$ is H or $C_{1-6}$alkyl, wherein the $C_{1-6}$alkyl is optionally substituted with hydroxyl;

$R^e$ and $R^f$ are, independently of each other and independently at each occurrence, selected from the group consisting of H, cyano, hydroxyl, $C_{1-6}$alkyl, $C_{2-6}$alkenyl, $C_{2-6}$alkynyl, $C_{1-6}$alkoxy, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl, wherein the $C_{1-6}$alkyl, $C_{2-6}$alkenyl, $C_{2-6}$alkynyl, $C_{3-10}$cycloalkyl, $C_{1-6}$alkyl-$C_{3-10}$cycloalkyl, 3-10 membered heterocyclyl, $C_{5-13}$spirocyclyl, $C_{6-20}$aryl, and 3-20 membered heteroaryl of $R^e$ and $R^f$ are each independently optionally substituted with one or more substituents selected from the group consisting of $C_{1-6}$alkyl, $C_{1-6}$haloalkyl, $C_{1-6}$alkoxy, oxo, cyano, halo, $NO_2$, and hydroxyl; and $R^g$ is halo, wherein the cancer is selected from: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

2. The method of claim 1, or a stereoisomer, tautomer, or pharmaceutically acceptable salt thereof, wherein $X_2$ is C—$R_5$ and $X_3$ is C—H.

3. The method of claim 1, or a stereoisomer, tautomer, or pharmaceutically acceptable salt thereof, wherein the compound is of formula (IA):

(IA)

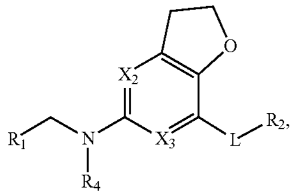

or a stereoisomer, tautomer, or pharmaceutically acceptable salt thereof.

4. The method of claim 3, or a stereoisomer, tautomer, or pharmaceutically acceptable salt thereof, wherein the compound of formula (IA) is a compound of formula (IA-1):

(IA-1)

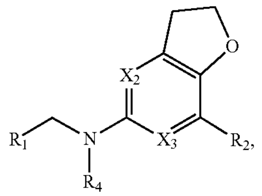

or a stereoisomer, tautomer, or pharmaceutically acceptable salt thereof.

5. The method of claim 3, or a stereoisomer, tautomer, or pharmaceutically acceptable salt thereof, wherein $X_2$ is C—$R_5$, wherein the $R_5$ of $X_2$ is H, cyano, halo, $C(O)NH_2$, $S(O)_2$—$C_{1-6}$alkyl, or $C_{1-6}$alkyl, wherein the $C_{1-6}$alkyl is optionally substituted with one or more hydroxyl.

6. The method of claim 5, or a stereoisomer, tautomer, or pharmaceutically acceptable salt thereof, wherein the $R_5$ of $X_2$ is cyano.

7. The method of claim 3, or a stereoisomer, tautomer, or pharmaceutically acceptable salt thereof, wherein $R_2$ is $C_{3-10}$cycloalkyl or $C_{6-20}$aryl, wherein the $C_{3-10}$cycloalkyl or $C_{6-20}$aryl of $R_2$ is independently optionally substituted with one or more $O(R^e)$, $S(R^g)_5$, or $C_{1-6}$alkyl, wherein the $C_{1-6}$alkyl is further optionally substituted with one or more halo.

8. The method of claim 3, or a stereoisomer, tautomer, or pharmaceutically acceptable salt thereof, wherein $R_2$ is $C_{6-20}$aryl, wherein the $C_{6-20}$aryl of $R_2$ is independently optionally substituted with one or more $C_{1-6}$alkyl.

9. The method of claim 3, or a stereoisomer, tautomer, or pharmaceutically acceptable salt thereof, wherein the compound has the structure of formula (IB):

(IB)

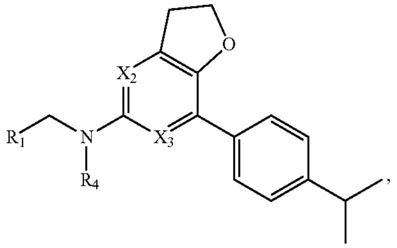

or a stereoisomer, tautomer, or pharmaceutically acceptable salt thereof.

10. The method of claim 1, or a stereoisomer, tautomer, or pharmaceutically acceptable salt thereof, wherein $R_1$ is

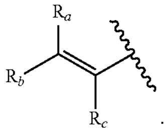

11. The method of claim 10, or a stereoisomer, tautomer, or pharmaceutically acceptable salt thereof, wherein at least two of $R_a$, $R_b$, and $R_c$ are H.

12. The method of claim 10, or a stereoisomer, tautomer, or pharmaceutically acceptable salt thereof, wherein exactly two of $R_a$, $R_b$, and $R_c$ are H, and exactly one of $R_a$, $R_b$, and $R_c$ is $B(OH)_2$, C(O)—OH, $C(O)—N(R^e)(R^f)$, C(O)—$C_{1-6}$ alkoxy, or C(O)—$C_{1-6}$alkyl.

13. The method of claim 12, or a stereoisomer, tautomer, or pharmaceutically acceptable salt thereof, wherein the $R^e$ and $R^f$ of $C(O)—N(R^e)(R^f)$ are each independently H, $C_{1-6}$alkyl, or hydroxyl.

14. The method of claim 1, or a stereoisomer, tautomer, or pharmaceutically acceptable salt thereof, wherein $R_4$ is H.

15. A method for treating cancer in a mammal, comprising administering a compound selected from the group consisting of:

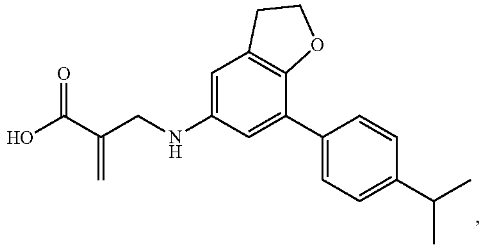

,

-continued

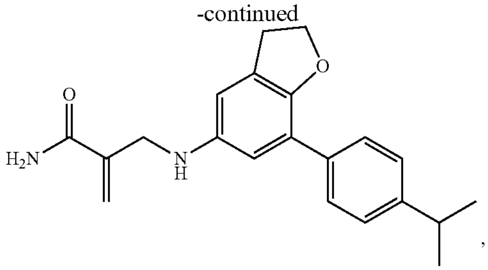

,

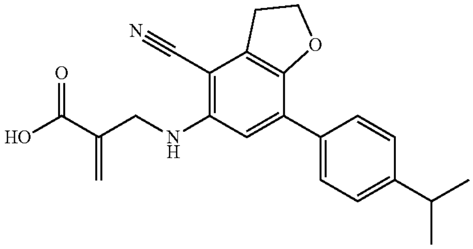

,

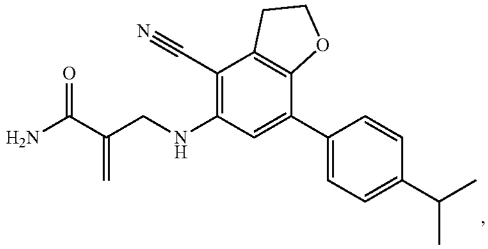

,

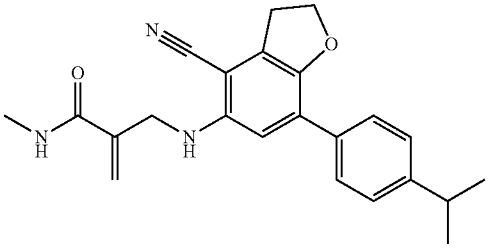

,

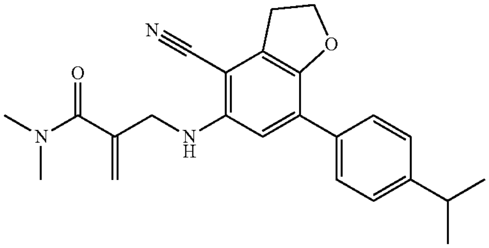

,

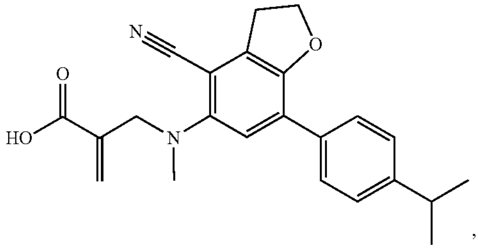

,

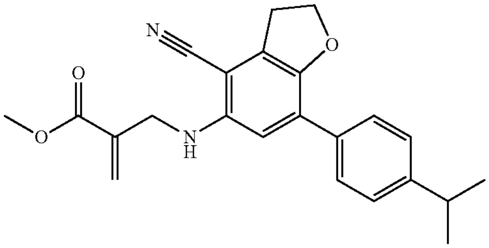

,

-continued
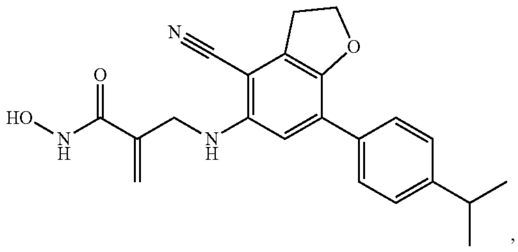
,
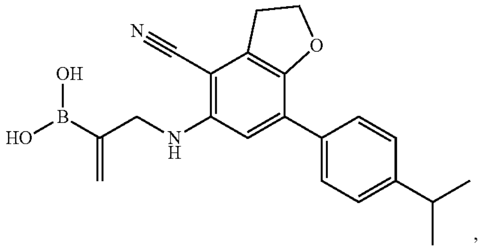
,
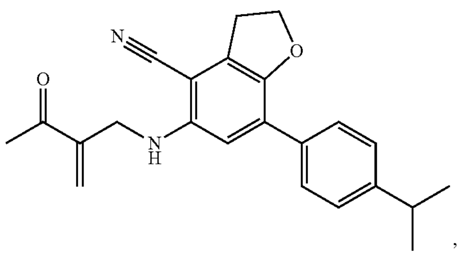
,
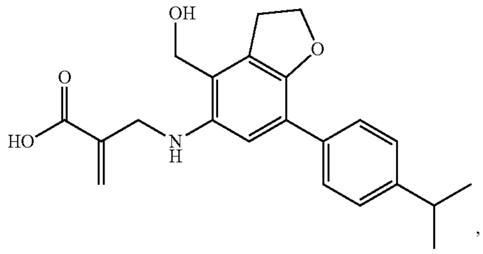
,
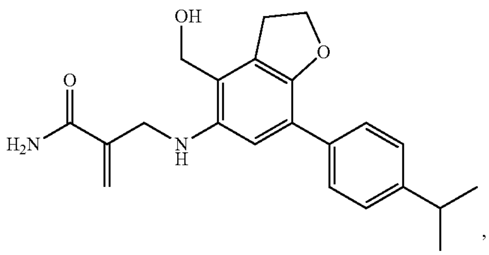
,
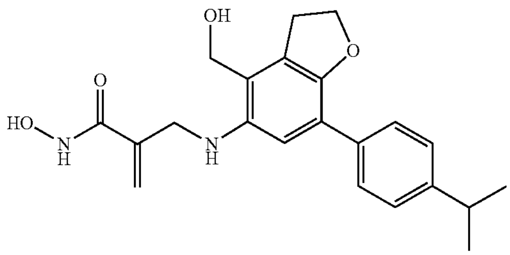
,
-continued
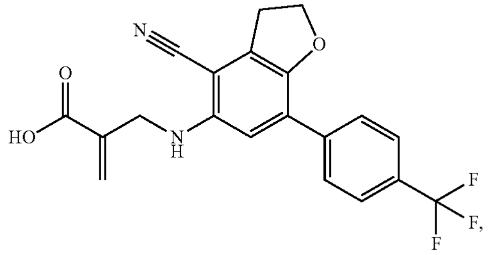
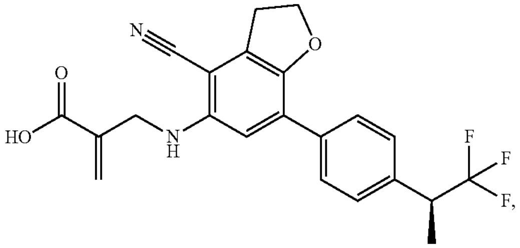
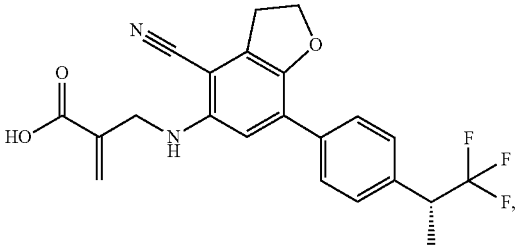
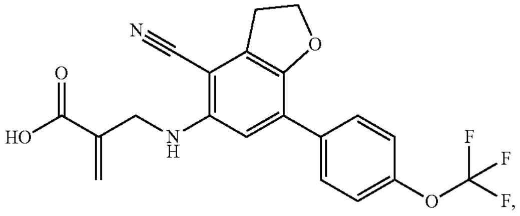
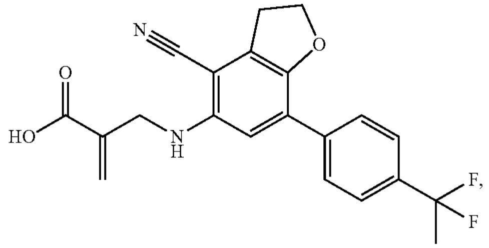
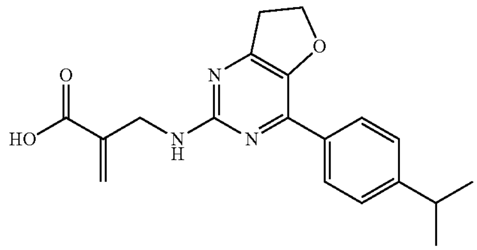
,
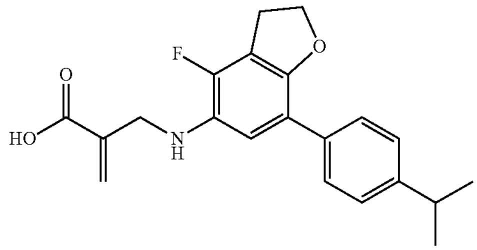
, -continued
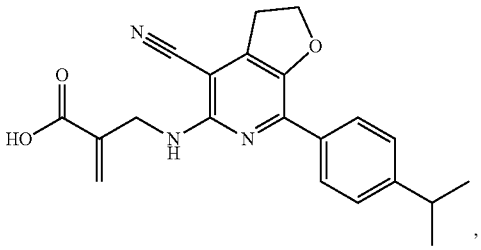
,
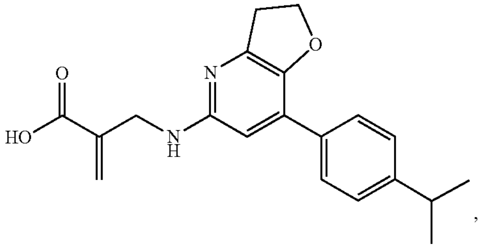
,
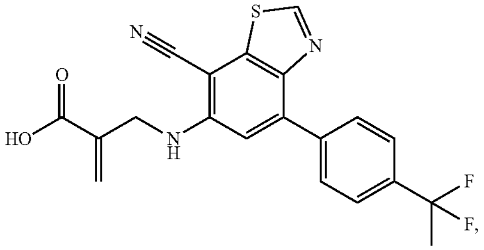
,
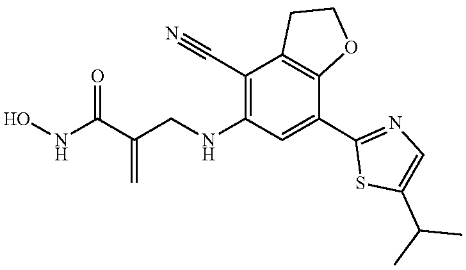
,
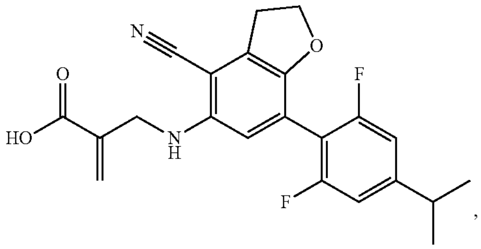
,
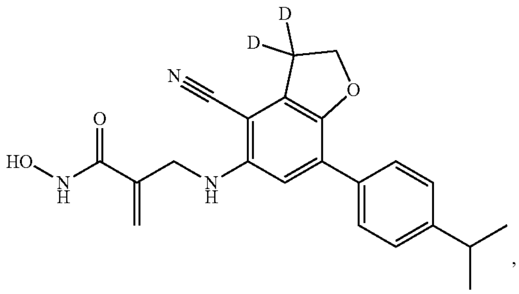
,
-continued
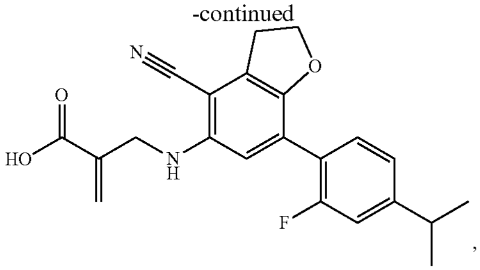
,
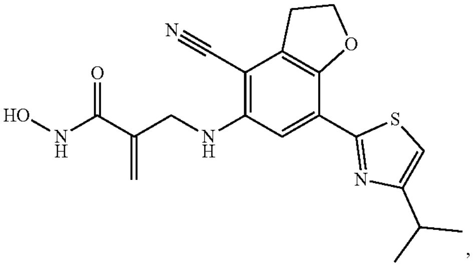
,
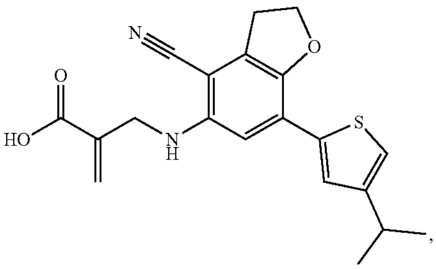
,
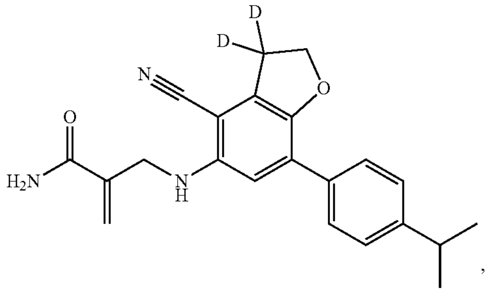
,
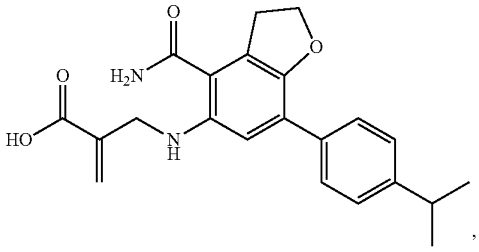
,
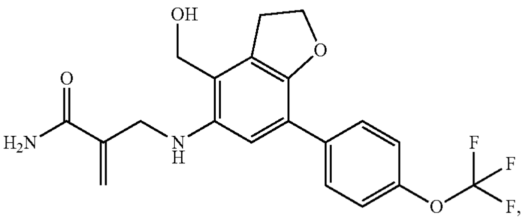
,

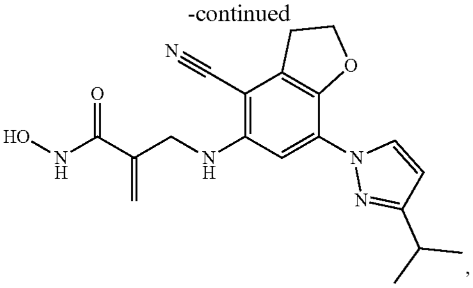
,
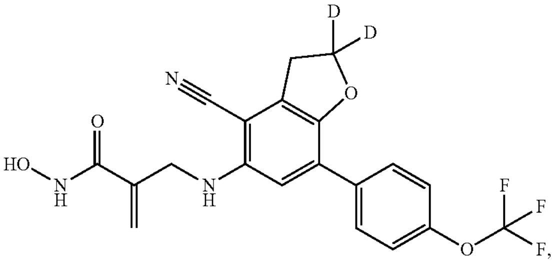
,
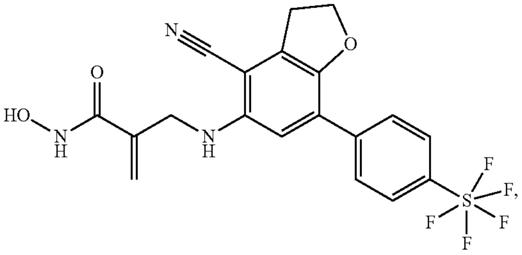
,
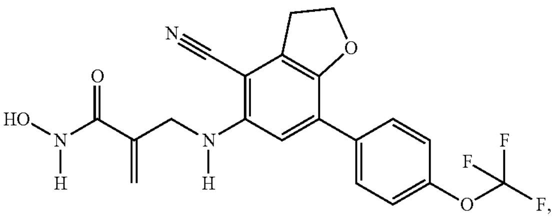
,
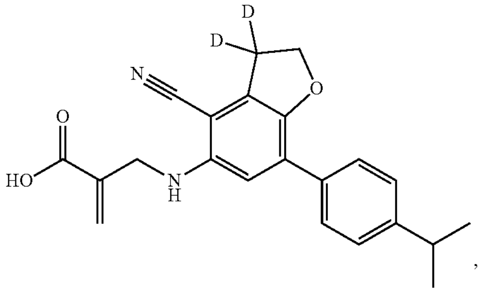
,
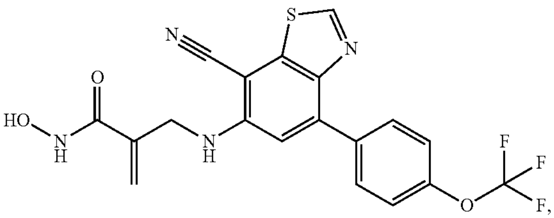
,
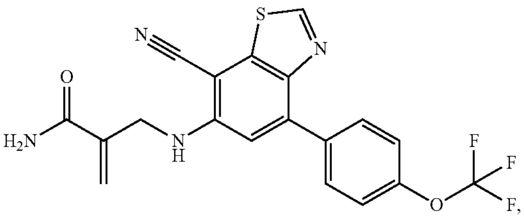
,
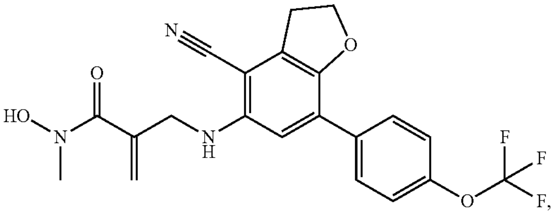
,
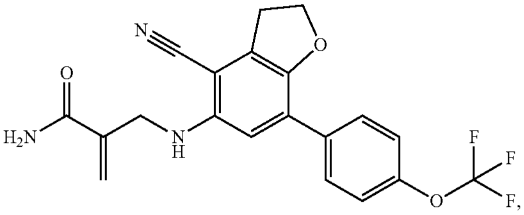
,
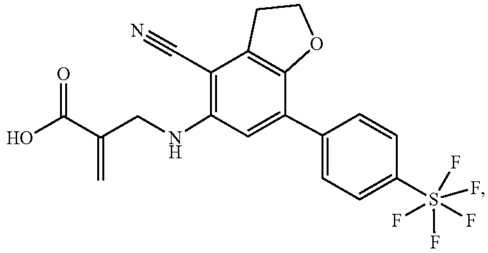
,
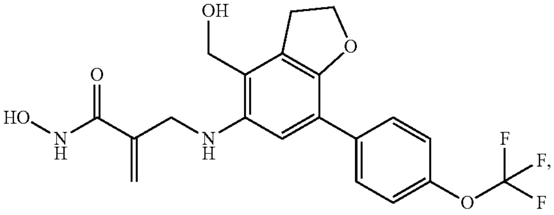
,
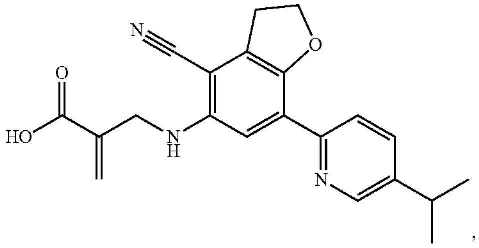
,
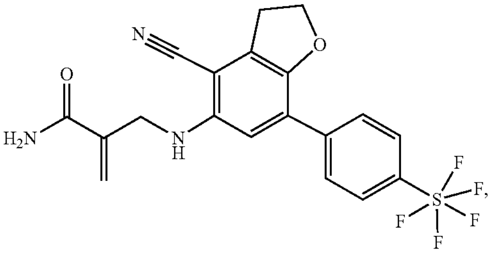
,
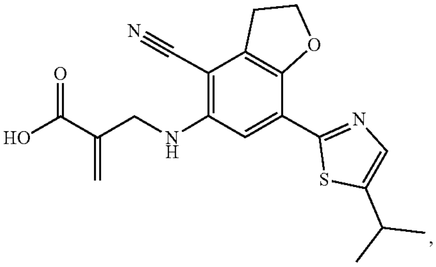
, -continued

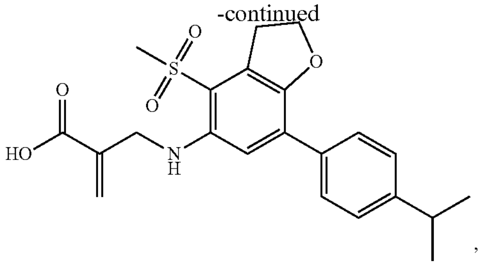

, and

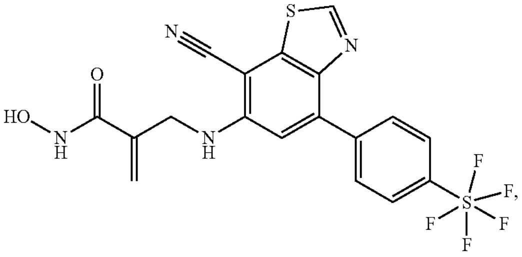

or a stereoisomer, tautomer, or pharmaceutically acceptable salt thereof, to the mammal, wherein the cancer is selected from: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

16. The method of claim 1, wherein the cancer is lung cancer, breast cancer, head and neck cancer, colon cancer, ovarian cancer, liver cancer, brain cancer, prostate cancer, mesothelioma, sarcomas, or leukemia.

17. The method of claim 1, wherein the cancer is a mesothelioma, sarcoma, or leukemia.

18. The method of claim 15, wherein the cancer is lung cancer, breast cancer, head and neck cancer, colon cancer, ovarian cancer, liver cancer, brain cancer, prostate cancer, mesothelioma, sarcomas, or leukemia.

19. The method of claim 15, wherein the cancer is a mesothelioma, sarcoma, or leukemia.

* * * * *